US008895504B2

(12) United States Patent
Schäffer et al.

(10) Patent No.: US 8,895,504 B2
(45) Date of Patent: Nov. 25, 2014

(54) AMYLIN DERIVATIVES

(75) Inventors: Lauge Schäffer, Lyngby (DK); Thomas Kruse, Herlev (DK); Jesper Lau, Farum (DK); Henning Thøgersen, Farum (DK)

(73) Assignee: Novo Nordisk A/S, Bagsvaerd (DK)

( * ) Notice: Subject to any disclaimer, the term of this patent is extended or adjusted under 35 U.S.C. 154(b) by 756 days.

(21) Appl. No.: 12/603,135

(22) Filed: Oct. 21, 2009

(65) Prior Publication Data

US 2011/0105394 A1 May 5, 2011

Related U.S. Application Data

(60) Provisional application No. 61/108,969, filed on Oct. 28, 2008, provisional application No. 61/184,099, filed on Jun. 4, 2009.

(30) Foreign Application Priority Data

Oct. 21, 2008 (EP) .................................... 08167154
May 28, 2009 (EP) .................................... 09161372

(51) Int. Cl.
*A61K 38/00* (2006.01)
*C07K 14/00* (2006.01)
*C07K 14/575* (2006.01)
*A61K 47/48* (2006.01)

(52) U.S. Cl.
CPC ............... *C07K 14/575* (2013.01); *A61K 38/00* (2013.01); *A61K 47/48284* (2013.01); *A61K 47/48038* (2013.01)
USPC .......................................... 514/6.9; 530/324

(58) Field of Classification Search
CPC ............ A61K 38/00; A61K 47/48038; A61K 47/48284; C07K 14/00; C07K 14/575
USPC .......................................... 514/6.9; 530/324
See application file for complete search history.

(56) References Cited

U.S. PATENT DOCUMENTS

| 5,710,024 A | 1/1998 | Adamou et al. |
| 2003/0130177 A1 | 7/2003 | Kolterman et al. |
| 2004/0022807 A1 | 2/2004 | Duft et al. |
| 2009/0099085 A1 | 4/2009 | Hansen et al. |
| 2010/0222269 A1 | 9/2010 | Schaffer et al. |
| 2011/0105394 A1 | 5/2011 | Schaffer et al. |

FOREIGN PATENT DOCUMENTS

| WO | WO 93/10147 | 5/1993 |
| WO | WO 01/45746 | 6/2001 |
| WO | WO 2005/027978 | 3/2005 |
| WO | WO 2005/028516 | 3/2005 |
| WO | WO 2005/077072 | 8/2005 |
| WO | WO 2005/097202 | 10/2005 |
| WO | WO 2005/118642 | 12/2005 |
| WO | WO 2006/005667 | 1/2006 |
| WO | WO 2006/059106 | 6/2006 |
| WO | WO 2006/105345 | 10/2006 |
| WO | 2007/055728 A1 | 5/2007 |
| WO | 2007/109354 A2 | 9/2007 |
| WO | WO 2007/104789 | 9/2007 |
| WO | WO 2009/034119 | 3/2009 |
| WO | WO 2010/046357 | 4/2010 |

OTHER PUBLICATIONS

Definition of Moiety from http://dictionary.reference.com/browse/moiety, pp. 1-3. Accessed Aug. 26, 2010.*
Dennis, M.S. et al., "Albumin Binding as a General Strategy for Improving the Pharmacokinetics of Proteins", Journal of Biological Chemistry, vol. 277, No. 38, pp. 35035-35043.
Andrew Young, Advances in Pharmacology, 2005, vol. 52, pp. 1-18.
Holz, George G., et al, Curr Med Chem (2003), "Glucagon-Like Peptide-1 Synthetic Analogs: New Therapeutic Agents for Use in the Treatment of Diabetes Mellitus," vol. 10, No. 22, pp. 2471-2483.
Colburn, W.A., J Clin Pharmacol, "Pharmacokinetics and pharmacodynamics of AC137 (25,28,29 tripro-amylin, human) after intravenous bolus and infusion doses in patients with insulin-dependent diabetes" 1996, vol. 36, pp. 13-24.
Kurtzhals, P., International Journal of Obesity, "Engineering predictability and protraction in a basal insulin analogue: the pharmacology of insulin detemir", 2004, vol. 28, Suppl 2, pp. S23-S28.
Veronese, Biomaterials, "Peptide and protein PEGylation: a review of problems and solutions", 2001, vol. 22, pp. 405-417.
Wan, L., et al, Journal of Pharmaceutical Sciences, "Improving Pharmacokinetic Properties of Adrenocorticotropin by Site-Specific Lipid Modification", 2003, vol. 92, Part 9, pp. 1882-1892.
Broadhead et al., Drug Development and Industrial Pharmacy, "The Spray Drying of Pharmaceuticals", 1992, vol. 18, Part 11-12, pp. 1169-1206.
Chien, Jianweiyu and Yie, Critical Reviews in Therapeutic Drug Carrier, "Pulmonary Drug Delivery: Physiologic and Mechanistic Aspect" 1997, vol. 14, Part 4, pp. 395-453.
Carpenter and Crowe, Cryobiology, "Modes of Stabilization of a Protein by Organic Solutes During Dessication", 1998, vol. 25, pp. 459-470.
Kurtzhals, P et al., Biochemical Journal, "Albumin Binding of Insulins Acylated With Fatty Acides . . . " 1995, vol. 312, pp. 725-731.
Mumenthaler et al., Pharmaceutical Research, "Feasibility Study on Spray-Drying Protein Pharmaceuticals: Recombinant Human Growth Hormane and Tissue-Type Plasminogen Activator", 1994, vol. 11, Part 1, pp. 12-20.
Roser, Biopharmaceutical, "Trehalsoe Drying: A Novel Replacement for Freeze Drying" 1991, vol. 4, pp. 47-53.
William and Polli, J. Parenteral Sci. Technol. 1984, vol. 38, pp. 48-59.
Spray Drying Handbook, 1991, pp. 491-676.
Yan, L M et al. "Design of a Mimic of Nonamyloidogenic" Proceedings of the National Academy of Sciences, 2006, vol. 103 (7), pp. 2046-2051.

\* cited by examiner

*Primary Examiner* — Julie Ha
(74) *Attorney, Agent, or Firm* — Jianjie Hu

(57) ABSTRACT

Amylin derivatives, pharmaceutical compositions containing such derivatives, as well as methods of treating diabetes and hyperglycaemia are disclosed.

11 Claims, 43 Drawing Sheets

AMYLIN DERIVATIVES

CROSS-REFERENCE TO RELATED APPLICATIONS

This application is a utility application which claims priority under 35U.S.C. § 119 of U.S. Provisional Application 61/108,969, filed 28 Oct. 2008 and U.S. Provisional Application 61/184,099, filed 4 Jun. 2009; this application further claims priority of European Patent Application No. 08167154.7, filed 21 Oct. 2008 and European Patent Application No. 09161372.9, filed 28 May 2009.

FIELD OF THE INVENTION

The invention relates to derivatives of human amylin or analogues thereof which bind to albumin and/or the amylin receptor, pharmaceutical compositions comprising these derivatives, and amylin derivatives for use as medicaments.

INCORPORATION-BY-REFERENCE OF THE SEQUENCE LISTING

In accordance with 37 C.F.R. § 1.52(e)(5), Applicants enclose herewith the Sequence Listing for the above-captioned application entitled "SEQUENCE LISTING", created on Oct. 20, 2009. The Sequence Listing is made up of 43 bytes, and the information contained in the attached "SEQUENCE LISTING" is identical to the information in the specification as originally filed. No new matter is added.

BACKGROUND OF THE INVENTION

A large and growing number of people suffer from diabetes mellitus and obesity. Diabetes mellitus is a metabolic disorder in which the ability to utilize glucose is partly or completely lost.

A number of treatment regimes are targeting excessive blood glucose whereas others are focused primarily on weight reduction. The most efficient anti-diabetic agent used to lower blood glucose is insulin and analogue(s) thereof. It has been known for a long time that when traditional insulin is used to treat diabetes, it is associated with an increase in body weight. Insulin has to be injected subcutaneously up to several times per day.

Type 2 diabetes is generally treated in the early phases with diet and exercise. As the condition progresses, various oral anti-diabetic agents are added. Injected agents such as GLP-1 analogues may also be used at this stage. In general, these agents are most efficient in patients with functioning beta-cells capable of releasing insulin and amylin.

Human amylin is a 37 amino acid long peptide which has physico-chemical properties that make its use as a drug troublesome. In particular, it has a tendency to fibrillate invitro and/or ex-vivo and become ineffective due to precipitation. Additionally amylin is difficult to formulate as it precipitates at physiologic pH. Therefore it is formulated in a acidic solution.

A drug product sold under the trademark Symlin® is currently on the market. The product contains an analogue of human amylin called pramlintide. Compared to human amylin the amino acids in position 25, 28 and 29 in pramlintide are substituted with proline. This modification reduces the fibrillating tendency of the protein. Pramlintide is difficult to keep in solution at neutral pH and it is therefore provided in an acidic solution i.e. Symlin®. Another disadvantage is that Symlin has to be injected at separate injection site three times daily.

International patent application no. EP2008/062036 discloses amylin derivatives having an albumin binding residue. Even though the amylin derivatives shows improved pharmacokinetic (PK) or pharmacodynamic (PD) properties compared to pramlintide they still tend to fibrillate and are difficult to keep in solution at pH 4.

SUMMARY OF THE INVENTION

It has surprisingly been found that amylin derivatives, wherein the amino acid in position 17 has been replaced with any natural amino acid except Val, Lys or Ala, has a reduced tendency to fibrillate and shows increased stability when formulated at acidic pH. The amylin derivatives of the present invention at the same time have a protracted pharmacokinetic profile and good pharmacodynamic properties. Therefore the amylin derivatives according to the present invention do not have to be injected as often as known amylin derivatives.

In one aspect the invention concerns a derivative of amylin, which is an human amylin analogue having a substituent attached to the α-amino group of the N-terminal amino acid residue or to a Lys residue in the human amylin analogue, wherein the substituent comprises an albumin binding moiety and the amino acid residue in position 17 of the human amylin analogue is any natural amino acid except Val, Lys or Ala and wherein the amino acid numbering of the human amylin analogue conforms with the amino acid numbering in SEQ ID NO:1

In one aspect the invention concerns an amylin derivative comprising an amino acid sequence of formula 1:

```
Formula (1)
                                    (SEQ ID No: 2)
Xaa₁-Cys-Xaa₃-Thr-Ala-Thr-Cys-Ala-Thr-Gln-Arg- Leu-Ala-Xaa₁₄-Phe-Leu-Xaa₁₇-Xaa₁₈-Ser-Ser-Xaa₂₁-

Asn-Phe-Xaa₂₄-Xaa₂₅-Xaa₂₆-Leu-Xaa₂₈-Xaa₂₉-Thr-

Xaa₃₁-Val-Gly-Ser-Asn-Thr-Tyr
``` wherein
$Xaa_1$ is deleted or independently selected from Lys, Arg, His and Glu;
$Xaa_3$ is independently selected from Asn and Lys;
$Xaa_{14}$ is independently selected from Glu, Asn, Gln and Asp;
$Xaa_{17}$ is independently selected from His, Ser, Gly, Arg and Pro;
$Xaa_{18}$ is independently selected from His or Arg;
$Xaa_{21}$ is independently selected from Asp, Asn and Gln;
$Xaa_{24}$ is independently selected from Glu and Gly;
$Xaa_{25}$ is independently selected from Ala and Pro;
$Xaa_{26}$ is independently selected from Pro and Ile;
$Xaa_{28}$ is independently selected from Ser and Pro;
$Xaa_{29}$ is independently selected from Ser and Pro;
$Xaa_{31}$ is independently selected from Glu and Asn;
the C-terminal may optionally be derivatized as an amide;
wherein a substituent is connected to the amino acid residue $Xaa_1$ or to Cys in position 2, which substituent comprises an albumin binding moiety.

In one aspect the invention concerns a pharmaceutical composition comprising an amylin derivative according to the invention and a pharmaceutically acceptable excipient.

In one aspect the invention concerns a derivative according to the invention for use as a medicament.

DEFINITIONS

Figure 1A:
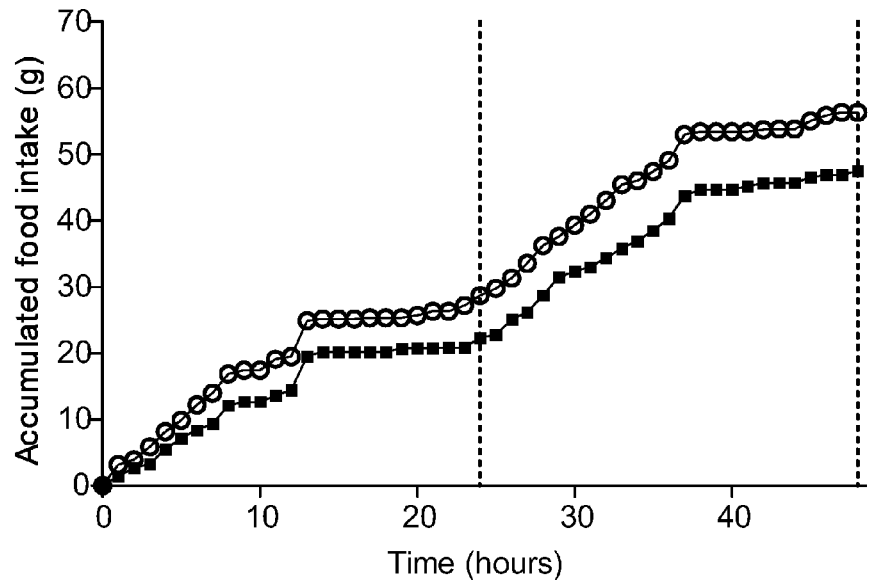
FIG. 1a shows food intake during 48 hours according to Pharmacological Assay (I). Data=mean. n=5-7. Open circle: vehicle. Black squares: 30 nmol/kg of compound 3.

The term "human amylin" as used herein refers to the peptide human amylin having the sequence as depicted in SEQ ID No 1. The term includes, but is not limited to, a human peptide hormone of 37 amino acids referred to as amylin, which in nature is co-secreted with insulin from β-cells of the pancreas. Human amylin has the following amino acid sequence: Lys-Cys-Asn-Thr-Ala-Thr-Cys-Ala-Thr-Gln-Arg-Leu-Ala-Asn-Phe-Leu-Val-His-Ser-Ser-Asn-Asn-Phe-Gly-Ala-Ile-Leu-Ser-Ser-Thr-Asn-Val-Gly-Ser-Asn-Thr-Tyr (SEQ ID NO: 1) which is shown below with a disulfide bridge between the two Cys residues and a C-terminal amide group.

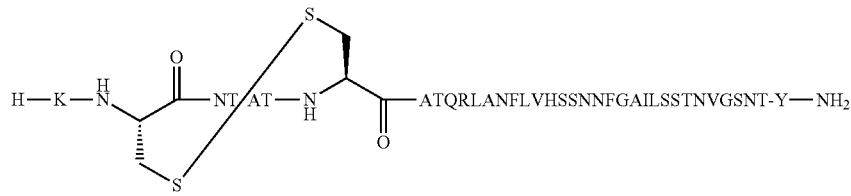

In the present text, the term "analogue of human amylin" or "human amylin analogue" is used to designate a peptide wherein one or more amino acid residues of human amylin independently have been modified by substituting with other amino acid residues and/or by deletion of one or more amino acid residues and/or by adding one or more amino acid residues. The number of amino acid insertions, additions, deletions, or substitutions may be at least 1, but up to 2, 3, 4, 5, 6, 7, 8, 9 or 10 amino acid insertions, additions, deletions, or substitutions may be present. The substitution or addition can be with any natural or unnatural amino acid, synthetic amino acids, peptidomimetics, or other chemical compounds. The addition or deletion of amino acid residues can take place at the N-terminal of the peptide and/or at the C-terminal of the peptide.

When used herein the term "natural amino acid" is an amino acid (with the usual three letter codes & one letter codes in parenthesis) selected from the group consisting of: Glycine (Gly & G), proline (Pro & P), alanine (Ala & A), valine (Val & V), leucine (Leu & L), isoleucine (Ile & I), methionine (Met & M), cysteine (Cys & C), phenylalanine (Phe & F), tyrosine (Tyr & Y), tryptophan (Trp & W), histidine (His & H), lysine (Lys & K), arginine (Arg & R), glutamine (Gln & Q), asparagine (Asn & N), glutamic acid (Glu & E), aspartic acid (Asp & D), serine (Ser & S) and threonine (Thr & T). If, due to typing errors, there are deviations from the commonly used codes, the commonly used codes apply. The amino acids present in the amylin derivatives of this invention are, preferably, amino acids which can be coded for by a nucleic acid.

The term "linker as used herein means chemical moiety which separates the albumin binding moiety and the human amylin analogue by having the linker in between. For example the linker can comprise one or two amino acids which at one end bind to the albumin binding moiety and at the other end binds to the amino acid in position 1 of the human amylin analogue, or when the amino acid in position 1 is deleted, the linker binds to Cys in position 2 of the human amylin analogue. The chemical moiety of the linker can contribute/enhance to the albumin binding effect of the substituent, e.g. a linker comprising γGlu enhances the albumin binding effect of the amylin derivative.

The term "potency" is used to describe the effect of a given compound in assays were a sigmoidal relationship between log concentration and the effect of a compound has been established. Furthermore, the response should be variable from 0 to 100%. EC(effective concentration)50 can be used to describe the concentration of a given compound yielding a response of 50% in the assay.

The term "activity" refers in one aspect to the ability to reduce appetite and/or increase satiety. The activity can be measured by the ability to reduce appetite as e.g. described in Pharmacological assays I and II under the heading ASSAYS.

The term "physical stability" of a amylin derivative according to the invention or a protein formulation according to the invention refers as used herein to the tendency of the protein not to form biologically inactive and/or insoluble aggregates of the protein as a result of exposure of the protein to thermo-mechanical stresses and/or interaction with interfaces and surfaces that are destabilizing, such as hydrophobic surfaces and interfaces. Physical stability of the aqueous protein formulations may be evaluated by means of visual inspection, ThT fibrillation assay and/or turbidity measurements as described elsewhere herein. Visual inspection of the formulations is performed in a sharp focused light with a dark background. The turbidity of the formulation is characterized by a visual score ranking the degree of turbidity for instance on a scale from 0 to 3 (a formulation showing no turbidity corresponds to a visual score 0, and a formulation showing visual turbidity in daylight corresponds to visual score 3). A formulation is classified physical unstable with respect to protein aggregation, when it shows visual turbidity in daylight. Alternatively, the turbidity of the formulation can be evaluated by simple turbidity measurements well-known to the skilled person.

The term "chemical stability" of a amylin derivative according to the invention or of the protein formulation or a pharmaceutical formulation refers to no chemical covalent changes in the protein structure which thereby do not lead to formation of chemical degradation products with potential less biological potency and/or potential increased immunogenic properties compared to the native protein structure. Various chemical degradation products can be formed depending on the type and nature of the native protein and the environment to which the protein is exposed. Elimination of chemical degradation can most probably not be completely avoided and increasing amounts of chemical degradation products is often seen during storage and use of the protein formulation as well-known by the person skilled in the art. Most proteins are prone to deamidation, a process in which the side chain amide group in glutaminyl or asparaginyl residues is hydrolysed to form a free carboxylic acid. Other degradations pathways involves formation of high molecular weight transformation products where two or more protein molecules are covalently bound to each other through transamidation and/or disulfide interactions leading to formation of covalently bound dimer, oligomer and polymer degradation products (*Stability of Protein Pharmaceuticals*, Ahern. T. J. & Manning M. C., Plenum Press, New York 1992). Oxidation (of for instance methionine residues) can be mentioned as another variant of chemical degradation. The chemical stability of the protein formulation can be evaluated by measuring the amount of the chemical degradation products at various time-points after exposure to different environmental conditions (the formation of degradation products can often be accelerated by for instance increasing temperature). The amount of each individual degradation product is often determined by separation of the degradation products depending on molecule size and/or charge using various chromatography techniques (e.g. SEC-HPLC and/or RP-HPLC).

The term "stabilized formulation" refers to a formulation with increased physical stability, increased chemical stability or increased physical and chemical stability compared to an aqueous solution of the peptide.

"Albumin binding affinity" may be determined by several methods known within the art. In one method the derivative to be measured is radiolabeled with e.g. $^{125}$I or $^3$H and incubated with immobilized albumin (Kurtzhals et. al., Biochem. J., 312, 725-731 (1995)). The binding of the derivative relative to a standard is calculated. In another method a related compound is radiolabeled and its binding to albumin immobilized on e.g. SPA beads is competed by a dilution series of the derivative to be measured. The EC50 value for the competition is a measure of the affinity of the derivative. In a third method, the receptor affinity or potency of a derivative is measured at different concentrations of albumin, and the shift in relative affinity or potency of the derivative as a function of albumin concentration reflects its affinity for albumin.

By using the term "Trx" or "trans-4-(aminomethyl)cyclohexanecarboxylic acid" is meant an amino acid with the following structure:

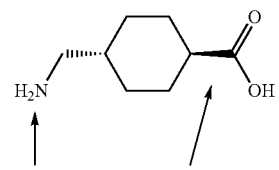

nitrogen and carboxy group
form the amide bonds to the two neighboring residues
trans-4-(aminomethyl)cyclohexanecarboxylic acid By using the term "γGlu" is meant an amino acid with the following structure:

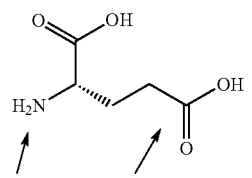

α-nitrogen and γ-carboxy group form the amide
bonds to the two neighboring residues The term "GABA" means Gamma amino butyric acid.

DESCRIPTION OF THE INVENTION

It has surprisingly been found that amylin derivatives, wherein the amino acid in position 17 has been replaced with an amino acid selected from the group consisting of His, Ser, Gly, Arg and Pro, has improved stability. The amylin derivatives have a reduced tendency to fibrillate and show improved stability when formulated at acidic pH. The amylin derivatives of the present invention at the same time have a protracted pharmacokinetic profile and good pharmacodynamic properties. Therefore the amylin derivatives according to the present invention do not have to be injected as often as known amylin derivatives. In one aspect the invention concerns a derivative of amylin, which is a human amylin analogue having a substituent attached to the α-amino group of the N-terminal amino acid residue or to a Lys residue in the human amylin analogue, wherein the substituent comprises an albumin binding moiety and the amino acid residue in position 17 of the human amylin analogue is any natural amino acid except Val, Lys or Ala and wherein the amino acid numbering of the human amylin analogue conforms with the amino acid numbering in SEQ ID NO:1 In one aspect the amino acid residue in position 17 is His, Ser, Gly, Pro or Arg. In one aspect the albumin binding residue is attached to the ε-amino group of the lysine residue. In one aspect the albumin binding residue is attached via the alpha-amino group of the lysine residue.

Amylin derivatives having a natural amino acid except Val, Lys or Ala in position 17 of the human amylin analogue, for example His, Ser, Gly, Arg or Pro in position 17 shows better biophysical properties eg. reduced tendency to fibrillate and shows increased solubility when formulated at pH 2.5 to 4, for example at pH 3 to 3.5.

In one aspect a derivative of human amylin analogue is provided which shows physical stability. In a further aspect a derivative of human amylin analogue is provided which has increased physical stability relative to human amylin.

In one aspect the amino acid in position 17 is His or Arg. Amylin derivatives having His or Arg in position 17 have been found to have reduced tendency to fibrillate and remain soluble at pH 2.5 to 4 while exhibiting even better protracted pharmacokinetic profile and better pharmacodynamic properties than the known amylin derivatives.

In one aspect the amino acids in position 25, 28 and 29 are Pro. In one aspect the human amylin analogue comprises 1-10 amino acid substitutions for example 1, 2, 3, 4, 5 or 6 substitutions.

In one aspect the amino acid in position 1 of the human amylin analogue is substituted with an amino acid such as the amino acids Glu, Arg and His or the amino acid in position 1 is deleted.

In one aspect the substituent comprises a linker.

In one aspect the linker comprises 1-10 amino acids which are attached to the α-amino group of the N-terminal amino acid residue or to a Lys residue in the human amylin analogue, In one aspect the amino acids are selected from the group consisting of γGlu, Arg, γGlu-Arg, γGlu-His, Trx-γGlu, γGlu-His, Glu-Lys, Glu-Glu, Glu-Arg, γGlu-His-His, γGlu-Arg-His, γGlu-His-Arg, γGlu-Glu-Arg, Glu-Glu-Arg, Glu-Lys-Arg, γGlu-Glu-His-His, γGlu-Glu-His-Arg, Glu-Glu-Arg-Glu and Glu-Glu-Glu-Glu.

The linker can further comprise —C(O)—(CH$_2$)$_l$—O—[CH$_2$CH$_2$—O]$_m$—(CH$_2$)$_p$—[NHC(O)—(CH$_2$)$_l$—O—[(CH$_2$)$_n$—O]$_m$—(CH$_2$)$_p$]$_q$—NH— wherein l, m, n, and p independently are 1-7, and q is 0-5. For example the linker can comprise —C(O)—CH$_2$—O—CH$_2$—CH$_2$—O—CH$_2$—CH$_2$—NH— or —C(O)—CH$_2$—O—CH$_2$—CH$_2$—O—CH$_2$—CH$_2$—[NHC(O)—CH$_2$—O—CH$_2$—CH$_2$—O—CH$_2$—CH$_2$—]$_1$—NH— and —C(O)—(CH$_2$)$_2$—O—[CH$_2$CH$_2$—O]$_7$—(CH$_2$)$_2$—NH—. In one aspect the linker further comprises γGlu or GABA.

In one aspect the albumin binding residue is an acyl group selected from the group comprising HOOC(CH$_2$)$_s$CO—, wherein s is an integer from 17 to 21, for example 18, 19 or 20.

In one aspect the linker comprises γGlu, γGlu-His or γGlu-His-His. In one aspect the derivative of human amylin analogue has His in position 1 and 17, the amino acid in position 25, 28 and 29 are Pro, the linker comprises γGlu-His-His or γGlu-His attached to the α-amino group of His in position 1 of the human amylin analogue and the albumin binding residue is attached to γGlu of the linker, wherein the albumin binding residue is HOOC(CH$_2$)$_{18}$CO or HOOC(CH$_2$)$_{16}$CO—.

In one aspect the invention concerns an amylin derivative comprising an amino acid sequence of formula I:

```
Formula (1)
                                          (SEQ ID No: 2)
Xaa₁-Cys-Xaa₃-Thr-Ala-Thr-Cys-Ala-Thr-Gln-Arg- Leu-Ala-Xaa₁₄-Phe-Leu-Xaa₁₇-Xaa₁₈-Ser-Ser-Xaa₂₁-

Asn-Phe-Xaa₂₄-Xaa₂₅-Xaa₂₆-Leu-Xaa₂₈-Xaa₂₉-Thr-

Xaa₃₁-Val-Gly-Ser-Asn-Thr-Tyr
``` wherein
Xaa$_1$ is deleted or independently selected from Lys, Arg, His and Glu;
Xaa$_3$ is independently selected from Asn and Lys;
Xaa$_{14}$ is independently selected from Glu, Asn, Gln and Asp;
Xaa$_{17}$ is independently selected from His, Ser, Gly, Arg and Pro;
Xaa$_{18}$ is independently selected from His or Arg;
Xaa$_{21}$ is independently selected from Asp, Asn and Gln;
Xaa$_{24}$ is independently selected from Glu and Gly;
Xaa$_{25}$ is independently selected from Ala and Pro;
Xaa$_{26}$ is independently selected from Pro and Ile;
Xaa$_{28}$ is independently selected from Ser and Pro;
Xaa$_{29}$ is independently selected from Ser and Pro;
Xaa$_{31}$ is independently selected from Glu and Asn;
the C-terminal may optionally be derivatized as an amide;
wherein a substituent is connected to the amino acid residue Xaa$_1$ or to Cys in position 2, which substituent comprises an albumin binding moiety.

In one aspect of the invention, the C-terminal of the amylin derivative may be terminated as either an acid or amide. In one aspect, the C-terminal of the amylin derivative is an amide.

In one aspect the albumin binding residue binds non-covalently to albumin.

In one aspect the albumin binding residue has a binding affinity towards human serum albumin that is below about 10 μM or below about 1 μM. The derivatives of the present invention are capable of binding to or otherwise directly or indirectly interacting with an amylin receptor, or other receptor or receptors with which amylin itself may interact to elicit a biological response, e.g., reducing food intake.

In one aspect the albumin binding residue has from 6 to 40 carbon atoms, from 8 to 26 carbon atoms or from 14 to 22 carbon atoms for example 17, 18, 19, 20 and 21 carbon atoms.

In one aspect the albumin binding residue is an acyl group selected from the group comprising CH$_3$(CH$_2$)$_r$CO—, wherein r is an integer from 4 to 38, preferably an integer from 4 to 24, more preferred selected from the group comprising $CH_3(CH_2)_6CO-$, $CH_3(CH_2)_8CO-$, $CH_3(CH_2)_{10}CO-$, $CH_3(CH_2)_{12}CO-$, $CH_3(CH_2)_{14}CO-$, $CH_3(CH_2)_{16}CO-$, $CH_3(CH_2)_{18}CO-$, $CH_3(CH_2)_{20}CO-$ and $CH_3(CH_2)_{22}CO-$.

In one aspect the albumin binding residue comprises a group which can be negatively charged at pH 7.4.

In one aspect the albumin binding residue comprises a carboxylic acid group, such as $HOOC(CH_2)_sCO-$, wherein s is an integer from 12 to 22, for example 17, 18, 19, 20, 21 or 22.

In one aspect of the invention, the albumin binding residue is a group of the formula $CH_3(CH_2)_vCO-NHCH(COOH)(CH_2)_2CO-$, wherein v is an integer from 10 to 24. In one aspect of the invention, the albumin binding residue is a group of the formula $CH_3(CH_2)_wCO-NHCH((CH_2)_2COOH)CO-$, wherein w is an integer from 8 to 24.

In one aspect the linker comprises 1-10 amino acids. The amino acids can be selected from the group consisting of γGlu, Arg, γGlu-Arg, γGlu-His, Trx-γGlu, γGlu-His, Glu-Lys, Glu-Glu, Glu-Arg, γGlu-His-His, γGlu-Arg-His, γGlu-His-Arg, γGlu-Glu-Arg, Glu-Glu-Arg, Glu-Lys-Arg, γGlu-Glu-His-His (SEQ ID: 36), γGlu-Glu-His-Arg (SEQ ID: 37), Glu-Glu-Arg-Glu (SEQ ID: 38) and Glu-Glu-Glu-Glu (SEQ ID: 39).

In one aspect the linker can further comprise $-C(O)-(CH_2)_l-O-[CH_2CH_2-O]_m-(CH_2)_p-[NHC(O)-(CH_2)_l-O-[(CH_2)_n-O]_m-(CH_2)_p]_q-NH-$ wherein l, m, n, and p independently are 1-7, and q is 0-5. The linker can for example the linker can be selected from the group consisting of $-C(O)-CH_2-O-CH_2-CH_2-O-CH_2-CH_2-NH-$ or $-C(O)-CH_2-O-CH_2-CH_2-O-CH_2-CH_2-[NHC(O)-CH_2-O-CH_2-CH_2-O-CH_2-CH_2-]_1-NH-$ and $-C(O)-(CH_2)_2-O-[CH_2CH_2-O]_7-(CH_2)_2-NH-$. In one aspect the linker further comprises γGlu. In one aspect the linker comprises GABA.

In one aspect the $Xaa_1$ is His, $Xaa_{17}$ is His, $Xaa_{25}$ is Pro, $Xaa_{28}$ is Pro, $Xaa_{29}$ is Pro, the albumin binding residue is $HOOC(CH_2)_{18}CO$ and the linker comprises γGlu-His-His, wherein the albumin binding residue is attached to the linker via the γGlu of the linker.

In one aspect the $Xaa_1$ is His, $Xaa_{17}$ is His, $Xaa_{25}$ is Pro, $Xaa_{28}$ is Pro, $Xaa_{29}$ is Pro, the albumin binding residue is $HOOC(CH_2)_{16}CO$ and the linker comprises γGlu-His, wherein the albumin binding residue is attached to the linker via the γGlu of the linker.

In one aspect derivative is selected from the group consisting of:

N-alpha-(19-carboxynonadecanoyl)-Glu-Glu-Arg-[Glu1,Glu14,His17,Glu31]-pramlintide, N-epsilon3-(19-carboxynonadecanoyl-Glu-Glu-Arg-Glu)-[Lys3,His17,Asp21]-pramlintide, N-epsilon3-{2-[2-(2-{(S)-4-Carboxy-2-[(S)-4-carboxy-2-(19-carboxynonadecanoylamino)butyrylamino]butyrylamino}ethoxy)ethoxy]acetyl}-[Lys3,His17,Asp21]-pramlintide, N-epsilon3-(19-carboxynonadecanoyl-Glu-Glu-Glu-Glu)-[Lys3,His17,Asp21]-pramlintide, N-alpha-[(S)-4-Carboxy-4-(19-carboxynonadecanoylamino)butyryl]-[His17]-pramlintide (2-37), N-alpha-[(S)-4-Carboxy-4-(19-carboxynonadecanoylamino)butyryl]-[Arg1,His17]-pramlintide, N-alpha-[(S)-4-Carboxy-4-(19-carboxynonadecanoylamino)butyryl]-[His17]-pramlintide, N-alpha-[19-carboxynonadecanoyl]-Glu-Lys-[Arg1,His17]-pramlintide, N-alpha-[19-carboxynonadecanoyl]-Glu-Lys-Arg-[His17]-pramlintide, N-alpha-[(S)-4-Carboxy-4-(17-carboxyheptadecanoylamino)butyryl]-[His17]-pramlintide (2-37), N-alpha-[(S)-4-Carboxy-4-(19-carboxynonadecanoylamino)butyryl]-[Ser17]-pramlintide (2-37), N-alpha-[(S)-4-Carboxy-4-(19-carboxynonadecanoylamino)butyryl]-[Ala17]-pramlintide (2-37), N-alpha-[(S)-4-Carboxy-4-(19-carboxynonadecanoylamino)butyryl]-[Gly17]-pramlintide (2-37), N-alpha-[(S)-4-Carboxy-4-(19-carboxynonadecanoylamino)butyryl]-[Arg17]-pramlintide (2-37), N-alpha-[(S)-4-Carboxy-4-(19-carboxynonadecanoylamino)butyryl]-[Pro17]-pramlintide (2-37), N-alpha-[2-(2-{2-[4-(S)-Carboxy-4-(19-carboxynonadecanoylamino)butyrylamino]ethoxy}ethoxy)acetyl]-[His17]-pramlintide (2-37), N-alpha-[(S)-4-Carboxy-4-(19-carboxynonadecanoylamino)butyryl]-Arg-[His17]-pramlintide, N-alpha-[(S)-4-Carboxy-4-(19-carboxynonadecanoylamino)butyryl]-Arg-[Gly17]-pramlintide, N-alpha-[(S)-4-Carboxy-4-(19-carboxynonadecanoylamino)butyryl]-Arg-[Ala17]-pramlintide, N-alpha-[(S)-4-Carboxy-4-(19-carboxynonadecanoylamino)butyryl]-Arg-[Ser17]-pramlintide, N-alpha-[(S)-4-Carboxy-4-(19-carboxynonadecanoylamino)butyryl]-Arg-[Pro17]-pramlintide, N-alpha-[(S)-4-Carboxy-4-(19-carboxynonadecanoylamino)butyryl]-Arg-[Arg17]-pramlintide, N-alpha-[2-(2-{2-[4-(S)-Carboxy-4-(19-carboxynonadecanoylamino)butyrylamino]ethoxy}ethoxy)acetyl]-Arg-[Arg17]-pramlintide, N-alpha-[2-(2-{2-[4-(S)-Carboxy-4-(19-carboxynonadecanoylamino)butyrylamino]ethoxy}ethoxy)acetyl]-Arg-[Ala17]-pramlintide, N-alpha-[4-(19-Carboxynonadecanoylamino)butyryl]-Arg-[Arg17]-pramlintide, N-alpha-[(S)-4-Carboxy-4-(17-carboxyheptadecanoylamino)butyryl]-Arg-[Arg17]-pramlintide, N-alpha-[(S)-4-Carboxy-4-(19-carboxynonadecanoylamino)butyryl]-His-[His1,His17]-pramlintide, N-alpha-[(S)-4-Carboxy-4-(19-carboxynonadecanoylamino)butyryl]-His-[His17]-pramlintide, N-alpha-[(S)-4-Carboxy-4-(19-carboxynonadecanoylamino)butyryl]-[His1,His17]-pramlintide, N-alpha-[4-(19-Carboxynonadecanoylamino)butyryl]-[His17]-pramlintide (2-37), N-alpha-[(S)-4-Carboxy-4-(17-carboxyheptadecanoylamino)butyryl]-His-[His1,His17]

N-alpha-[(S)-4-Carboxy-4-(17-carboxyheptadecanoylamino)butyryl]-[His1,His17]-pramlintide, N-alpha-[4-Carboxy-4-({4-[(19-carboxynonadecanoylamino)methyl]transcyclohexanecarbonyl}amino)butyryl]-[His1,His17]-pramlintide, N-alpha-[2-(2-{2-[4-(S)-Carboxy-4-(19-carboxynonadecanoylamino)butyrylamino]ethoxy}ethoxy)acetyl]-His-[His1,Arg17]-pramlintide, N-alpha-[(S)-4-Carboxy-4-(19-carboxynonadecanoylamino)butyryl]-His-[His1,Arg17]-pramlintide, N-alpha-[(S)-4-Carboxy-4-(19-carboxynonadecanoylamino)butyryl]-[His1,Arg17]-pramlintide, N-alpha-[2-(2-{2-[4-(S)-Carboxy-4-(19-carboxynonadecanoylamino)butyrylamino]ethoxy}ethoxy)acetyl]-[His1,His17]-pramlintide, N-alpha-[2-(2-{2-[4-(S)-Carboxy-4-(19-carboxynonadecanoylamino)butyrylamino]ethoxy}ethoxy)acetyl]-His-[His1,His17]-pramlintide, N-alpha-[(S)-4-Carboxy-4-(19-carboxynonadecanoylamino)butyryl]-His-His-[His1,His17]-pramlintide,
N-alpha-[(S)-4-Carboxy-4-(19-carboxynonadecanoylamino)butyryl]-His-Arg-[His17]-pramlintide,
N-alpha-[(S)-4-Carboxy-4-(19-carboxynonadecanoylamino)butyryl]-Glu-Arg-[Glu1,His17,Gln21,Ala25,Pro26,Ser28,Ser29]-pramlintide,
N-alpha-[(S)-4-Carboxy-4-(19-carboxynonadecanoylamino)butyryl]-Glu-Arg-[Glu1,Asp14,His17,Ala25,Pro26,Ser28,Ser29]-pramlintide,
N-alpha-[(S)-4-Carboxy-4-(19-carboxynonadecanoylamino)butyryl]-[Asp14,His17]-pramlintide (2-37),
N-alpha-[(S)-4-Carboxy-4-(19-carboxynonadecanoylamino)butyryl]-[His17,Glu24]-pramlintide (2-37),
N-alpha-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl][Arg1,His17]-pramlintide,
N-alpha-[(S)-4-Carboxy-4-(19-carboxynonadecanoylamino)butyryl]-Glu-Arg-[Glu1,Arg17,Ala25,Pro26,Ser28,Ser29]-pramlintide,
N-alpha-[(S)-4-Carboxy-4-(19-carboxynonadecanoylamino)butyryl]-His-[His1,His17,Arg18]-pramlintide,
N-alpha-[(S)-4-Carboxy-4-(19-carboxynonadecanoylamino)butyryl]-Glu-Arg-[Glu1,Asp14,His17,Gln21,Ala25,Pro26,Ser28,Ser29]-pramlintide,
N-alpha-[(S)-4-Carboxy-4-(19-carboxynonadecanoylamino)butyryl]-Glu-[Glu1,Arg17]-pramlintide,
N-alpha-[(S)-4-Carboxy-4-(19-carboxynonadecanoylamino)butyryl]-Glu-[Glu 1,His17]-pramlintide,
N-alpha-[(S)-4-Carboxy-4-(19-carboxynonadecanoylamino)butyryl]-[Glu 1,His17]-pramlintide,
N-alpha-[3-(2-{2-[2-(2-{2-[2-(2-{2-[(S)-4-Carboxy-4-(17-carboxyheptadecanoylamino) butyrylamino]ethoxy}ethoxy)ethoxy]ethoxy}ethoxy)ethoxy]ethoxy}ethoxy)propionylamino][Arg1,His17]-pramlintide,
N-alpha-[(S)-4-Carboxy-4-(19-carboxynonadecanoylamino)butyryl]-[His17,Asp31]-pramlintide (2-37),
N-alpha-[(S)-4-Carboxy-4-(19-carboxynonadecanoylamino)butyryl]-Glu-His-His-[His1,His17]-pramlintide,
N-alpha-[(S)-4-Carboxy-4-(19-carboxynonadecanoylamino)butyryl]-Glu-His-Arg-[Arg1,His17]-pramlintide,
N-alpha-[2-(2-{2-[4-(S)-Carboxy-4-(19-carboxynonadecanoylamino)butyrylamino]ethoxy}ethoxy)acetyl]-His-His-[Arg 1,His17]-pramlintide,
N-alpha-[2-(2-{2-[4-(S)-Carboxy-4-(19-carboxynonadecanoylamino)butyrylamino]ethoxy}ethoxy)acetyl]-His-His-[Arg1,Arg17]-pramlintide,
N-alpha-[(S)-4-Carboxy-4-(19-carboxynonadecanoylamino)butyryl]-Glu-His-His-[Arg1,Arg17]-pramlintide,
N-alpha-[2-(2-{2-[4-(S)-Carboxy-4-(19-carboxynonadecanoylamino)butyrylamino]ethoxy}ethoxy)acetyl]-His-His-[Arg1His17,Gln21]-pramlintide,
N-alpha-[(S)-4-Carboxy-4-(17-carboxyheptadecanoylamino)butyryl]-His-His-[His1,His17]-pramlintide,
N-alpha-[(S)-4-Carboxy-4-(5-carboxypentanoylamino)butyryl]-His-His-[His1,His17]-pramlintide
N-alpha-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl][His17]-pramlintide (2-37),
N-alpha-[(S)-4-Carboxy-4-(19-carboxynonadecanoylamino)butyryl]-Glu His-His-[Arg1,His17,Gln21]-pramlintide,
N-alpha-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[His17]-pramlintide (2-37),
N-alpha-[2-(2-{2-[4-(S)-Carboxy-4-(19-carboxynonadecanoylamino)butyrylamino]ethoxy}ethoxy)acetyl]-His-His-[Arg1,Arg17,Gln21]-pramlintide,
N-alpha-[(S)-4-Carboxy-4-(19-carboxynonadecanoylamino)butyryl]-Glu-His-Arg-[His1,His17]-pramlintide,
N-alpha-[(S)-4-Carboxy-4-(19-carboxynonadecanoylamino)butyryl]-Glu-His-His-[Arg1,His17]-pramlintide,
N-alpha-[(S)-4-Carboxy-4-(19-carboxynonadecanoylamino)butyryl]-Glu-His-His-[Arg1,Arg17,Gln21]-pramlintide,
N-alpha-[(S)-4-Carboxy-4-(19-carboxynonadecanoylamino)butyryl]-Glu-Arg-His-[Arg1,His17]-pramlintide,
N-alpha-[(S)-4-Carboxy-4-(19-carboxynonadecanoylamino)butyryl]-Arg-His[Arg1,His17]-pramlintide,
N-alpha-[(S)-4-Carboxy-4-(19-carboxynonadecanoylamino)butyryl]-His-His-[Arg1,His17]-pramlintide,
N-alpha-[(S)-4-Carboxy-4-(19-carboxynonadecanoylamino)butyryl]-His-Arg-[His1,His17]-pramlintide.

In one aspect the invention concerns a pharmaceutical composition comprising a derivative according of the invention, and a pharmaceutically acceptable excipient. The composition are suited for parenteral administration.

In one aspect the derivative according to the invention can be used as a medicament.

In one aspect the derivative can be used as a medicament for the treatment or prevention of hyperglycemia, type 2 diabetes, impaired glucose tolerance, type 1 diabetes, obesity, hypertension, syndrome X, dyslipidemia, cognitive disorders, atherosclerosis, myocardial infarction, coronary heart disease and other cardiovascular disorders, stroke, inflammatory bowel syndrome, dyspepsia and gastric ulcers.

In one aspect the medicament for delaying or preventing disease progression in type 2 diabetes.

In one aspect the medicament can be used for decreasing food intake, treating obesity, decreasing β-cell apoptosis, increasing β-cell function and β-cell mass, and/or for restoring glucose sensitivity to β-cells.

In one aspect the derivative according to the invention can be used for the preparation of a medicament.

In one aspect the derivative can be used for the preparation of a medicament for the treatment or prevention of hyperglycemia, type 2 diabetes, impaired glucose tolerance, type 1 diabetes, obesity, hypertension, syndrome X, dyslipidemia, cognitive disorders, atherosclerosis, myocardial infarction, coronary heart disease and other cardiovascular disorders, stroke, inflammatory bowel syndrome, dyspepsia and gastric ulcers.

In one aspect the derivative can be used for the preparation of a medicament for delaying or preventing disease progression in type 2 diabetes.

In one aspect the derivative can be used for the preparation of a medicament for decreasing food intake, decreasing β-cell apoptosis, increasing β-cell function and β-cell mass, and/or for restoring glucose sensitivity to β-cells.

The treatment with a derivative according to the present invention may also be combined with a second or more pharmacologically active substances, e.g. selected from antidiabetic agents, antiobesity agents, appetite regulating agents, antihypertensive agents, agents for the treatment and/or prevention of complications resulting from or associated with diabetes and agents for the treatment and/or prevention of complications and disorders resulting from or associated with obesity. Examples of these pharmacologically active substances are: Insulin, insulin derivative, insulin analogues, GLP-1, GLP-1 derivatives, GLP-1 analogues, oxyntomodulin derivatives, sulphonylureas, biguanides, meglitinides, glucosidase inhibitors, glucagon antagonists, DPP-IV (dipeptidyl peptidase-IV) inhibitors, inhibitors of hepatic enzymes involved in stimulation of gluconeogenesis and/or glycogenolysis, glucose uptake modulators, compounds modifying the lipid metabolism such as antihyperlipidemic agents as HMG CoA inhibitors (statins), compounds lowering food intake, RXR agonists and agents acting on the ATP-dependent potassium channel of the β-cells; Cholestyramine, colestipol, clofibrate, gemfibrozil, lovastatin, pravastatin, simvastatin, probucol, dextrothyroxine, neteglinide, repaglinide; β-blockers such as alprenolol, atenolol, timolol, pindolol, propranolol and metoprolol, ACE (angiotensin converting enzyme) inhibitors such as benazepril, captopril, enalapril, fosinopril, lisinopril, alatriopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin; CART (coCaine amphetamine regulated transcript) agonists, NPY (neuropeptide Y) antagonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, β3 agonists, MSH (melanocyte-stimulating hormone) agonists, MCH (melanocyte-concentrating hormone) antagonists, CCK (cholecystokinin) agonists, serotonin re-uptake inhibitors, serotonin and noradrenaline re-uptake inhibitors, mixed serotonin and noradrenergic compounds, 5HT (serotonin) agonists, bombesin agonists, galanin antagonists, growth hormone, growth hormone releasing compounds, TRH (thyrotropin releasing hormone) agonists, UCP 2 or 3 (uncoupling protein 2 or 3) modulators, leptin agonists, DA agonists (bromocriptin, doprexin), lipase/amylase inhibitors, RXR (retinoid X receptor) modulators, TR β agonists; histamine H3 antagonists, gastrin and gastrin analogs.

It should be understood that any suitable combination of the derivatives according to the invention with one or more of the above-mentioned compounds and optionally one or more further pharmacologically active substances are considered to be within the scope of the present invention.

In one aspect a process for preparing a pharmaceutical composition comprising the derivative according to the invention comprises mixing a derivative according to the invention with at least one pharmaceutically acceptable excipient.

In one aspect according to the invention, the amylin derivative has a protracted pharmaco-kinetic profile compared to pramlintide as measured by Assay (V) as described in the section Assays. In one aspect of the invention, the amylin derivative has a plasma T½ of at least 30 hour. In another aspect, of the invention the plasma T½ is at least 40 hour. In another aspect of the invention, the amylin derivative has a plasma T½ of at least 50 hours. In another aspect of the invention, the amylin derivative has a plasma T½ of at least 60 hours. In another aspect of the invention, the amylin derivative has a plasma T½ of at least 70 hours. In another aspect of the invention, the amylin derivative has a plasma T½ of at least 75 hours. In another aspect of the invention, the amylin derivative has a plasma T½ of at least 80 hours. In another aspect of the invention, the amylin derivative has a plasma T½ of at least 85 hours. In another aspect of the invention, the amylin derivative has a plasma T½ of at least 90 hours. In one aspect of the invention, the amylin derivative has a plasma T½ of at least 95 hours. In one aspect of the invention, the amylin derivative has a plasma T½ of at least 100 hours.

The production of peptides such as human amylin or analogues thereof is well known in the art. The peptides of the invention can thus be produced by classical peptide synthesis, e.g. solid phase peptide synthesis using t-Boc or Fmoc chemistry or other well established techniques, see e.g. Greene and Wuts, "Protective Groups in Organic Synthesis", John Wiley & Sons, 1999. The peptides may also be produced by a method which comprises culturing a host cell containing a DNA sequence encoding the polypeptide and capable of expressing the polypeptide in a suitable nutrient medium under conditions permitting the expression of the peptide. For peptides comprising non-natural amino acid residues, the recombinant cell should b modified such that the non-natural amino acids are incorporated into the peptide, for instance by use of tRNA mutants.

Pharmaceutical Compositions

One object of the present invention is to provide a pharmaceutical formulation comprising a peptide according to the present invention. In one aspect, the peptide is present in the formulation at a concentration of from about 0.1 mg/ml to about 25 mg/ml. In another aspect, the peptide is present in the formulation at a concentration of from about 1 mg/ml to about 10 mg/ml.

In one aspect, the formulation has a pH from 2.0 to 10.0. In one aspect, the formulation has a pH from 2.0 to 7.0. In one aspect, the formulation has a pH from 2.5-4.5. In one aspect, the formulation has a pH from 2.5-4.0.

Pharmaceutical compositions containing a derivative according to the present invention may be prepared by conventional techniques, e.g. as described in *Remington's Pharmaceutical Sciences*, 1985 or in *Remington: The Science and Practice of Pharmacy*, 19$^{th}$ edition, 1995.

The formulation may further comprise a buffer system, preservative(s), isotonicity agent(s), chelating agent(s), stabilizers and/or surfactants. The use of such excipients in pharmaceutical compositions is well-known to the skilled person. For convenience reference is made to Remington: *The Science and Practice of Pharmacy*, 19$^{th}$ edition, 1995.

In one aspect of the invention the pharmaceutical formulation is an aqueous formulation, i.e. formulation comprising water. Such formulation is typically a solution or a suspension. In a further aspect of the invention the pharmaceutical formulation is an aqueous solution. The term "aqueous formulation" is defined as a formulation comprising at least 50% w/w water. Likewise, the term "aqueous solution" is defined as a solution comprising at least 50% w/w water, and the term "aqueous suspension" is defined as a suspension comprising at least 50% w/w water.

In another aspect the pharmaceutical formulation is a freeze-dried formulation, whereto the physician or the patient adds solvents and/or diluents prior to use. In another aspect the pharmaceutical formulation is a dried formulation (e.g. freeze-dried or spray-dried) ready for use without any prior dissolution.

By "dried form" is intended the liquid pharmaceutical composition or formulation is dried either by freeze drying (i.e., lyophilization; see, for example, Williams and Polli (1984) J. Parenteral Sci. Technol. 38:48-59), spray drying (see Masters (1991) in Spray-Drying Handbook (5th ed; Longman Scientific and Technical, Essez, U.K.), pp. 491-676; Broadhead et al. (1992) Drug Devel. Ind. Pharm. 18:1169-1206; and Mumenthaler et al. (1994) Pharm. Res. 11:12-20), or air drying (Carpenter and Crowe (1988) Cryobiology 25:459-470; and Roser Biopharm. 4:47-53). Aggregate formation by a polypeptide during storage of a liquid pharmaceutical composition can adversely affect biological activity of that polypeptide, resulting in loss of therapeutic efficacy of the pharmaceutical composition. Furthermore, aggregate formation may cause other problems such as blockage of tubing, membranes, or pumps when the polypeptide-containing pharmaceutical composition is administered using an infusion system.

In a further aspect of the invention the buffer is selected from the group consisting of sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, bicine, tricine, malic acid, lactic acid, succinate, maleic acid, fumaric acid, tartaric acid, aspartic acid or mixtures thereof. Each one of these specific buffers constitutes an alternative aspect of the invention.

In a further aspect of the invention the formulation further comprises a pharmaceutically acceptable preservative. In a further aspect of the invention the formulation further comprises an isotonic agent, e.g. propylene glycol, mannitol or glycerol. In a further aspect of the invention the formulation further comprises a chelating agent.

In a further aspect of the invention the formulation further comprises a stabilizer. The use of a stabilizer in pharmaceutical compositions is well-known to the skilled person. For convenience reference is made to Remington: *The Science and Practice of Pharmacy*, 19$^{th}$ edition, 1995.

More particularly, compositions of the invention are stabilized liquid pharmaceutical compositions whose therapeutically active components include a polypeptide that possibly exhibits aggregate formation during storage in liquid pharmaceutical formulations. By "aggregate formation" is intended a physical interaction between the polypeptide molecules that results in formation of oligomers, which may remain soluble, or large visible aggregates that precipitate from the solution. By "during storage" is intended a liquid pharmaceutical composition or formulation once prepared, is not immediately administered to a subject. Rather, following preparation, it is packaged for storage, either in a liquid form, in a frozen state, or in a dried form for later reconstitution into a liquid form or other form suitable for administration to a subject.

The pharmaceutical compositions of the invention may further comprise an amount of an amino acid base sufficient to decrease aggregate formation by the polypeptide during storage of the composition. By "amino acid base" is intended an amino acid or a combination of amino acids, where any given amino acid is present either in its free base form or in its salt form. Where a combination of amino acids is used, all of the amino acids may be present in their free base forms, all may be present in their salt forms, or some may be present in their free base forms while others are present in their salt forms. In one aspect, amino acids to use in preparing the compositions of the invention are those carrying a charged side chain, such as arginine, lysine, aspartic acid, and glutamic acid. Any stereoisomer (i.e., L, D, or a mixture thereof) of a particular amino acid (e.g. methionine, histidine, imidazole, arginine, lysine, isoleucine, aspartic acid, tryptophan, threonine and mixtures thereof) or combinations of these stereoisomers, may be present in the pharmaceutical compositions of the invention so long as the particular amino acid is present either in its free base form or its salt form. In one aspect the L-stereoisomer is used. Compositions of the invention may also be formulated with analogues of these amino acids and derivatives thereof. Suitable arginine analogues include, for example, aminoguanidine, ornithine and N-monoethyl L-arginine, suitable methionine analogues include ethionine and buthionine and suitable cysteine analogues include S-methyl-L cysteine. As with the other amino acids, the amino acid analogues are incorporated into the compositions in either their free base form or their salt form.

In a further aspect of the invention the amino acids or amino acid analogues and derivatives thereof are used in a concentration, which is sufficient to prevent or delay aggregation of the protein.

In a further aspect of the invention the formulation further comprises a surfactant. In a further aspect of the invention the formulation further comprises protease inhibitors. The use of a protease inhibitor is particular useful in pharmaceutical compositions comprising zymogens of proteases in order to inhibit autocatalysis.

It is possible that other ingredients may be present in the peptide pharmaceutical formulation of the present invention. Such additional ingredients may include wetting agents, emulsifiers, antioxidants, bulking agents, tonicity modifiers, chelating agents, metal ions, oleaginous vehicles, proteins (e.g., human serum albumin, gelatine or proteins) and a zwitterion (e.g., an amino acid such as betaine, taurine, arginine, glycine, lysine and histidine). Such additional ingredients, of course, should not adversely affect the overall stability of the pharmaceutical formulation of the present invention.

Pharmaceutical compositions containing a derivative of human amylin or an analogue thereof according to the present invention may be administered to a patient in need of such treatment at several sites, for example, at topical sites, for example, skin and mucosal sites, at sites which bypass absorption, for example, administration in an artery, in a vein, in the heart, and at sites which involve absorption, for example, administration in the skin, under the skin, in a muscle or in the abdomen.

Administration of pharmaceutical compositions according to the invention may be through several routes of administration, for example, lingual, sublingual, buccal, in the mouth, oral, in the stomach and intestine, nasal, pulmonary, for example, through the bronchioles and alveoli or a combination thereof, epidermal, dermal, transdermal, vaginal, rectal, ocular, for examples through the conjunctiva, uretal, and parenteral to patients in need of such a treatment.

Compositions of the current invention may be administered in several dosage forms, for example, as solutions, suspensions, emulsions, microemulsions, multiple emulsion, foams, salves, pastes, plasters, ointments, tablets, coated tablets, rinses, capsules, for example, hard gelatine capsules and soft gelatine capsules, suppositories, rectal capsules, drops, gels, sprays, powder, aerosols, inhalants, eye drops, ophthalmic ointments, ophthalmic rinses, vaginal pessaries, vaginal rings, vaginal ointments, injection solution, in situ transforming solutions, for example in situ gelling, in situ setting, in situ precipitating, in situ crystallization, infusion solution, and implants.

Compositions of the invention may further be compounded in, or attached to, for example through covalent, hydrophobic and electrostatic interactions, a drug carrier, drug delivery system and advanced drug delivery system in order to further enhance stability of the derivative of human amylin or an analogue thereof increase bioavailability, increase solubility, decrease adverse effects, achieve chronotherapy well known to those skilled in the art, and increase patient compliance or any combination thereof.

Compositions of the current invention are useful in the formulation of solids, semisolids, powder and solutions for pulmonary administration of the derivative of human amylin or an analogue thereof, using, for example a metered dose inhaler, dry powder inhaler and a nebulizer, all being devices well known to those skilled in the art.

Compositions of the current invention are useful in the formulation of controlled, sustained, protracting, retarded, and slow release drug delivery systems.

Parenteral administration may be performed by subcutaneous, intramuscular, intraperitoneal or intravenous injection by means of a syringe, optionally a pen-like syringe. Alternatively, parenteral administration can be performed by means of an infusion pump. A further option is a composition which may be a solution or suspension for the administration of the derivative of human amylin or an analogue thereof in the form of a nasal or pulmonal spray. As a still further option, the pharmaceutical compositions containing the derivative of human amylin or an analogue thereof of the invention can also be adapted to transdermal administration, e.g. by needle-free injection or from a patch, optionally an iontophoretic patch, or transmucosal, e.g. buccal, administration.

The derivative of human amylin or an analogue thereof can be administered via the pulmonary route in a vehicle, as a solution, suspension or dry powder using any of known types of devices suitable for pulmonary drug delivery. Examples of these comprise of, but are not limited to, the three general types of aerosol-generating for pulmonary drug delivery, and may include jet or ultrasonic nebulizers, metered-dose inhalers, or dry powder inhalers (Cf. Yu J, Chien Y W. Pulmonary drug delivery: Physiologic and mechanistic aspects. Crit. Rev Ther Drug Carr Sys 14(4) (1997) 395-453).

In one aspect of the invention the pharmaceutical formulation comprising the derivative of human amylin or an analogue thereof is stable for more than 6 weeks of usage and for more than 3 years of storage.

In another aspect of the invention the pharmaceutical formulation comprising the derivative of human amylin or an analogue thereof is stable for more than 4 weeks of usage and for more than 3 years of storage.

In a further aspect of the invention the pharmaceutical formulation comprising the derivative of human amylin or an analogue thereof is stable for more than 4 weeks of usage and for more than two years of storage.

In an even further aspect of the invention the pharmaceutical formulation comprising the derivative of human amylin or an analogue thereof is stable for more than 2 weeks of usage and for more than two years of storage.

The invention is summarized in the following paragraphs:

1. A derivative of amylin, which is a human amylin analogue having a substituent attached to the α-amino group of the N-terminal amino acid residue or to a Lys residue in the human amylin analogue, wherein the substituent comprises an albumin binding moiety and the amino acid residue in position 17 of the human amylin analogue is any natural amino acid except Val, Lys or Ala and wherein the amino acid numbering of the human amylin analogue conforms with the amino acid numbering in SEQ ID NO:1
2. A derivative according to paragraph 1, wherein the amino acid residue in position 17 is His, Ser, Gly, Pro or Arg.
3. A derivative according to paragraphs 1-2, wherein the amino acids in position 25, 28 and 29 are Pro.
4. A derivative according to paragraphs 1-3, wherein the human amylin analogue comprises 1-10 amino acid substitutions for example 1, 2, 3, 4, 5 or 6 substitutions.
5. A derivative according to paragraphs 1-4, wherein the amino acid in position 1 of the human amylin analogue is substituted or is deleted.
6. A derivative according to paragraphs 1-5, wherein the amino acid in position 1 is selected from the group consisting of Lys, Glu, Arg and His.
7. A derivative according to paragraphs 1-6, wherein the substituent comprises a linker.
8. A derivative according to paragraphs 1-7, wherein the linker comprises 1-10 amino acids which are attached to the α-amino group of the N-terminal amino acid residue or to a Lys residue in the human amylin analogue.
9. A derivative according to paragraph 8, wherein the amino acids are selected from the group consisting of γGlu, Arg, γGlu-Arg, γGlu-His, Trx-γGlu, γGlu-His, Glu-Lys, Glu-Glu, Glu-Arg, γGlu-His-His, γGlu-Arg-His, γGlu-His-Arg, γGlu-Glu-Arg, Glu-Glu-Arg, Glu-Lys-Arg, γGlu-Glu-His-His, γGlu-Glu-His-Arg, Glu-Glu-Arg-Glu and Glu-Glu-Glu-Glu.
10. A derivative according to paragraphs 1-9, wherein the linker comprises —C(O)—(CH$_2$)$_l$—O—[CH$_2$CH$_2$—O]$_m$—(CH$_2$)$_p$—[NHC(O)—(CH$_2$)$_l$—O—[(CH$_2$)$_n$—O]$_m$—(CH$_2$)$_p$]$_q$—NH— wherein l, m, n, and p independently are 1-7, and q is 0-5.
11. A derivative according to paragraphs 1-10, wherein the linker is selected from the group consisting of —C(O)—CH$_2$—O—CH$_2$—CH$_2$—O—CH$_2$—CH$_2$—NH— or —C(O)—CH$_2$—O—CH$_2$—CH$_2$—O—CH$_2$—CH$_2$—[NHC(O)—CH$_2$—O—CH$_2$—CH$_2$—O—CH$_2$—CH$_2$—]$_1$—NH— and —C(O)—(CH$_2$)$_2$—O—[CH$_2$CH$_2$—O]$_7$—(CH$_2$)$_2$—NH—.
12. A derivative according to paragraphs 1-11, wherein the linker comprises γGlu, γGlu-His or γGlu-His-His.
13. A derivative according to paragraphs 1-12, wherein the linker comprises GABA.
14. A derivative according to any of paragraphs 1-13, wherein the albumin binding residue is an acyl group selected from the group comprising HOOC(CH$_2$)$_s$CO—, wherein s is an integer from 17 to 21, for example 18, 19 or 20.
15. A derivative according to paragraphs 1-14, wherein the amino acid in position 1 and 17 of the human amylin analogue is His, the amino acid in position 25, 28 and 29 are Pro, a linker comprising γGlu-His-His or γGlu-His is attached to the α-amino group of His in position 1 of the human amylin analogue and an albumin binding residue is attached to γGlu of the linker, wherein the albumin binding residue is HOOC(CH$_2$)$_{18}$CO or HOOC(CH$_2$)$_{16}$CO—.
16. A derivative according to paragraph 1, comprising an amino acid sequence of formula 1:

```
Formula (1)
                                         (SEQ ID No: 2)
Xaa₁-Cys-Xaa₃-Thr-Ala-Thr-Cys-Ala-Thr-Gln-Arg- Leu-Ala-Xaa₁₄-Phe-Leu-Xaa₁₇-Xaa₁₈-Ser-Ser-Xaa₂₁-

Asn-Phe-Xaa₂₄-Xaa₂₅-Xaa₂₆-Leu-Xaa₂₈-Xaa₂₉-Thr-

Xaa₃₁-Val-Gly-Ser-Asn-Thr-Tyr
``` wherein
$Xaa_1$ is deleted or independently selected from Lys, Arg, His and Glu;
$Xaa_3$ is independently selected from Asn and Lys;
$Xaa_{14}$ is independently selected from Glu, Asn, Gln and Asp;
$Xaa_{17}$ is independently selected from His, Ser, Gly, Arg and Pro;
$Xaa_{18}$ is independently selected from His or Arg;
$Xaa_{21}$ is independently selected from Asp, Asn and Gln;
$Xaa_{24}$ is independently selected from Glu and Gly;
$Xaa_{25}$ is independently selected from Ala and Pro;
$Xaa_{26}$ is independently selected from Pro and Ile;
$Xaa_{28}$ is independently selected from Ser and Pro;

Xaa$_{29}$ is independently selected from Ser and Pro;
Xaa$_{31}$ is independently selected from Glu and Asn;
the C-terminal may optionally be derivatized as an amide;
wherein a substituent is connected to the amino acid residue Xaa$_1$ or to Cys in position 2, which substituent comprises an albumin binding moiety.

17. A derivative according to any of paragraphs 1 and 16, wherein the albumin binding residue binds non-covalently to albumin.

18. A derivative according to any of paragraphs 1 and 16-17, wherein the albumin binding residue has a binding affinity towards human serum albumin that is below about 10 μM or below about 1 μM.

19. A derivative according to any of paragraphs 1 and 16-18, wherein the albumin binding residue is a lipophilic moiety.

20. A derivative according to any of paragraphs 1 and 16-19, wherein the albumin binding residue has from 6 to 40 carbon atoms, from 8 to 26 carbon atoms or from 14 to 22 carbon atoms for example 17, 18, 19, 20 and 21 carbon atoms.

21. A derivative according to any of paragraphs 1 and 16-20, wherein the albumin binding residue comprises a group which can be negatively charged at pH 7.4.

22. A derivative according to any of paragraphs 1 and 16-21, wherein the albumin binding residue comprises a carboxylic acid group.

23. A derivative according to any of paragraphs 1, 16-22, wherein the albumin binding residue is an acyl group selected from the group comprising HOOC(CH$_2$)$_s$CO—, wherein s is an integer from 12 to 22, for example 17, 18, 19, 20, 21 or 22.

24. A derivative according to paragraphs 1 and 16-23, wherein the substituent comprises a linker 25. A derivative according to paragraphs 1 and 16-24, wherein the linker comprises 1-10 amino acids.

26. A derivative according to paragraph 1 and 16-25, wherein the amino acids are selected from the group consisting of γGlu, Arg, γGlu-Arg, γGlu-His, Trx-γGlu, γGlu-His, Glu-Lys, Glu-Glu, Glu-Arg, γGlu-His-His, γGlu-Arg-His, γGlu-His-Arg, γGlu-Glu-Arg, Glu-Glu-Arg, Glu-Lys-Arg, γGlu-Glu-His-His, γGlu-Glu-His-Arg, Glu-Glu-Arg-Glu and Glu-Glu-Glu-Glu.

27. A derivative according to paragraphs 1 and 16-26, wherein the linker comprises —C(O)—(CH$_2$)$_l$—O—[CH$_2$CH$_2$—O]$_m$—(CH$_2$)$_p$—[NHC(O)—(CH$_2$)$_l$—O—[(CH$_2$)$_n$—O]$_m$—(CH$_2$)$_p$]$_q$—NH— wherein l, m, n, and p independently are 1-7, and q is 0-5.

28. A derivative according to paragraphs 1 and 16-27, wherein the linker is selected from the group consisting of —C(O)—CH$_2$—O—CH$_2$—CH$_2$—O—CH$_2$—CH$_2$—NH— or —C(O)—CH$_2$—O—CH$_2$—CH$_2$—O—CH$_2$—CH$_2$—[NHC(O)—CH$_2$—O—CH$_2$—CH$_2$—O]$_1$—CH$_2$—CH$_2$—]$_1$—NH— and —C(O)—(CH$_2$)$_2$—O—[CH$_2$CH$_2$—O]$_7$—(CH$_2$)$_2$—NH—.

29. A derivative according to paragraphs 1 and 16-28, wherein the linker comprises γGlu-His-His or γGlu-His.

30. A derivative according to paragraphs 1, 16-26 and 29, wherein Xaa$_1$ is His, Xaa$_{17}$ is His, Xaa$_{25}$ is Pro, Xaa$_{28}$ is Pro, Xaa$_{29}$ is Pro.

31. A derivative according to paragraphs 1, 16-26 and 29-30, wherein γGlu-His-His is attached to an albumin binding residue via the γGlu of the linker and wherein the albumin binding residue is HOOC(CH$_2$)$_{18}$CO.

32. A derivative according to paragraphs 1, 16-26 and 29-30, wherein γGlu-His is attached to an albumin binding residue via the γGlu of the linker and wherein the albumin binding residue is HOOC(CH$_2$)$_{16}$CO.

33. A derivative according to paragraphs 1 and 16-30, wherein the linker comprises GABA.

34. A derivative according to paragraph 1, wherein the derivative is selected from the group consisting of:
N-alpha-(19-carboxynonadecanoyl)-Glu-Glu-Arg-[Glu1,Glu14,His17,Glu31]-pramlintide,
N-epsilon3-(19-carboxynonadecanoyl-Glu-Glu-Arg-Glu)-[Lys3,His17,Asp21]-pramlintide,
N-epsilon3-{2-[2-(2-{(S)-4-Carboxy-2-[(S)-4-carboxy-2-(19-carboxynonadecanoylamino)butyrylamino]butyrylamino}ethoxy)ethoxy]acetyl}-[Lys3,His17,Asp21]-pramlintide,
N-epsilon3-(19-carboxynonadecanoyl-Glu-Glu-Glu-Glu)-[Lys3,His17,Asp21]-pramlintide,
N-alpha-[(S)-4-Carboxy-4-(19-carboxynonadecanoylamino)butyryl]-[His17]-pramlintide (2-37),
N-alpha-[(S)-4-Carboxy-4-(19-carboxynonadecanoylamino)butyryl]-[Arg1,His17]-pramlintide,
N-alpha-[(S)-4-Carboxy-4-(19-carboxynonadecanoylamino)butyryl]-[His17]-pramlintide,
N-alpha-[19-carboxynonadecanoyl]-Glu-Lys-[Arg1,His17]-pramlintide,
N-alpha-[19-carboxynonadecanoyl]-Glu-Lys-Arg-[His17]-pramlintide,
N-alpha-[(S)-4-Carboxy-4-(17-carboxyheptadecanoylamino)butyryl]-[His17]-pramlintide (2-37),
N-alpha-[(S)-4-Carboxy-4-(19-carboxynonadecanoylamino)butyryl]-[Ser17]-pramlintide (2-37),
N-alpha-[(S)-4-Carboxy-4-(19-carboxynonadecanoylamino)butyryl]-[Ala17]-pramlintide (2-37),
N-alpha-[(S)-4-Carboxy-4-(19-carboxynonadecanoylamino)butyryl]-[Gly17]-pramlintide (2-37),
N-alpha-[(S)-4-Carboxy-4-(19-carboxynonadecanoylamino)butyryl]-[Arg17]-pramlintide (2-37),
N-alpha-[(S)-4-Carboxy-4-(19-carboxynonadecanoylamino)butyryl]-[Pro17]-pramlintide (2-37),
N-alpha-[2-(2-{2-[4-(S)-Carboxy-4-(19-carboxynonadecanoylamino)butyrylamino]ethoxy}ethoxy)acetyl]-[His17]-pramlintide (2-37),
N-alpha-[(S)-4-Carboxy-4-(19-carboxynonadecanoylamino)butyryl]-Arg-[His17]-pramlintide,
N-alpha-[(S)-4-Carboxy-4-(19-carboxynonadecanoylamino)butyryl]-Arg-[Gly17]-pramlintide,
N-alpha-[(S)-4-Carboxy-4-(19-carboxynonadecanoylamino)butyryl]-Arg-[Ala17]-pramlintide,
N-alpha-[(S)-4-Carboxy-4-(19-carboxynonadecanoylamino)butyryl]-Arg-[Ser17]-pramlintide,
N-alpha-[(S)-4-Carboxy-4-(19-carboxynonadecanoylamino)butyryl]-Arg-[Pro17]-pramlintide,
N-alpha-[(S)-4-Carboxy-4-(19-carboxynonadecanoylamino)butyryl]-Arg-[Arg17]-pramlintide,
N-alpha-[2-(2-{2-[4-(S)-Carboxy-4-(19-carboxynonadecanoylamino)butyrylamino]ethoxy}ethoxy)acetyl]-Arg-[Arg17]-pramlintide,
N-alpha-[2-(2-{2-[4-(S)-Carboxy-4-(19-carboxynonadecanoylamino)butyrylamino]ethoxy}ethoxy)acetyl]-Arg-[Ala17]-pramlintide,
N-alpha-[4-(19-Carboxynonadecanoylamino)butyryl]-Arg-[Arg17]-pramlintide,
N-alpha-[(S)-4-Carboxy-4-(17-carboxyheptadecanoylamino)butyryl]-Arg-[Arg17]-pramlintide,
N-alpha-[(S)-4-Carboxy-4-(19-carboxynonadecanoylamino)butyryl]-His-[His1,His17]-pramlintide,
N-alpha-[(S)-4-Carboxy-4-(19-carboxynonadecanoylamino)butyryl]-His-[His17]-pramlintide, N-alpha-[(S)-4-Carboxy-4-(19-carboxynonadecanoy-
lamino)butyryl]-[His1,His17]-pramlintide,
N-alpha-[4-(19-Carboxynonadecanoylamino)butyryl]-
[His17]-pramlintide (2-37),
N-alpha-[(S)-4-Carboxy-4-(17-carboxyheptadecanoy-
lamino)butyryl]-His-[His1,His17]-pramlintide,
N-alpha-[(S)-4-Carboxy-4-(17-carboxyheptadecanoy-
lamino)butyryl]-[His1,His17]-pramlintide,
N-alpha-[4-Carboxy-4-({4-[(19-carboxynonadecanoy-
lamino)methyl]transcyclohexanecarbonyl}amino)bu-
tyryl]-[His1,His17]-pramlintide,
N-alpha-[2-(2-{2-[4-(S)-Carboxy-4-(19-carboxynonade-
canoylamino)butyrylamino]ethoxy}ethoxy)acetyl]-His-
[His1,Arg17]-pramlintide,
N-alpha-[(S)-4-Carboxy-4-(19-carboxynonadecanoy-
lamino)butyryl]-His-[His1,Arg17]-pramlintide,
N-alpha-[(S)-4-Carboxy-4-(19-carboxynonadecanoy-
lamino)butyryl]-[His1,Arg17]-pramlintide,
N-alpha-[2-(2-{2-[4-(S)-Carboxy-4-(19-carboxynonade-
canoylamino)butyrylamino]ethoxy}ethoxy)acetyl]-[His1,
His17]-pramlintide,
N-alpha-[2-(2-{2-[4-(S)-Carboxy-4-(19-carboxynonade-
canoylamino)butyrylamino]ethoxy}ethoxy)acetyl]-His-
[His1,His17]-pramlintide,
N-alpha-[(S)-4-Carboxy-4-(19-carboxynonadecanoy-
lamino)butyryl]-His-His-[His1,His 17]-pramlintide,
N-alpha-[(S)-4-Carboxy-4-(19-carboxynonadecanoy-
lamino)butyryl]-His-Arg-[His17]-pramlintide,
N-alpha-[(S)-4-Carboxy-4-(19-carboxynonadecanoy-
lamino)butyryl]-Glu-Arg-[Glu1,His17,Gln21,Ala25,
Pro26,Ser28,Ser29]-pramlintide,
N-alpha-[(S)-4-Carboxy-4-(19-carboxynonadecanoy-
lamino)butyryl]-Glu-Arg-[Glu1,Asp14,His17,Ala25,
Pro26,Ser28,Ser29]-pramlintide,
N-alpha-[(S)-4-Carboxy-4-(19-carboxynonadecanoy-
lamino)butyryl]-[Asp14,His17]-pramlintide (2-37),
N-alpha-[(S)-4-Carboxy-4-(19-carboxynonadecanoy-
lamino)butyryl]-[His17,Glu24]-pramlintide (2-37),
N-alpha-[2-(2-{2-[2-(2-{2-[(S)-4-Carboxy-4-(17-carboxy-
heptadecanoylamino)butyrylamino]ethoxy}ethoxy)acety-
lamino]ethoxy}ethoxy)acetyl][Arg1,His17]-pramlintide,
N-alpha-[(S)-4-Carboxy-4-(19-carboxynonadecanoy-
lamino)butyryl]-Glu-Arg-[Glu1,Arg17,Ala25,Pro26,
Ser28,Ser29]-pramlintide,
N-alpha-[(S)-4-Carboxy-4-(19-carboxynonadecanoy-
lamino)butyryl]-His-[His1,His17,Arg18]-pramlintide,
N-alpha-[(S)-4-Carboxy-4-(19-carboxynonadecanoy-
lamino)butyryl]-Glu-Arg-[Glu1,Asp14,His17,Gln21,
Ala25,Pro26,Ser28,Ser29]-pramlintide,
N-alpha-[(S)-4-Carboxy-4-(19-carboxynonadecanoy-
lamino)butyryl]-Glu-[Glu1,Arg17]-pramlintide,
N-alpha-[(S)-4-Carboxy-4-(19-carboxynonadecanoy-
lamino)butyryl]-Glu-[Glu1,His17]-pramlintide,
N-alpha-[(S)-4-Carboxy-4-(19-carboxynonadecanoy-
lamino)butyryl]-[Glu1,His17]-pramlintide,
N-alpha-[3-(2-{2-[2-(2-{2-[2-(2-{2-[(S)-4-Carboxy-4-(17-
carboxyheptadecanoylamino) butyrylamino]
ethoxy}ethoxy)ethoxy]ethoxy}ethoxy)ethoxy]
ethoxy}ethoxy)propionylamino][Arg1,His17]-
pramlintide,
N-alpha-[(S)-4-Carboxy-4-(19-carboxynonadecanoy-
lamino)butyryl]-[His17,Asp31]-pramlintide (2-37),
N-alpha-[(S)-4-Carboxy-4-(19-carboxynonadecanoy-
lamino)butyryl]-Glu-His-His-[His1,His17]-pramlintide,
N-alpha-[(S)-4-Carboxy-4-(19-carboxynonadecanoy-
lamino)butyryl]-Glu-His-Arg-[Arg1,His17]-pramlintide,
N-alpha-[2-(2-{2-[4-(S)-Carboxy-4-(19-carboxynonade-
canoylamino)butyrylamino]ethoxy}ethoxy)acetyl]-His-
His-[Arg1,His17]-pramlintide,
N-alpha-[2-(2-{2-[4-(S)-Carboxy-4-(19-carboxynonade-
canoylamino)butyrylamino]ethoxy}ethoxy)acetyl]-His-
His-[Arg1,Arg17]-pramlintide,
N-alpha-[(S)-4-Carboxy-4-(19-carboxynonadecanoy-
lamino)butyryl]-Glu-His-His-[Arg1,Arg17]-pramlintide,
N-alpha-[2-(2-{2-[4-(S)-Carboxy-4-(19-carboxynonade-
canoylamino)butyrylamino]ethoxy}ethoxy)acetyl]-His-
His-[Arg1His17,Gln21]-pramlintide,
N-alpha-[(S)-4-Carboxy-4-(17-carboxyheptadecanoy-
lamino)butyryl]-His-His-[His1,His17]-pramlintide,
N-alpha-[(S)-4-Carboxy-4-(5-carboxypentanoylamino)bu-
tyryl]-His-His-[His1,His17]-pramlintide
N-alpha-[2-(2-{2-[2-(2-{2-[(S)-4-Carboxy-4-(17-carboxy-
heptadecanoylamino)butyrylamino]ethoxy}ethoxy)acety-
lamino]ethoxy}ethoxy)acetyl][His17]-pramlintide (2-37),
N-alpha-[(S)-4-Carboxy-4-(19-carboxynonadecanoy-
lamino)butyryl]-GluHis-His-[Arg1,His17,Gln21]-pram-
lintide,
N-alpha-[2-(2-{2-[2-(2-{2-[(S)-4-Carboxy-4-(19-carboxy-
heptadecanoylamino)butyrylamino]ethoxy}ethoxy)acety-
lamino]ethoxy}ethoxy)acetyl]-[His17]-pramlintide
(2-37),
N-alpha-[2-(2-{2-[4-(S)-Carboxy-4-(19-carboxynonade-
canoylamino)butyrylamino]ethoxy}ethoxy)acetyl]-His-
His-[Arg1,Arg17,Gln21]-pramlintide,
N-alpha-[(S)-4-Carboxy-4-(19-carboxynonadecanoy-
lamino)butyryl]-Glu-His-Arg-[His1,His17]-pramlintide,
N-alpha-[(S)-4-Carboxy-4-(19-carboxynonadecanoy-
lamino)butyryl]-Glu-His-His-[Arg 1,His17]-pramlintide,
N-alpha-[(S)-4-Carboxy-4-(19-carboxynonadecanoy-
lamino)butyryl]-Glu-His-His-[Arg1,Arg17,Gln21]-pram-
lintide,
N-alpha-[(S)-4-Carboxy-4-(19-carboxynonadecanoy-
lamino)butyryl]-Glu-Arg-His-[Arg1,His17]-pramlintide,
N-alpha-[(S)-4-Carboxy-4-(19-carboxynonadecanoy-
lamino)butyryl]-Arg-His[Arg1,His17]-pramlintide,
N-alpha-[(S)-4-Carboxy-4-(19-carboxynonadecanoy-
lamino)butyryl]-His-His-[Arg1,His17]-pramlintide,
N-alpha-[(S)-4-Carboxy-4-(19-carboxynonadecanoy-
lamino)butyryl]-His-Arg-[His1,His17]-pramlintide.

35. A pharmaceutical composition comprising a derivative according to any of paragraphs 1-34, and a pharmaceutically acceptable excipient.

36. The pharmaceutical composition according to paragraph 35, which is suited for parenteral administration.

37. A derivative according to any one of the paragraphs 1-34 for use as a medicament.

38. A derivative according to any one of the paragraphs 1-34 for use as a medicament for the treatment or prevention of hyperglycemia, type 2 diabetes, impaired glucose tolerance, type 1 diabetes, obesity, hypertension, syndrome X, dyslipidemia, cognitive disorders, atherosclerosis, myocardial infarction, coronary heart disease and other cardiovascular disorders, stroke, inflammatory bowel syndrome, dyspepsia and gastric ulcers.

39. A derivative according to any one of the paragraphs 1-34 for use as a medicament for delaying or preventing disease progression in type 2 diabetes.

40. A derivative according to any one of the paragraphs 1-34 for use as a medicament for decreasing food intake, decreasing β-cell apoptosis, increasing β-cell function and β-cell mass, and/or for restoring glucose sensitivity to β-cells.

41. Use of a derivative according to any one of the paragraphs 1-34 for the preparation of a medicament.
42. Use of a derivative according to any one of the paragraphs 1-34 for the preparation of a medicament for the treatment or prevention of hyperglycemia, type 2 diabetes, impaired glucose tolerance, type 1 diabetes, obesity, hypertension, syndrome X, dyslipidemia, cognitive disorders, atherosclerosis, myocardial infarction, coronary heart disease and other cardiovascular disorders, stroke, inflammatory bowel syndrome, dyspepsia and gastric ulcers.
43. Use of a derivative according to any one of the paragraphs 1-34 for the preparation of a medicament for delaying or preventing disease progression in type 2 diabetes.
44. Use of a derivative according to any one of the paragraphs 1-34 for the preparation of a medicament for decreasing food intake, decreasing β-cell apoptosis, increasing β-cell function and β-cell mass, and/or for restoring glucose sensitivity to β-cells.
45. A process for preparing a pharmaceutical composition according to paragraphs 35-36 comprising mixing a derivative according to any one of paragraphs 1-34 with at least one pharmaceutically acceptable excipient.
46. Derivative of amylin according to the examples
47. A derivative according to paragraph 34 wherein the derivative is N-alpha-[(S)-4-Carboxy-4-(19-carboxynonadecanoylamino)butyryl]-His-His-[His1,His17]-pramlintide All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

EXAMPLES

The peptide sequences SEQ ID No. 1-35 were prepared according to the below-mentioned peptide synthesis and the compounds of examples 1-72 were prepared according to the below-mentioned Synthesis:

One method of peptide synthesis was by Fmoc chemistry on a microwave-based Liberty peptide synthesizer (CEM Corp., North Carolina). The resin was Tentagel S RAM with a loading of 0.25 mmol/g. The coupling chemistry was DIC/HOAt in NMP using amino acid solutions of 0.3 M in NMP and a molar excess of 6-8 fold. Coupling conditions was 5 minutes at up to 70° C. Deprotection was with 5% piperidine in NMP at up to 70° C. The protected amino acids used were standard Fmoc-amino acids (supplied from e.g. Anaspec or Novabiochem) dissolved at 0.3 M in NMP containing 0.3 M HOAt.

Another method of peptide synthesis was on an Applied Biosystems 433 peptide synthesizer in 0.25 mmol or 1.0 mmol scale using the manufacturer supplied FastMoc UV protocols which employ HBTU(2-(1H-Benzotriazol-1-yl-)-1,1,3,3 tetramethyluronium hexafluorophosphate) or HATU (O-(7-azabenzotriazol-1-yl)-1,1,3,3-tetramethyluronium hexafluorophosphate) mediated couplings in NMP, and UV monitoring of the deprotection of the Fmoc protection group. The starting resin used for the synthesis of the peptide amides was Rink-Amide resin. The protected amino acid derivatives used were standard Fmoc-amino acids (supplied from e.g. Anaspec, or Novabiochem) supplied in preweighed cartridges suitable for the AB1433A synthesizer.

When a chemical modification of a lysine side chain was desired, the lysine was incorporated as Lys(Mtt) and the N-terminal amino acid was either incorporated into the sequence as a Boc-amino acid or, if the N-terminal amino acid was incorporated as an Fmoc-amino acid, the Fmoc group was removed and the N-terminal was protected by treatment with 6 equivalents of Boc-carbonate and 6 equivalents of DIPEA in NMP for 30 minutes. The resin was washed with NMP and DCM and the Mtt group was removed by suspending the resin in neat hexafluoroisopropanol for 20 minutes followed by washing with DCM and NMP. The chemical modification of the lysine was performed by adding one or more of the building blocks listed below by the same methods as used for the peptide synthesis, i.e. by one or more automated steps on the Liberty or the ABI 433 or by one or more manual coupling steps at room temperature. After synthesis the resin was washed with DCM and dried, and the peptide was cleaved from the resin by a 2 hour treatment with TFA/TIPS/water (92.5/5/2.5) followed by precipitation with 4 volumes of diethylether. After further washing with diethylether and drying, the peptide was redissolved in water at 1-2 mg/ml, pH adjusted to about 4.5, and the disulfide bridge formed by treatment with 1.1 eq. of [Pt(IV)ethylenediamine$_2$Cl$_2$]Cl$_2$ overnight. Alternatively, the disulfide bridge was formed on the resin by treatment with 10 equivalents of iodine in NMP for 1 hour. In this case the crude peptide was purified directly after cleavage and diethylether precipitation.

Purification: The crude peptide was purified by semi-preparative HPLC on a 20 mm×250 mm column packed with either 5µ, or 7µ, C-18 silica. Peptide solutions were pumped onto the HPLC column and precipitated peptides were dissolved in 5 ml 50% acetic acid H$_2$O and diluted to 20 ml with H$_2$O and injected on the column which then was eluted with a gradient of 40-60% CH$_3$CN in 0.1% TFA 10 ml/min during 50 min at 40° C. The peptide containing fractions were collected. The purified peptide was lyophilized after dilution of the eluate with water.

For analysis of HPLC-fractions and final product RP-HPLC analysis was performed using UV detection at 214 nm and e.g. a Vydac 218TP54 4.6 mm×250 mm 5µ, C-18 silica column (The Separations Group, Hesperia, USA) and eluted at e.g. 1 ml/min at 42° C. Most often one of four different elution conditions was used:

A1: Equilibration of the column with a buffer consisting of 0.1M (NH$_4$)$_2$SO$_4$, which was adjusted to pH 2.5 with concentrated H$_2$SO$_4$ and elution by a gradient of 0% to 60% CH$_3$CN in the same buffer during 50 min.

B1: Equilibration of the column with 0.1% TFA/H$_2$O and elution by a gradient of 0% CH$_3$CN/0.1% TFA/H$_2$O to 60% CH$_3$CN/0.1% TFA/H$_2$O during 50 min.

B6: Equilibration of the column with 0.1% TFA/H₂O and elution by a gradient of 0% CH₃CN/0.1% TFA/H₂O to 90% CH₃CN/0.1% TFA/H₂O during 50 min.

Alternatively the RP-HPLC analysis was performed using UV detection at 214 nm and a Symmetry300, 3.6 mm×150 mm, 3.5μ C-18 silica column (Waters) which was eluted at 1 ml/min at 42° C.

B4: Equilibration of the column with 0.05% TFA/H₂O and elution by a gradient of 5% CH₃CN/0.05% TFA/H₂O to 95% CH₃CN/0.05% TFA/H₂O during 15 min.

The identity of the peptide was confirmed by MALDI-MS on a Bruker Microflex.

Abbreviations used:
HBTU: 2-(1H-Benzotriazol-1-yl-)-1,1,3,3 tetramethyluronium hexafluorophosphate
Fmoc: 9 H-fluoren-9-ylmethoxycarbonyl
Boc: tert butyloxycarbonyl
Mtt: 4-methyltrityl
DCM: dichloromethane
TIPS: triisopropylsilane
TFA: trifluoroacetic acid
NMP: 1-Methyl-pyrrolidin-2-one
HOAt: 1-Hydroxy-7-azabenzotriazole
DIC: Diisopropylcarbodiimide
Trt: triphenylmethyl The term "Compound X" refers to the compound according to example X. Compound 3 therefore means the compound N-epsilon3-{2-[2-(2-{(S)-4-Carboxy-2-[(S)-4-carboxy-2-(19-carboxynonadecanoylamino)butyrylamino]butyrylamino}ethoxy)ethoxy]acetyl}-[Lys3,His17,Asp21]-pramlintide.

Example 1

N-alpha-(19-carboxynonadecanoyl)-Glu-Glu-Arg-[Glu1,Glu14,His17,Glu31]-pramlintide

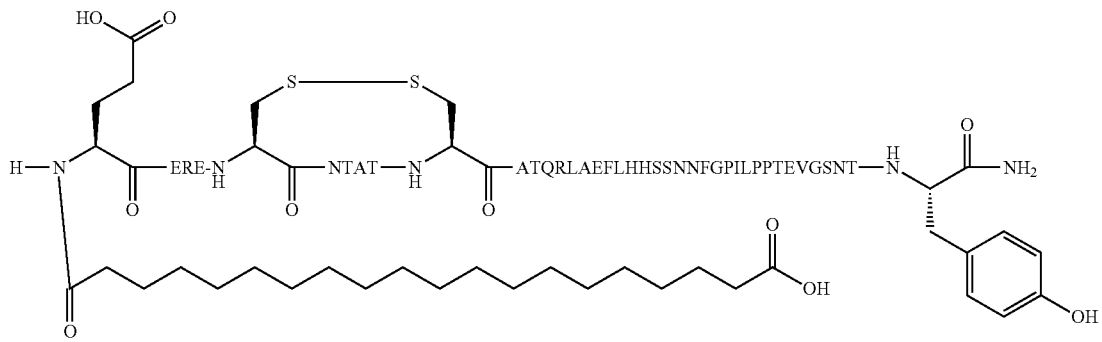

Example 2

N-epsilon3-(19-carboxynonadecanoyl-Glu-Glu-Arg-Glu)-[Lys3,His17,Asp21]-pramlintide

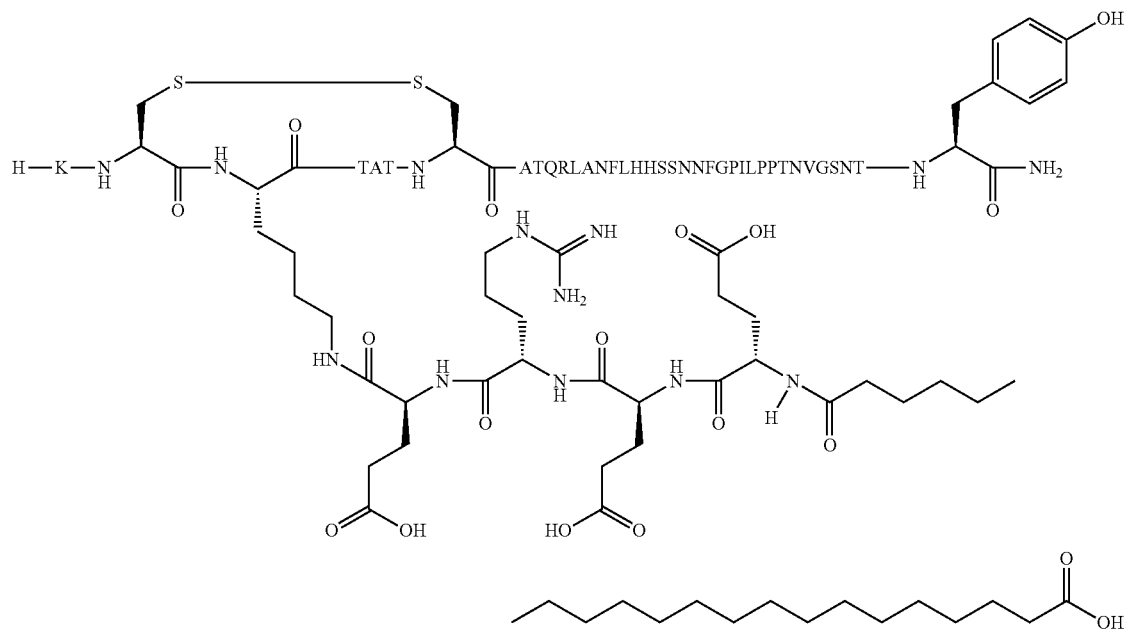

Example 3

N-epsilon3-{2-[2-(2-{(S)-4-Carboxy-2-[(S)-4-carboxy-2-(19-carboxynonadecanoylamino)butyrylamino]butyrylamino}ethoxy)ethoxy]acetyl}-[Lys3,His17,Asp21]-pramlintide

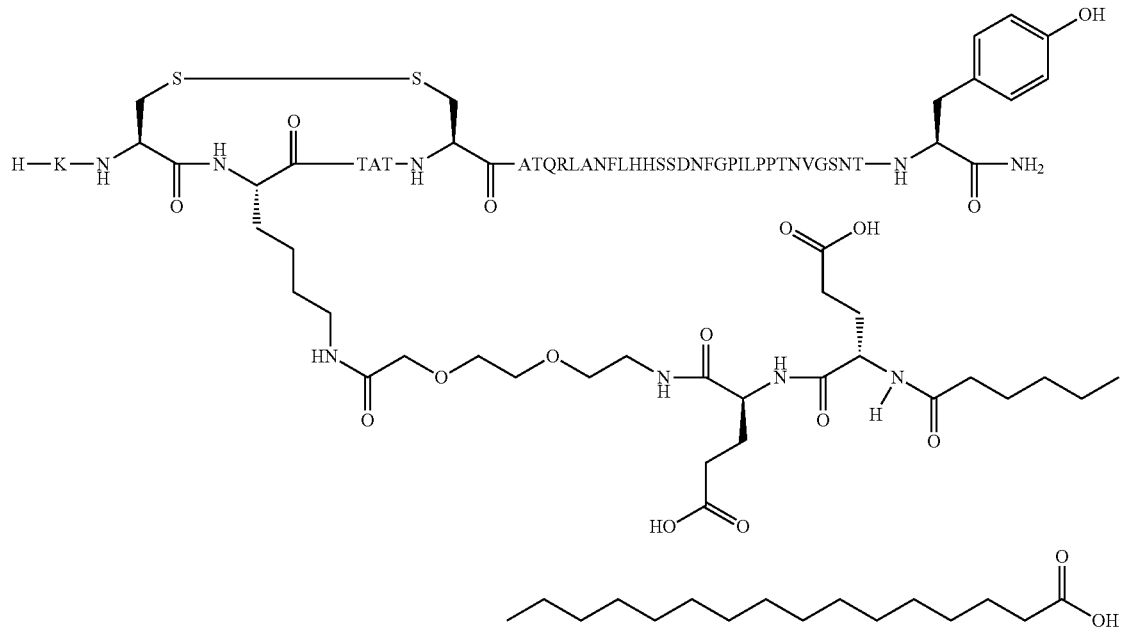

Figure 1B:
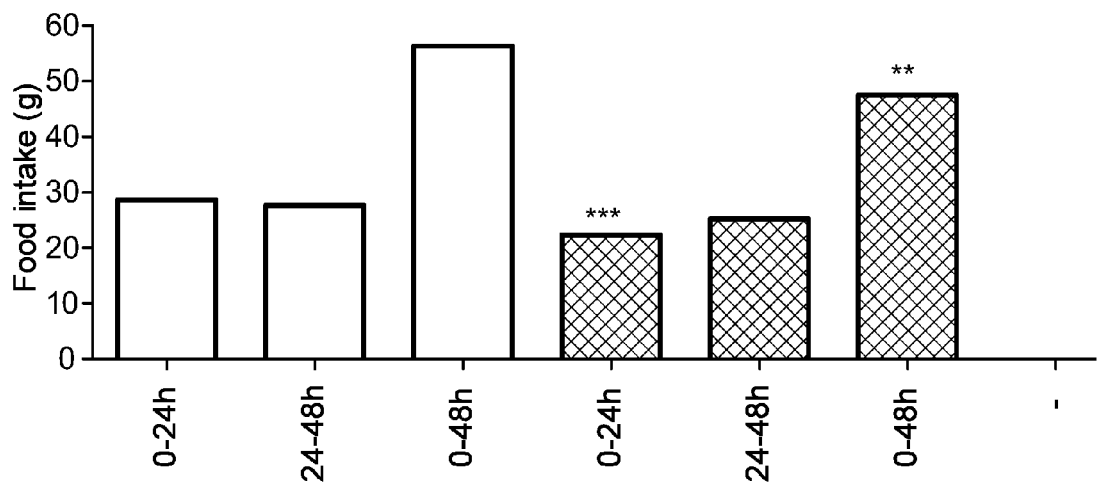
FIG. 1b shows accumulated food intake according to Pharmacological Assay (I) in the first 24 hours, the period from 24 to 48 hours, and the whole 48 hour period. Data=mean. n=5-7. Grey bars: vehicle. Black bars: 30 nmol/kg of compound 3.

From the FIG. 1a showing food intake over a period of 48 hours, it is seen that compound 3 is effectively reducing food intake. This is also illustrated in FIG. 1b, showing accumulated food intake in the periods 0-24 hours, 24-48 hours, and 0-48 hours, respectively. Food intake was compared using two-sided Student's t-test, alpha=0.05.

Example 4

N-epsilon3-(19-carboxynonadecanoyl-Glu-Glu-Glu-Glu)-[Lys3,His17,Asp21]-pramlintide

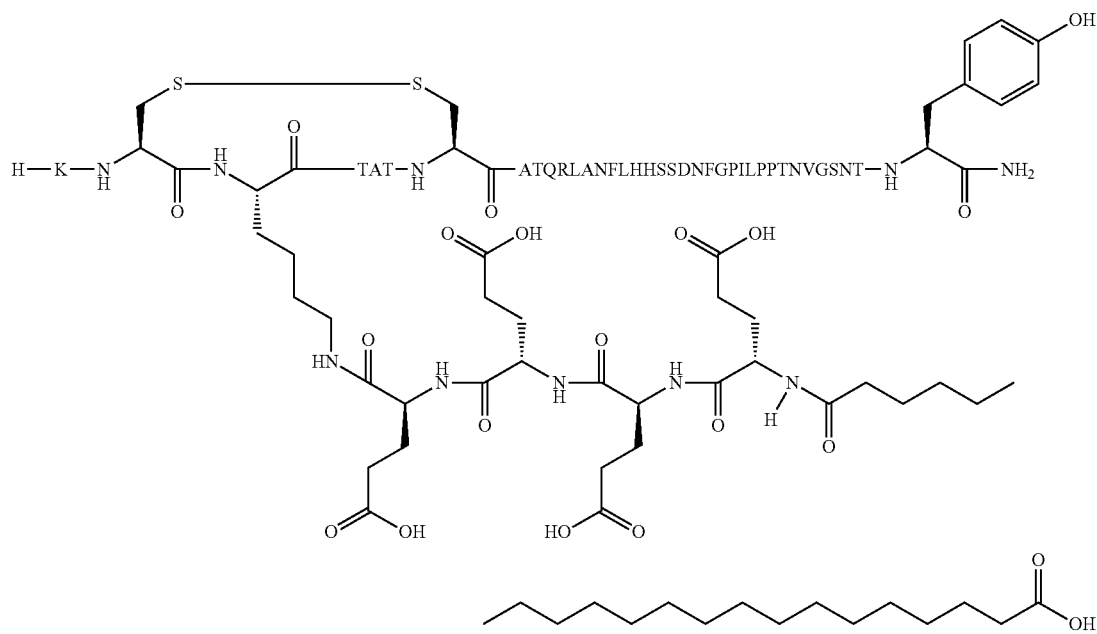

Example 5

N-alpha-[(S)-4-Carboxy-4-(19-carboxynonade-canoylamino)butyryl]-[His17]-pramlintide

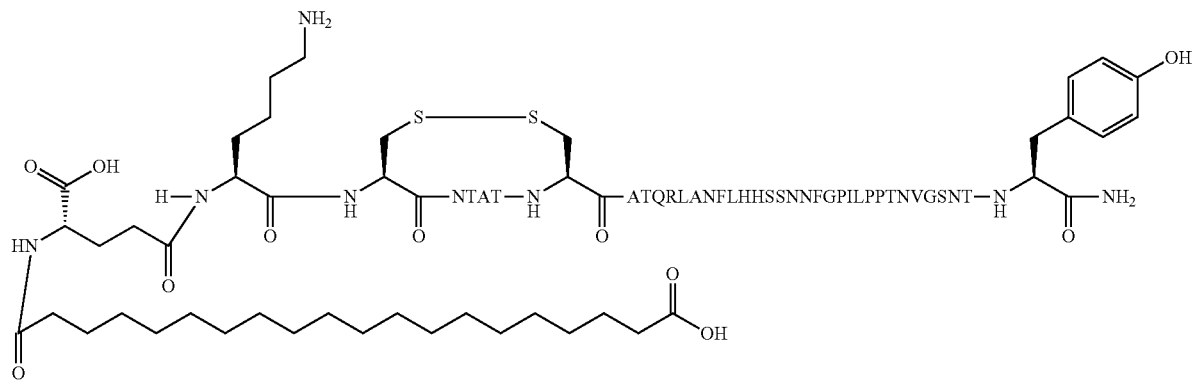

Figure 2A:
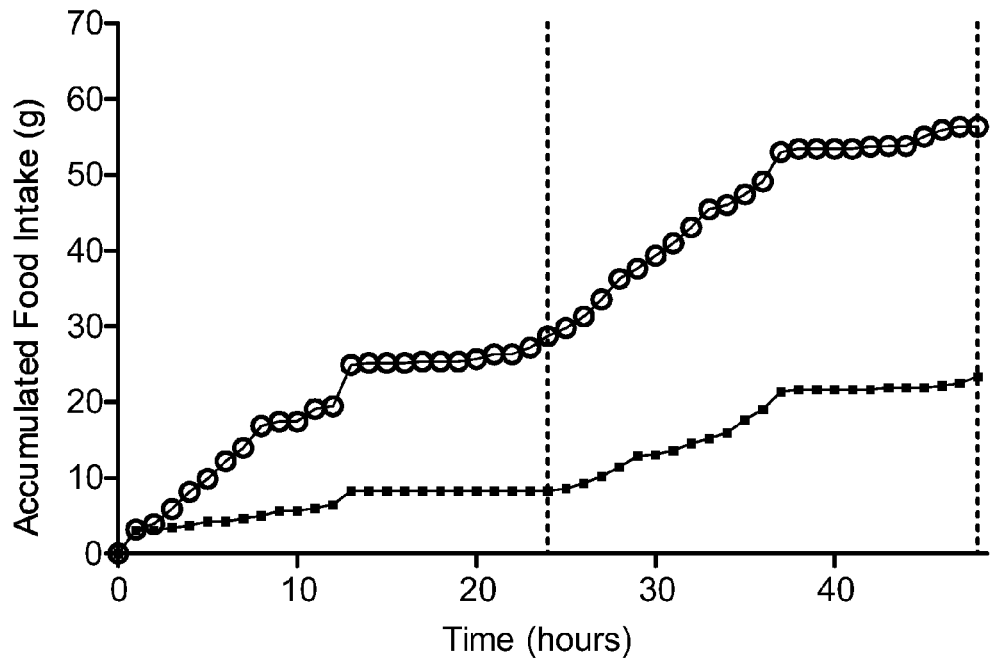
FIG. 2a shows food intake during 48 hours according to Pharmacological Assay (I). Data=mean. n=5-7. Open circle: vehicle. Black squares: 30 nmol/kg of compound 5.
Figure 2B:
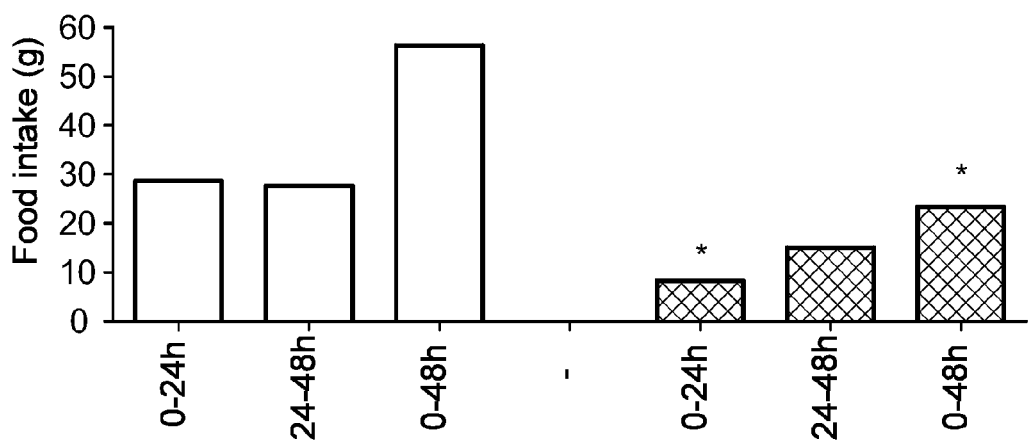
FIG. 2b shows accumulated food intake according to Pharmacological Assay (I) in the first 24 hours, the period from 24 to 48 hours, and the whole 48 hour period. Data=mean. n=5-7. Grey bars: vehicle. Black bars: 30 nmol/kg of compound 5.

From the FIG. 2a showing food intake over a period of 48 hours, it is seen that compound 5 is effectively reducing food intake. This is also illustrated in FIG. 2b, showing accumulated food intake in the periods 0-24 hours, 24-48 hours, and 0-48 hours, respectively. Food intake was compared using two-sided Student's t-test, alpha=0.05.

Example 6

N-alpha-[(S)-4-Carboxy-4-(19-carboxynonade-canoylamino)butyryl]-[Arg1,His17]-pramlintide

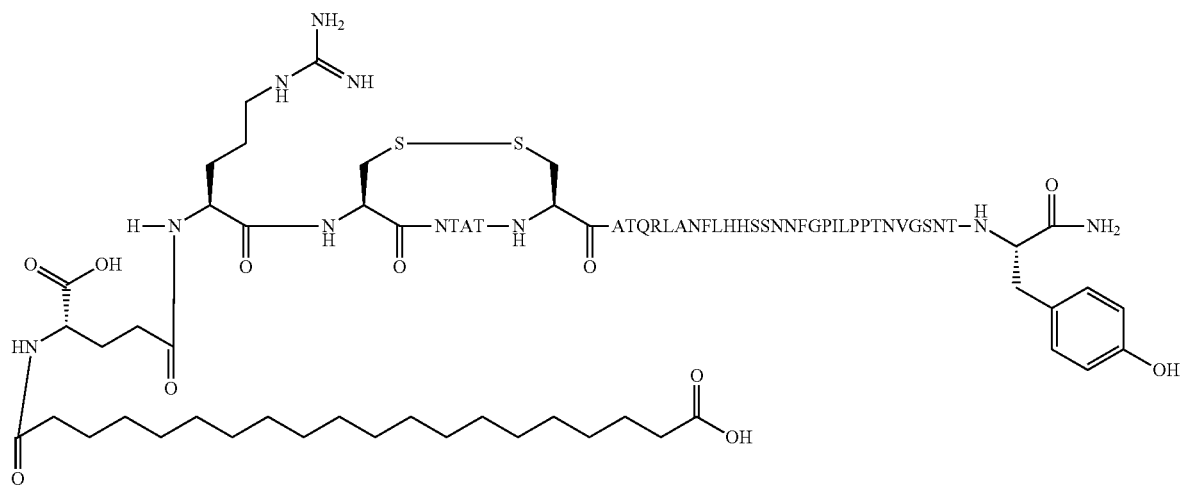

Figure 3A:
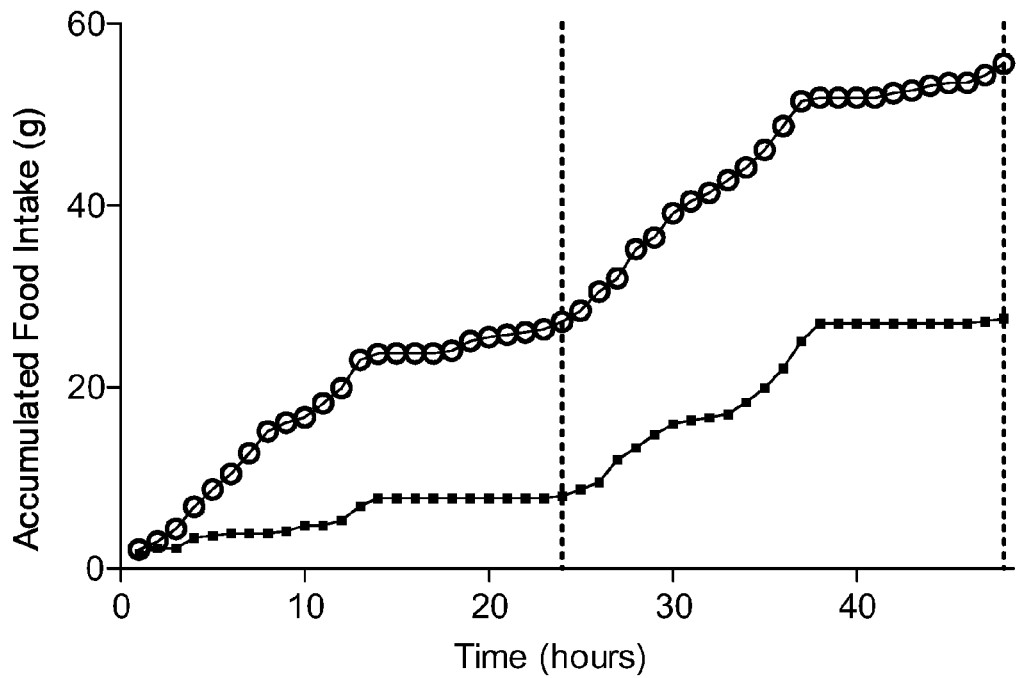
FIG. 3a shows food intake during 48 hours according to Pharmacological Assay (I). Data=mean. n=5-7. Open circle: vehicle. Black squares: 30 nmol/kg of compound 6.
Figure 3B:
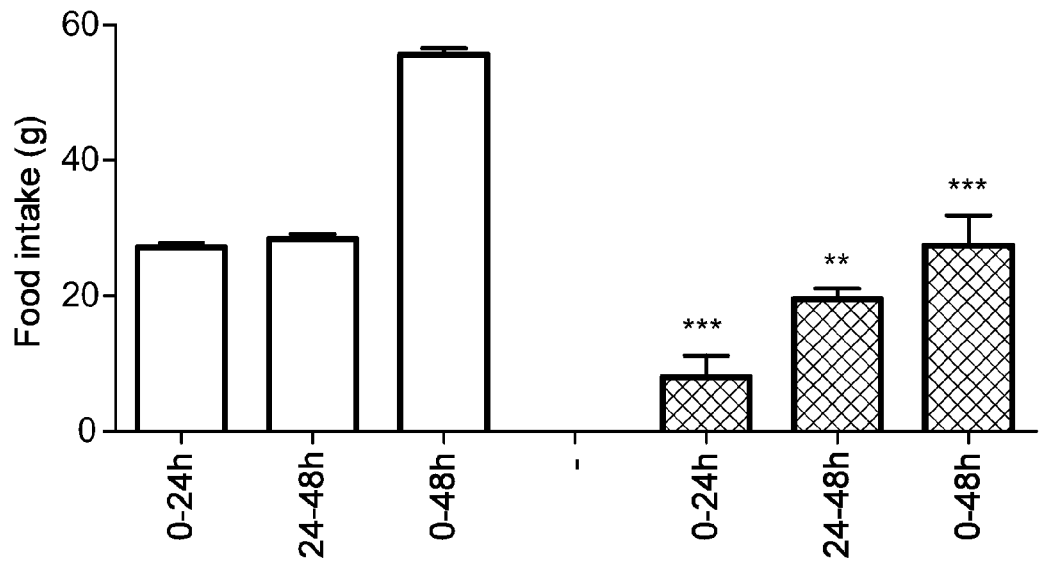
FIG. 3b shows accumulated food intake according to Pharmacological Assay (I) in the first 24 hours, the period from 24 to 48 hours, and the whole 48 hour period. Data=mean. n=5-7. Grey bars: vehicle. Black bars: 30 nmol/kg of compound 6.

From the FIG. 3a showing food intake over a period of 48 hours, it is seen that compound 5 is effectively reducing food intake. This is also illustrated in FIG. 3b, showing accumulated food intake in the periods 0-24 hours, 24-48 hours, and 0-48 hours, respectively. Food intake was compared using two-sided Student's t-test, alpha=0.05.

Example 7

N-alpha-[(S)-4-Carboxy-4-(19-carboxynonade-canoylamino)butyryl]-[His17]-pramlintide

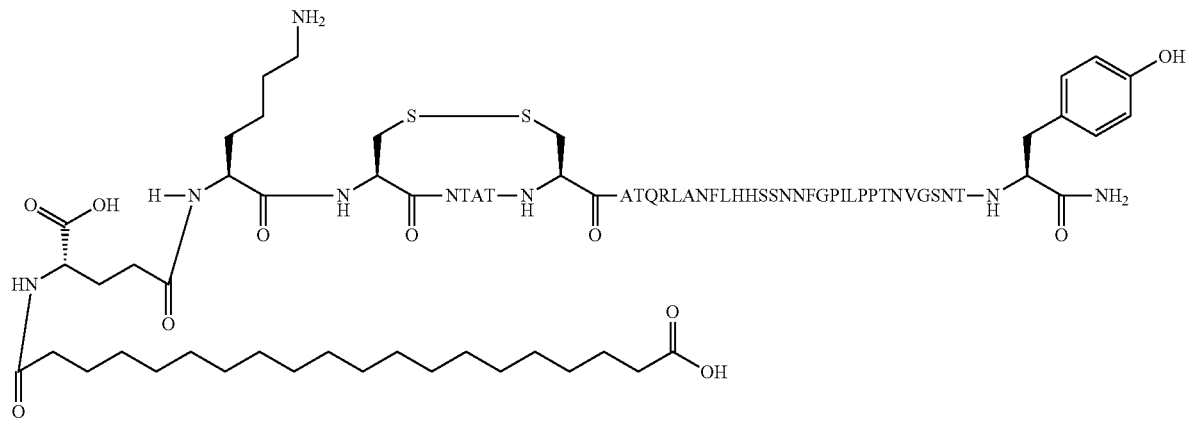

Figure 4A:
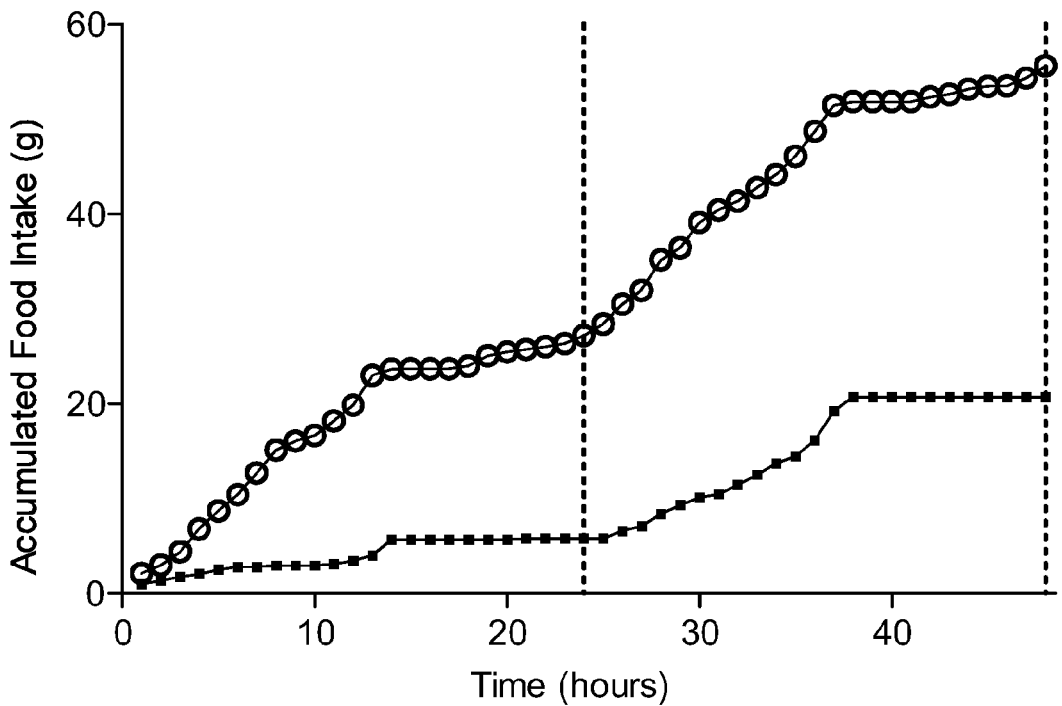
FIG. 4a shows food intake during 48 hours according to Pharmacological Assay (I). Data=mean. n=5-7. Open circle: vehicle. Black squares: 30 nmol/kg of compound 7.
Figure 4B:
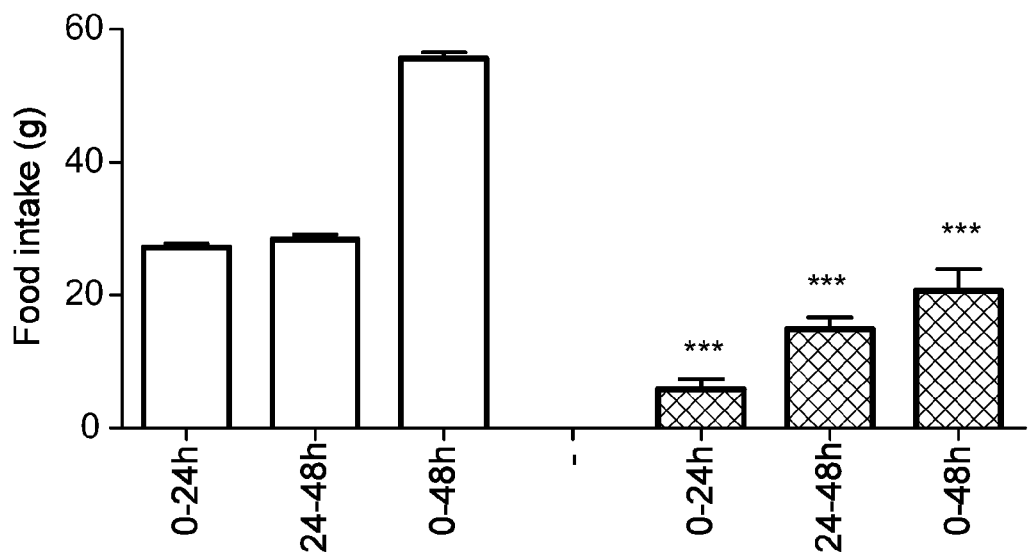
FIG. 4b shows accumulated food intake according to Pharmacological Assay (I) 4a in the first 24 hours, the period from 24 to 48 hours, and the whole 48 hour period. Data=mean. n=5-7. Grey bars: vehicle. Black bars: 30 nmol/kg of compound 7.

From the FIG. 4a showing food intake over a period of 48 hours, it is seen that compound 7 is effectively reducing food intake. This is also illustrated in FIG. 4b, showing accumulated food intake in the periods 0-24 hours, 24-48 hours, and 0-48 hours, respectively. Food intake was compared using two-sided Student's t-test, alpha=0.05.

Example 8

N-alpha-[19-carboxynonadecanoyl]-Glu-Lys-[Arg1, His17]-pramlintide

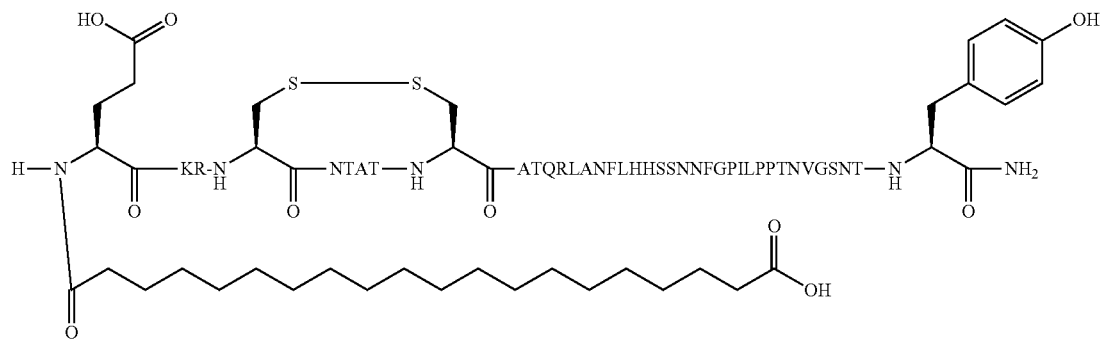

Figure 5A:
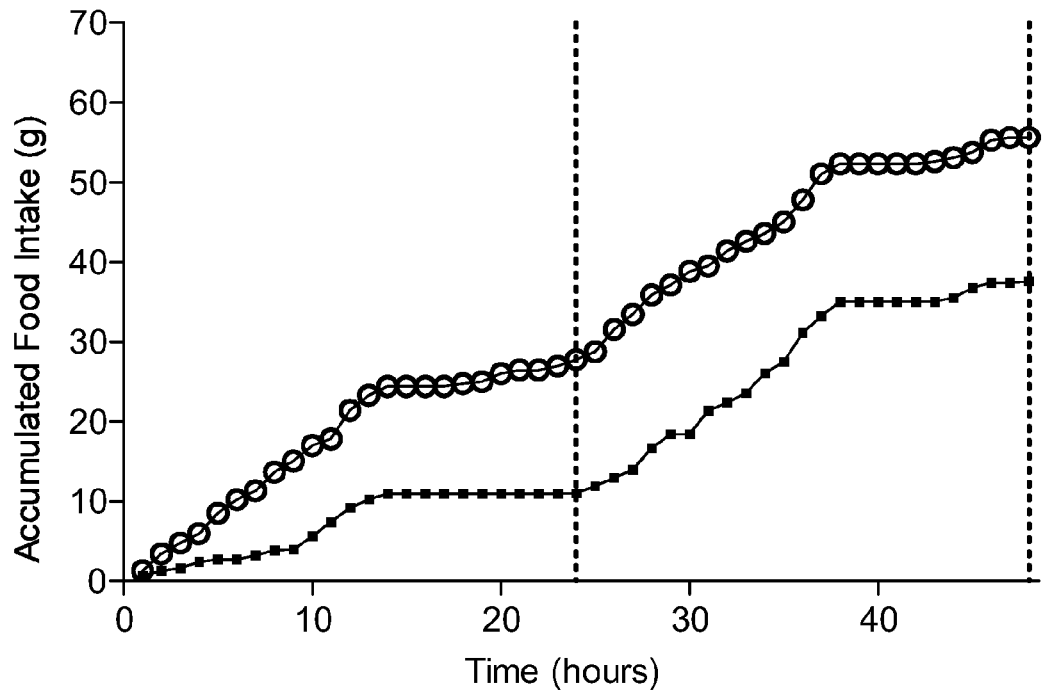
FIG. 5a shows food intake during 48 hours according to Pharmacological Assay (I). Data=mean. n=5-7. Open circle: vehicle. Black squares: 30 nmol/kg of compound 8.
Figure 5B:
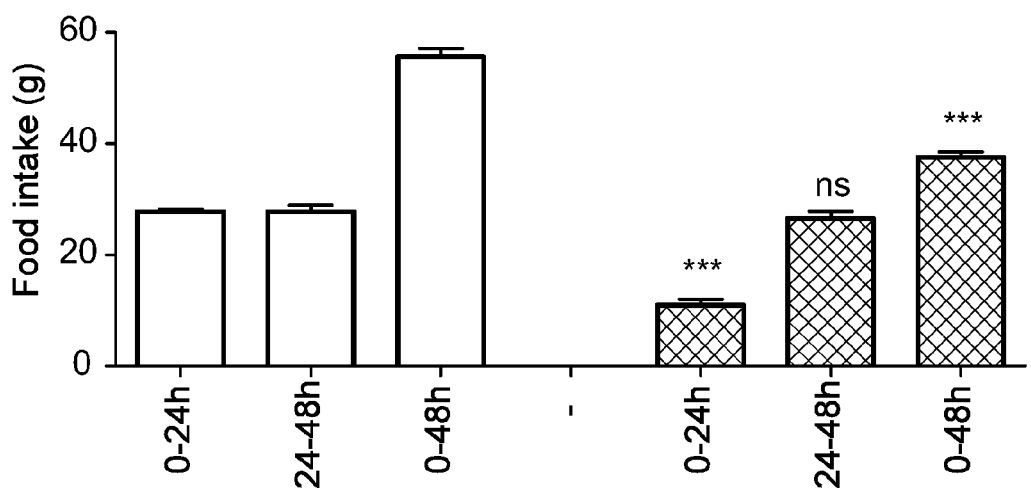
FIG. 5b shows accumulated food intake according to Pharmacological Assay (I) in the first 24 hours, the period from 24 to 48 hours, and the whole 48 hour period. Data=mean. n=5-7. Grey bars: vehicle. Black bars: 30 nmol/kg of compound 8.

From the FIG. 5a showing food intake over a period of 48 hours, it is seen that compound 8 is effectively reducing food intake. This is also illustrated in FIG. 5b, showing accumulated food intake in the periods 0-24 hours, 24-48 hours, and 0-48 hours, respectively. Food intake was compared using two-sided Student's t-test, alpha=0.05.

Example 9

N-alpha-[19-carboxynonadecanoyl]-Glu-Lys-Arg-[His17]-pramlintide

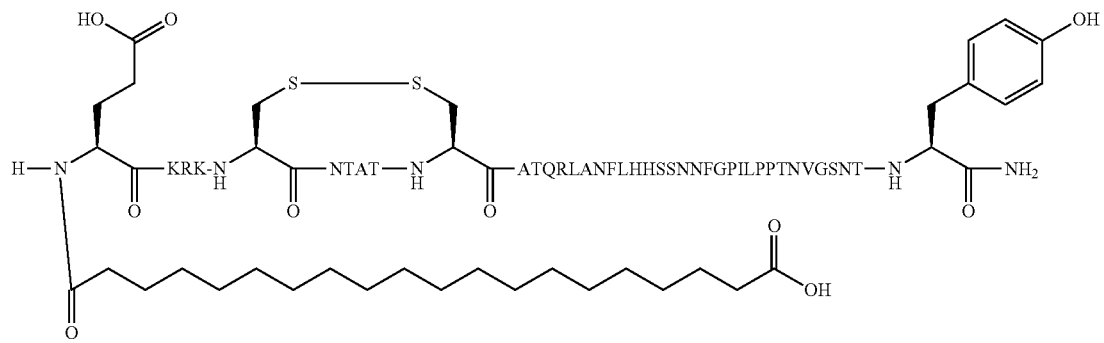

Figure 6A:
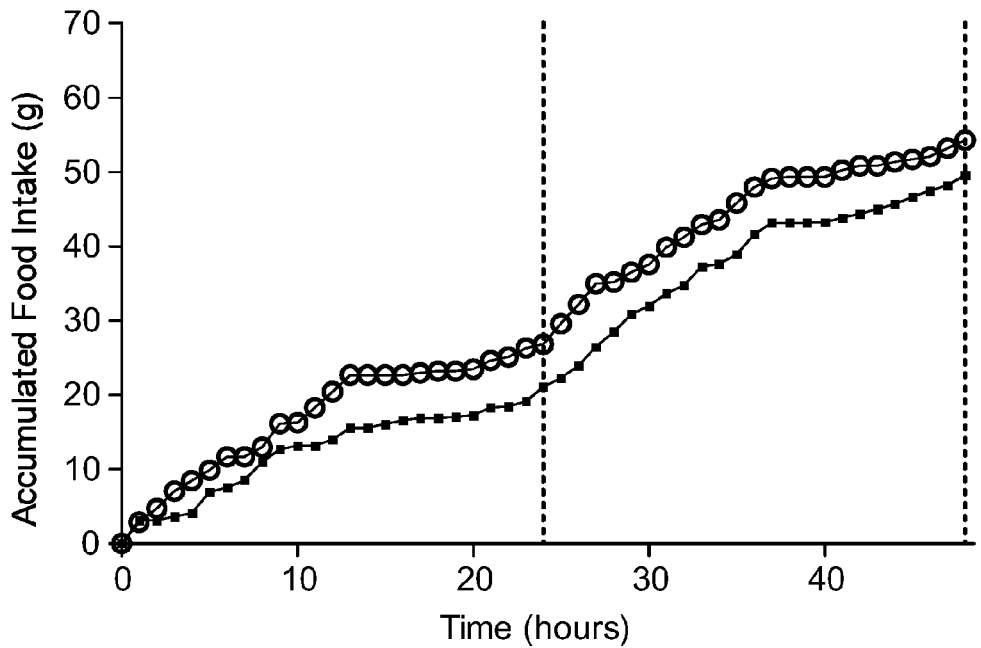
FIG. 6a shows food intake during 48 hours according to Pharmacological Assay (I). Data=mean. n=5-7. Open circle: vehicle. Black squares: 30 nmol/kg of compound 9.
Figure 6B:
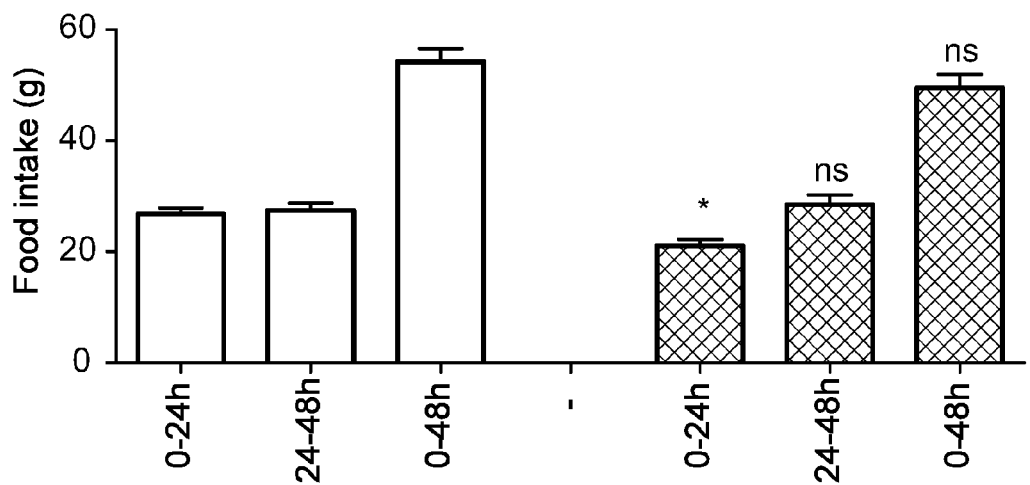
FIG. 6b shows accumulated food intake according to Pharmacological Assay (I) in the first 24 hours, the period from 24 to 48 hours, and the whole 48 hour period. Data=mean. n=5-7. Grey bars: vehicle. Black bars: 30 nmol/kg of compound 9.

From the FIG. 6a showing food intake over a period of 48 hours, it is seen that compound 9 is effectively reducing food intake. This is also illustrated in FIG. 6b, showing accumulated food intake in the periods 0-24 hours, 24-48 hours, and 0-48 hours, respectively. Food intake was compared using two-sided student's t-test, alpha=0.05.

Example 10

N-alpha-[(S)-4-Carboxy-4-(17-carboxyheptadecanoylamino)butyryl]-[His17]-pramlintide (2-37)

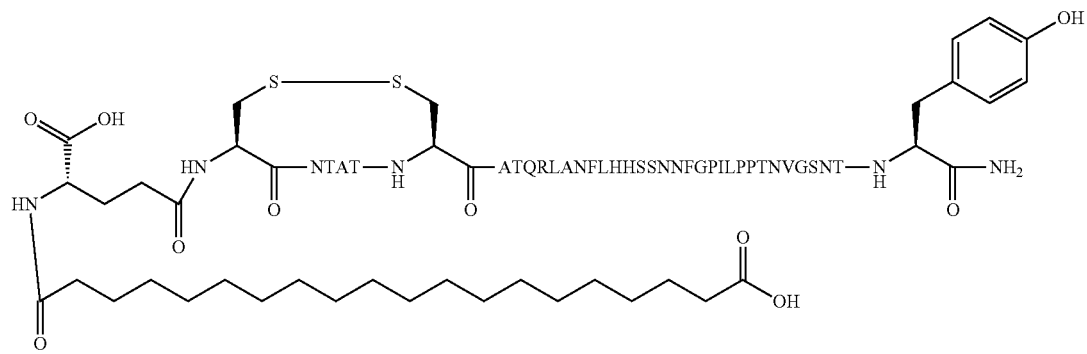

Figure 7A:
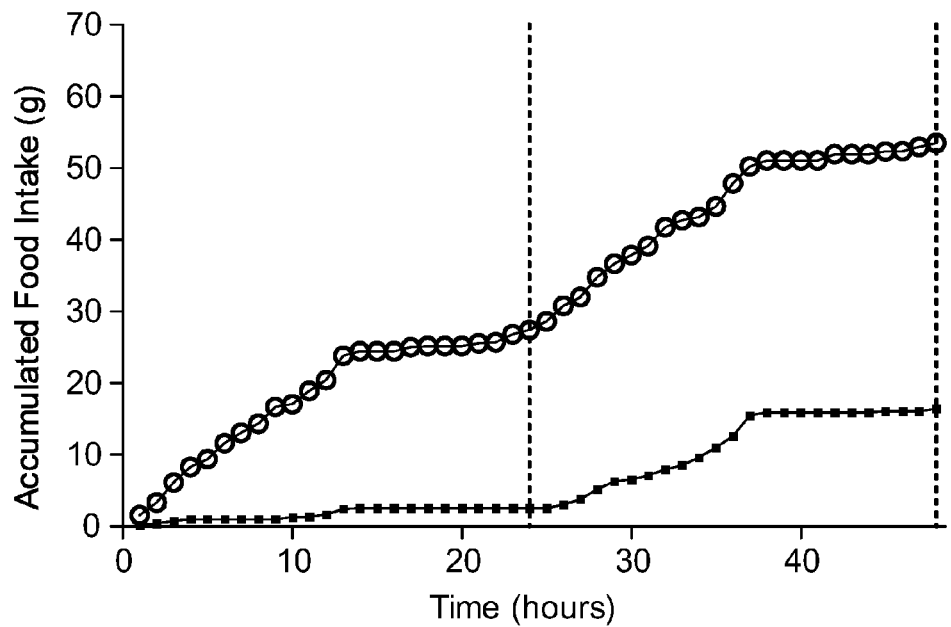
FIG. 7a shows food intake during 48 hours according to Pharmacological Assay (I). Data=mean. n=5-7. Open circle: vehicle. Black squares: 30 nmol/kg of compound 10.
Figure 7B:
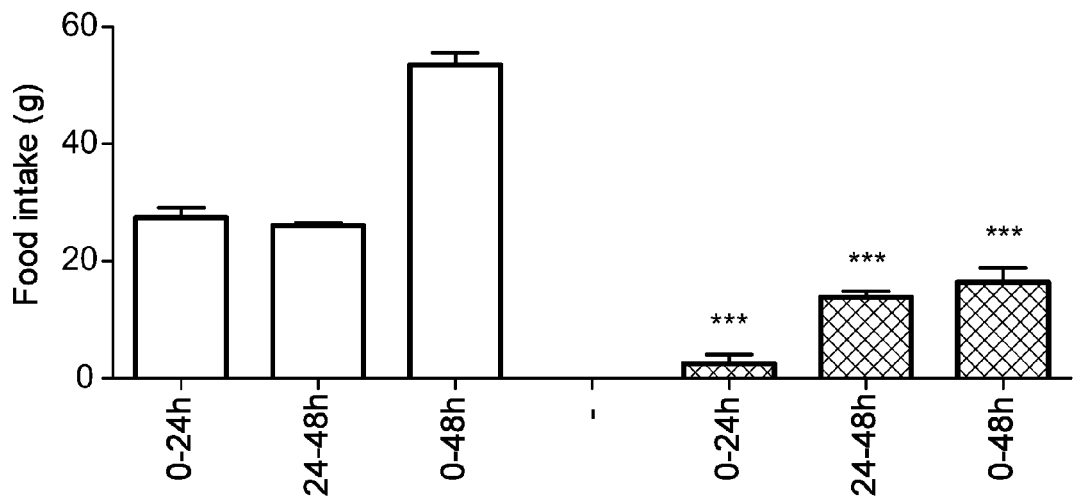
FIG. 7b shows accumulated food intake according to Pharmacological Assay (I) in the first 24 hours, the period from 24 to 48 hours, and the whole 48 hour period. Data=mean. n=5-7. Grey bars: vehicle. Black bars: 30 nmol/kg of compound 10.

From the FIG. 7a showing food intake over a period of 48 hours, it is seen that compound 10 is effectively reducing food intake. This is also illustrated in FIG. 7b, showing accumulated food intake in the periods 0-24 hours, 24-48 hours, and 0-48 hours, respectively. Food intake was compared using two-sided Student's t-test, alpha=0.05.

Example 11

N-alpha-[(S)-4-Carboxy-4-(19-carboxynonade-canoylamino)butyryl]-[Ser17]-pramlintide (2-37)

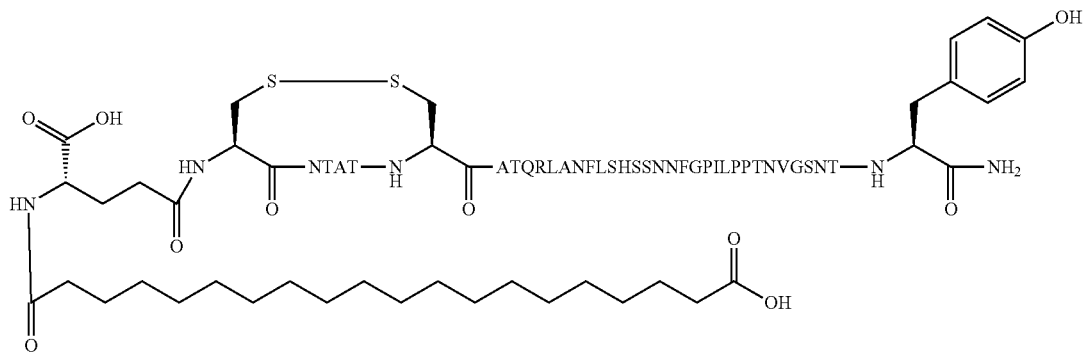

Figure 8A:
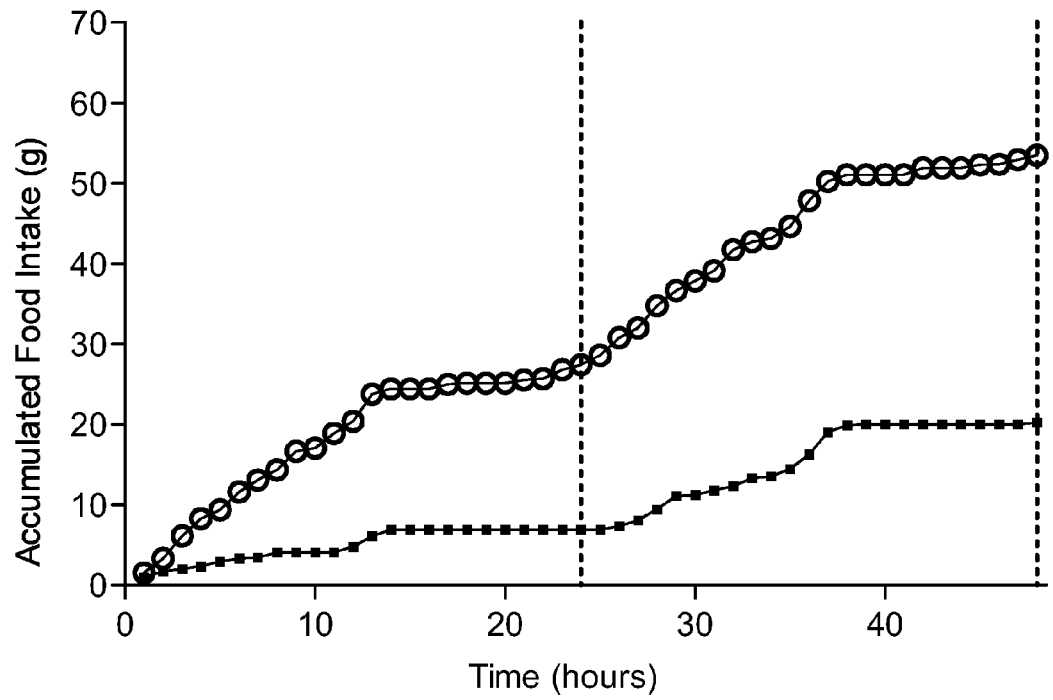
FIG. 8a shows food intake during 48 hours according to Pharmacological Assay (I). Data=mean. n=5-7. Open circle: vehicle. Black squares: 30 nmol/kg of compound 11.
Figure 8B:
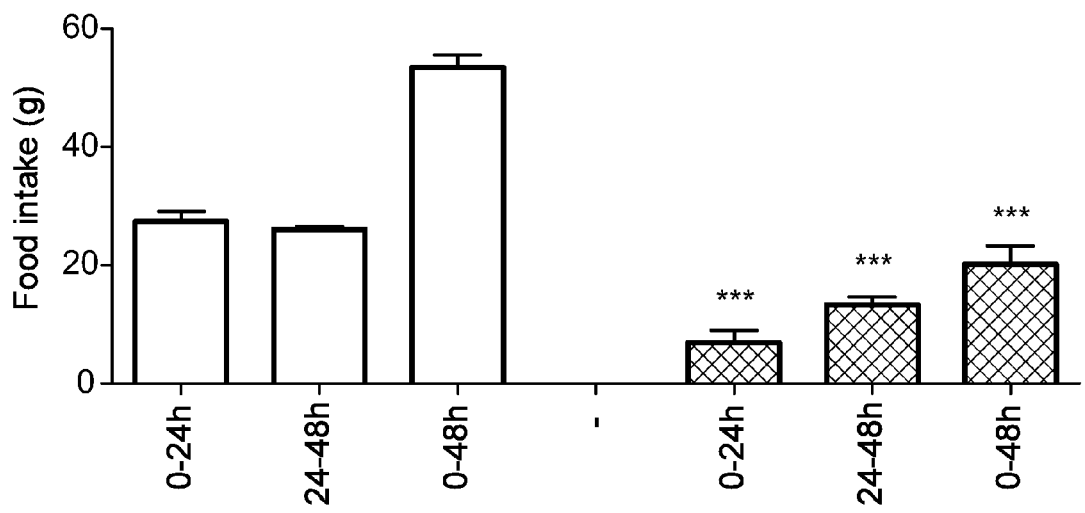
FIG. 8b shows accumulated food intake according to Pharmacological Assay (I) in the first 24 hours, the period from 24 to 48 hours, and the whole 48 hour period. Data=mean. n=5-7. Grey bars: vehicle. Black bars: 30 nmol/kg of compound 11.

From the FIG. 8a showing food intake over a period of 48 hours, it is seen that compound 11 is effectively reducing food intake. This is also illustrated in FIG. 8b, showing accumulated food intake in the periods 0-24 hours, 24-48 hours, and 0-48 hours, respectively. Food intake was compared using two-sided Student's t-test, alpha=0.05.

Example 12

N-alpha-[(S)-4-Carboxy-4-(19-carboxynonade-canoylamino)butyryl]-[Ala17]-pramlintide (2-37)

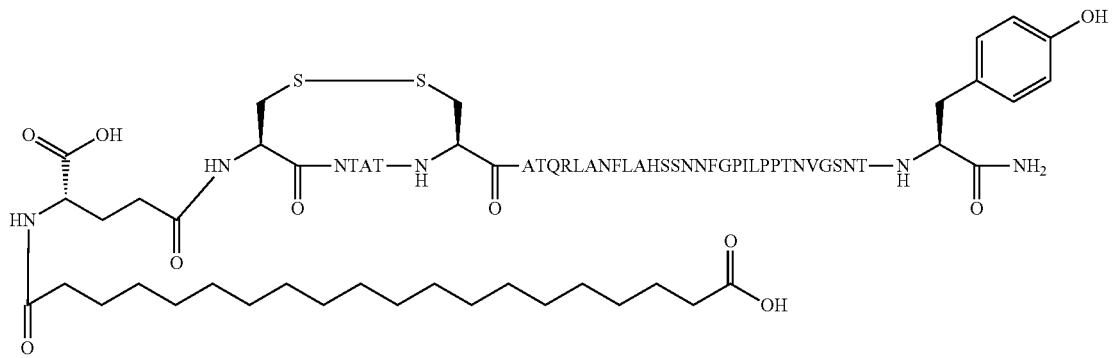

Figure 9A:
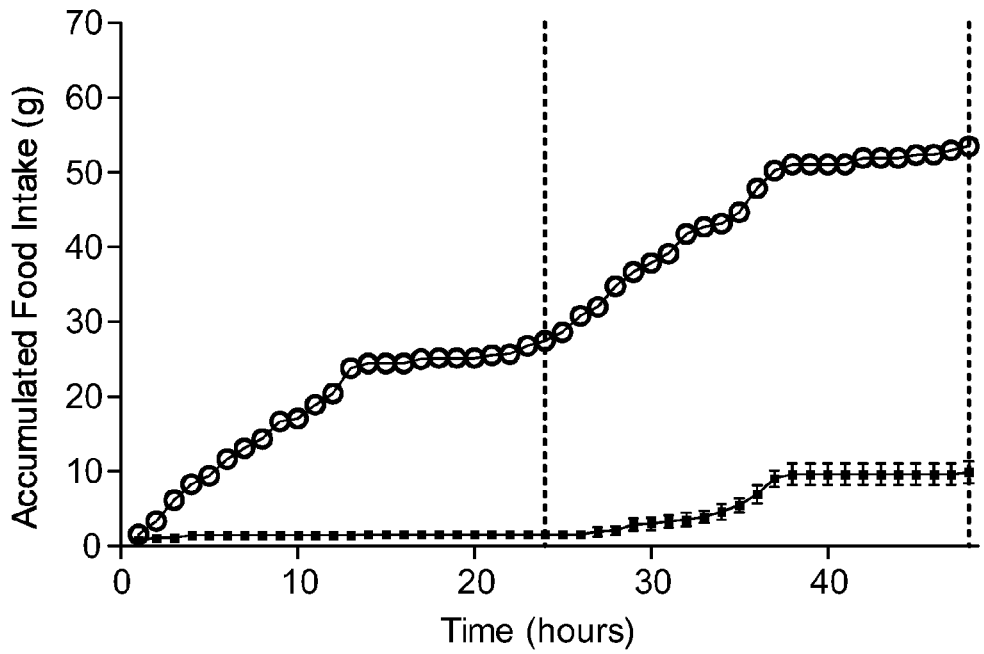
FIG. 9a shows food intake during 48 hours according to Pharmacological Assay (I). Data=mean. n=5-7. Open circle: vehicle. Black squares: 30 nmol/kg of compound 12.
Figure 9B:
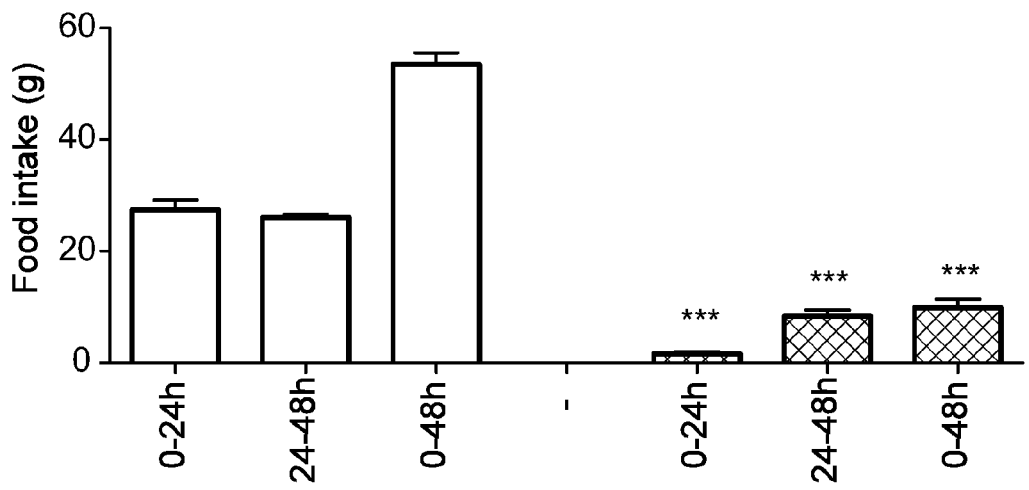
FIG. 9b shows accumulated food intake according to Pharmacological Assay (I) in the first 24 hours, the period from 24 to 48 hours, and the whole 48 hour period. Data=mean. n=5-7. Grey bars: vehicle. Black bars: 30 nmol/kg of compound 12.

From the FIG. 9a showing food intake over a period of 48 hours, it is seen that compound 12 is effectively reducing food intake. This is also illustrated in FIG. 9b, showing accumulated food intake in the periods 0-24 hours, 24-48 hours, and 0-48 hours, respectively. Food intake was compared using two-sided Student's t-test, alpha=0.05.

Example 13

N-alpha-[(S)-4-Carboxy-4-(19-carboxynonade-canoylamino)butyryl]-[Gly17]-pramlintide (2-37)

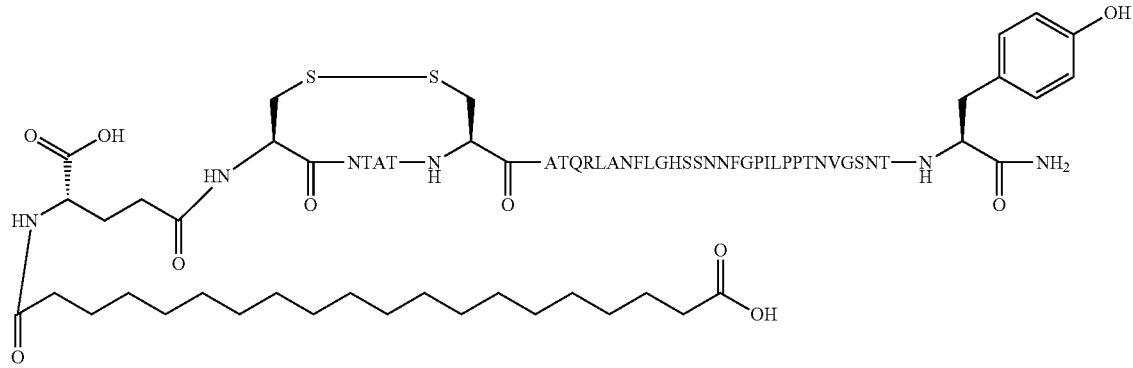

Example 14

N-alpha-[(S)-4-Carboxy-4-(19-carboxynonade-canoylamino)butyryl]-[Arg17]-pramlintide (2-37)

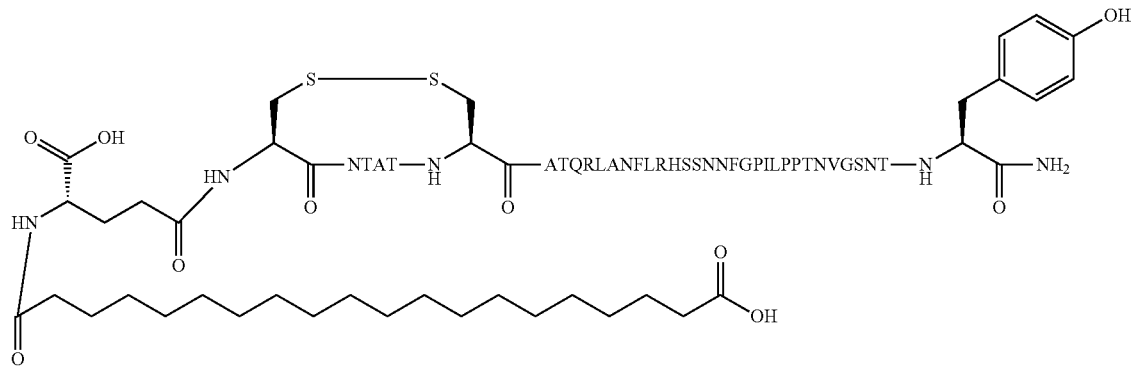

Figure 10A:
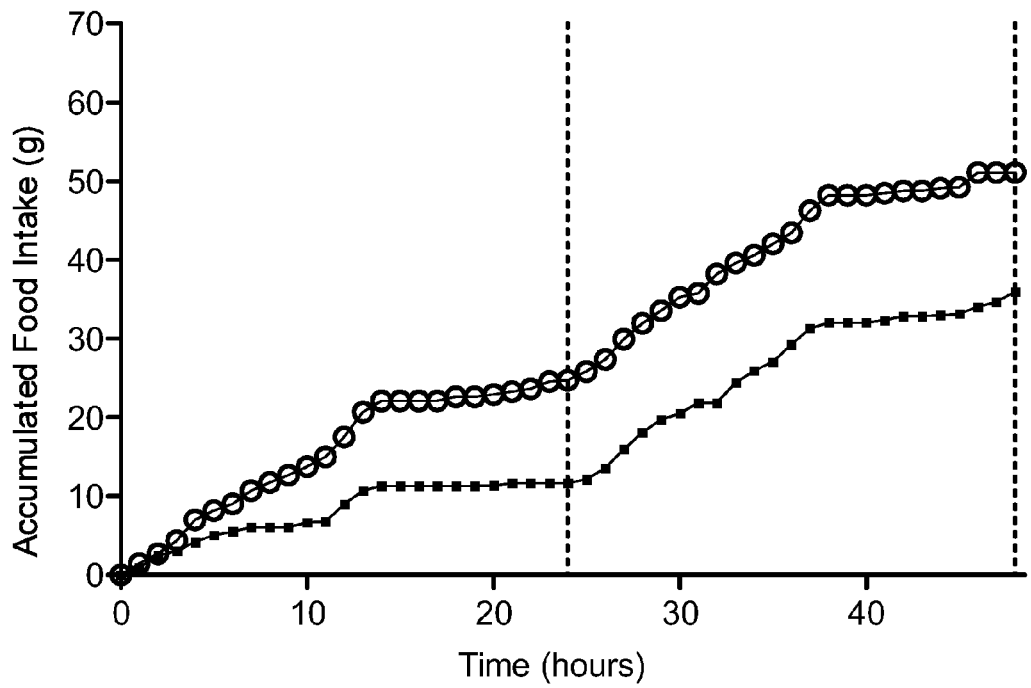
FIG. 10a shows food intake during 48 hours according to Pharmacological Assay (I). Data=mean. n=5-7. Open circle: vehicle. Black squares: 30 nmol/kg of compound 14.
Figure 10B:
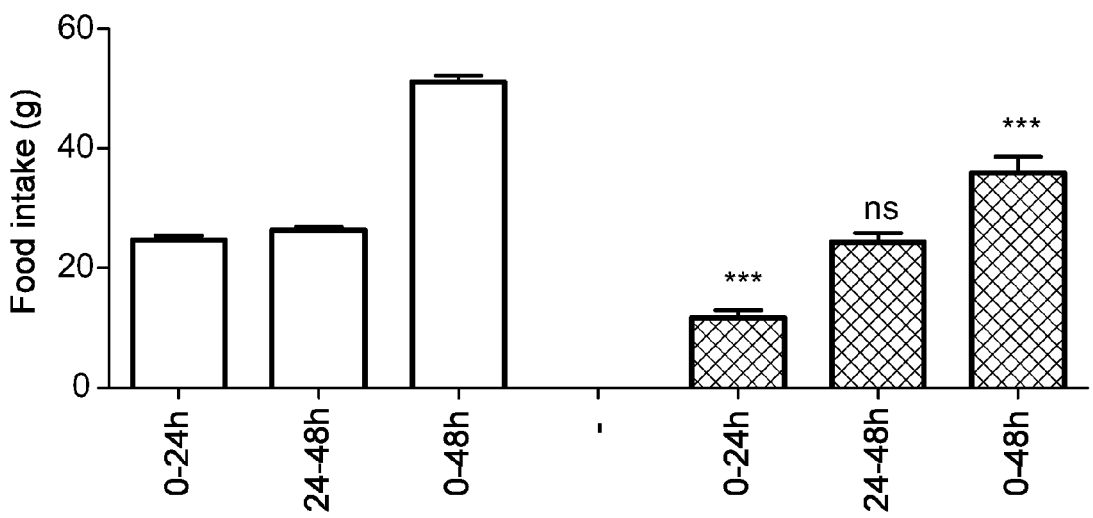
FIG. 10b shows accumulated food intake according to Pharmacological Assay (I) in the first 24 hours, the period from 24 to 48 hours, and the whole 48 hour period. Data=mean. n=5-7. Grey bars: vehicle. Black bars: 30 nmol/kg of compound 14.

From the FIG. 10a showing food intake over a period of 48 hours, it is seen that compound 14 is effectively reducing food intake. This is also illustrated in FIG. 10b, showing accumulated food intake in the periods 0-24 hours, 24-48 hours, and 0-48 hours, respectively. Food intake was compared using two-sided student's t-test, alpha=0.05.

Example 15

N-alpha-[(S)-4-Carboxy-4-(19-carboxynonade-canoylamino)butyryl]-[Pro17]-pramlintide (2-37)

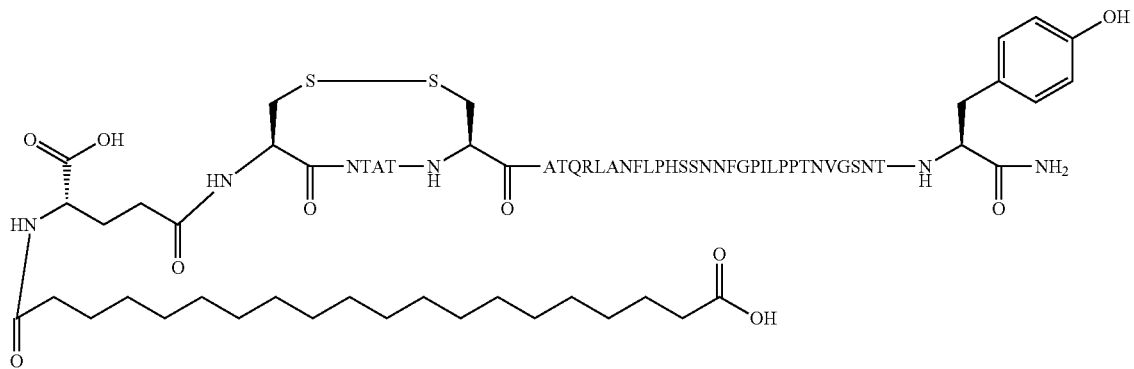

Example 16

N-alpha-[2-(2-{2-[4-(S)-Carboxy-4-(19-carboxynonadecanoylamino)butyrylamino]ethoxy}ethoxy)acetyl]-[His17]-pramlintide (2-37)

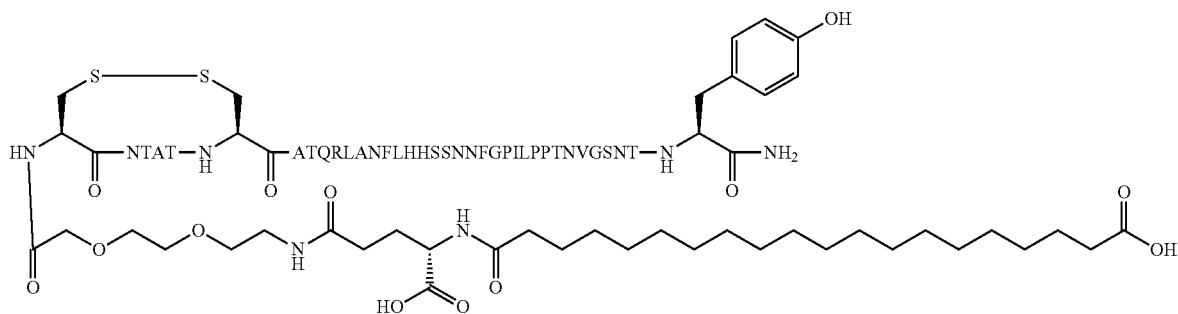

Figure 11A:
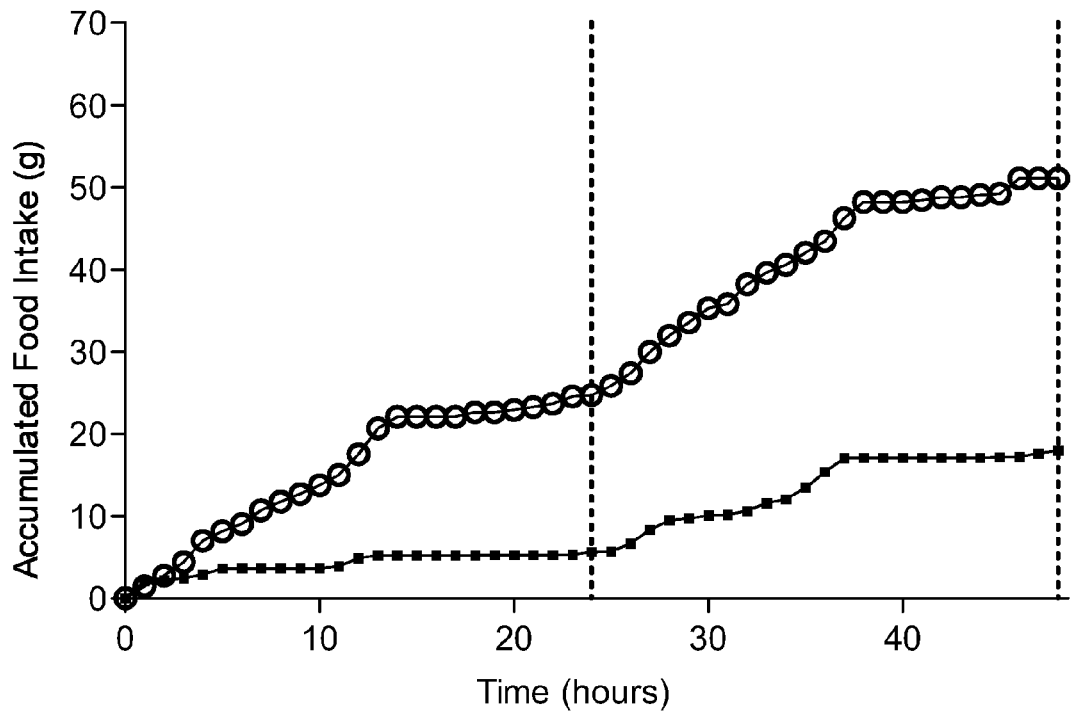
FIG. 11a shows food intake during 48 hours according to Pharmacological Assay (I). Data=mean. n=5-7. Open circle: vehicle. Black squares: 30 nmol/kg of compound 16.
Figure 11B:
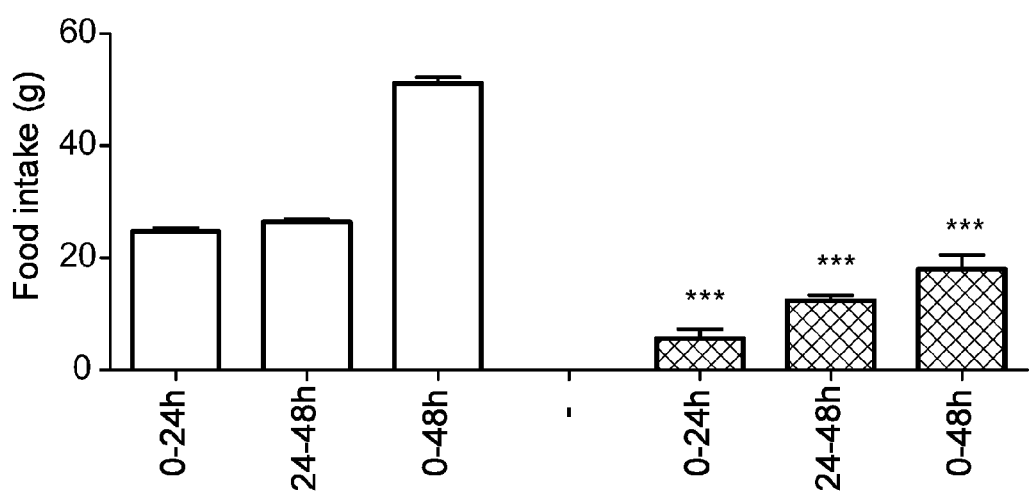
FIG. 11b shows accumulated food intake according to Pharmacological Assay (I) in the first 24 hours, the period from 24 to 48 hours, and the whole 48 hour period. Data=mean. n=5-7. Grey bars: vehicle. Black bars: 30 nmol/kg of compound 16.

From the FIG. 11a showing food intake over a period of 48 hours, it is seen that compound 16 is effectively reducing food intake. This is also illustrated in FIG. 11b, showing accumulated food intake in the periods 0-24 hours, 24-48 hours, and 0-48 hours, respectively. Food intake was compared using two-sided Student's t-test, alpha=0.05.

Example 17

N-alpha-[(S)-4-Carboxy-4-(19-carboxynonadecanoylamino)butyryl]-Arg-[His17]-pramlintide

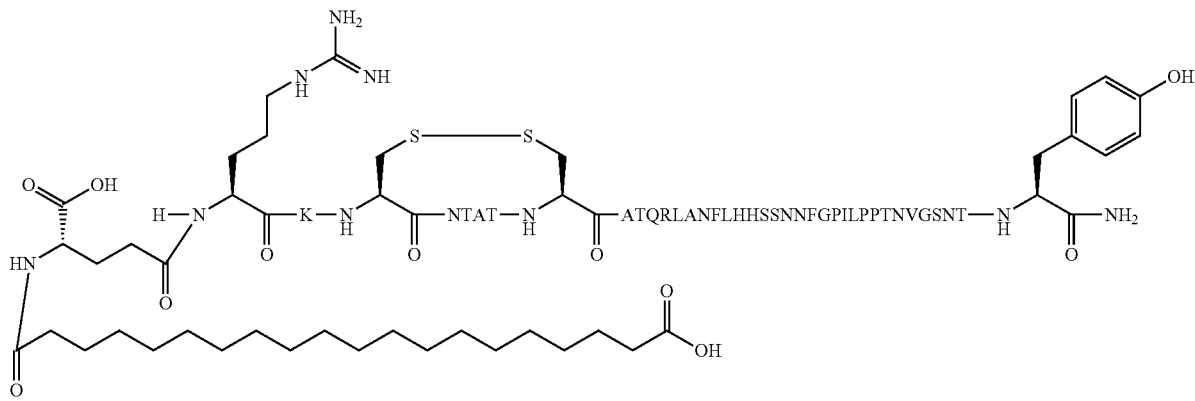

Figure 12A:
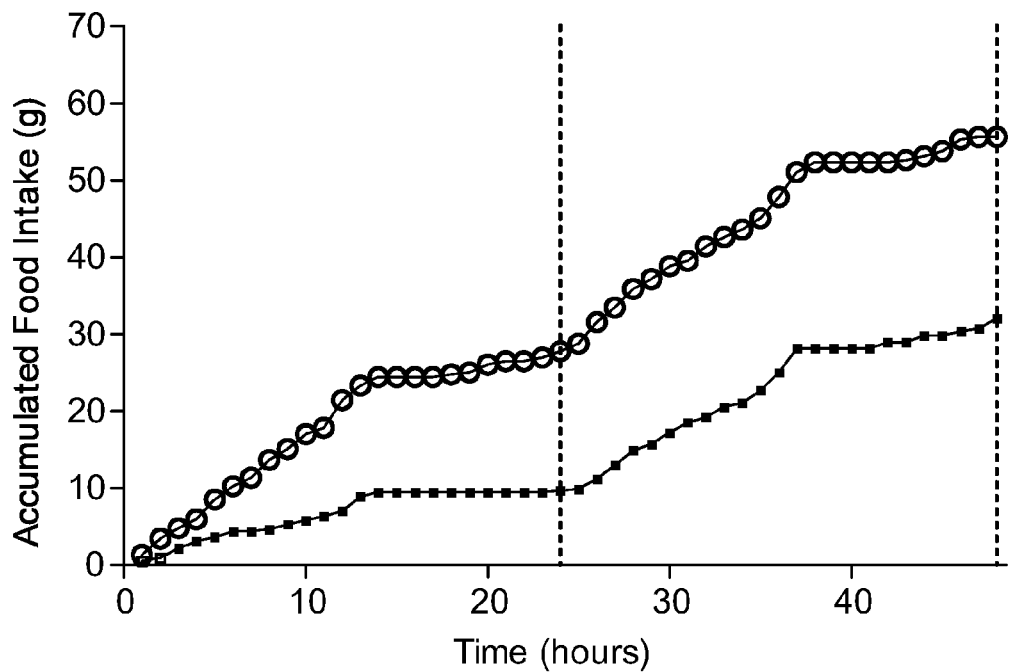
FIG. 12a shows food intake during 48 hours according to Pharmacological Assay (I). Data=mean. n=5-7. Open circle: vehicle. Black squares: 30 nmol/kg of compound 17.
Figure 12B:
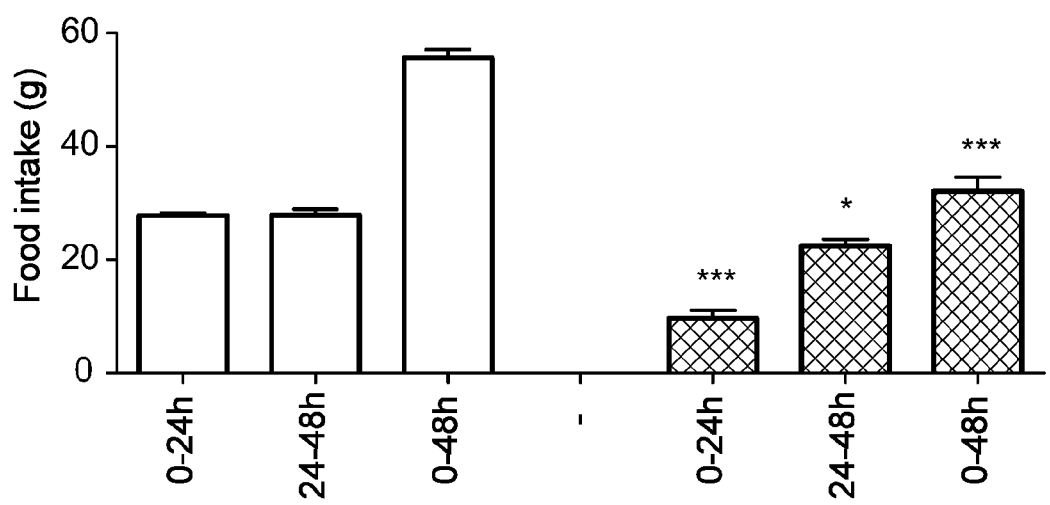
FIG. 12b shows accumulated food intake according to Pharmacological Assay (I) in the first 24 hours, the period from 24 to 48 hours, and the whole 48 hour period. Data=mean. n=5-7. Grey bars: vehicle. Black bars: 30 nmol/kg of compound 17.

From the FIG. 12a showing food intake over a period of 48 hours, it is seen that compound 17 is effectively reducing food intake. This is also illustrated in FIG. 12b, showing accumulated food intake in the periods 0-24 hours, 24-48 hours, and 0-48 hours, respectively. Food intake was compared using two-sided Student's t-test, alpha=0.05.

Example 18

N-alpha-[(S)-4-Carboxy-4-(19-carboxynonadecanoylamino)butyryl]-Arg-[Gly17]-pramlintide

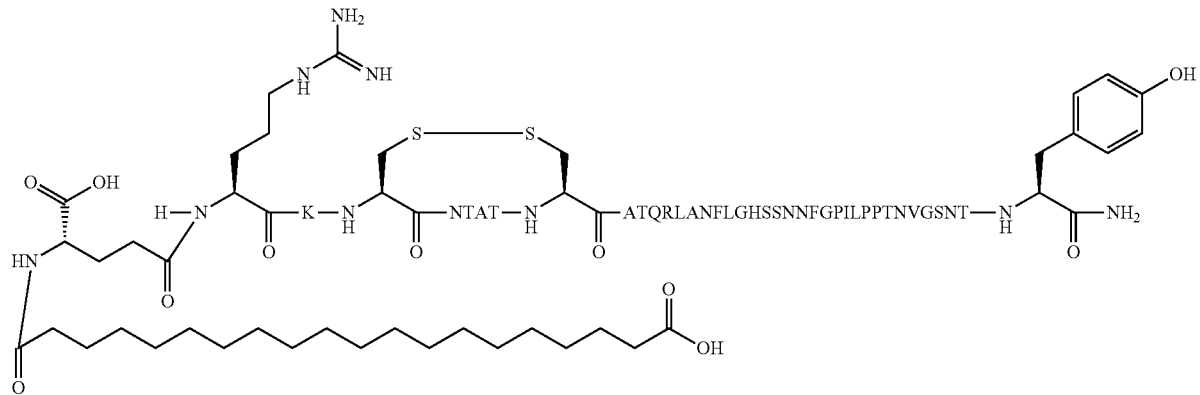

Figure 13A:
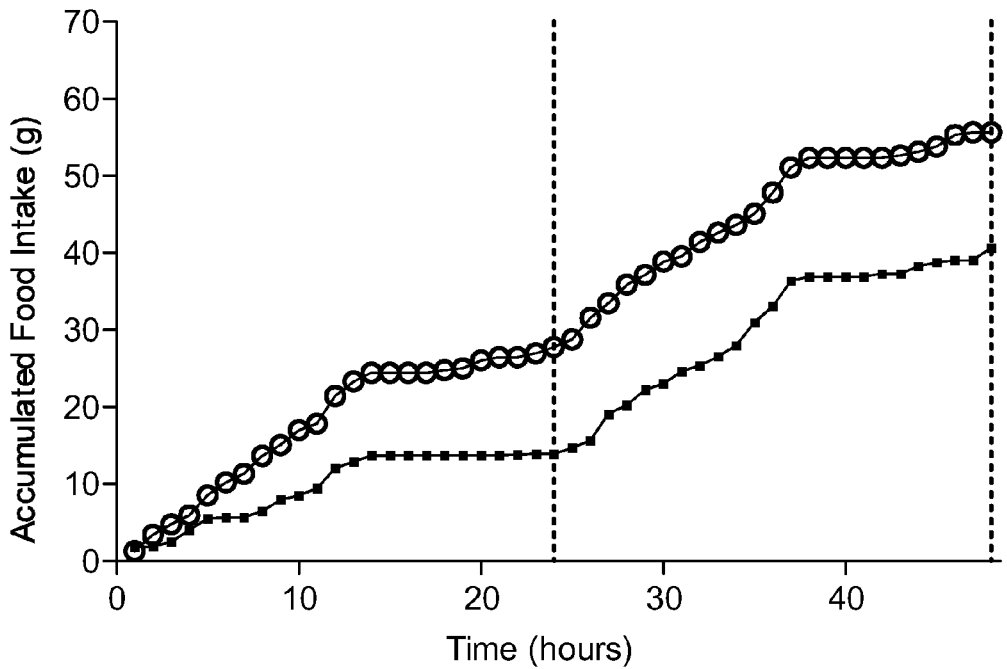
FIG. 13a shows food intake during 48 hours according to Pharmacological Assay (I). Data=mean. n=5-7. Open circle: vehicle. Black squares: 30 nmol/kg of compound 18.
Figure 13B:
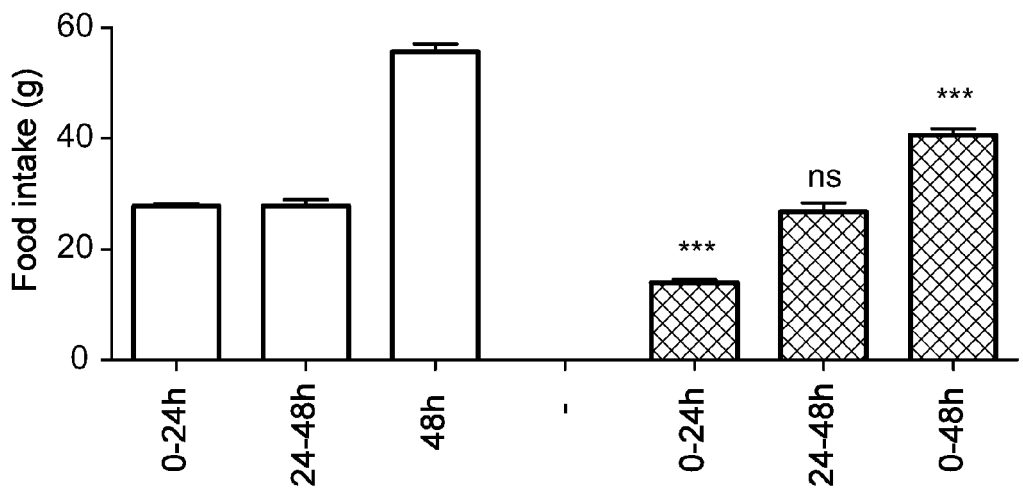
FIG. 13b shows accumulated food intake according to Pharmacological Assay (I) in the first 24 hours, the period from 24 to 48 hours, and the whole 48 hour period. Data=mean. n=5-7. Grey bars: vehicle. Black bars: 30 nmol/kg of compound 18.

From the FIG. 13a showing food intake over a period of 48 hours, it is seen that compound 18 is effectively reducing food intake. This is also illustrated in FIG. 13b, showing accumulated food intake in the periods 0-24 hours, 24-48 hours, and 0-48 hours, respectively. Food intake was compared using two-sided Student's t-test, alpha=0.05.

Example 19

N-alpha-[(S)-4-Carboxy-4-(19-carboxynonadecanoylamino)butyryl]-Arg-[Ala17]-pramlintide

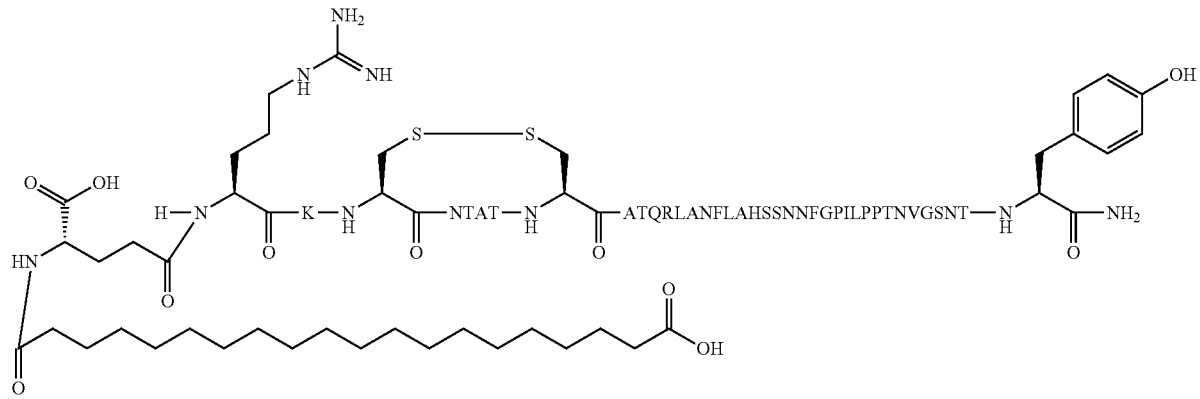

Figure 14A:
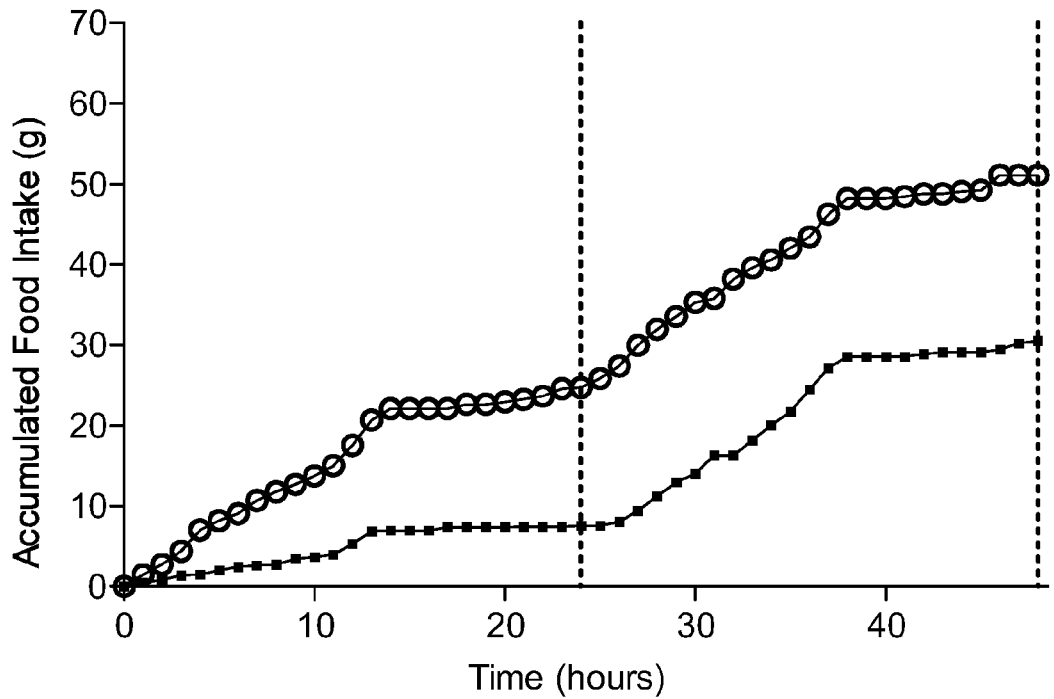
FIG. 14a shows food intake during 48 hours according to Pharmacological Assay (I). Data=mean. n=5-7. Open circle: vehicle. Black squares: 30 nmol/kg of compound 19.
Figure 14B:
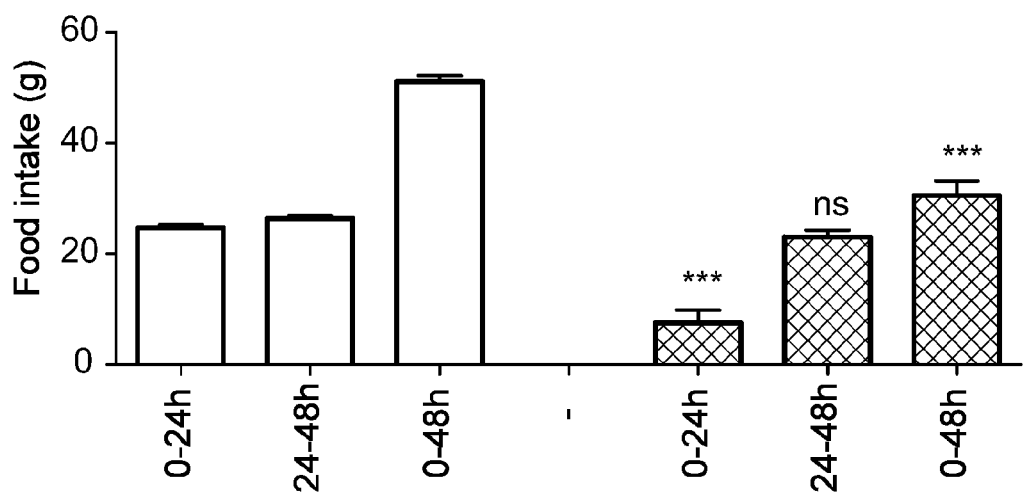
FIG. 14b shows accumulated food intake according to Pharmacological Assay (I) in the first 24 hours, the period from 24 to 48 hours, and the whole 48 hour period. Data=mean. n=5-7. Grey bars: vehicle. Black bars: 30 nmol/kg of compound 19.

From the FIG. 14a showing food intake over a period of 48 hours, it is seen that compound 19 is effectively reducing food intake. This is also illustrated in FIG. 14b, showing accumulated food intake in the periods 0-24 hours, 24-48 hours, and 0-48 hours, respectively. Food intake was compared using two-sided Student's t-test, alpha=0.05.

Example 20

N-alpha-[(S)-4-Carboxy-4-(19-carboxynonade-canoylamino)butyryl]-Arg-[Ser17]-pramlintide

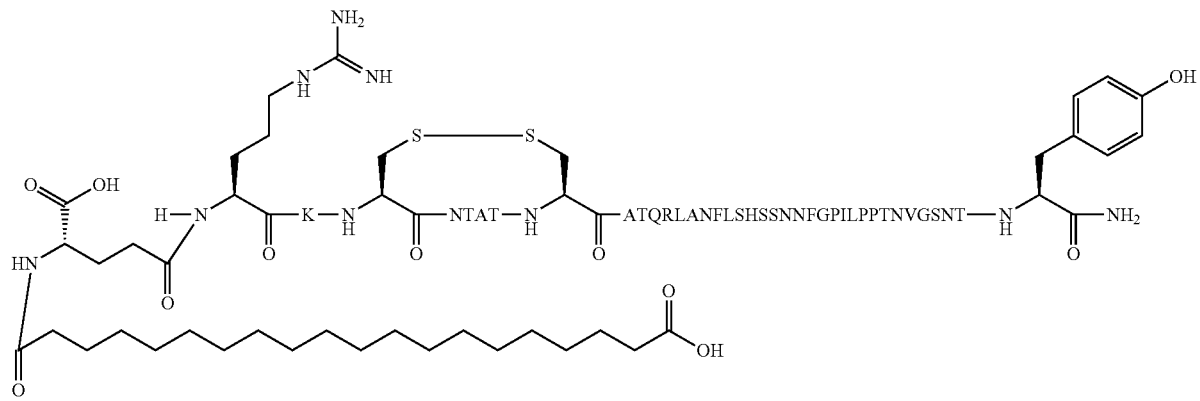

Figure 15A:
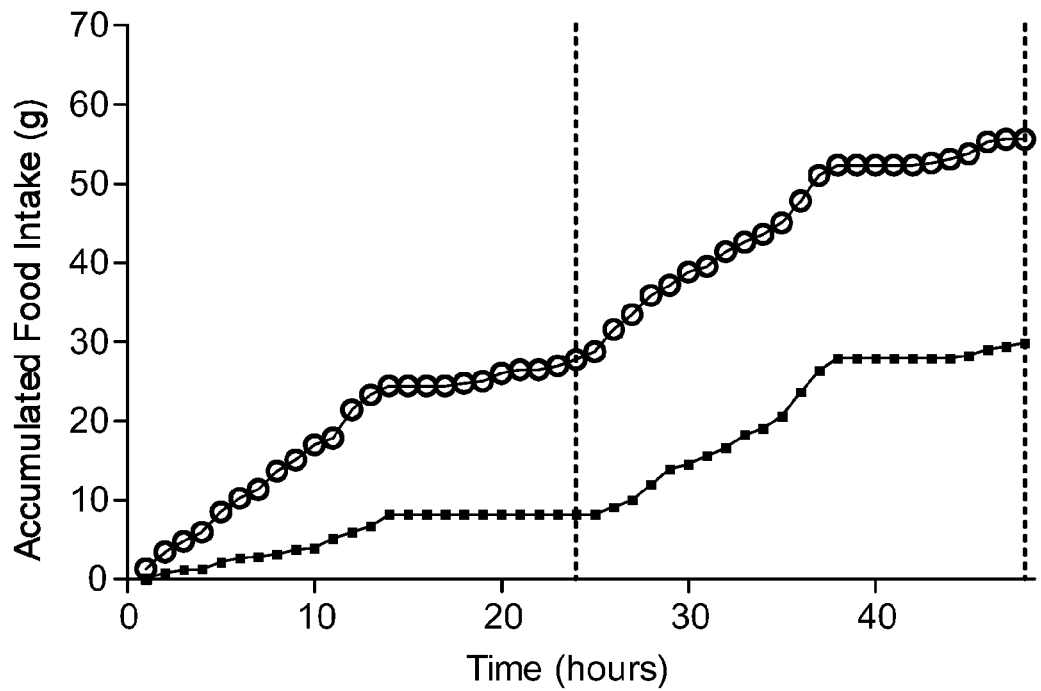
FIG. 15a shows food intake during 48 hours according to Pharmacological Assay (I). Data=mean. n=5-7. Open circle: vehicle. Black squares: 30 nmol/kg of compound 20.
Figure 15B:
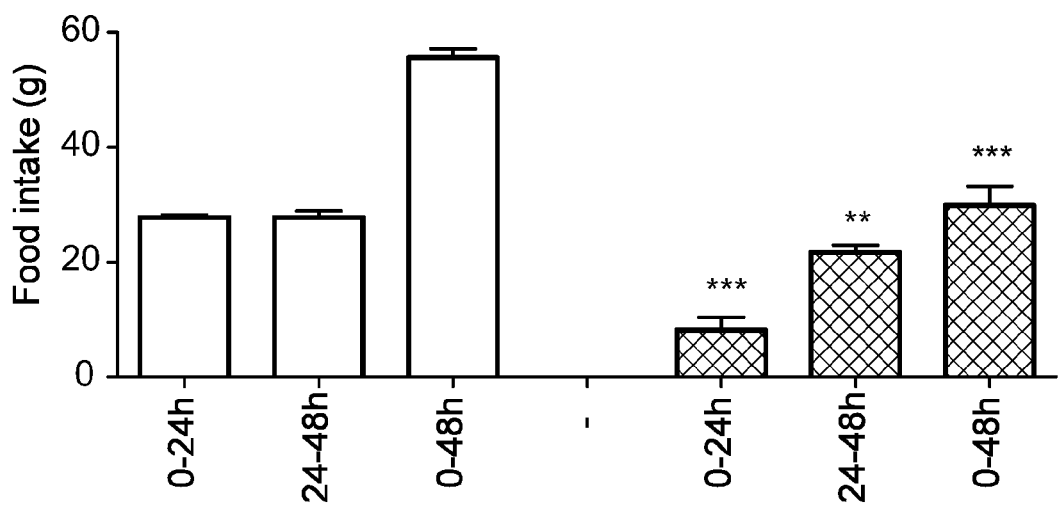
FIG. 15b shows accumulated food intake according to Pharmacological Assay (I) in the first 24 hours, the period from 24 to 48 hours, and the whole 48 hour period. Data=mean. n=5-7. Grey bars: vehicle. Black bars: 30 nmol/kg of compound 20.

From the FIG. 15*a* showing food intake over a period of 48 hours, it is seen that compound 20 is effectively reducing food intake. This is also illustrated in FIG. 15*b*, showing accumulated food intake in the periods 0-24 hours, 24-48 hours, and 0-48 hours, respectively. Food intake was compared using two-sided Student's t-test, alpha=0.05.

Example 21

N-alpha-[(S)-4-Carboxy-4-(19-carboxynonade-canoylamino)butyryl]-Arg-[Pro17]-pramlintide

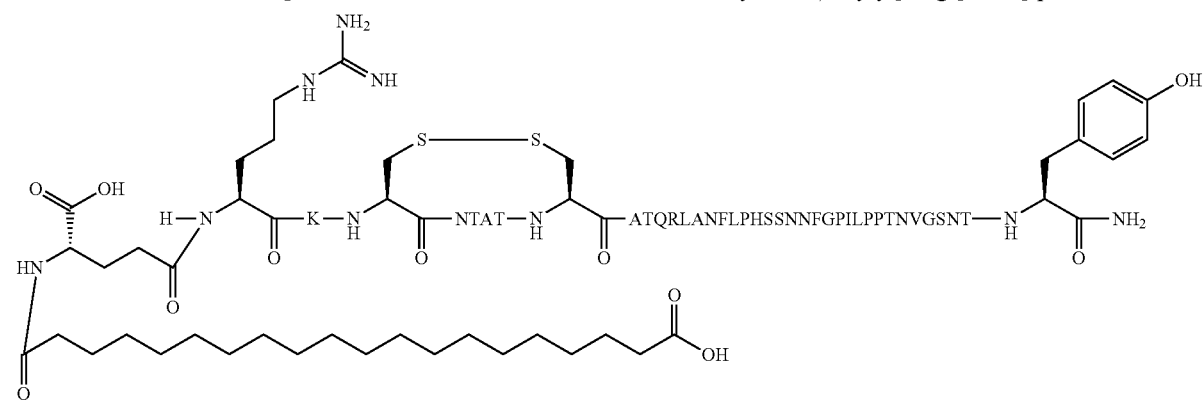

Example 22

N-alpha-[(S)-4-Carboxy-4-(19-carboxynonade-canoylamino)butyryl]-Arg-[Arg17]-pramlintide

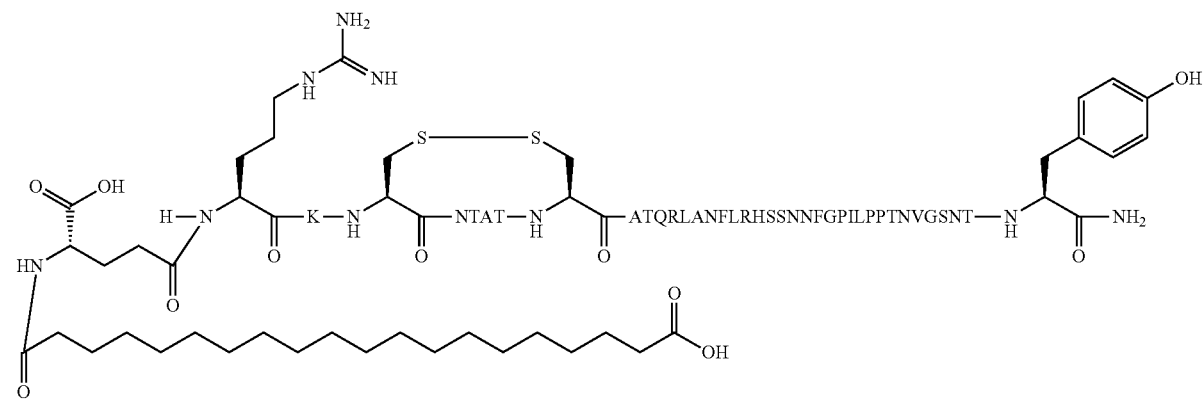

Figure 16A:
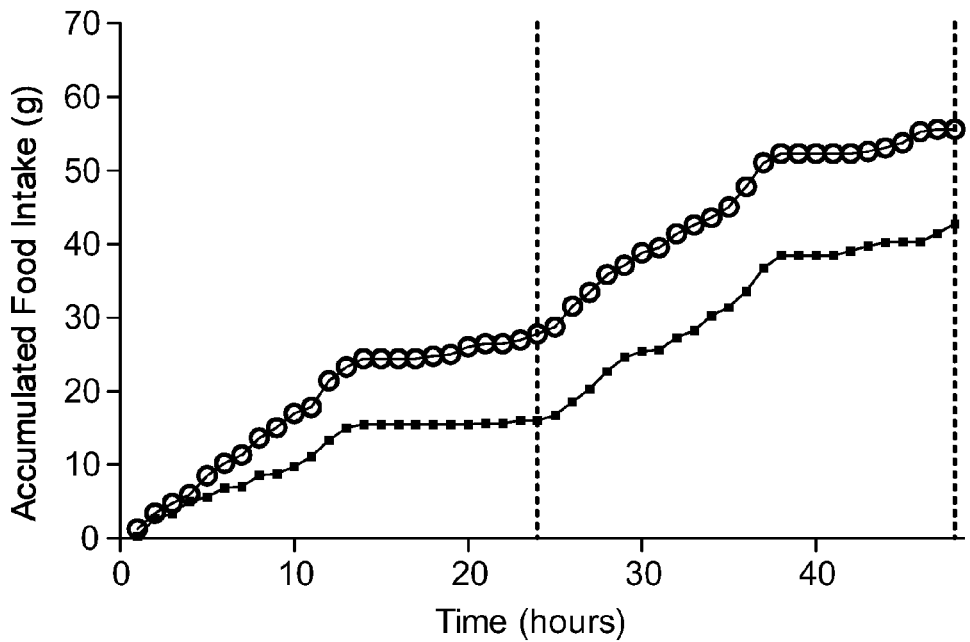
FIG. 16a shows food intake during 48 hours according to Pharmacological Assay (I). Data=mean. n=5-7. Open circle: vehicle. Black squares: 30 nmol/kg of compound 22.
Figure 16B:
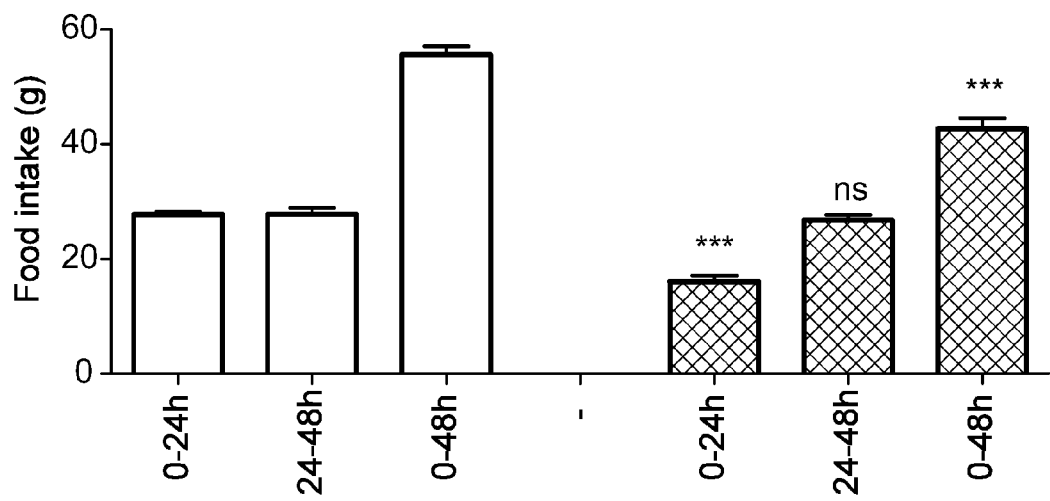
FIG. 16b shows accumulated food intake according to Pharmacological Assay (I) in the first 24 hours, the period from 24 to 48 hours, and the whole 48 hour period. Data=mean. n=5-7. Grey bars: vehicle. Black bars: 30 nmol/kg of compound 22.

From the FIG. 16a showing food intake over a period of 48 hours, it is seen that compound 22 is effectively reducing food intake. This is also illustrated in FIG. 16b, showing accumulated food intake in the periods 0-24 hours, 24-48 hours, and 0-48 hours, respectively. Food intake was compared using two-sided Student's t-test, alpha=0.05.

Example 23

N-alpha-[2-(2-{2-[4-(S)-Carboxy-4-(19-carboxynonadecanoylamino)butyrylamino]ethoxy}ethoxy)acetyl]-Arg-[Arg17]-pramlintide

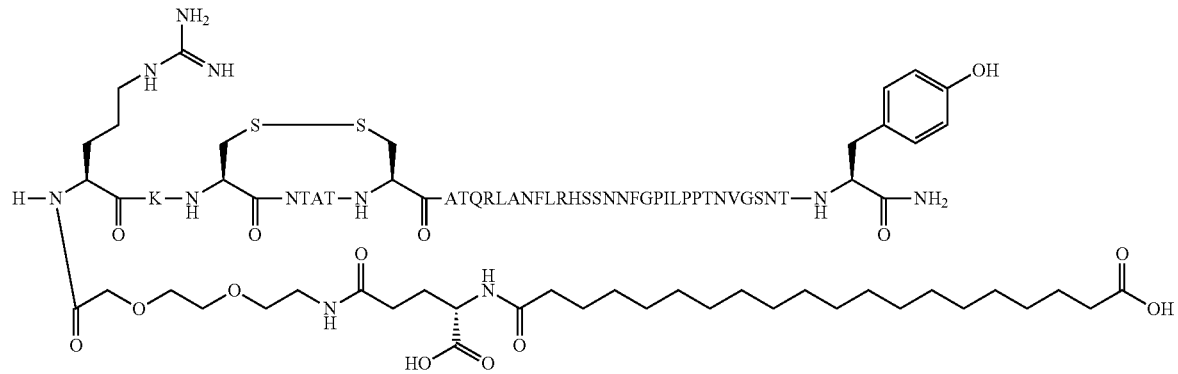

Figure 17A:
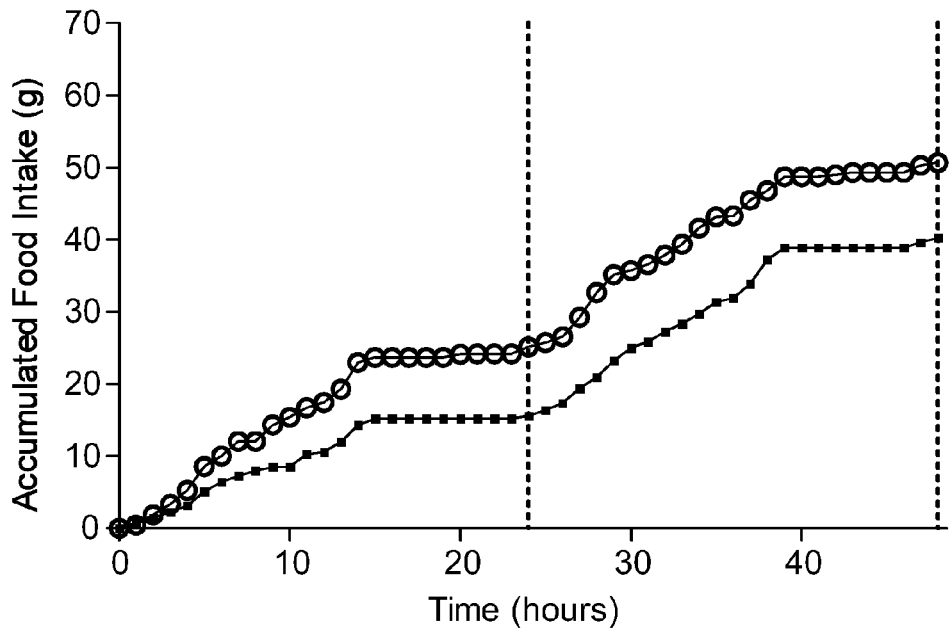
FIG. 17a shows food intake during 48 hours according to Pharmacological Assay (I). Data=mean. n=5-7. Open circle: vehicle. Black squares: 30 nmol/kg of compound 23.
Figure 17B:
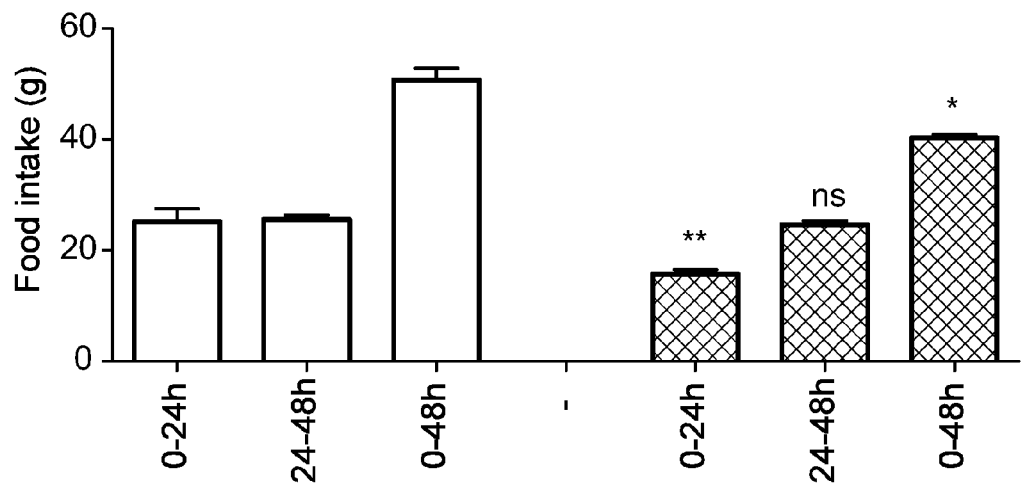
FIG. 17b shows accumulated food intake according to Pharmacological Assay (I) in the first 24 hours, the period from 24 to 48 hours, and the whole 48 hour period. Data=mean. n=5-7. Grey bars: vehicle. Black bars: 30 nmol/kg of compound 23.

From the FIG. 17a showing food intake over a period of 48 hours, it is seen that compound 23 is effectively reducing food intake. This is also illustrated in FIG. 17b, showing accumulated food intake in the periods 0-24 hours, 24-48 hours, and 0-48 hours, respectively. Food intake was compared using two-sided Student's t-test, alpha=0.05.

Example 24

N-alpha-[2-(2-{2-[4-(S)-Carboxy-4-(19-carboxynonadecanoylamino)butyrylamino]ethoxy}ethoxy)acetyl]-Arg-[Ala17]-pramlintide

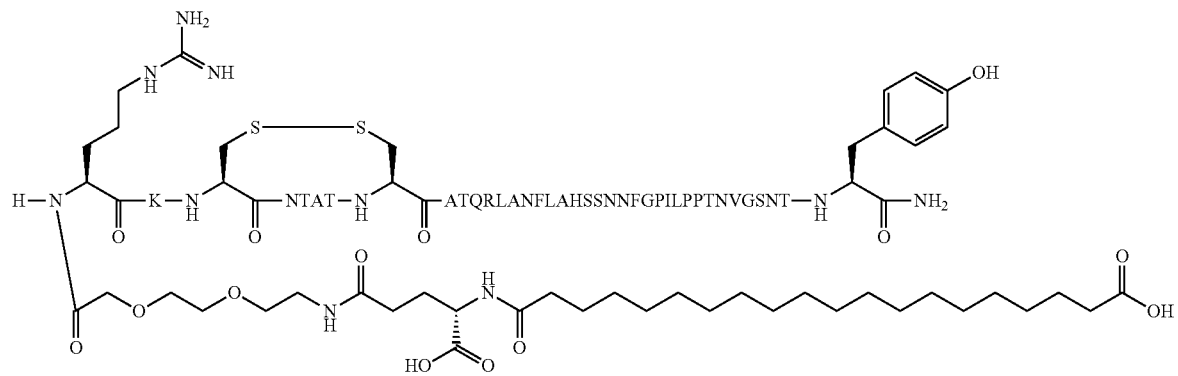

Figure 18A:
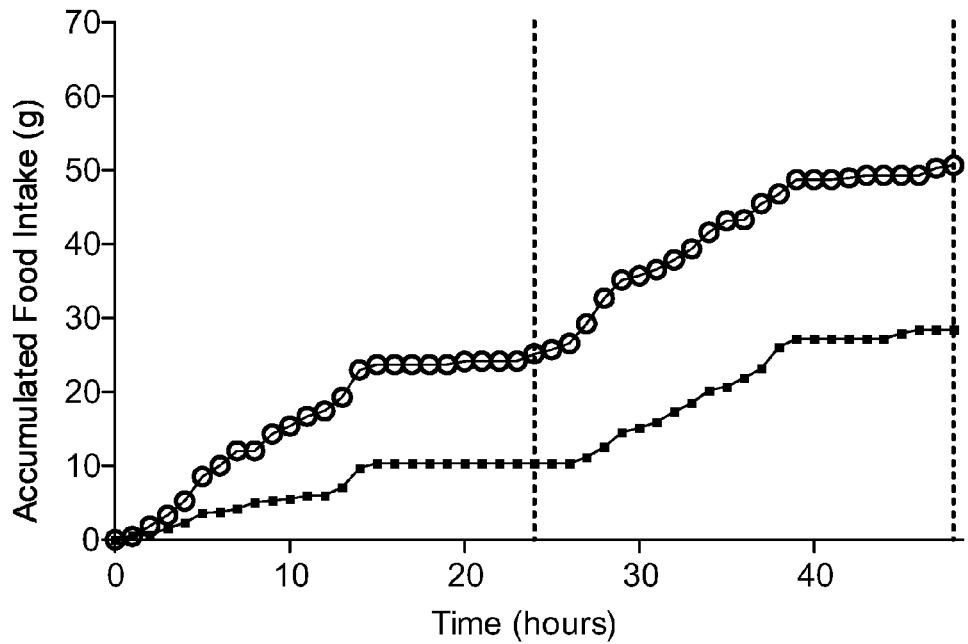
FIG. 18a shows food intake during 48 hours according to Pharmacological Assay (I). Data=mean. n=5-7. Open circle: vehicle. Black squares: 30 nmol/kg of compound 24.
Figure 18B:
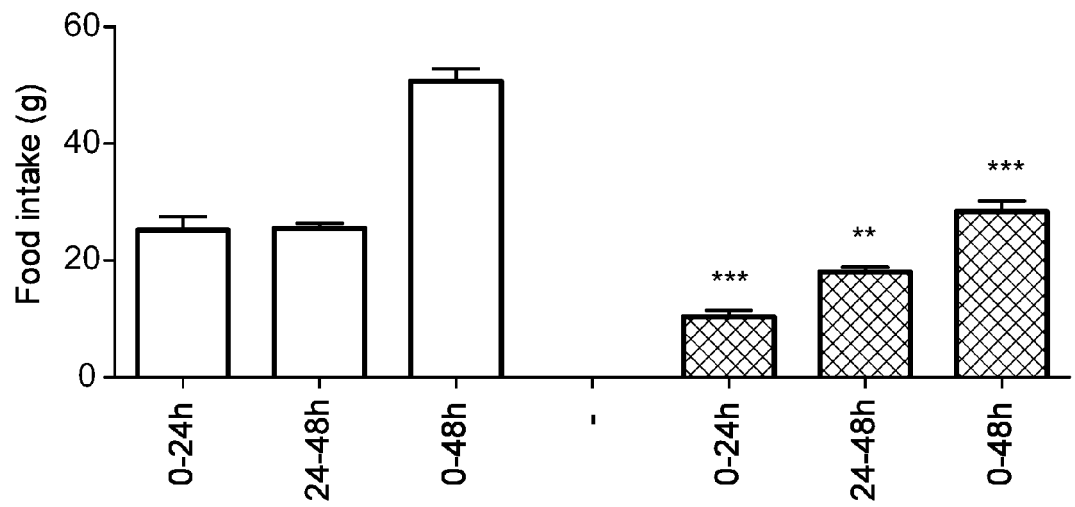
FIG. 18b shows accumulated food intake according to Pharmacological Assay (I) in the first 24 hours, the period from 24 to 48 hours, and the whole 48 hour period. Data=mean. n=5-7. Grey bars: vehicle. Black bars: 30 nmol/kg of compound 24.

From the FIG. 18a showing food intake over a period of 48 hours, it is seen that compound 24 is effectively reducing food intake. This is also illustrated in FIG. 18b, showing accumulated food intake in the periods 0-24 hours, 24-48 hours, and 0-48 hours, respectively. Food intake was compared using two-sided Student's t-test, alpha=0.05.

Example 25
N-alpha-[4-(19-Carboxynonadecanoylamino)butyryl]-Arg-[Arg17]-pramlintide
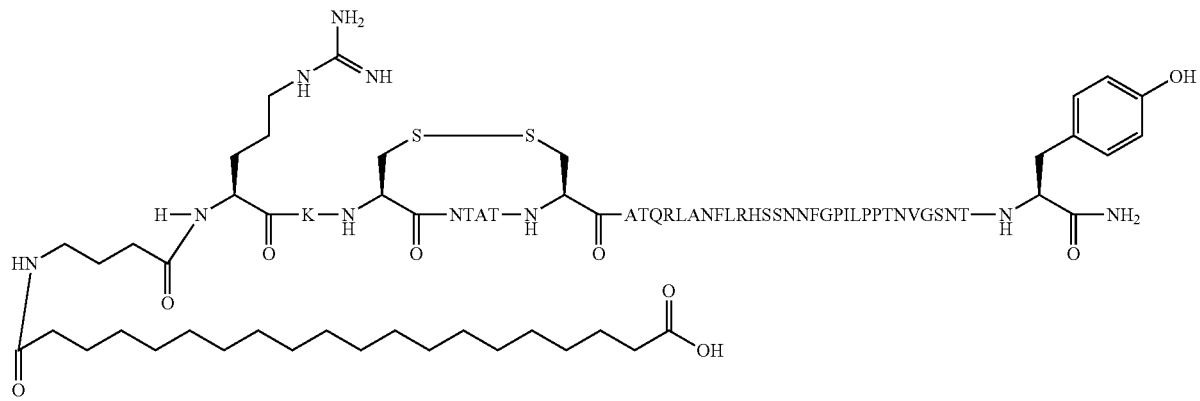
Example 26
N-alpha-[(S)-4-Carboxy-4-(17-carboxyheptadecanoylamino)butyryl]-Arg-[Arg17]-pramlintide
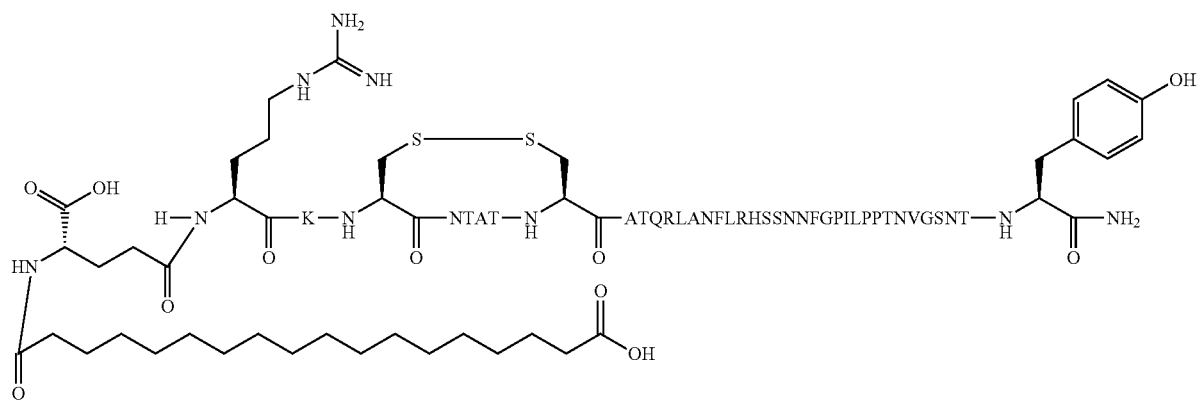
Example 27
N-alpha-[(S)-4-Carboxy-4-(19-carboxynonadecanoylamino)butyryl]-His-[His1,His17]-pramlintide
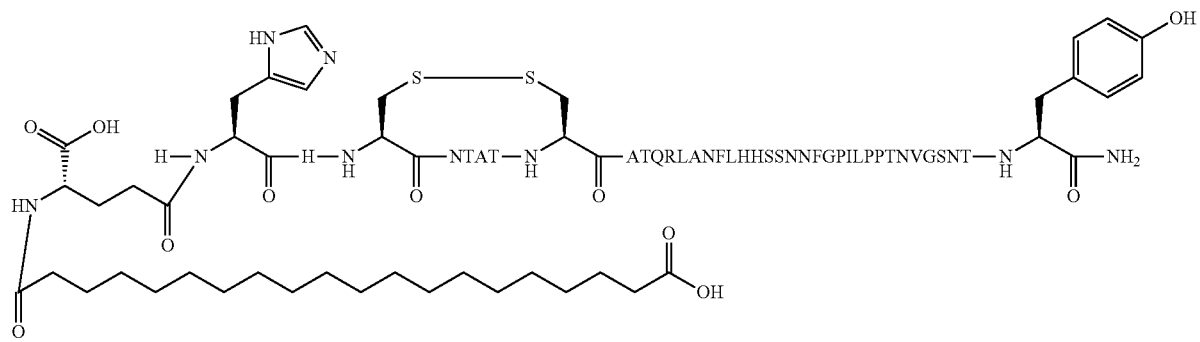

Figure 19A:
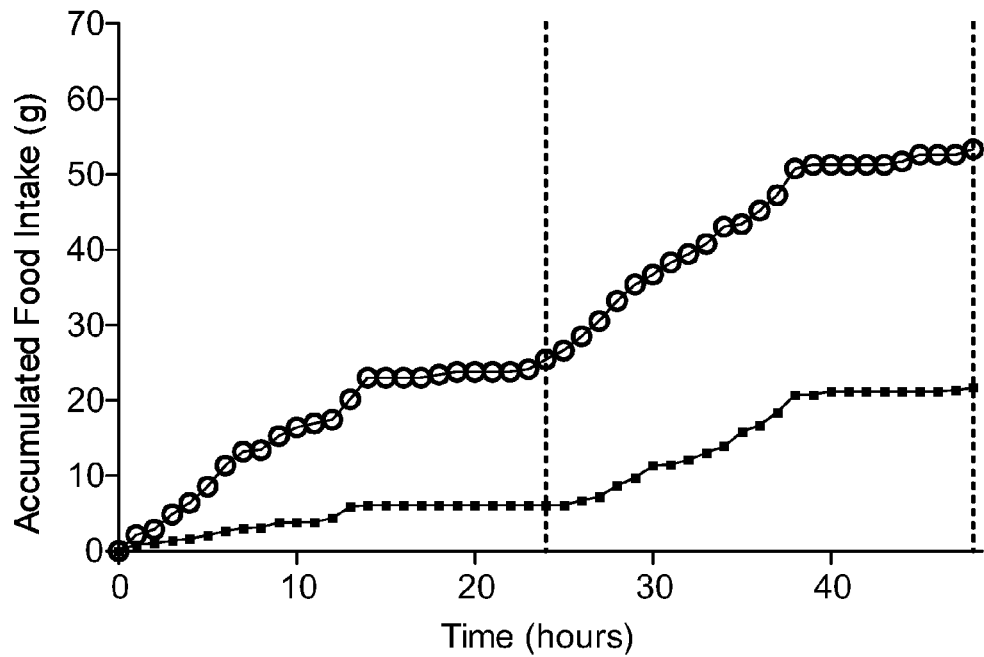
FIG. 19a shows food intake during 48 hours according to Pharmacological Assay (I). Data=mean. n=5-7. Open circle: vehicle. Black squares: 30 nmol/kg of compound 27.
Figure 19B:
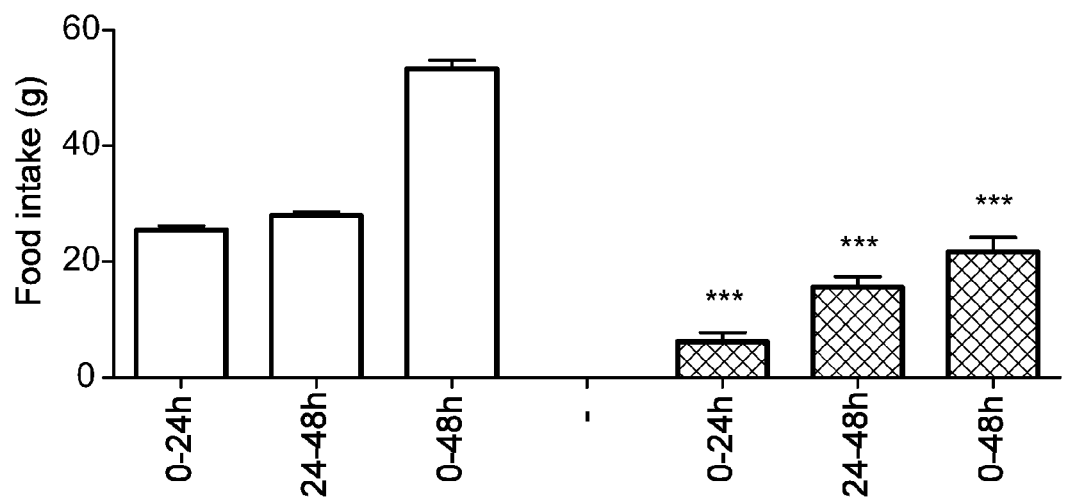
FIG. 19b shows accumulated food intake according to Pharmacological Assay (I) in the first 24 hours, the period from 24 to 48 hours, and the whole 48 hour period. Data=mean. n=5-7. Grey bars: vehicle. Black bars: 30 nmol/kg of compound 27.

From the FIG. 19a showing food intake over a period of 48 hours, it is seen that compound 27 is effectively reducing food intake. This is also illustrated in FIG. 19b, showing accumulated food intake in the periods 0-24 hours, 24-48 hours, and 0-48 hours, respectively. Food intake was compared using two-sided Student's t-test, alpha=0.05.

Example 28

N-alpha-[(S)-4-Carboxy-4-(19-carboxynonadecanoylamino)butyryl]-His-[His17]-pramlintide

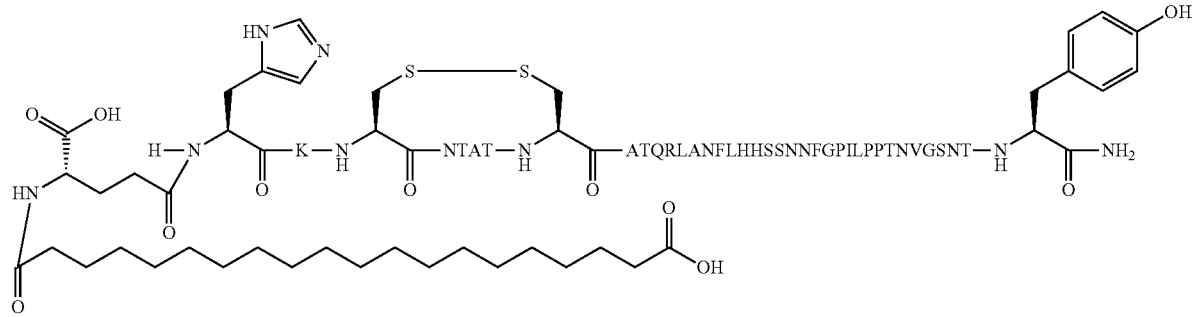

Figure 20A:
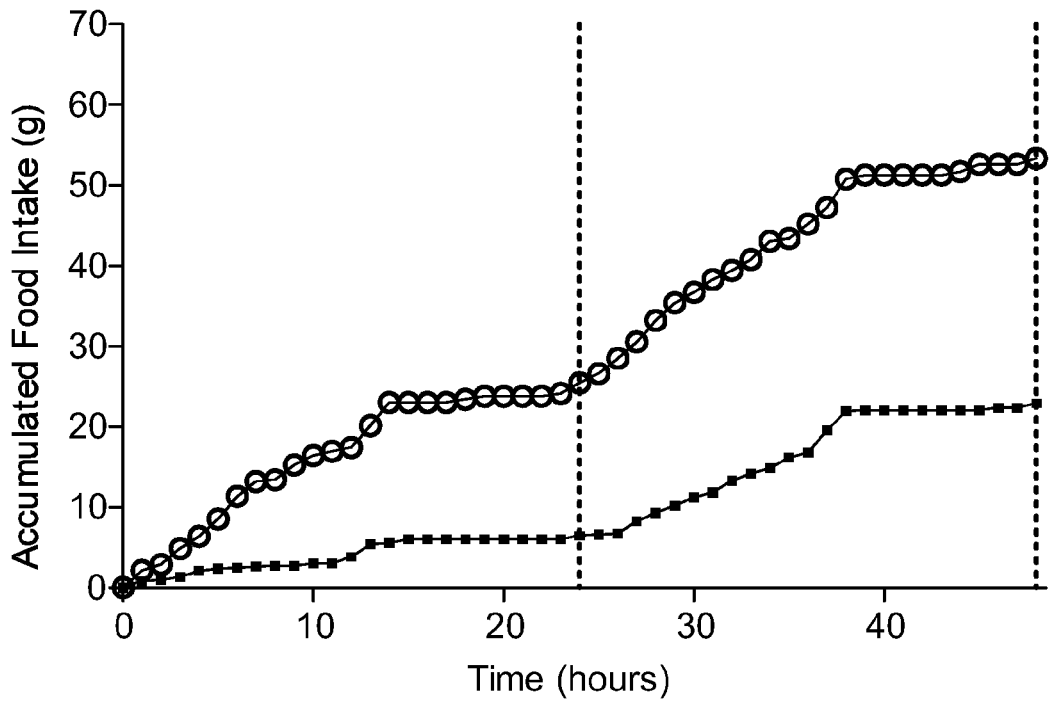
FIG. 20a shows food intake during 48 hours according to Pharmacological Assay (I). Data=mean. n=5-7. Open circle: vehicle. Black squares: 30 nmol/kg of compound 28.
Figure 20B:
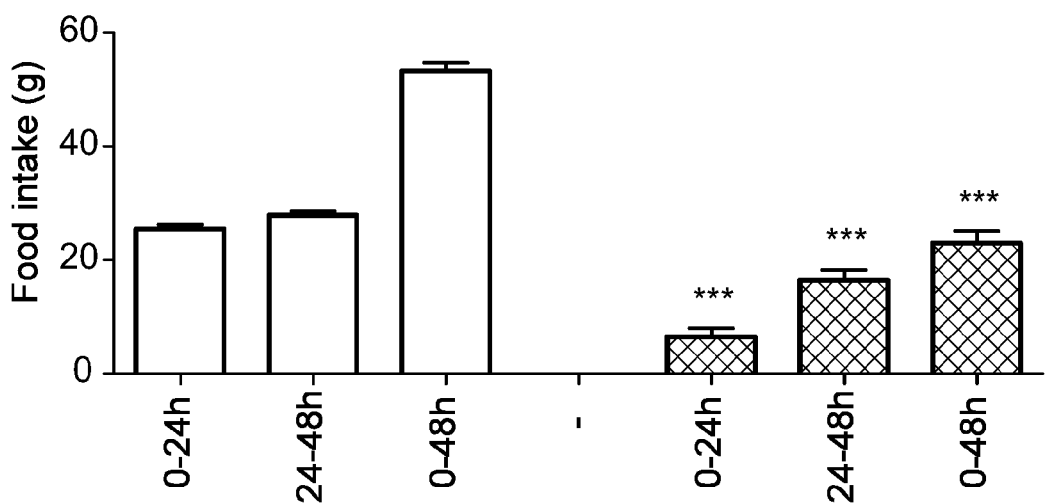
FIG. 20b shows accumulated food intake according to Pharmacological Assay (I) in the first 24 hours, the period from 24 to 48 hours, and the whole 48 hour period. Data=mean. n=5-7. Grey bars: vehicle. Black bars: 30 nmol/kg of compound 28.

From the FIG. 20a showing food intake over a period of 48 hours, it is seen that compound 28 is effectively reducing food intake. This is also illustrated in FIG. 20b, showing accumulated food intake in the periods 0-24 hours, 24-48 hours, and 0-48 hours, respectively. Food intake was compared using two-sided Student's t-test, alpha=0.05.

Example 29

N-alpha-[(S)-4-Carboxy-4-(19-carboxynonadecanoylamino)butyryl]-[His1,His17]-pramlintide

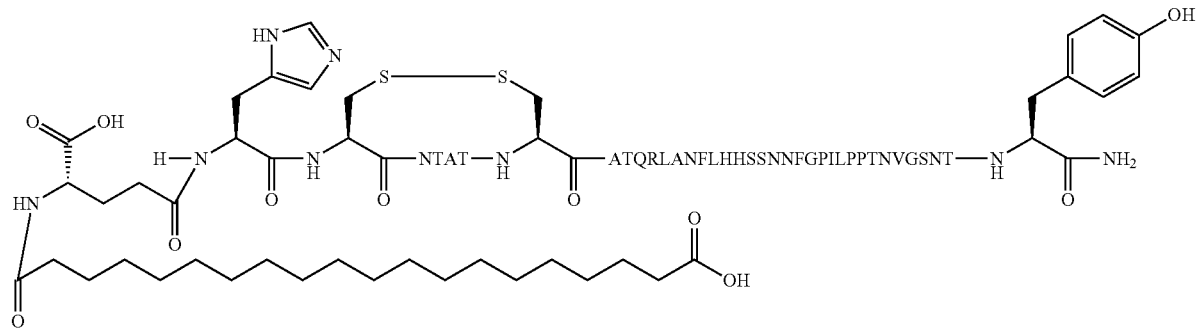

Figure 21A:
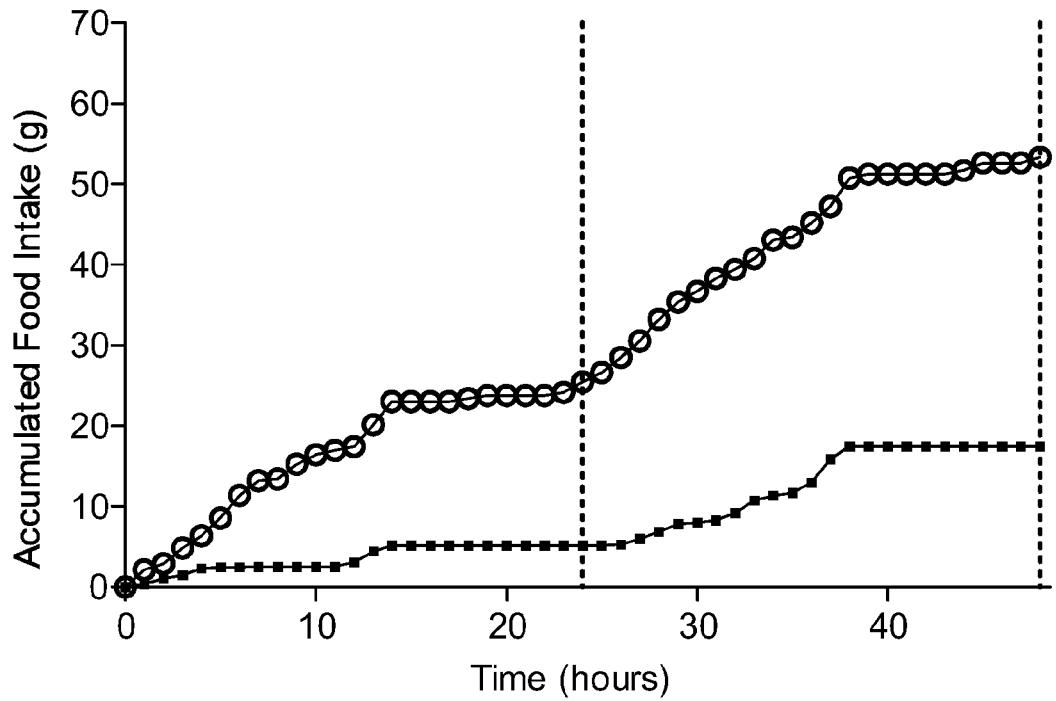
FIG. 21a shows food intake during 48 hours according to Pharmacological Assay (I). Data=mean. n=5-7. Open circle: vehicle. Black squares: 30 nmol/kg of compound 29.
Figure 21B:
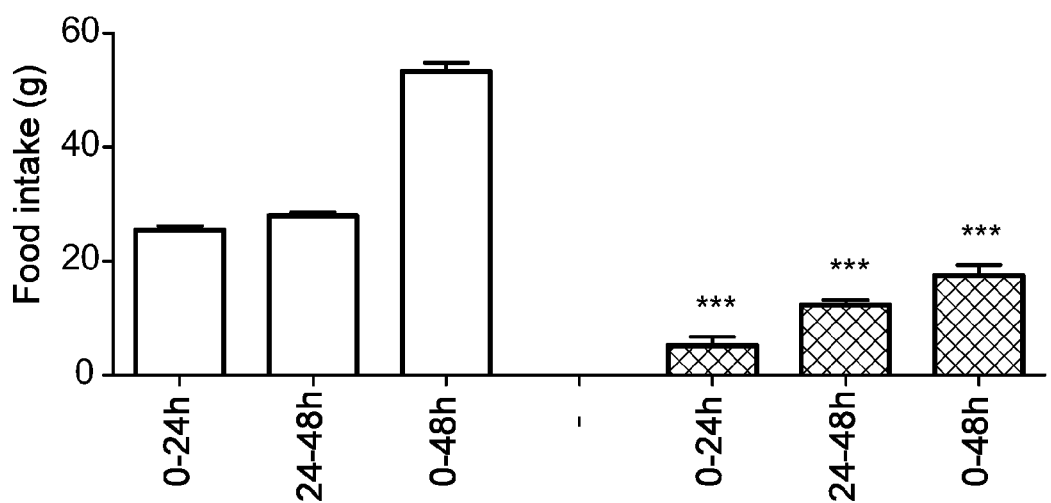
FIG. 21b shows accumulated food intake according to Pharmacological Assay (I) in the first 24 hours, the period from 24 to 48 hours, and the whole 48 hour period. Data=mean. n=5-7. Grey bars: vehicle. Black bars: 30 nmol/kg of compound 29.

From the FIG. 21a showing food intake over a period of 48 hours, it is seen that compound 29 is effectively reducing food intake. This is also illustrated in FIG. 21b, showing accumulated food intake in the periods 0-24 hours, 24-48 hours, and 0-48 hours, respectively. Food intake was compared using two-sided Student's t-test, alpha=0.05.

Example 30

N-alpha-[4-(19-Carboxynonadecanoylamino)butyryl]-[His17]-pramlintide (2-37)

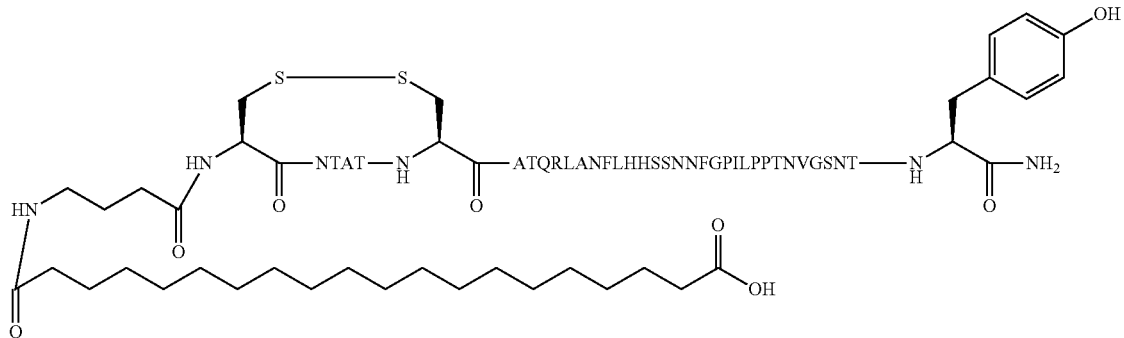

Figure 22A:
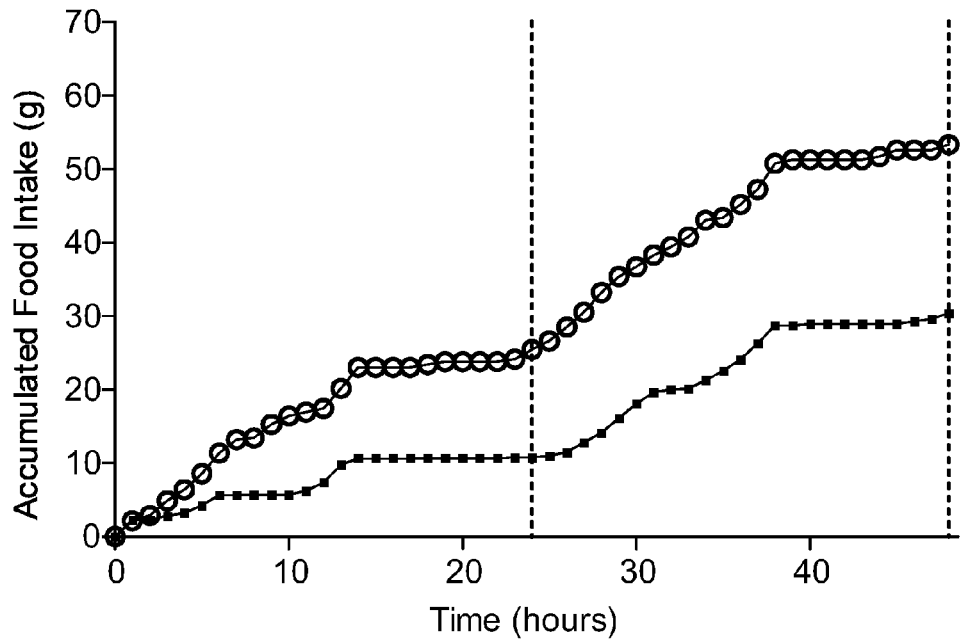
FIG. 22a shows food intake during 48 hours according to Pharmacological Assay (I). Data=mean. n=5-7. Open circle: vehicle. Black squares: 30 nmol/kg of compound 30.
Figure 22B:
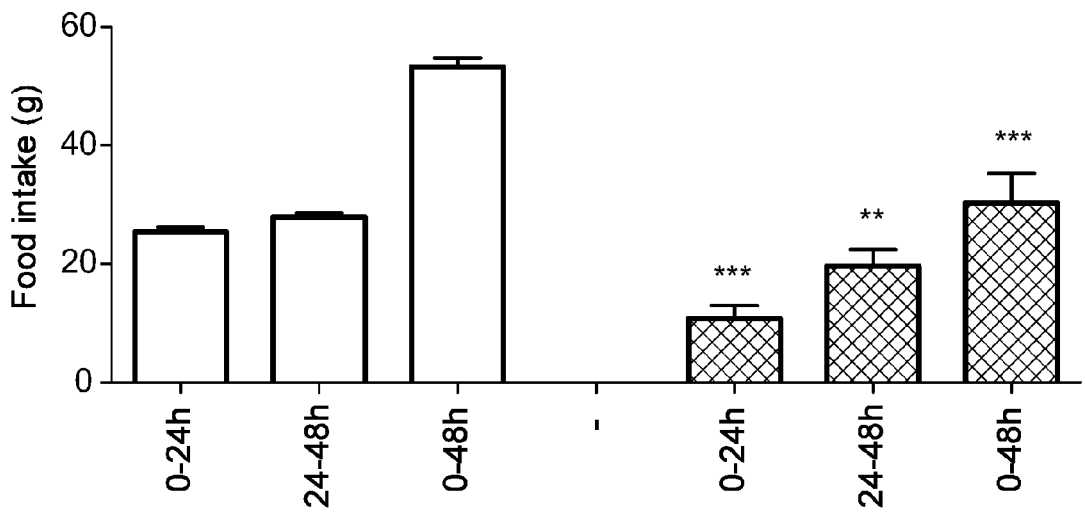
FIG. 22b shows accumulated food intake according to Pharmacological Assay (I) in the first 24 hours, the period from 24 to 48 hours, and the whole 48 hour period. Data=mean. n=5-7. Grey bars: vehicle. Black bars: 30 nmol/kg of compound 30.

From the FIG. 22a showing food intake over a period of 48 hours, it is seen that compound 30 is effectively reducing food intake. This is also illustrated in FIG. 22b, showing accumulated food intake in the periods 0-24 hours, 24-48 hours, and 0-48 hours, respectively. Food intake was compared using two-sided Student's t-test, alpha=0.05.

Example 31

N-alpha-[(S)-4-Carboxy-4-(17-carboxyheptadecanoylamino)butyryl]-His-[His1,His17]-pramlintide

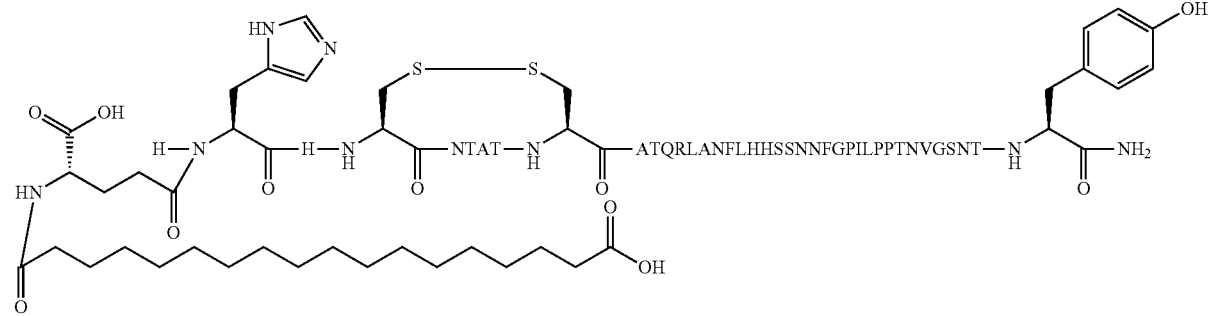

Figure 23A:
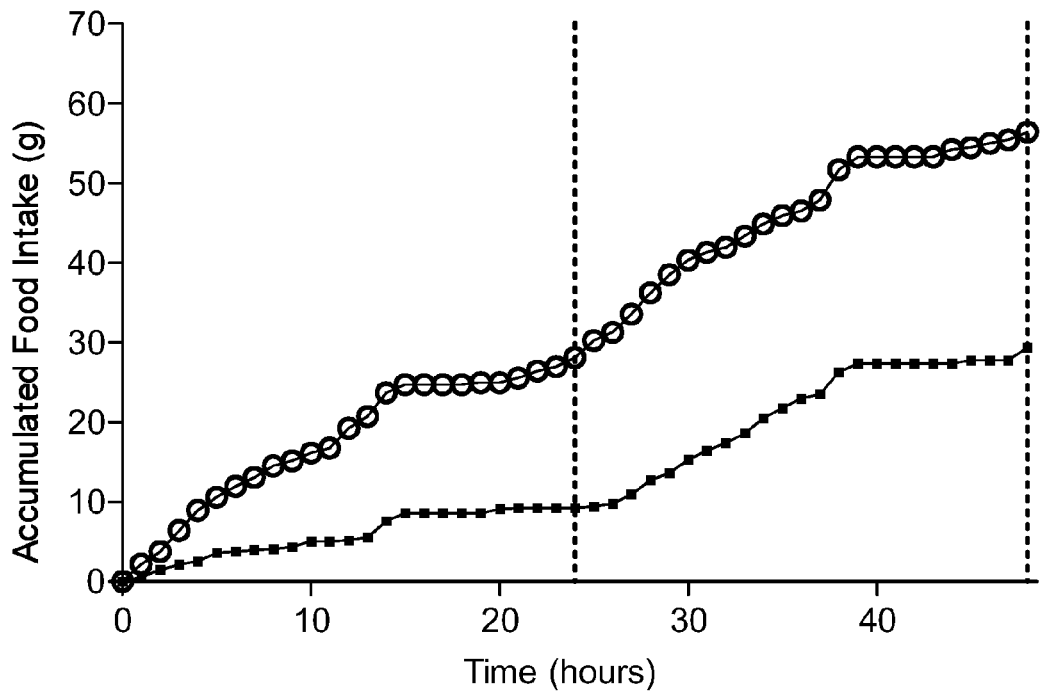
FIG. 23a shows food intake during 48 hours according to Pharmacological Assay (I). Data=mean. n=5-7. Open circle: vehicle. Black squares: 30 nmol/kg of compound 31.
Figure 23B:
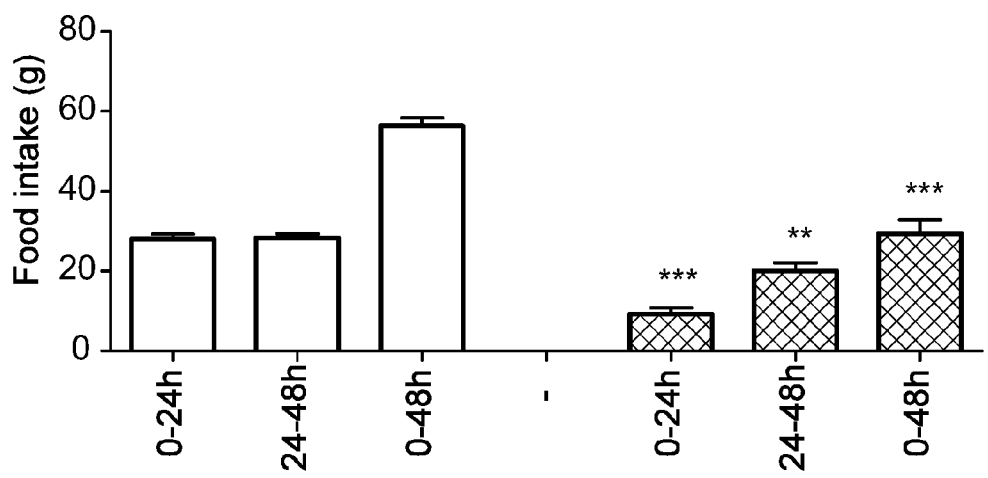
FIG. 23b shows accumulated food intake according to Pharmacological Assay (I) in the first 24 hours, the period from 24 to 48 hours, and the whole 48 hour period. Data=mean. n=5-7. Grey bars: vehicle. Black bars: 30 nmol/kg of compound 31.

From the FIG. 23a showing food intake over a period of 48 hours, it is seen that compound 31 is effectively reducing food intake. This is also illustrated in FIG. 23b, showing accumulated food intake in the periods 0-24 hours, 24-48 hours, and 0-48 hours, respectively. Food intake was compared using two-sided Student's t-test, alpha=0.05.

Example 32

N-alpha-[(S)-4-Carboxy-4-(17-carboxyheptadecanoylamino)butyryl]-[His1,His17]-pramlintide

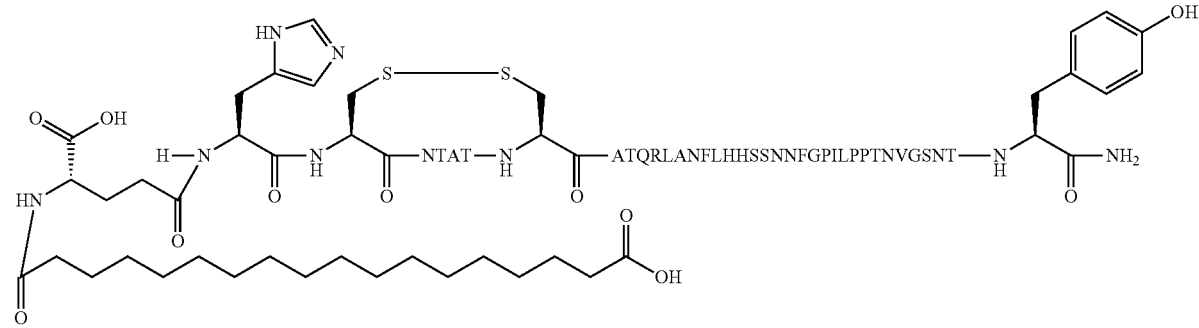

Figure 24A:
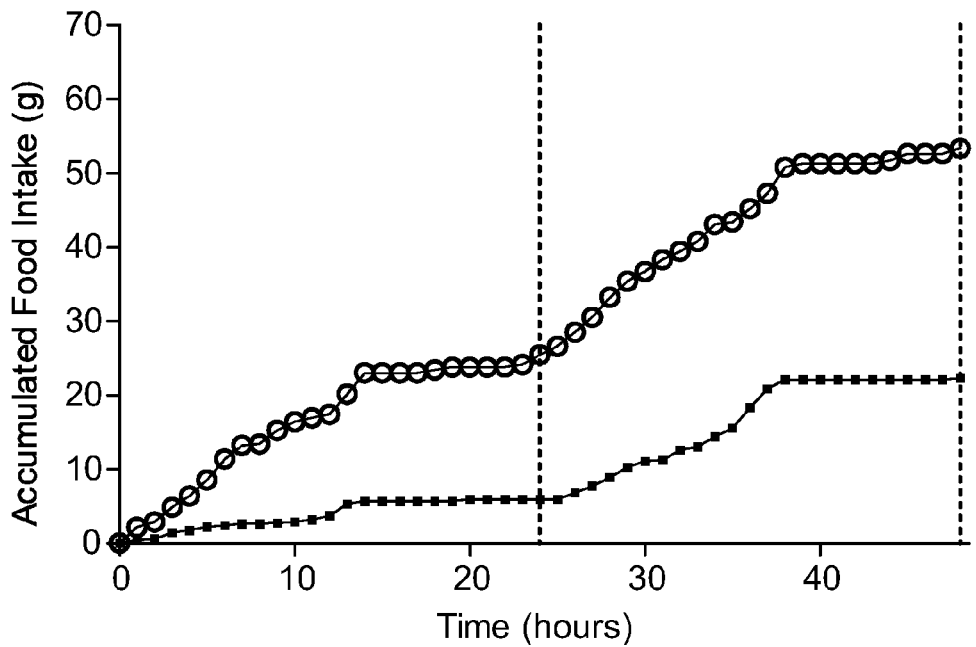
FIG. 24a shows food intake during 48 hours according to Pharmacological Assay (I). Data=mean. n=5-7. Open circle: vehicle. Black squares: 30 nmol/kg of compound 32.
Figure 24B:
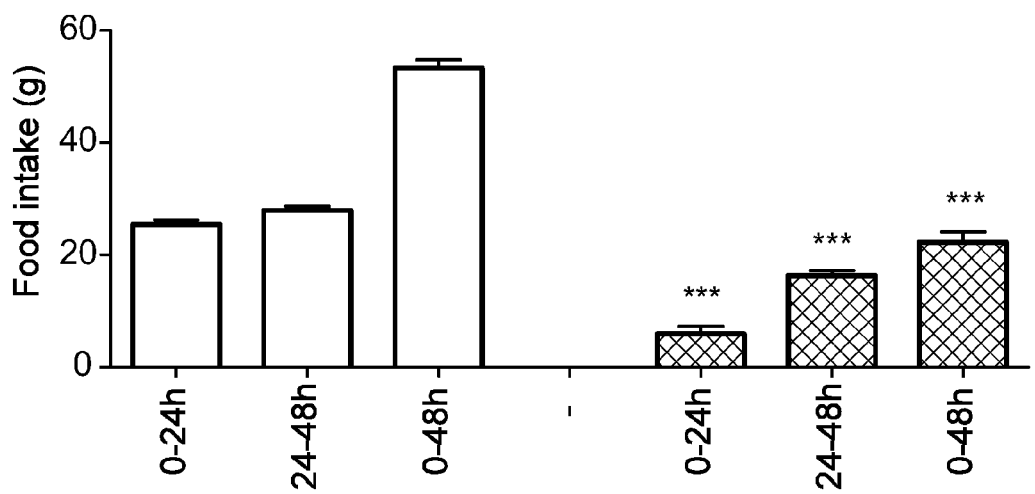
FIG. 24b shows accumulated food intake according to Pharmacological Assay (I) in the first 24 hours, the period from 24 to 48 hours, and the whole 48 hour period. Data=mean. n=5-7. Grey bars: vehicle. Black bars: 30 nmol/kg of compound 32.

From the FIG. 24a showing food intake over a period of 48 hours, it is seen that compound 32 is effectively reducing food intake. This is also illustrated in FIG. 24b, showing accumulated food intake in the periods 0-24 hours, 24-48 hours, and 0-48 hours, respectively. Food intake was compared using two-sided Student's t-test, alpha=0.05.

Example 33

N-alpha-[4-Carboxy-4-({4-[(19-carboxynonade-canoylamino)methyl]transcyclohexanecarbonyl}amino)butyryl]-[His1,His17]-pramlintide

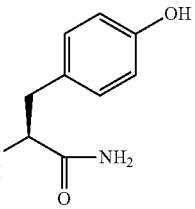
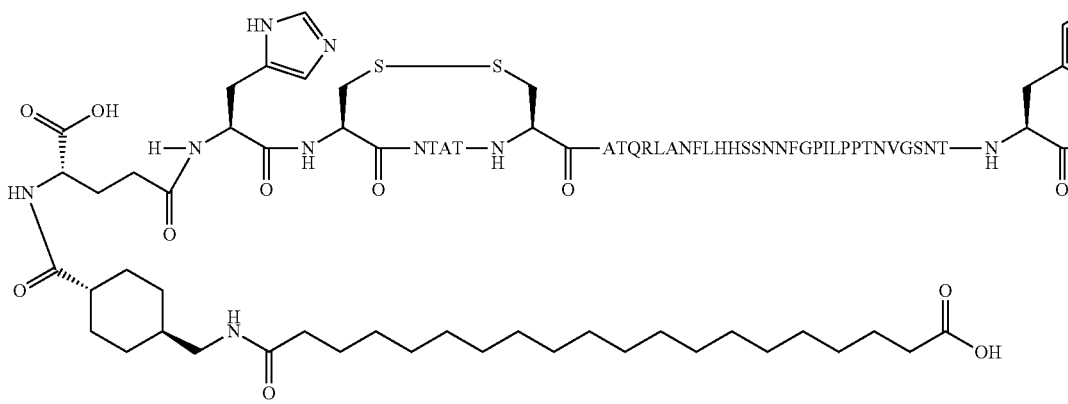

Figure 25A:
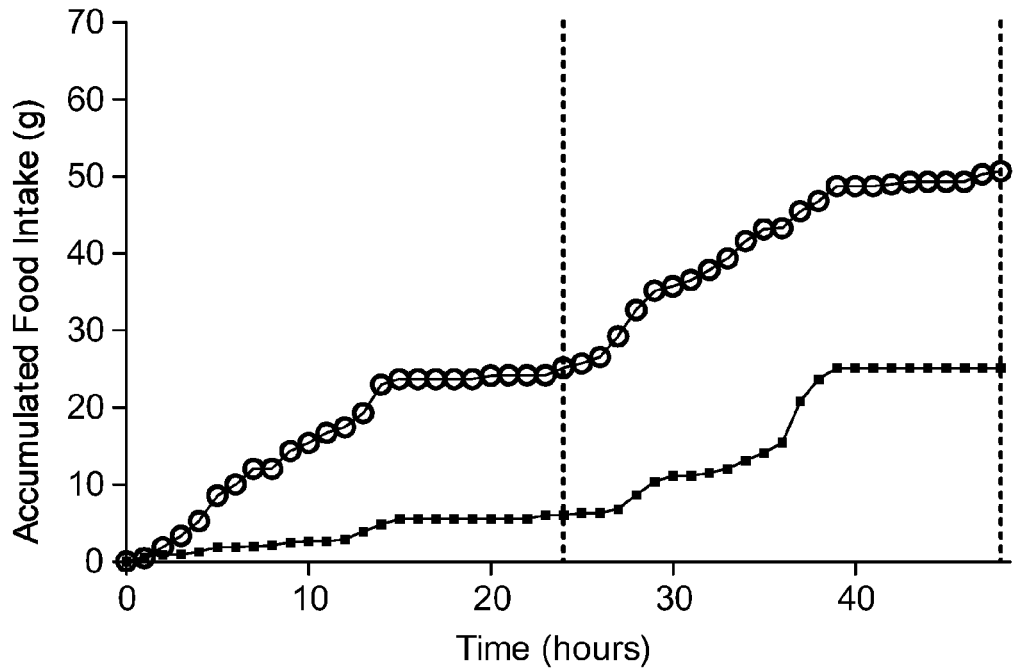
FIG. 25a shows food intake during 48 hours according to Pharmacological Assay (I). Data=mean. n=5-7. Open circle: vehicle. Black squares: 30 nmol/kg of compound 33.
Figure 25B:
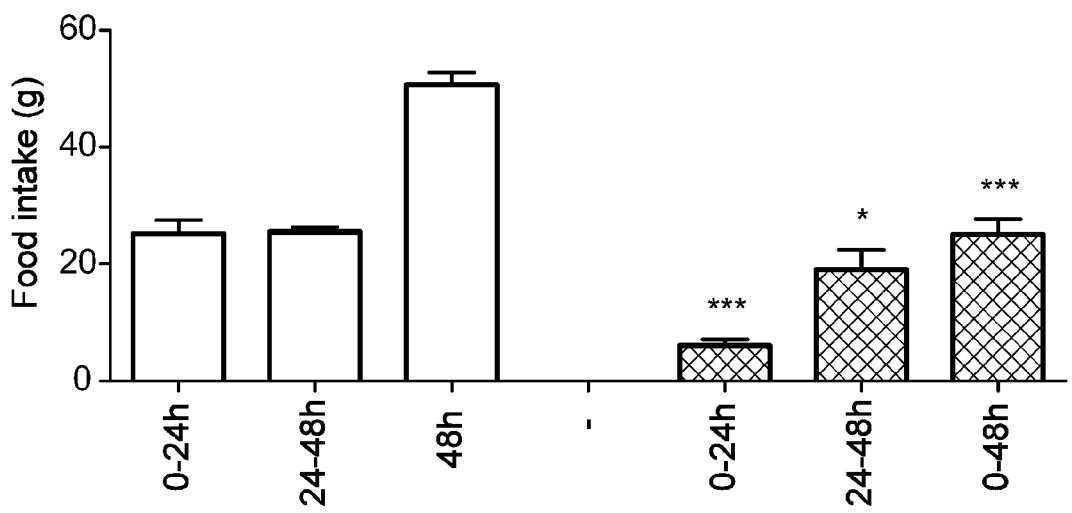
FIG. 25b shows accumulated food intake according to Pharmacological Assay (I) in the first 24 hours, the period from 24 to 48 hours, and the whole 48 hour period. Data=mean. n=5-7. Grey bars: vehicle. Black bars: 30 nmol/kg of compound 33.

From the FIG. 25a showing food intake over a period of 48 hours, it is seen that compound 33 is effectively reducing food intake. This is also illustrated in FIG. 25b, showing accumulated food intake in the periods 0-24 hours, 24-48 hours, and 0-48 hours, respectively. Food intake was compared using two-sided Student's t-test, alpha=0.05.

Example 34

N-alpha-[2-(2-{2-[4-(S)-Carboxy-4-(19-carbox-ynonadecanoylamino)butyrylamino]ethoxy}ethoxy)acetyl]-His-[His1,Arg17]-pramlintide

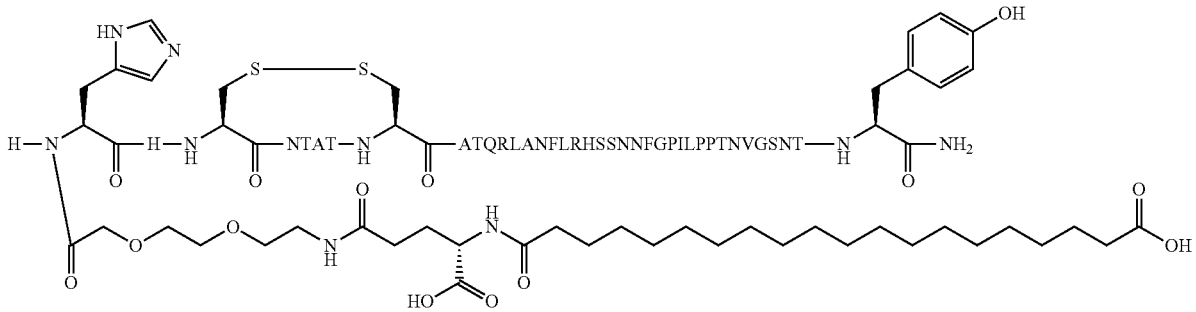

Example 35

N-alpha-[(S)-4-Carboxy-4-(19-carboxynonade-canoylamino)butyryl]-His-[His1,Arg17]-pramlintide

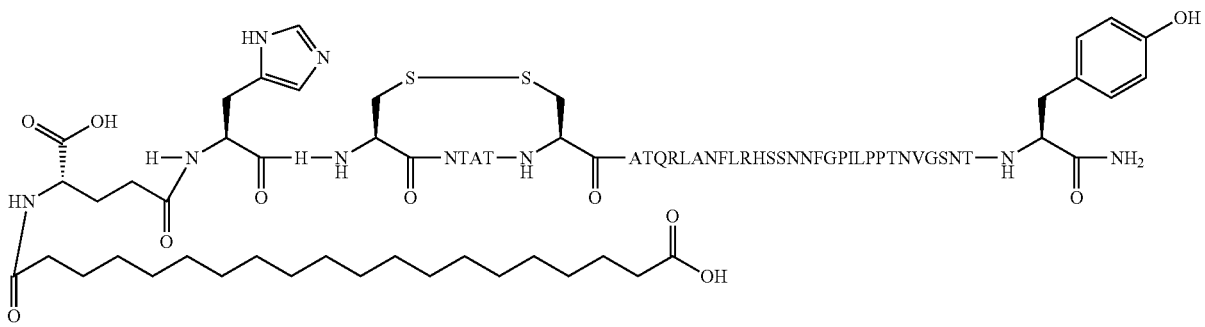

Example 36

N-alpha-[(S)-4-Carboxy-4-(19-carboxynonade-canoylamino)butyryl]-[His1,Arg17]-pramlintide

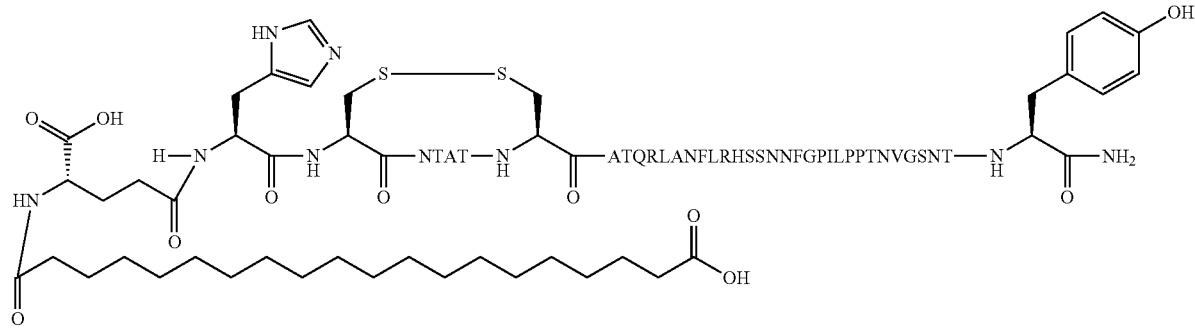

Example 37

N-alpha-[2-(2-{2-[4-(S)-Carboxy-4-(19-carbox-ynonadecanoylamino)butyrylamino]ethoxy}ethoxy)acetyl]-[His1,His17]-pramlintide

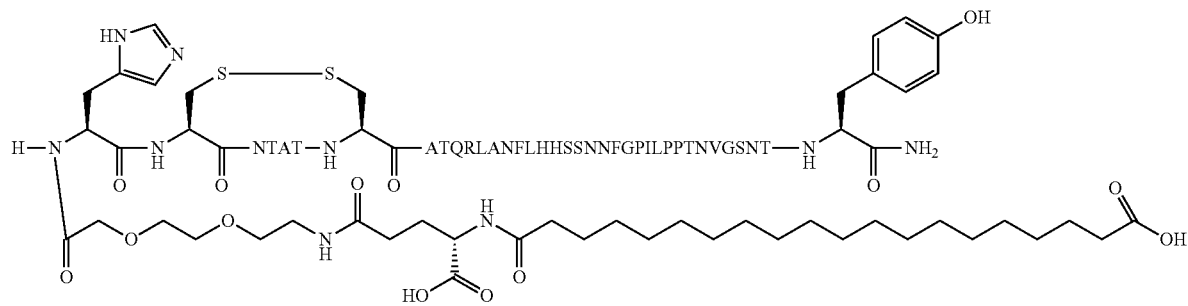

Figure 26A:
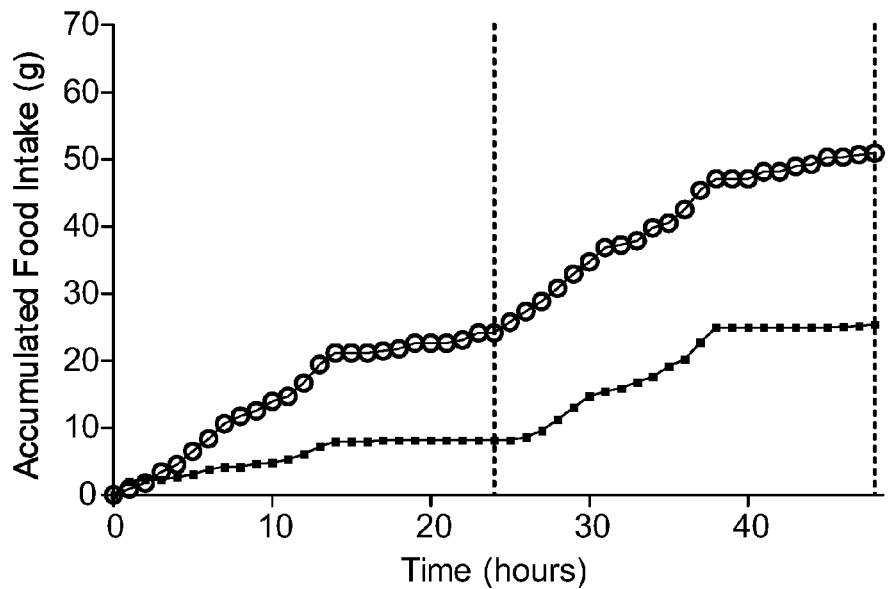
FIG. 26a shows food intake during 48 hours according to Pharmacological Assay (I). Data=mean. n=5-7. Open circle: vehicle. Black squares: 30 nmol/kg of compound 37.
Figure 26B:
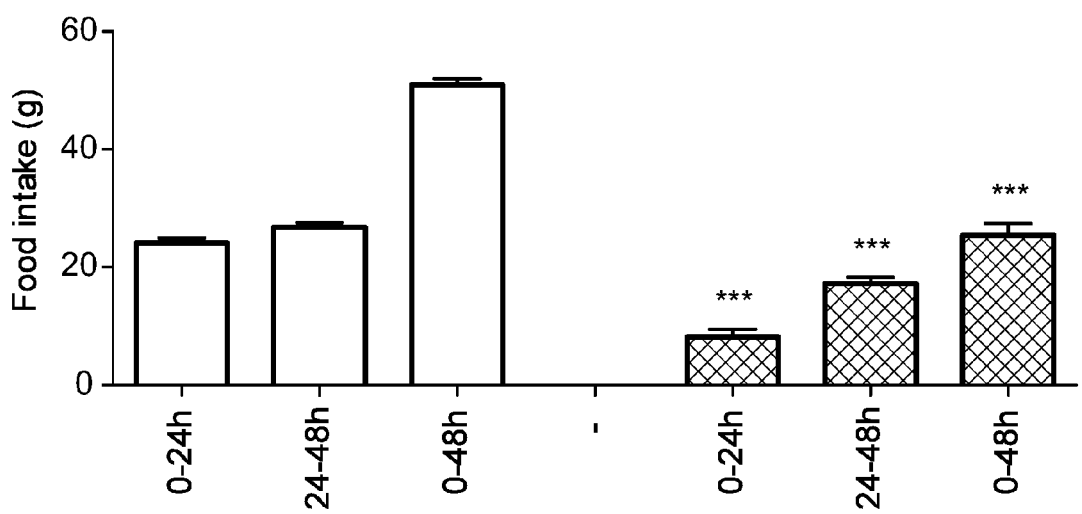
FIG. 26b shows accumulated food intake according to Pharmacological Assay (I) in the first 24 hours, the period from 24 to 48 hours, and the whole 48 hour period. Data=mean. n=5-7. Grey bars: vehicle. Black bars: 30 nmol/kg of compound 37.

From the FIG. 26a showing food intake over a period of 48 hours, it is seen that compound 37 is effectively reducing food intake. This is also illustrated in FIG. 26b, showing accumulated food intake in the periods 0-24 hours, 24-48 hours, and 0-48 hours, respectively. Food intake was compared using two-sided Student's t-test, alpha=0.05.

Example 38

N-alpha-[2-(2-{2-[4-(S)-Carboxy-4-(19-carbox-ynonadecanoylamino)butyrylamino]ethoxy}ethoxy)acetyl]-His-[His1,His17]-pramlintide

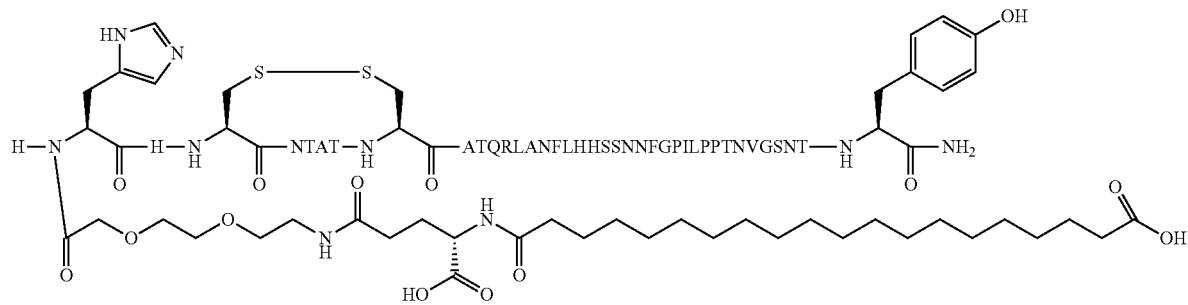

Figure 27A:
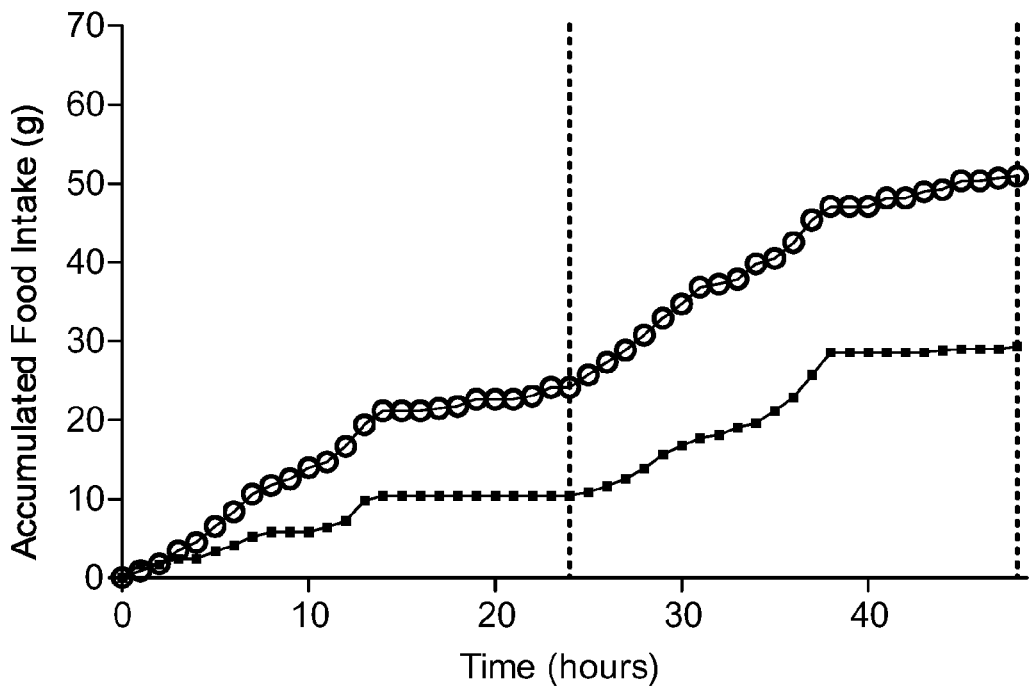
FIG. 27a shows food intake during 48 hours according to Pharmacological Assay (I). Data=mean. n=5-7. Open circle: vehicle. Black squares: 30 nmol/kg of compound 38.
Figure 27B:
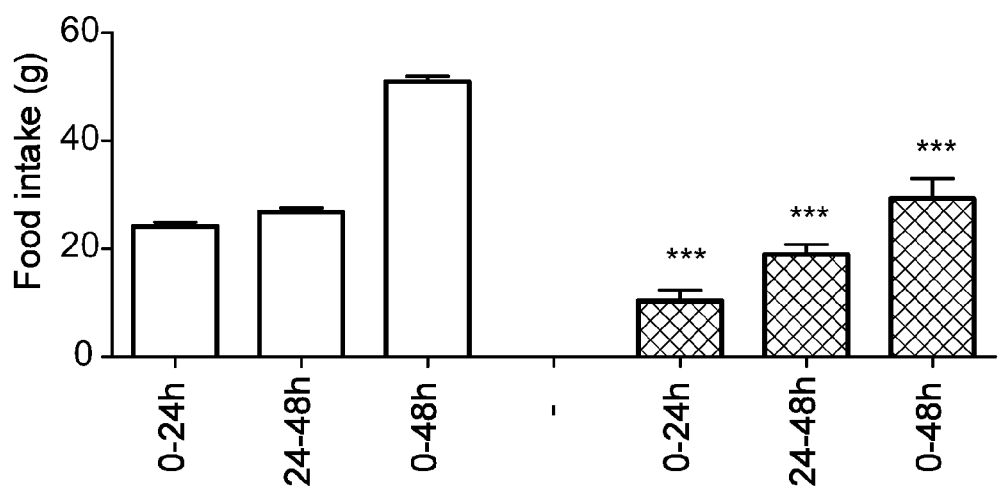
FIG. 27b shows accumulated food intake according to Pharmacological Assay (I) in the first 24 hours, the period from 24 to 48 hours, and the whole 48 hour period. Data=mean. n=5-7. Grey bars: vehicle. Black bars: 30 nmol/kg of compound 38.

From the FIG. 27*a* showing food intake over a period of 48 hours, it is seen that compound 38 is effectively reducing food intake. This is also illustrated in FIG. 27*b*, showing accumulated food intake in the periods 0-24 hours, 24-48 hours, and 0-48 hours, respectively. Food intake was compared using two-sided Student's t-test, alpha=0.05.

Example 39

N-alpha-[(S)-4-Carboxy-4-(19-carboxynonadecanoylamino)butyryl]-His-His-[His1,His17]-pramlintide

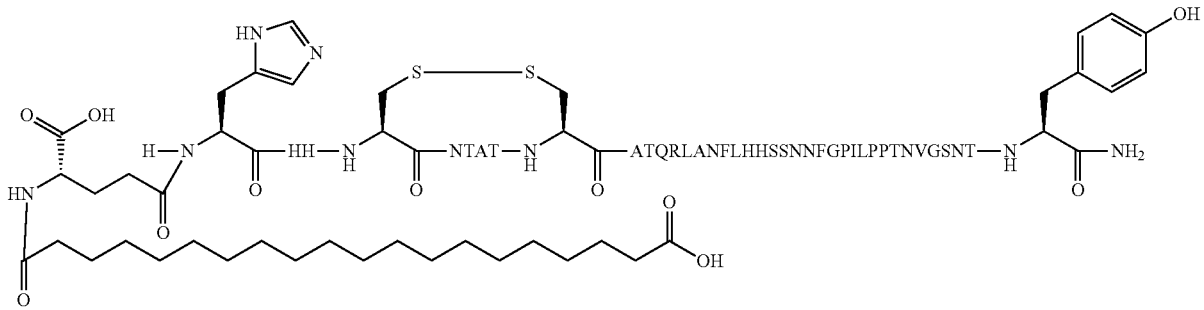

Figure 28A:
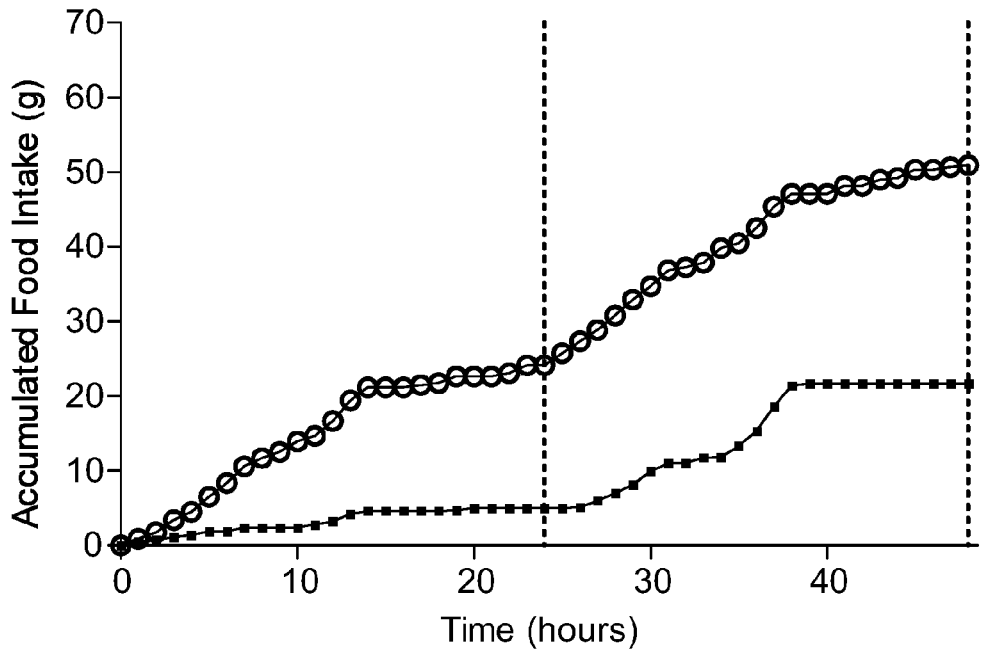
FIG. 28a shows food intake during 48 hours according to Pharmacological Assay (I). Data=mean. n=5-7. Open circle: vehicle. Black squares: 30 nmol/kg of compound 39.
Figure 28B:
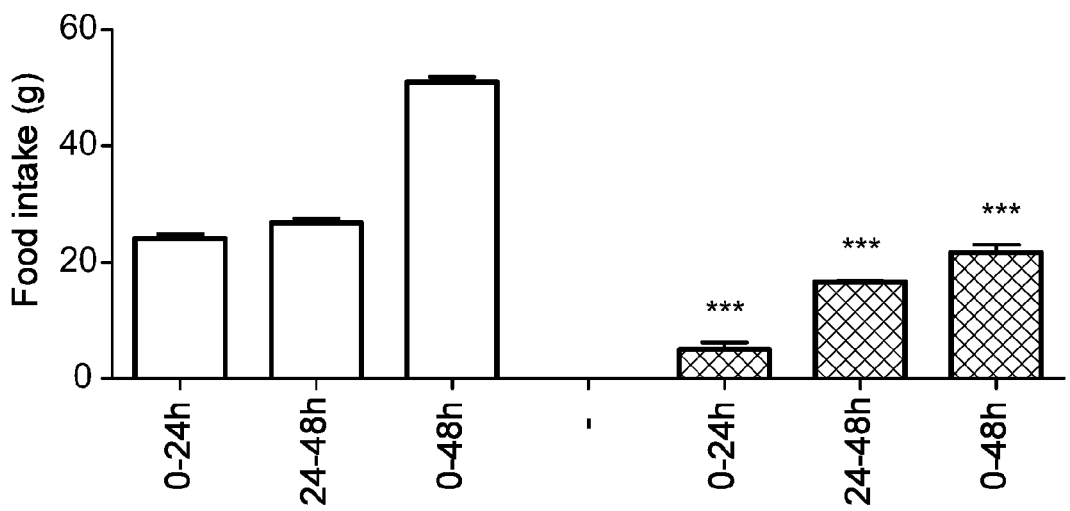
FIG. 28b shows accumulated food intake according to Pharmacological Assay (I) in the first 24 hours, the period from 24 to 48 hours, and the whole 48 hour period. Data=mean. n=5-7. Grey bars: vehicle. Black bars: 30 nmol/kg of compound 39.

From the FIG. 28*a* showing food intake over a period of 48 hours, it is seen that compound 39 is effectively reducing food intake. This is also illustrated in FIG. 28*b*, showing accumulated food intake in the periods 0-24 hours, 24-48 hours, and 0-48 hours, respectively. Food intake was compared using two-sided Student's t-test, alpha=0.05.

Example 40

N-alpha-[(S)-4-Carboxy-4-(19-carboxynonadecanoylamino)butyryl]-His-Arg-[His17]-pramlintide

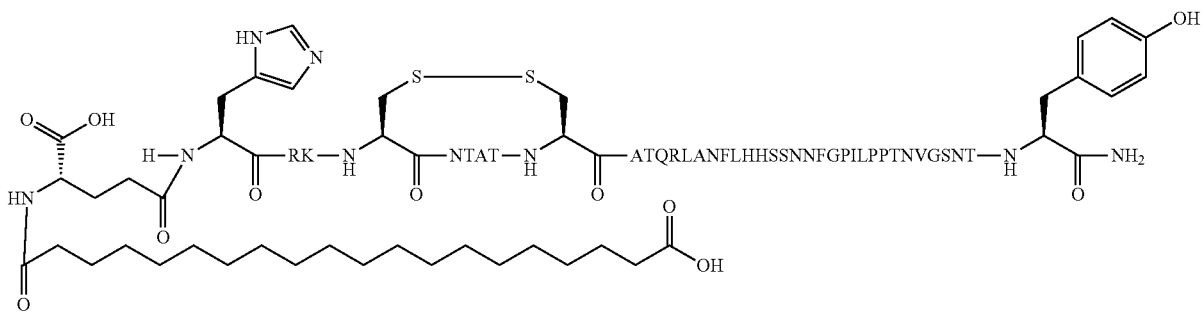

Figure 29A:
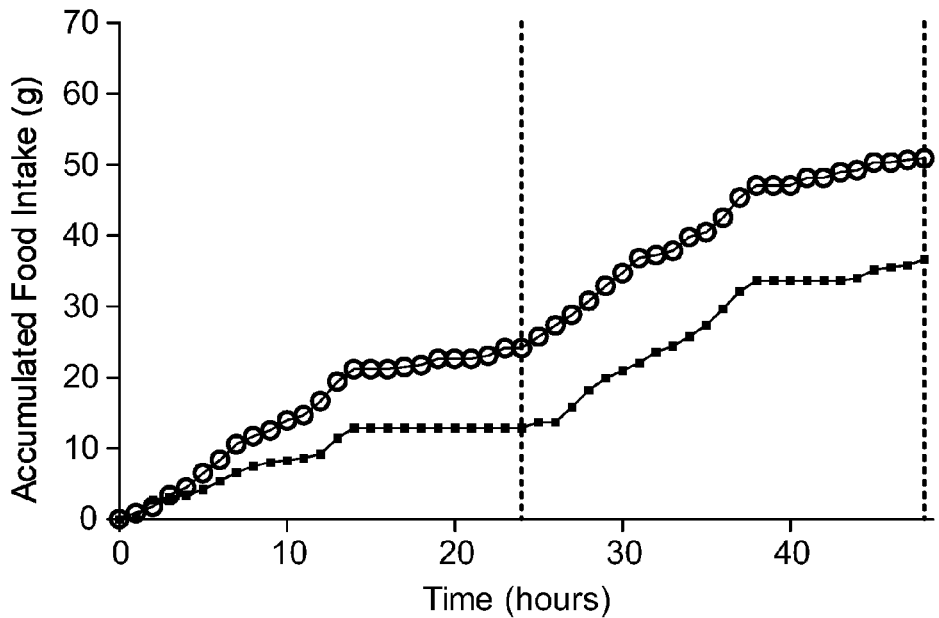
FIG. 29a shows food intake during 48 hours according to Pharmacological Assay (I). Data=mean. n=5-7. Open circle: vehicle. Black squares: 30 nmol/kg of compound 40.
Figure 29B:
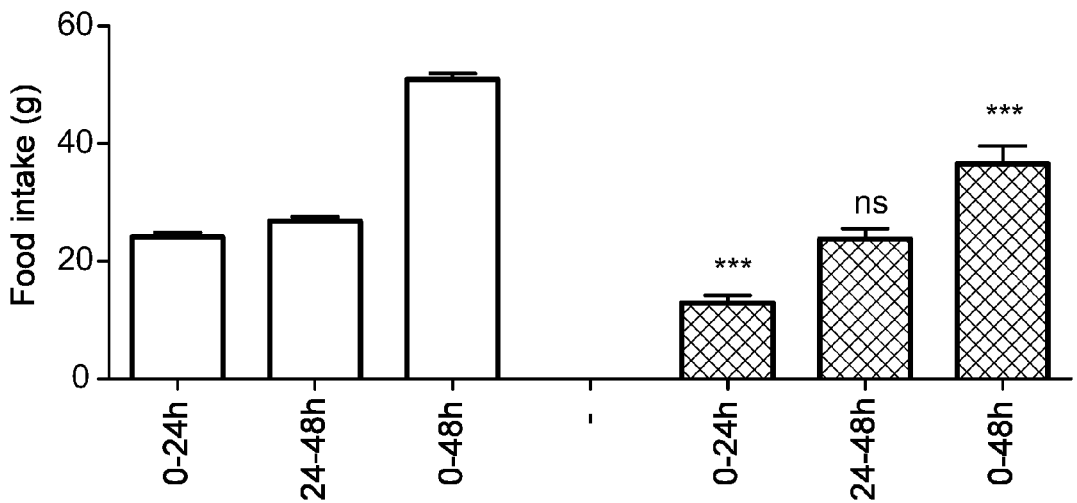
FIG. 29b shows accumulated food intake according to Pharmacological Assay (I) in the first 24 hours, the period from 24 to 48 hours, and the whole 48 hour period. Data=mean. n=5-7. Grey bars: vehicle. Black bars: 30 nmol/kg of compound 40.

From the FIG. 29*a* showing food intake over a period of 48 hours, it is seen that compound 40 is effectively reducing food intake. This is also illustrated in FIG. 29*b*, showing accumulated food intake in the periods 0-24 hours, 24-48 hours, and 0-48 hours, respectively. Food intake was compared using two-sided Student's t-test, alpha=0.05.

Example 41

N-alpha-[(S)-4-Carboxy-4-(19-carboxynonade-
canoylamino)butyryl]-Glu-Arg-[Glu1,His17,Gln21,
Ala25,Pro26,Ser28,Ser29]-pramlintide

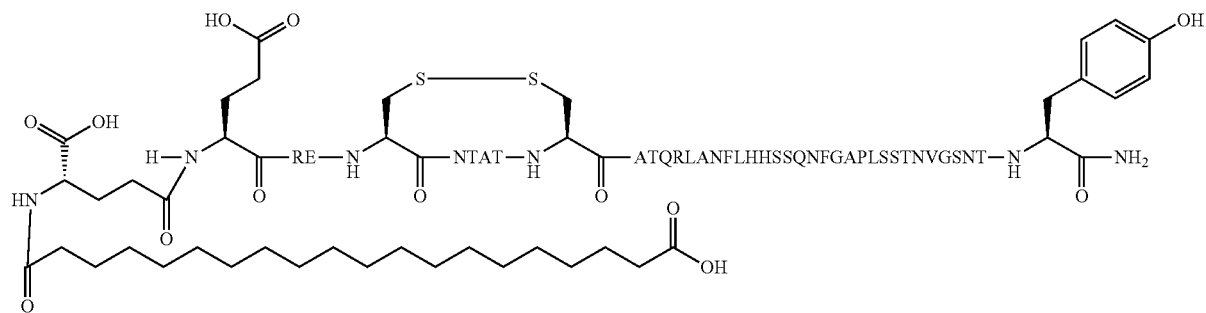

Figure 30A:
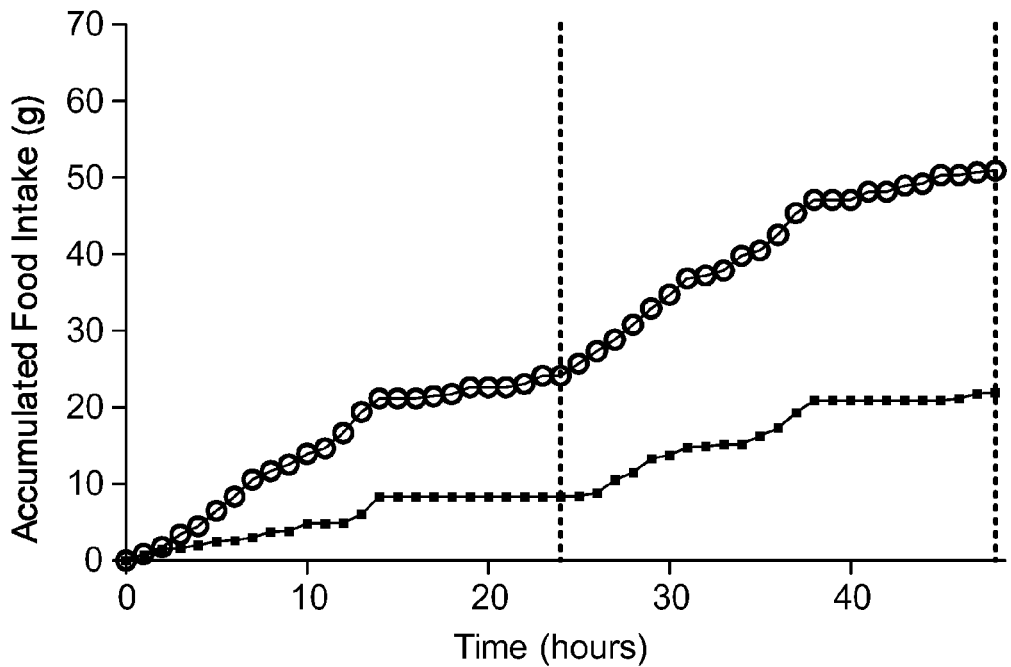
FIG. 30a shows food intake during 48 hours according to Pharmacological Assay (I). Data=mean. n=5-7. Open circle: vehicle. Black squares: 30 nmol/kg of compound 41.
Figure 30B:
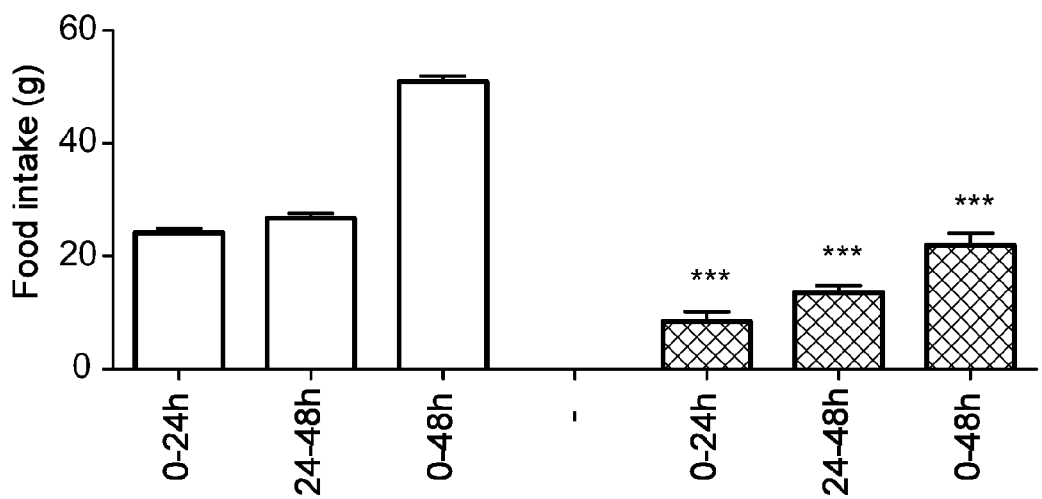
FIG. 30b shows accumulated food intake according to Pharmacological Assay (I) in the first 24 hours, the period from 24 to 48 hours, and the whole 48 hour period. Data=mean. n=5-7. Grey bars: vehicle. Black bars: 30 nmol/kg of compound 41.

From the FIG. 30a showing food intake over a period of 48 hours, it is seen that compound 41 is effectively reducing food intake. This is also illustrated in FIG. 30b, showing accumulated food intake in the periods 0-24 hours, 24-48 hours, and 0-48 hours, respectively. Food intake was compared using two-sided Student's t-test, alpha=0.05.

Example 42

N-alpha-[(S)-4-Carboxy-4-(19-carboxynonade-
canoylamino)butyryl]-Glu-Arg-[Glu1,Asp14,His17,
Ala25,Pro26,Ser28,Ser29]-pramlintide

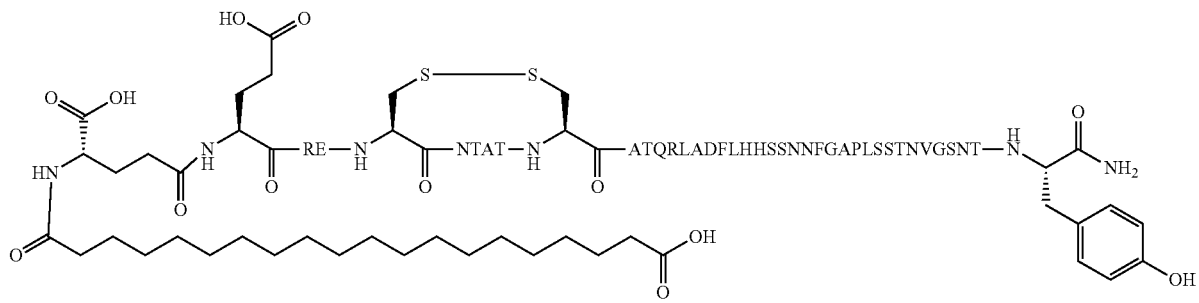

Example 43

N-alpha-[(S)-4-Carboxy-4-(19-carboxynonade-
canoylamino)butyryl]-[Asp14,His17]-pramlintide
(2-37)

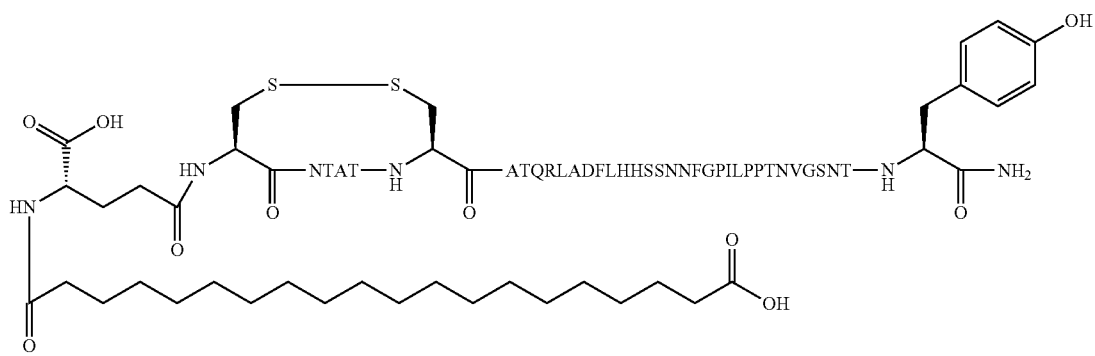

Example 44

N-alpha-[(S)-4-Carboxy-4-(19-carboxynonade-canoylamino)butyryl]-[His17,Glu24]-pramlintide (2-37)

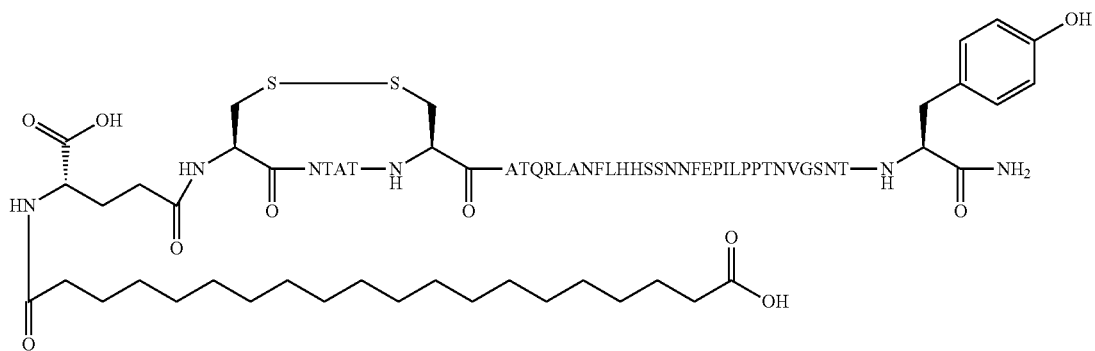

Example 45

N-alpha-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl][Arg1,His17]-pramlintide

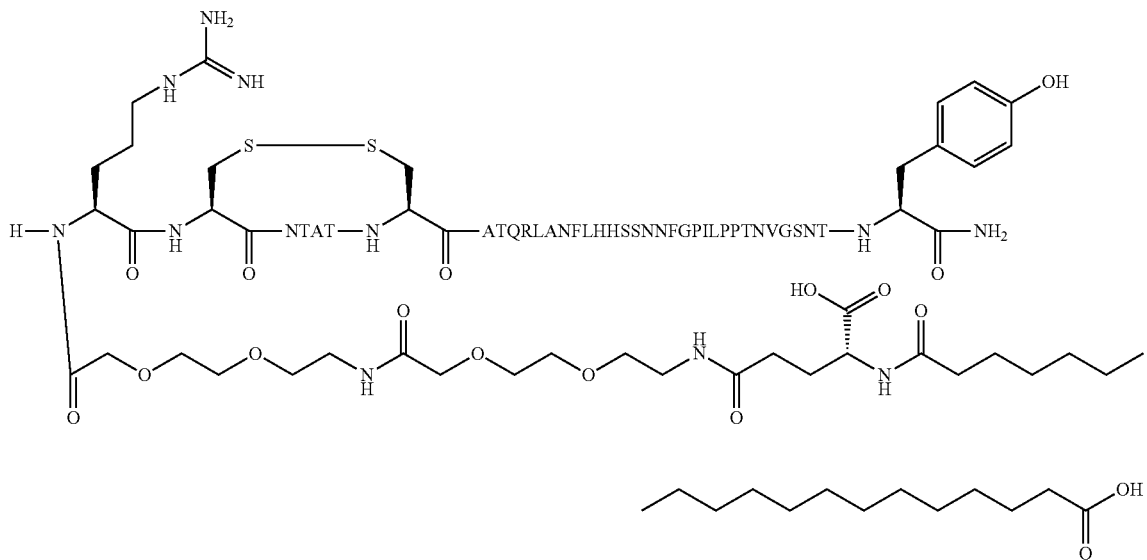

Figure 31A:
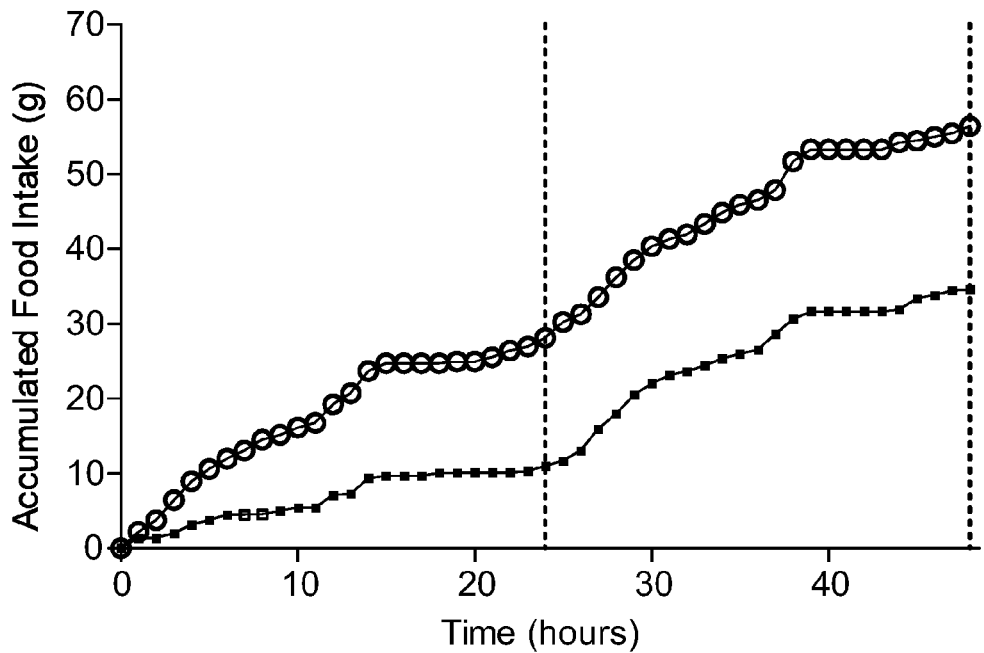
FIG. 31a shows food intake during 48 hours according to Pharmacological Assay (I). Data=mean. n=5-7. Open circle: vehicle. Black squares: 30 nmol/kg of compound 45.
Figure 31B:
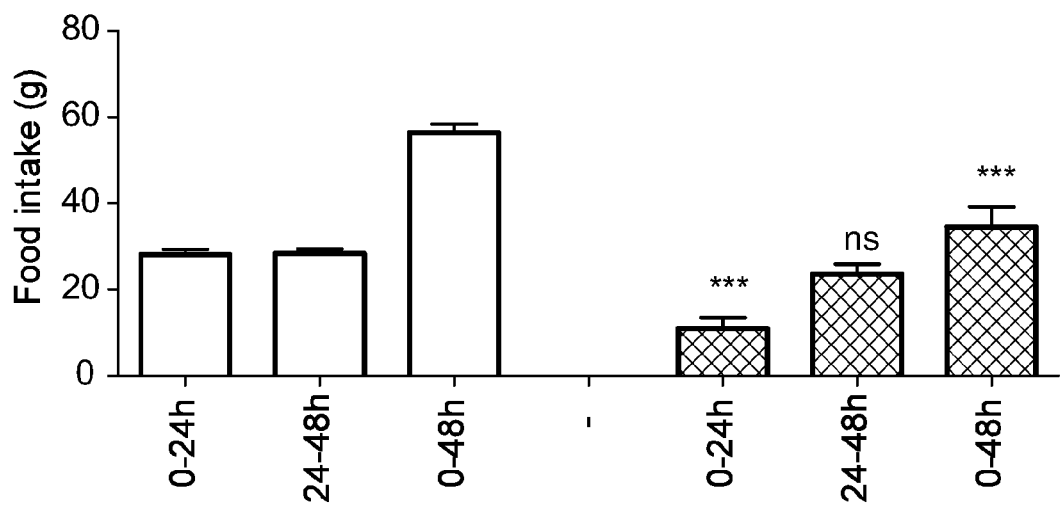
FIG. 31b shows accumulated food intake according to Pharmacological Assay (I) in the first 24 hours, the period from 24 to 48 hours, and the whole 48 hour period. Data=mean. n=5-7. Grey bars: vehicle. Black bars: 30 nmol/kg of compound 45.

From the FIG. 31a showing food intake over a period of 48 hours, it is seen that compound 45 is effectively reducing food intake. This is also illustrated in FIG. 31b, showing accumulated food intake in the periods 0-24 hours, 24-48 hours, and 0-48 hours, respectively. Food intake was compared using two-sided Student's t-test, alpha=0.05.

Example 46

N-alpha-[(S)-4-Carboxy-4-(19-carboxynonade-
canoylamino)butyryl]-Glu-Arg-[Glu1,Arg17,Ala25,
Pro26,Ser28,Ser29]-pramlintide

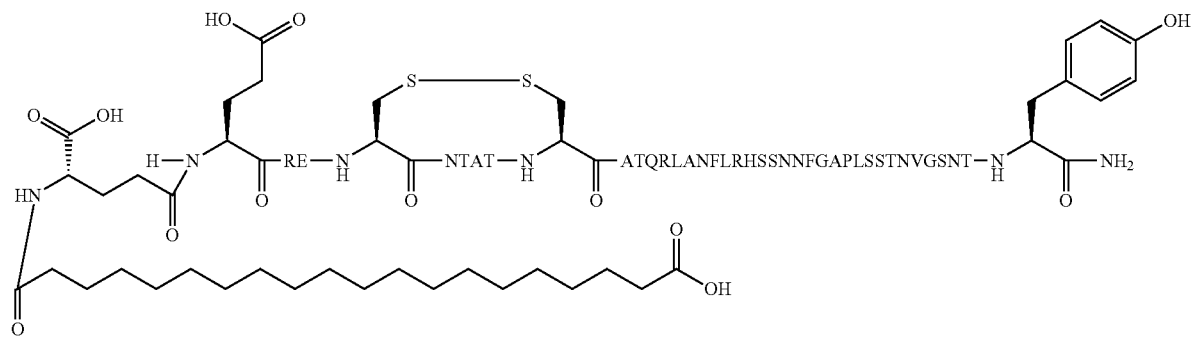

Example 47

N-alpha-[(S)-4-Carboxy-4-(19-carboxynonade-
canoylamino)butyryl]-His-[His1,His17,Arg18]-
pramlintide

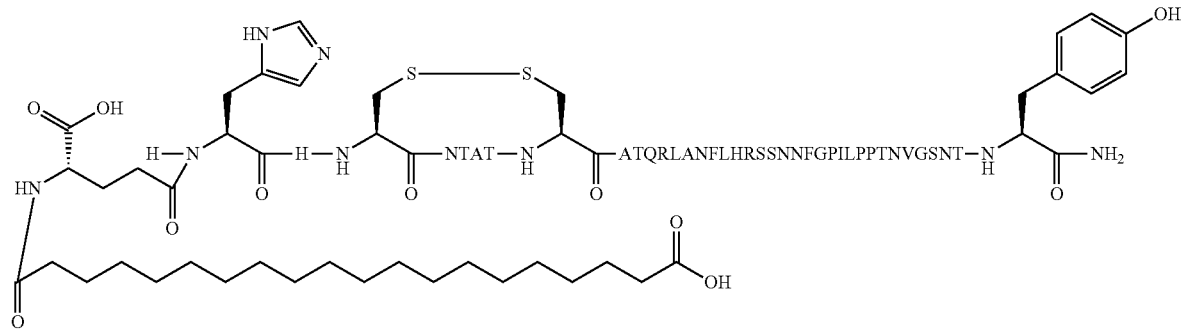

Figure 32A:
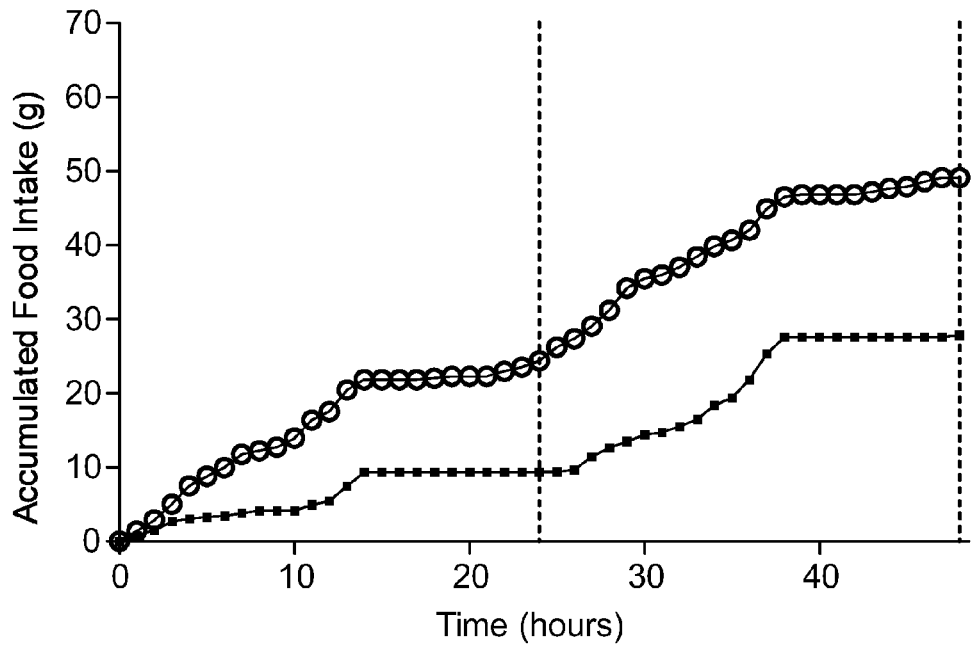
FIG. 32a shows food intake during 48 hours according to Pharmacological Assay (I). Data=mean. n=5-7. Open circle: vehicle. Black squares: 30 nmol/kg of compound 47.
Figure 32B:
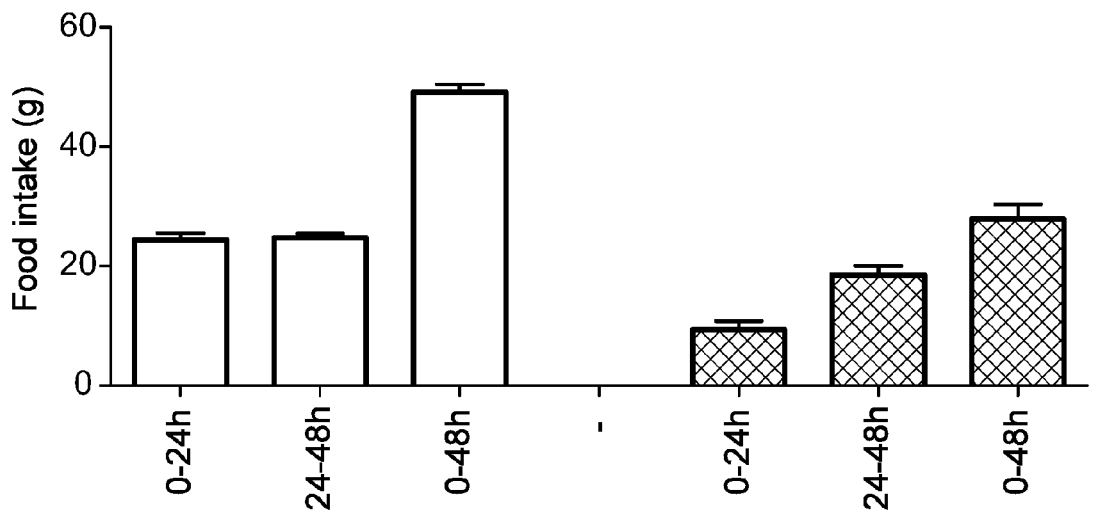
FIG. 32b shows accumulated food intake according to Pharmacological Assay (I) in the first 24 hours, the period from 24 to 48 hours, and the whole 48 hour period. Data=mean. n=5-7. Grey bars: vehicle. Black bars: 30 nmol/kg of compound 47.

From the FIG. 32*a* showing food intake over a period of 48 hours, it is seen that compound 47 is effectively reducing food intake. This is also illustrated in FIG. 32*b*, showing accumulated food intake in the periods 0-24 hours, 24-48 hours, and 0-48 hours, respectively. Food intake was compared using two-sided Student's t-test, alpha=0.05.

Example 48

N-alpha-[(S)-4-Carboxy-4-(19-carboxynonade-
canoylamino)butyryl]-Glu-Arg-[Glu1,Asp14,His17,
Gln21,Ala25,Pro26,Ser28,Ser29]-pramlintide

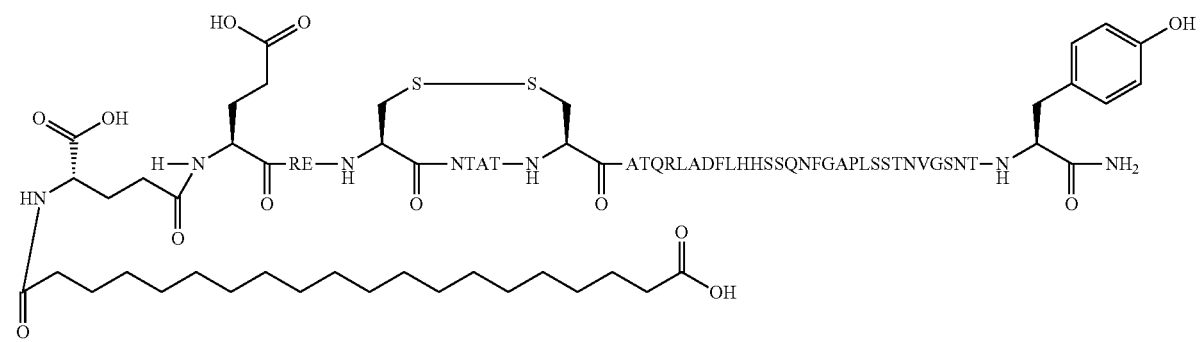

Example 49
N-alpha-[(S)-4-Carboxy-4-(19-carboxynonade-canoylamino)butyryl]-Glu-[Glu1,Arg17]-pramlintide
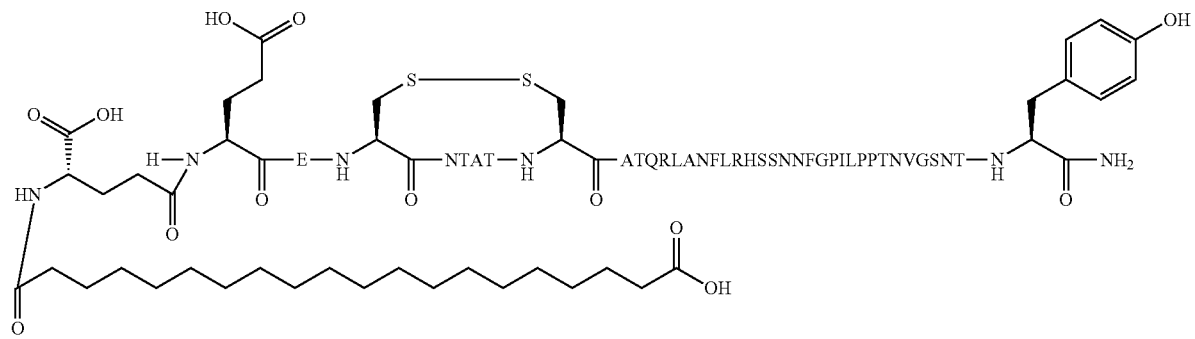
Example 50
N-alpha-[(S)-4-Carboxy-4-(19-carboxynonade-canoylamino)butyryl]-Glu-[Glu1,His17]-pramlintide
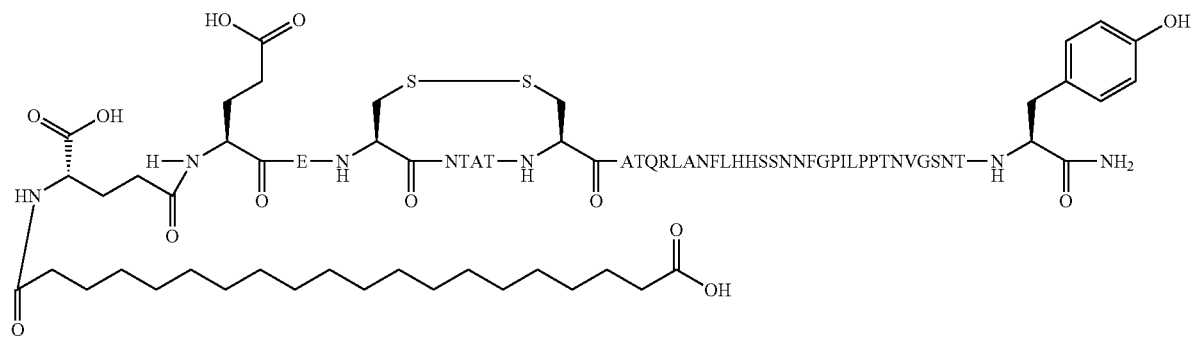
Example 51
N-alpha-[(S)-4-Carboxy-4-(19-carboxynonade-canoylamino)butyryl]-[Glu 1,His17]-pramlintide
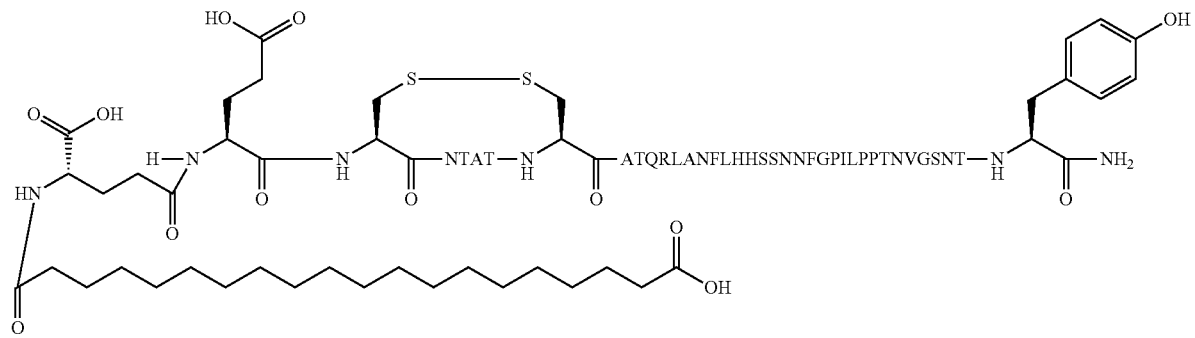

Example 52
N-alpha-[3-(2-{2-[2-(2-{2-[2-(2-{2-[(S)-4-Carboxy-4-(17-carboxyheptadecanoylamino) butyrylamino]ethoxy}ethoxy)ethoxy]ethoxy}ethoxy)ethoxy]ethoxy}ethoxy)propionylamino][Arg1,His17]-pramlintide
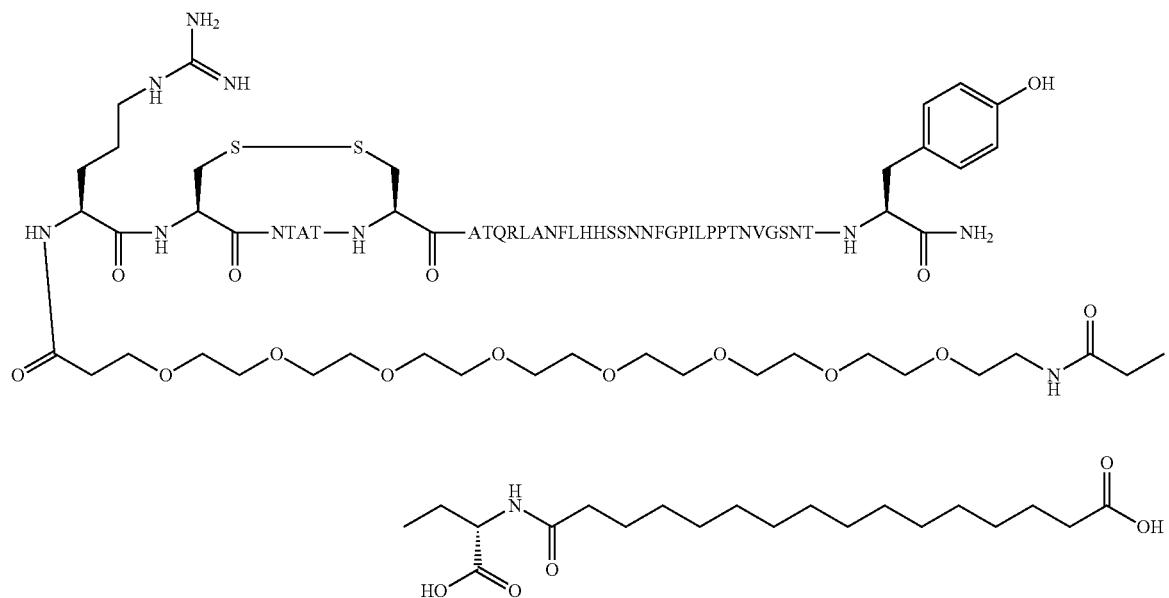
Example 53
N-alpha-[(S)-4-Carboxy-4-(19-carboxynonadecanoylamino)butyryl]-[His17,Asp31]-pramlintide (2-37)
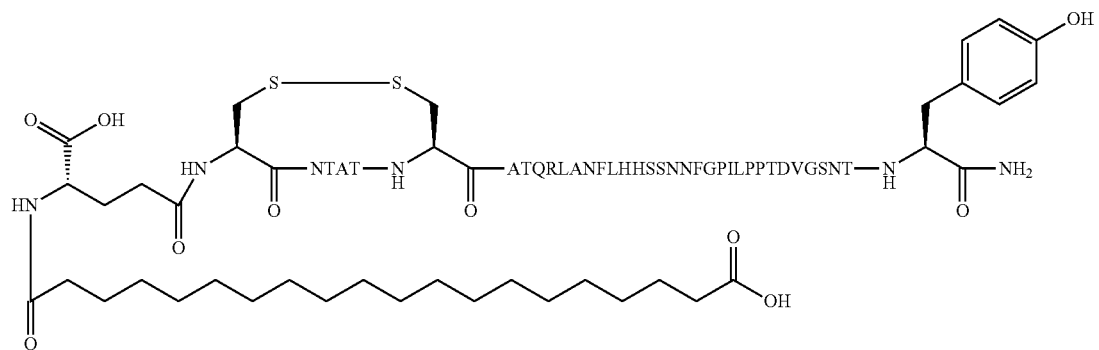

Example 54

N-alpha-[(S)-4-Carboxy-4-(19-carboxynonade-
canoylamino)butyryl]-Glu-His-His-[His1,His17]-
pramlintide

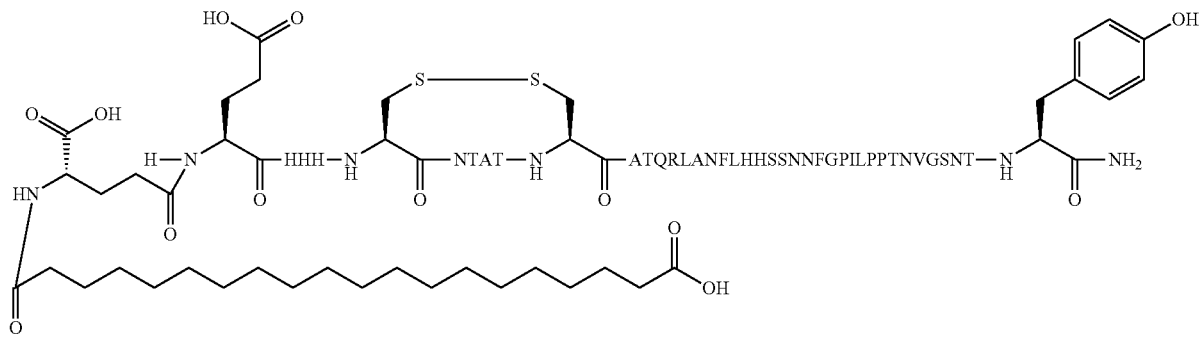

Figure 33A:
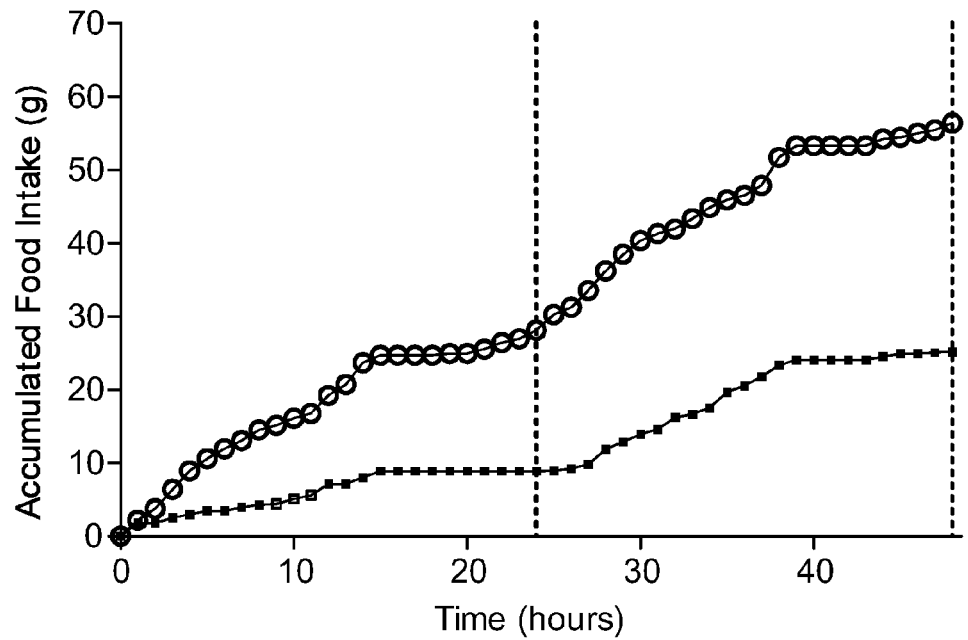
FIG. 33a shows food intake during 48 hours according to Pharmacological Assay (I). Data=mean. n=5-7. Open circle: vehicle. Black squares: 30 nmol/kg of compound 54.
Figure 33B:
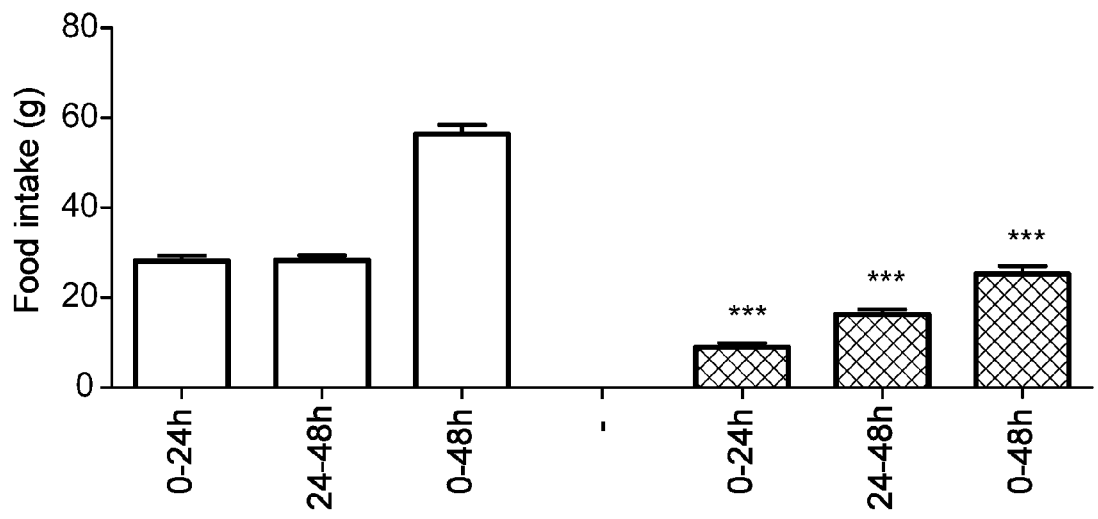
FIG. 33b shows accumulated food intake according to Pharmacological Assay (I) in the first 24 hours, the period from 24 to 48 hours, and the whole 48 hour period. Data=mean. n=5-7. Grey bars: vehicle. Black bars: 30 nmol/kg of compound 54.

From the FIG. 33a showing food intake over a period of 48 hours, it is seen that compound 54 is effectively reducing food intake. This is also illustrated in FIG. 33b, showing accumulated food intake in the periods 0-24 hours, 24-48 hours, and 0-48 hours, respectively. Food intake was compared using two-sided Student's t-test, alpha=0.05.

Example 55

N-alpha-[(S)-4-Carboxy-4-(19-carboxynonade-
canoylamino)butyryl]-Glu-His-Arg-[Arg1,His17]-
pramlintide

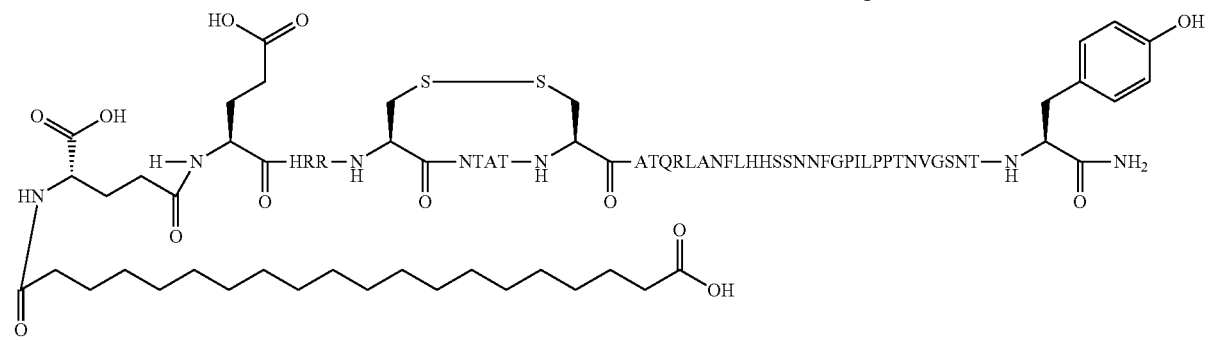

Figure 34A:
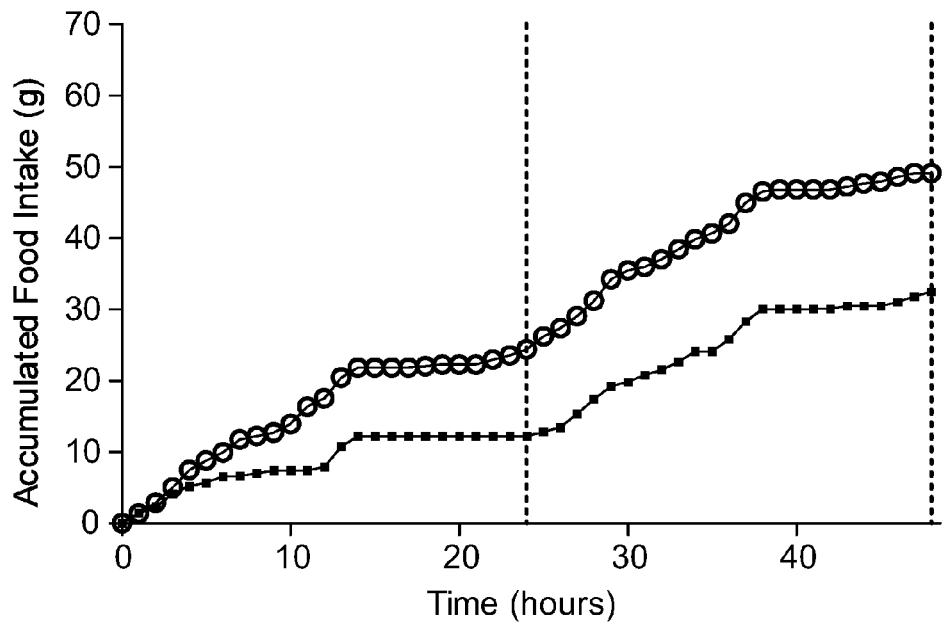
FIG. 34a shows food intake during 48 hours according to Pharmacological Assay (I). Data=mean. n=5-7. Open circle: vehicle. Black squares: 30 nmol/kg of compound 55.
Figure 34B:
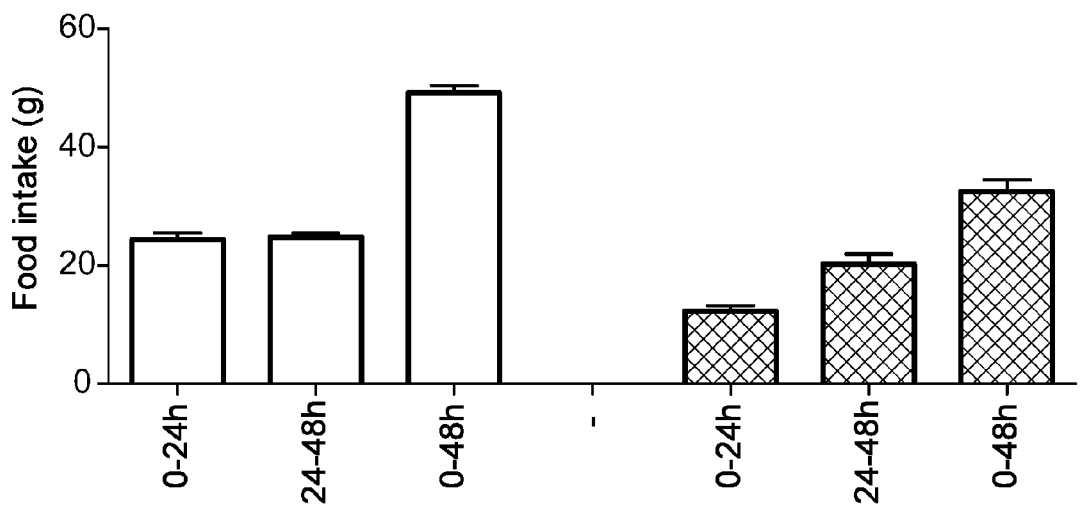
FIG. 34b shows accumulated food intake according to Pharmacological Assay (I) in the first 24 hours, the period from 24 to 48 hours, and the whole 48 hour period. Data=mean. n=5-7. Grey bars: vehicle. Black bars: 30 nmol/kg of compound 55.

From the FIG. 34a showing food intake over a period of 48 hours, it is seen that compound 55 is effectively reducing food intake. This is also illustrated in FIG. 34b, showing accumulated food intake in the periods 0-24 hours, 24-48 hours, and 0-48 hours, respectively. Food intake was compared using two-sided Student's t-test, alpha=0.05.

Example 56

N-alpha-[2-(2-{2-[4-(S)-Carboxy-4-(19-carbox-
ynonadecanoylamino)butyrylamino]ethoxy}ethoxy)
acetyl]-His-His-[Arg1,His17]-pramlintide

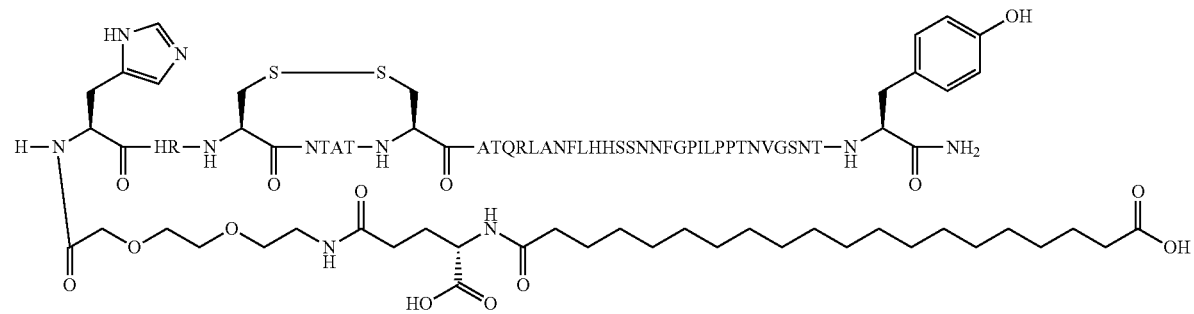

Figure 35A:
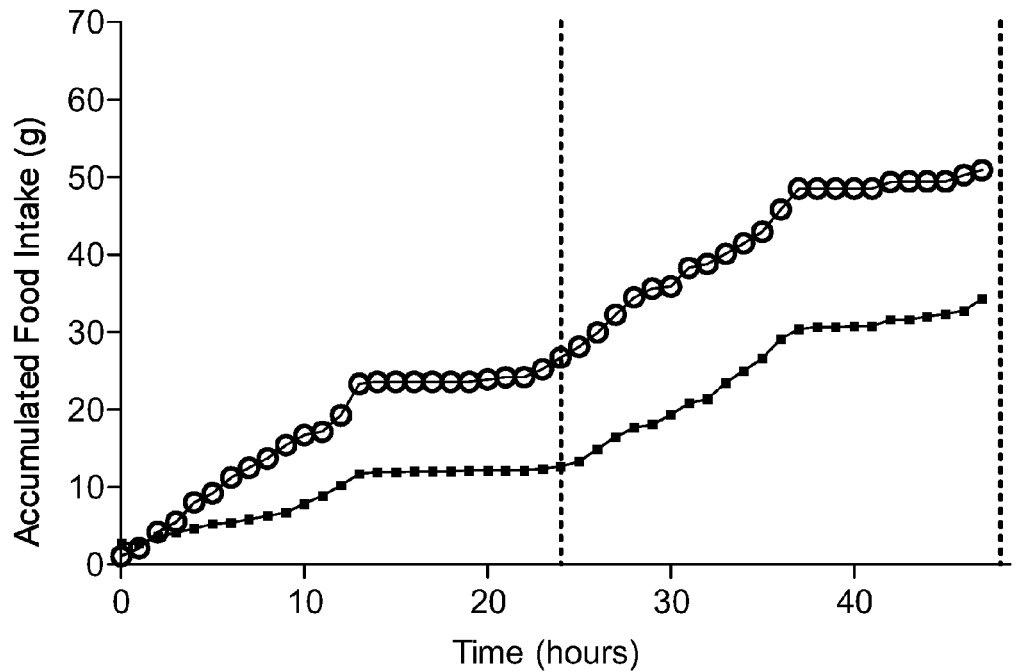
FIG. 35a shows food intake during 48 hours according to Pharmacological Assay (I). Data=mean. n=5-7. Open circle: vehicle. Black squares: 30 nmol/kg of compound 56.
Figure 35B:
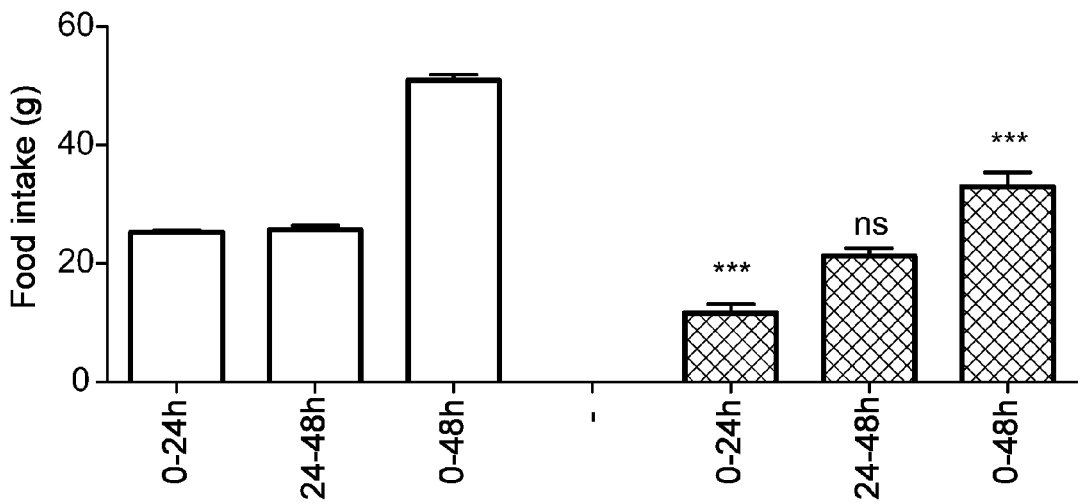
FIG. 35b shows accumulated food intake according to Pharmacological Assay (I) in the first 24 hours, the period from 24 to 48 hours, and the whole 48 hour period. Data=mean. n=5-7. Grey bars: vehicle. Black bars: 30 nmol/kg of compound 56.

From the FIG. 35a showing food intake over a period of 48 hours, it is seen that compound 56 is effectively reducing food intake. This is also illustrated in FIG. 35b, showing accumulated food intake in the periods 0-24 hours, 24-48 hours, and 0-48 hours, respectively. Food intake was compared using two-sided Student's t-test, alpha=0.05.

Example 57

N-alpha-[2-(2-{2-[4-(S)-Carboxy-4-(19-carboxynonadecanoylamino)butyrylamino]ethoxy}ethoxy)acetyl]-His-His-[Arg1,Arg17]-pramlintide

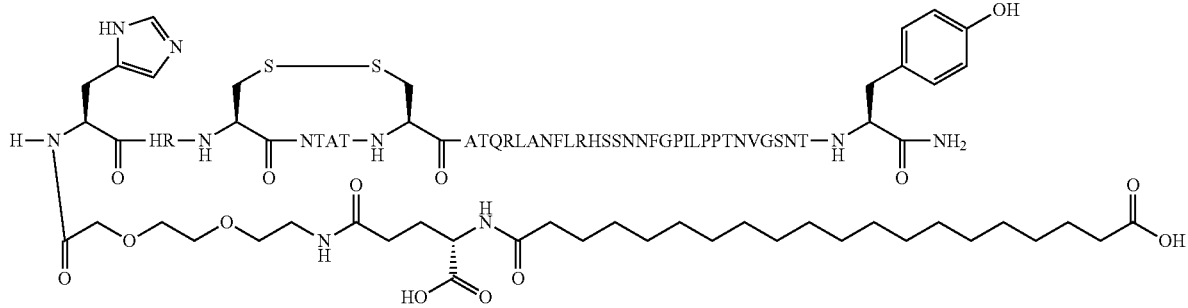

Figure 36A:
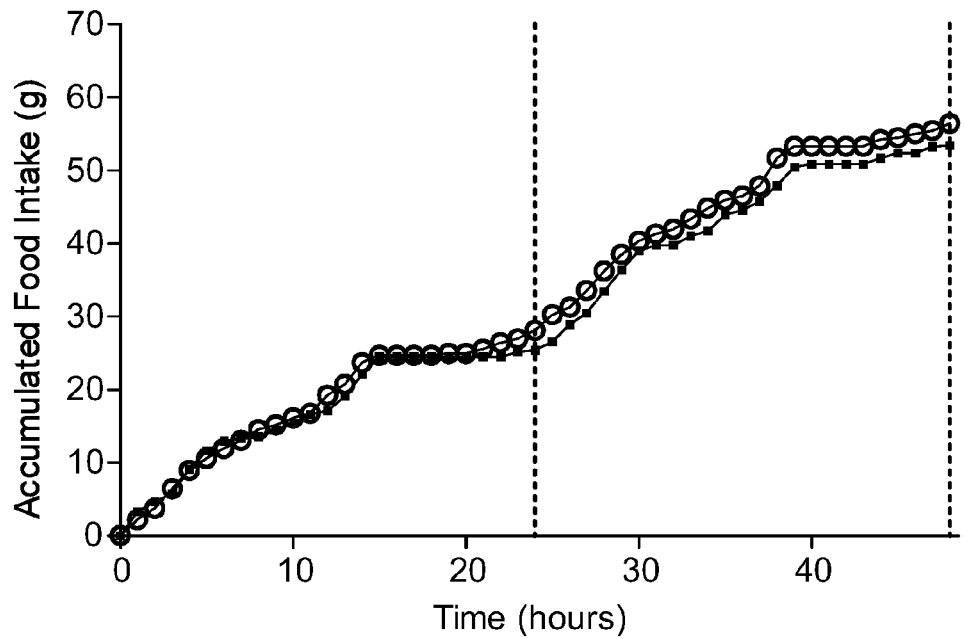
FIG. 36a shows food intake during 48 hours according to Pharmacological Assay (I). Data=mean. n=5-7. Open circle: vehicle. Black squares: 30 nmol/kg of compound 57.
Figure 36B:
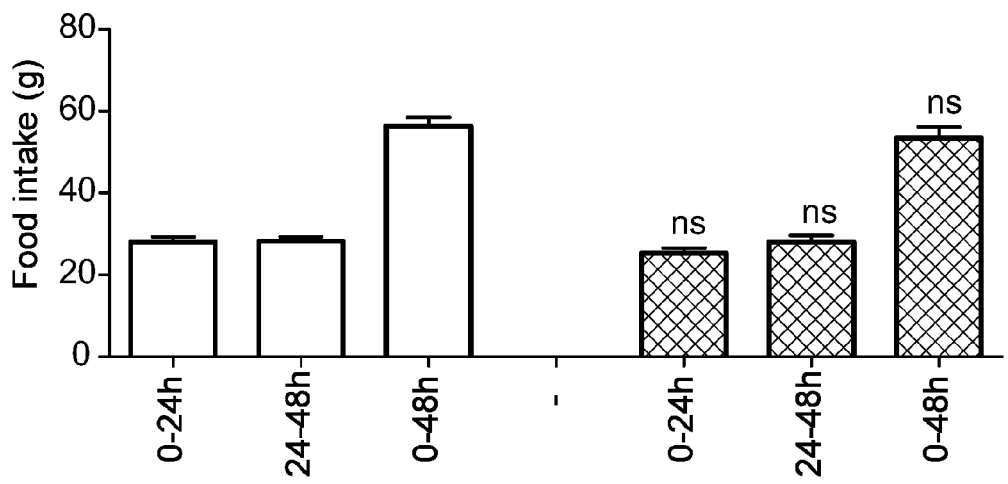
FIG. 36b shows accumulated food intake according to Pharmacological Assay (I) in the first 24 hours, the period from 24 to 48 hours, and the whole 48 hour period. Data=mean. n=5-7. Grey bars: vehicle. Black bars: 30 nmol/kg of compound 57.

From the FIG. 36a showing food intake over a period of 48 hours, it is seen that compound 57 shows a minor reduction in food intake. FIG. 36b shows accumulated food intake in the periods 0-24 hours, 24-48 hours, and 0-48 hours, respectively. Food intake was compared using two-sided Student's t-test, alpha=0.05.

Example 58

N-alpha-[(S)-4-Carboxy-4-(19-carboxynonadecanoylamino)butyryl]-Glu-His-His-[Arg1,Arg17]-pramlintide

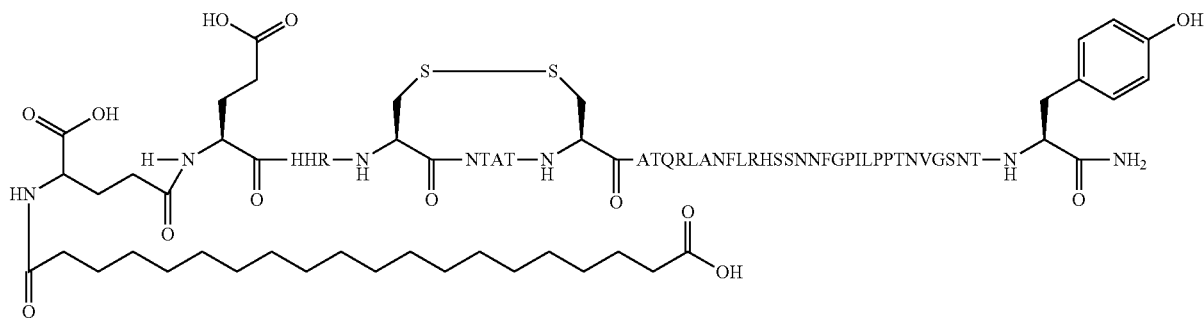

Figure 37A:
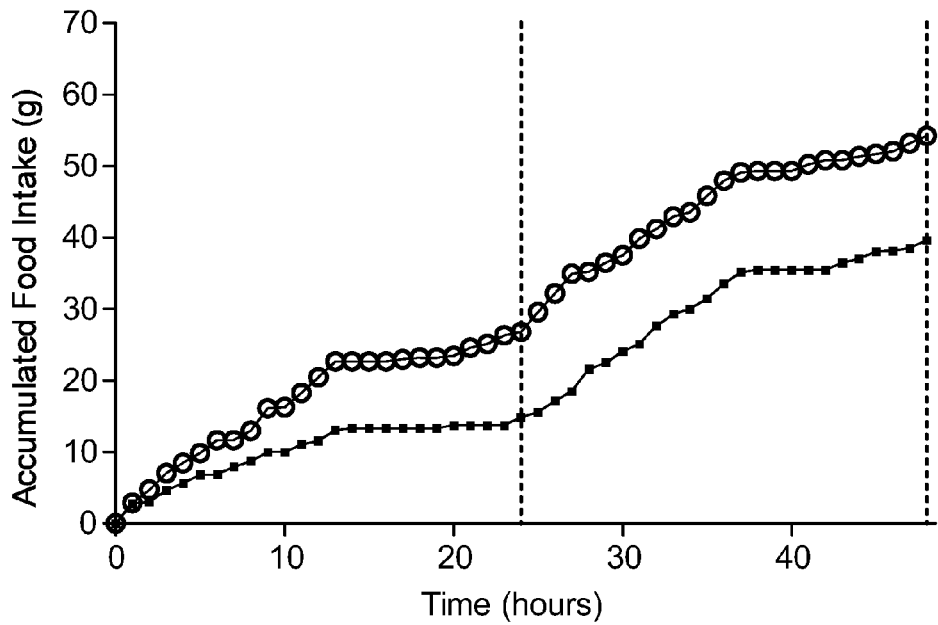
FIG. 37a shows food intake during 48 hours according to Pharmacological Assay (I). Data=mean. n=5-7. Open circle: vehicle. Black squares: 30 nmol/kg of compound 58.
Figure 37B:
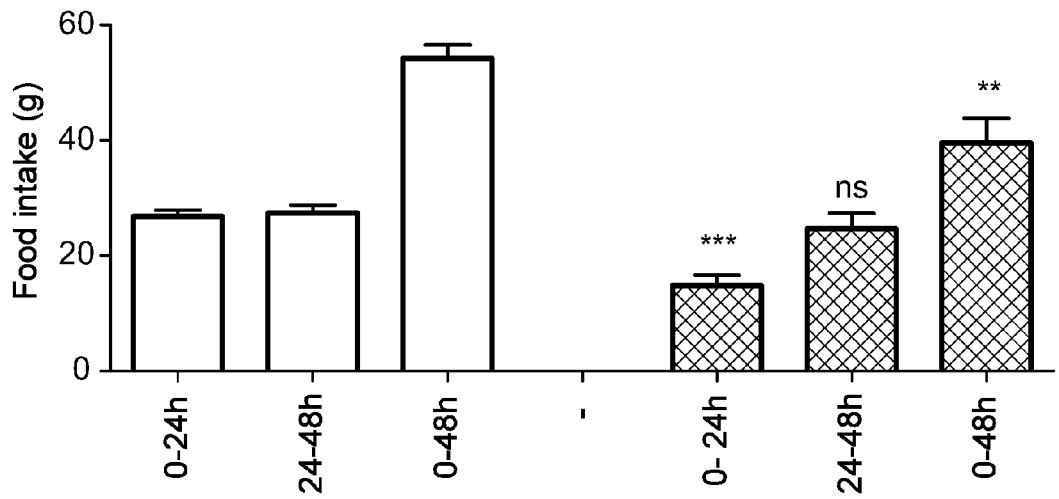
FIG. 37b shows accumulated food intake according to Pharmacological Assay (I) in the first 24 hours, the period from 24 to 48 hours, and the whole 48 hour period. Data=mean. n=5-7. Grey bars: vehicle. Black bars: 30 nmol/kg of compound 58.

From the FIG. 37a showing food intake over a period of 48 hours, it is seen that compound 58 is effectively reducing food intake. This is also illustrated in FIG. 37b, showing accumulated food intake in the periods 0-24 hours, 24-48 hours, and 0-48 hours, respectively. Food intake was compared using two-sided Student's t-test, alpha=0.05.

Example 59

N-alpha-[2-(2-{2-[4-(S)-Carboxy-4-(19-carboxynonadecanoylamino)butyrylamino]ethoxy}ethoxy)acetyl]-His-His-[Arg1His17,Gln21]-pramlintide

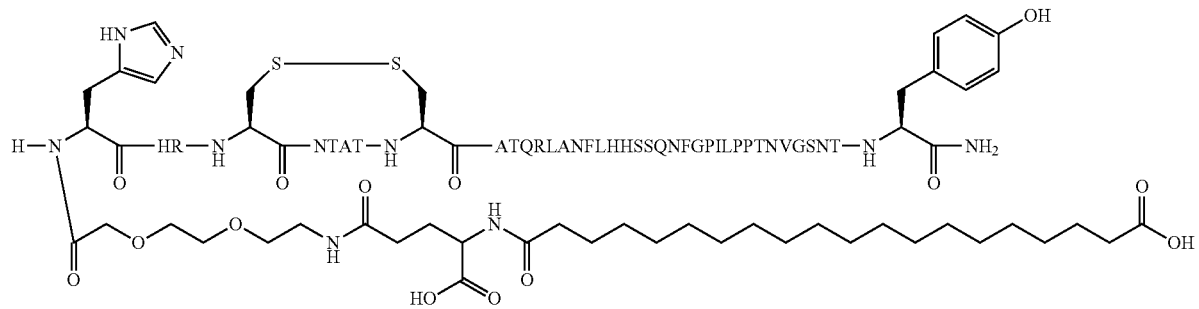

Figure 38A:
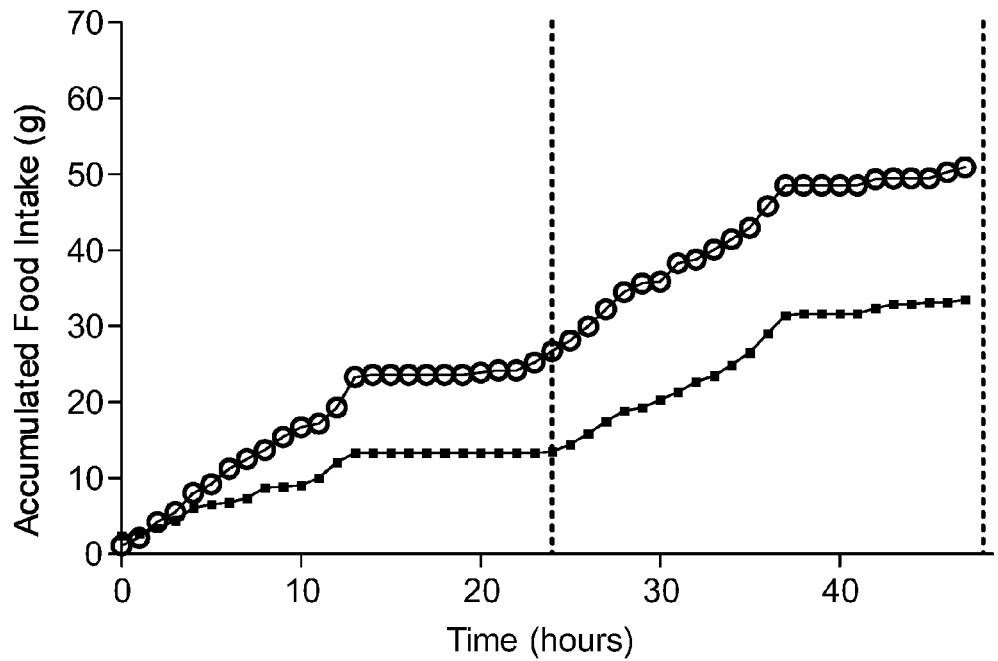
FIG. 38a shows food intake during 48 hours according to Pharmacological Assay (I). Data=mean. n=5-7. Open circle: vehicle. Black squares: 30 nmol/kg of compound 59.
Figure 38B:
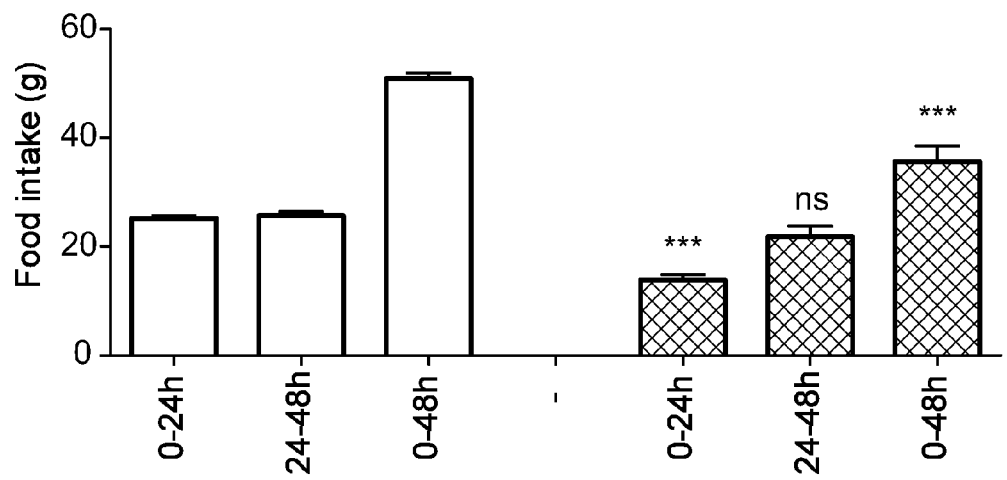
FIG. 38b shows accumulated food intake according to Pharmacological Assay (I) in the first 24 hours, the period from 24 to 48 hours, and the whole 48 hour period. Data=mean. n=5-7. Grey bars: vehicle. Black bars: 30 nmol/kg of compound 59.

From the FIG. 38a showing food intake over a period of 48 hours, it is seen that compound 59 is effectively reducing food intake. This is also illustrated in FIG. 38b, showing accumulated food intake in the periods 0-24 hours, 24-48 hours, and 0-48 hours, respectively. Food intake was compared using two-sided Student's t-test, alpha=0.05.

Example 60

N-alpha-[(S)-4-Carboxy-4-(17-carboxyheptadecanoylamino)butyryl]-His-His-[His1,His17]-pramlintide

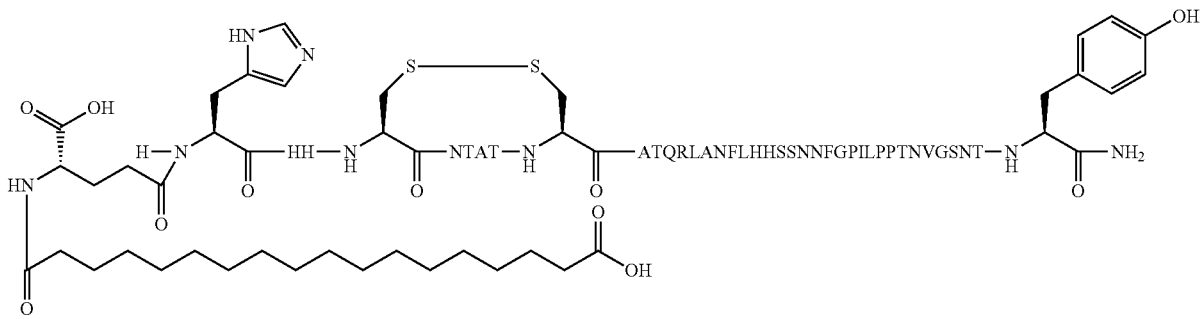

Example 61

N-alpha-[(S)-4-Carboxy-4-(5-carboxypentanoylamino)butyryl]-His-His-[His1,His17]-pramlintide

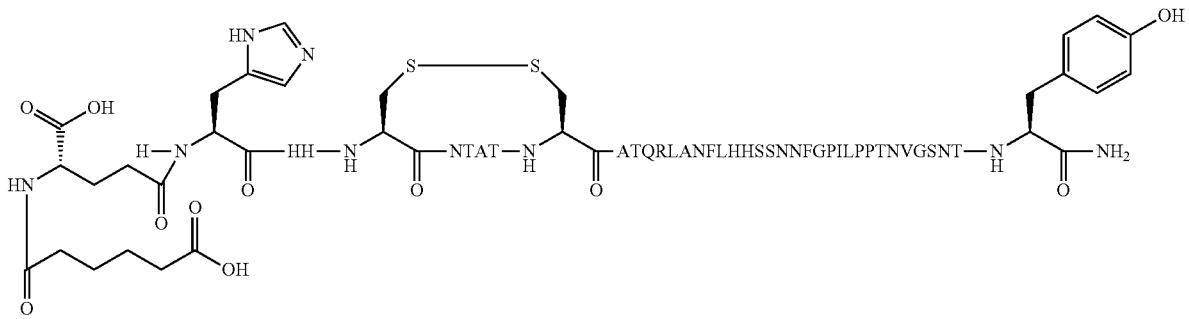

Example 62

N-alpha-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl][His17]-pramlintide (2-37)

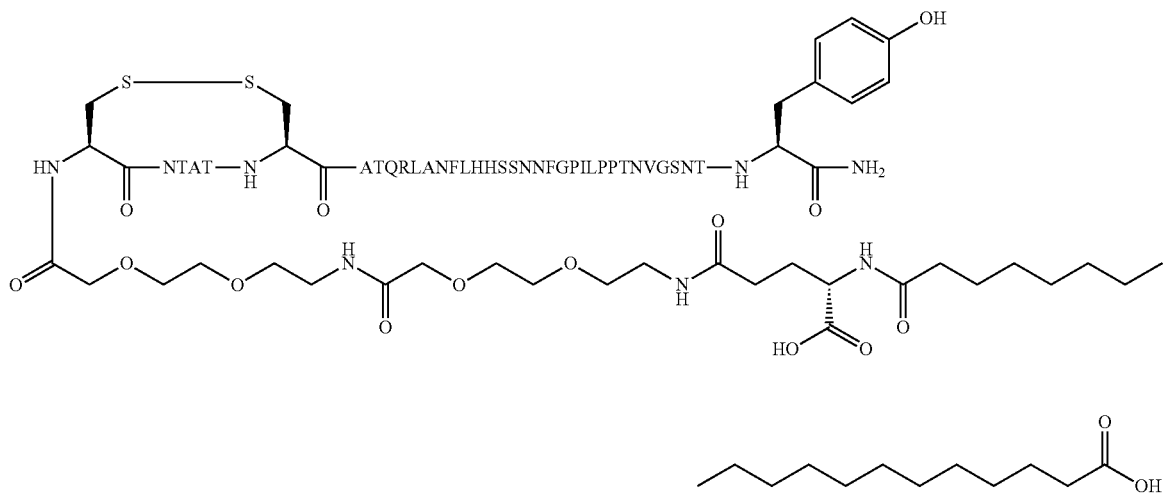

Example 63

N-alpha-[(S)-4-Carboxy-4-(19-carboxynonadecanoylamino)butyryl]-GluHis-His-[Arg1,His17,Gln21]-pramlintide

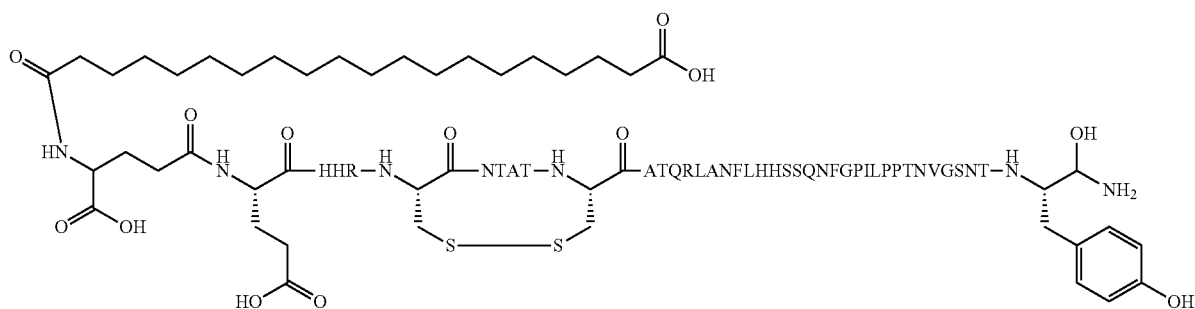

Figure 39A:
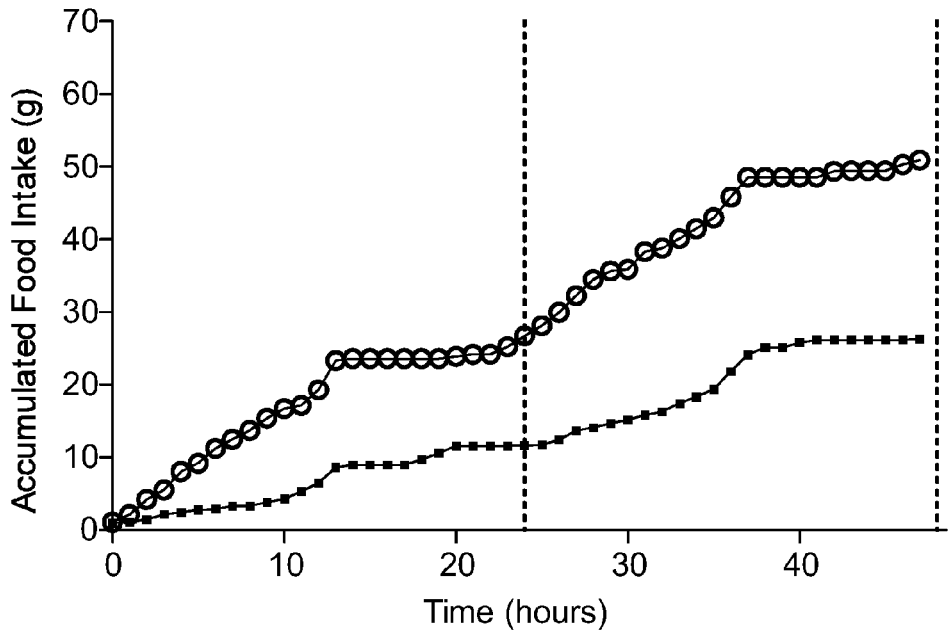
FIG. 39a shows food intake during 48 hours according to Pharmacological Assay (I). Data=mean. n=5-7. Open circle: vehicle. Black squares: 30 nmol/kg of compound 63.
Figure 39B:
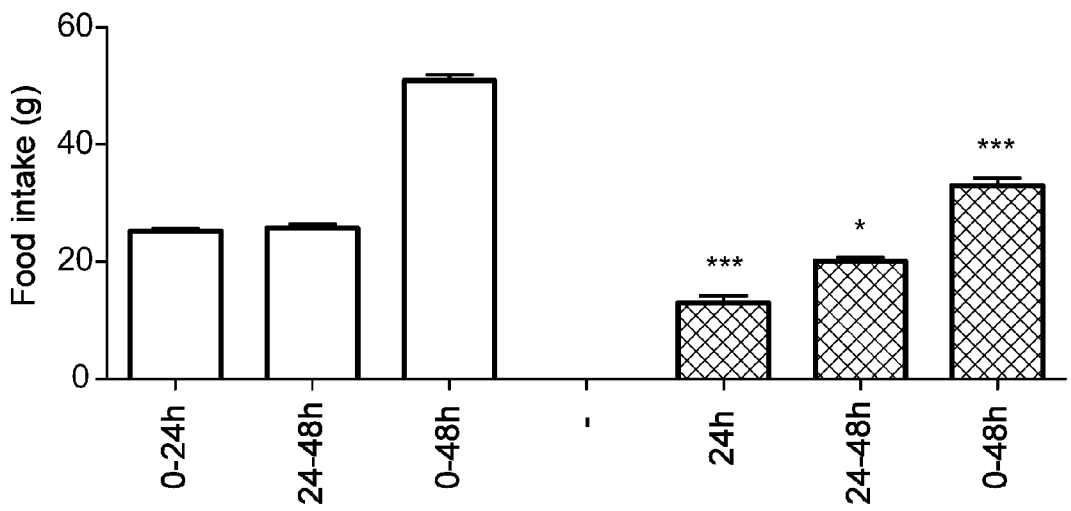
FIG. 39b shows accumulated food intake according to Pharmacological Assay (I) in the first 24 hours, the period from 24 to 48 hours, and the whole 48 hour period. Data=mean. n=5-7. Grey bars: vehicle. Black bars: 30 nmol/kg of compound 63.

From the FIG. 39a showing food intake over a period of 48 hours, it is seen that compound 63 is effectively reducing food intake. This is also illustrated in FIG. 39b, showing accumulated food intake in the periods 0-24 hours, 24-48 hours, and 0-48 hours, respectively. Food intake was compared using two-sided Student's t-test, alpha=0.05.

Example 64

N-alpha-[2-(2-{2-[2-(2-{2-[(S)-4-Carboxy-4-(19-carboxyheptadecanoylamino)butyrylamino]ethoxy}ethoxy)acetylamino]ethoxy}ethoxy)acetyl]-[His17]-pramlintide (2-37)

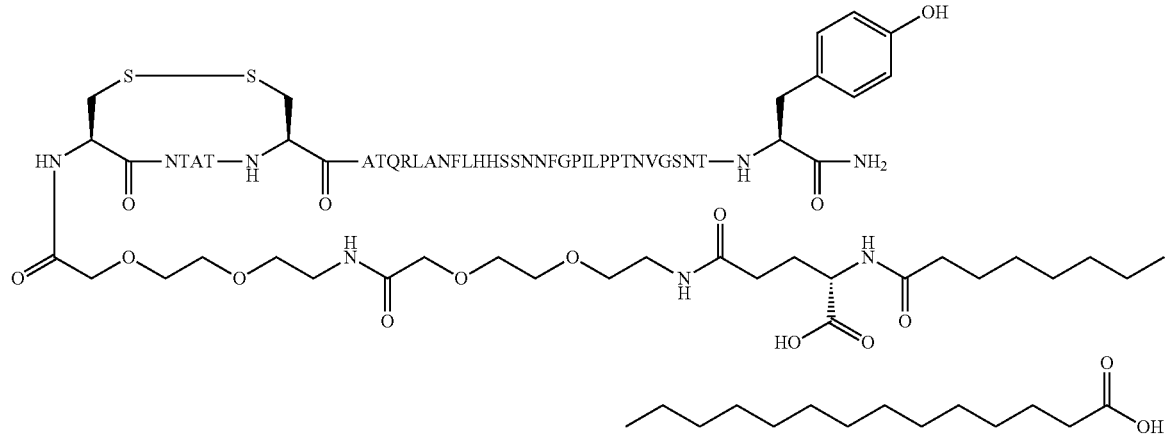

Figure 40A:
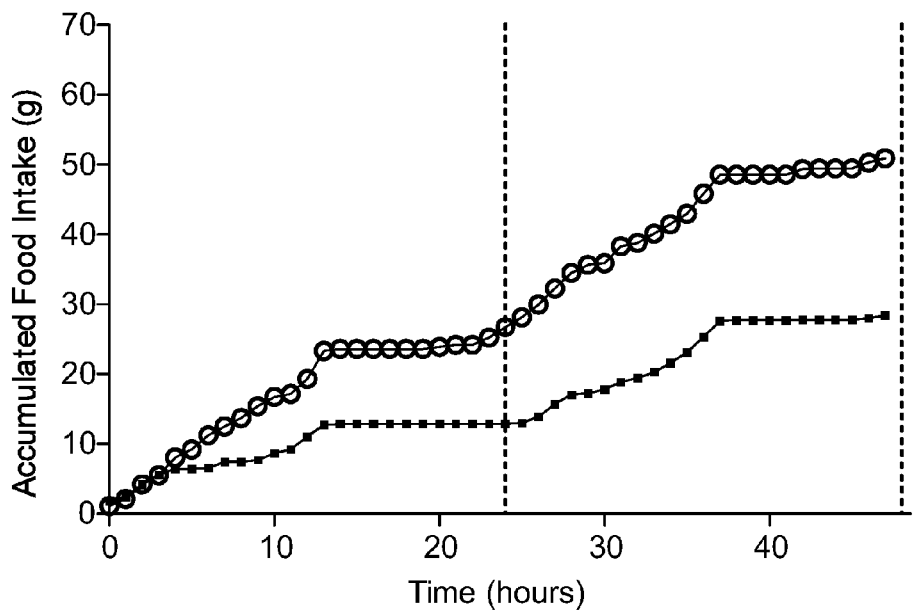
FIG. 40a shows food intake during 48 hours according to Pharmacological Assay (I). Data=mean. n=5-7. Open circle: vehicle. Black squares: 30 nmol/kg of compound 64.
Figure 40B:
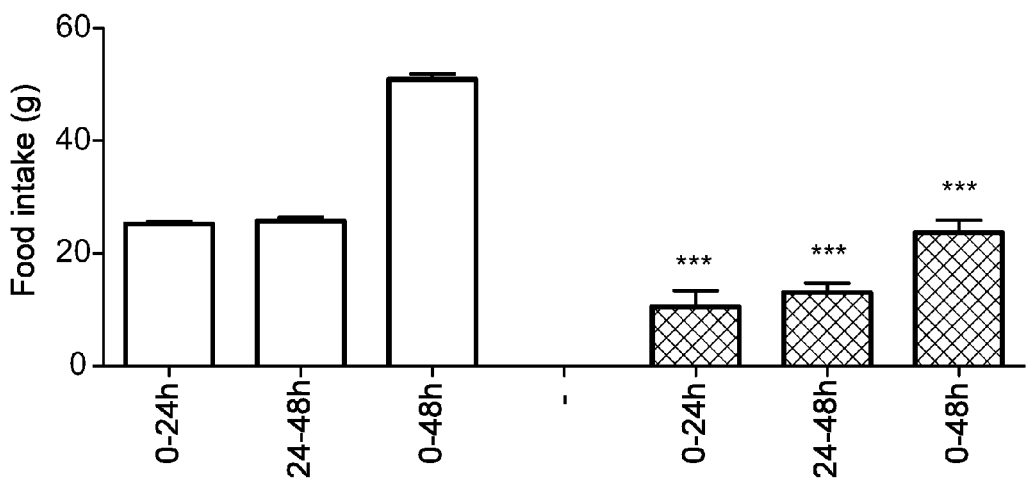
FIG. 40b shows accumulated food intake according to Pharmacological Assay (I) in the first 24 hours, the period from 24 to 48 hours, and the whole 48 hour period. Data=mean. n=5-7. Grey bars: vehicle. Black bars: 30 nmol/kg of compound 64.

From the FIG. 40a showing food intake over a period of 48 hours, it is seen that compound 64 is effectively reducing food intake. This is also illustrated in FIG. 40b, showing accumulated food intake in the periods 0-24 hours, 24-48 hours, and 0-48 hours, respectively. Food intake was compared using two-sided Student's t-test, alpha=0.05.

Example 65

N-alpha-[2-(2-{2-[4-(S)-Carboxy-4-(19-carboxynonadecanoylamino)butyrylamino]ethoxy}ethoxy)acetyl]-His-His-[Arg1,Arg17,Gln21]-pramlintide

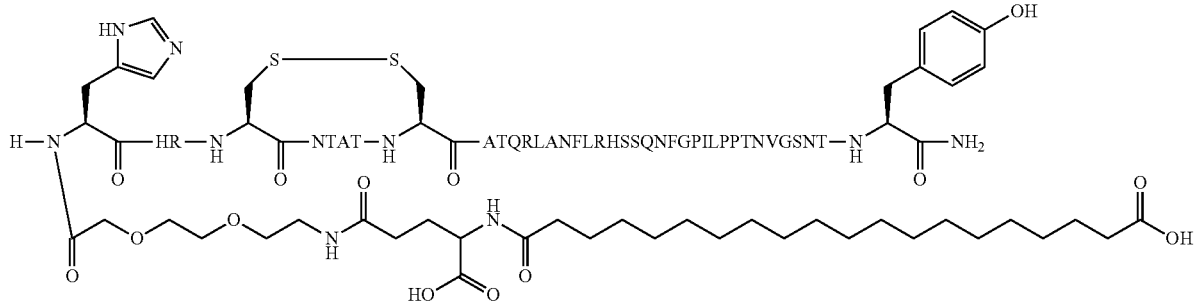

Example 66

N-alpha-[(S)-4-Carboxy-4-(19-carboxynonadecanoylamino)butyryl]-Glu-His-Arg-[His1,His17]-pramlintide

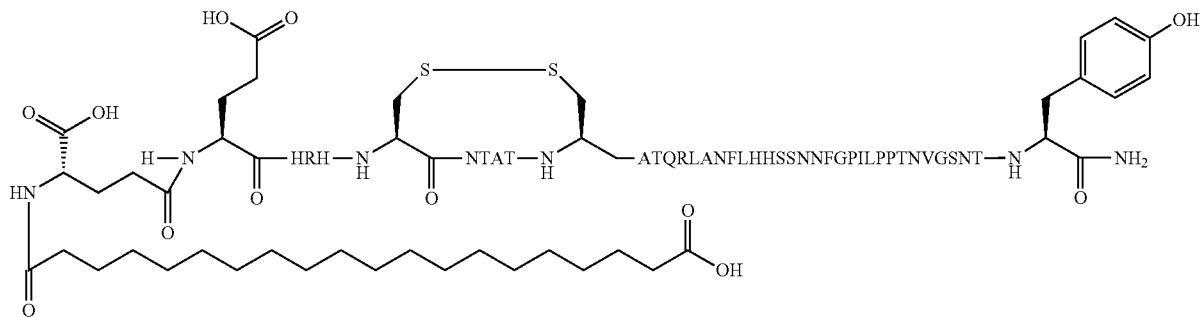

Figure 41A:
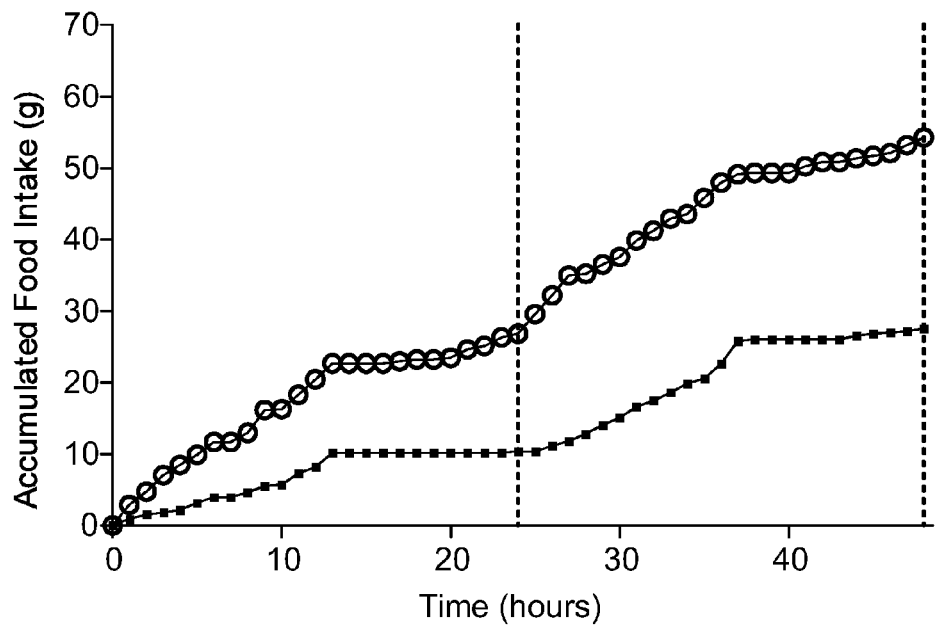
FIG. 41a shows food intake during 48 hours according to Pharmacological Assay (I). Data=mean. n=5-7. Open circle: vehicle. Black squares: 30 nmol/kg of compound 66.
Figure 41B:
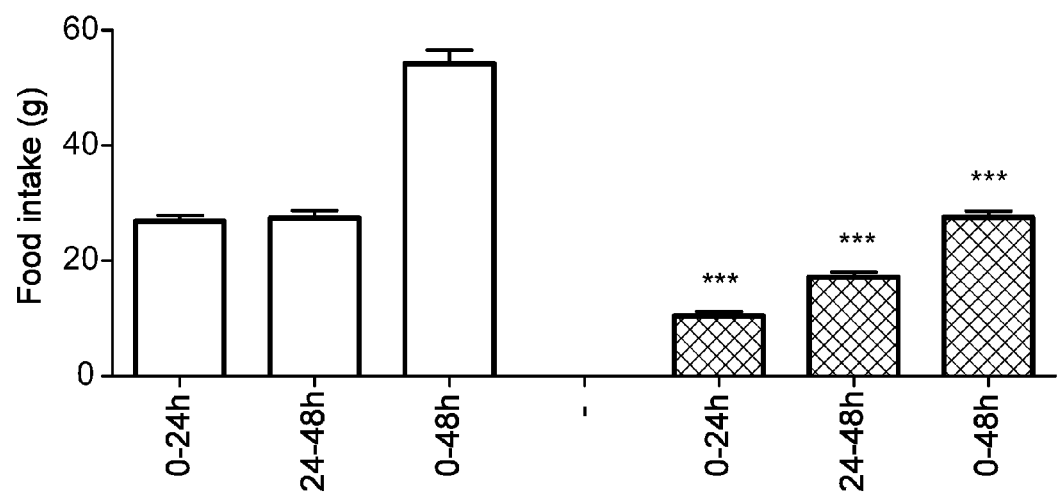
FIG. 41b shows accumulated food intake according to Pharmacological Assay (I) in the first 24 hours, the period from 24 to 48 hours, and the whole 48 hour period. Data=mean. n=5-7. Grey bars: vehicle. Black bars: 30 nmol/kg of compound 66.

From the FIG. 41a showing food intake over a period of 48 hours, it is seen that compound 66 is effectively reducing food intake. This is also illustrated in FIG. 41b, showing accumulated food intake in the periods 0-24 hours, 24-48 hours, and 0-48 hours, respectively. Food intake was compared using two-sided Student's t-test, alpha=0.05.

Example 67

N-alpha-[(S)-4-Carboxy-4-(19-carboxynonade-canoylamino)butyryl]-Glu-His-His-[Arg1,His17]-pramlintide

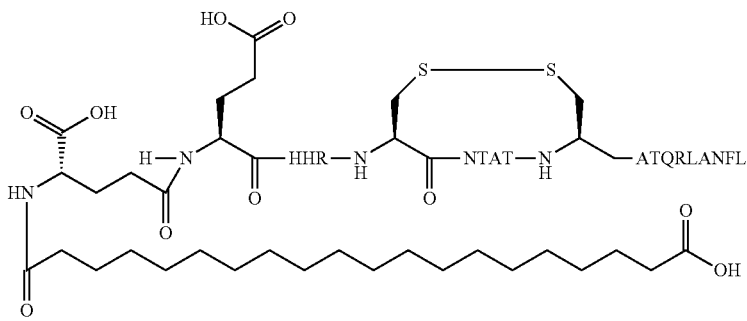
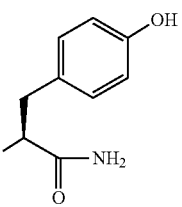

Figure 42A:
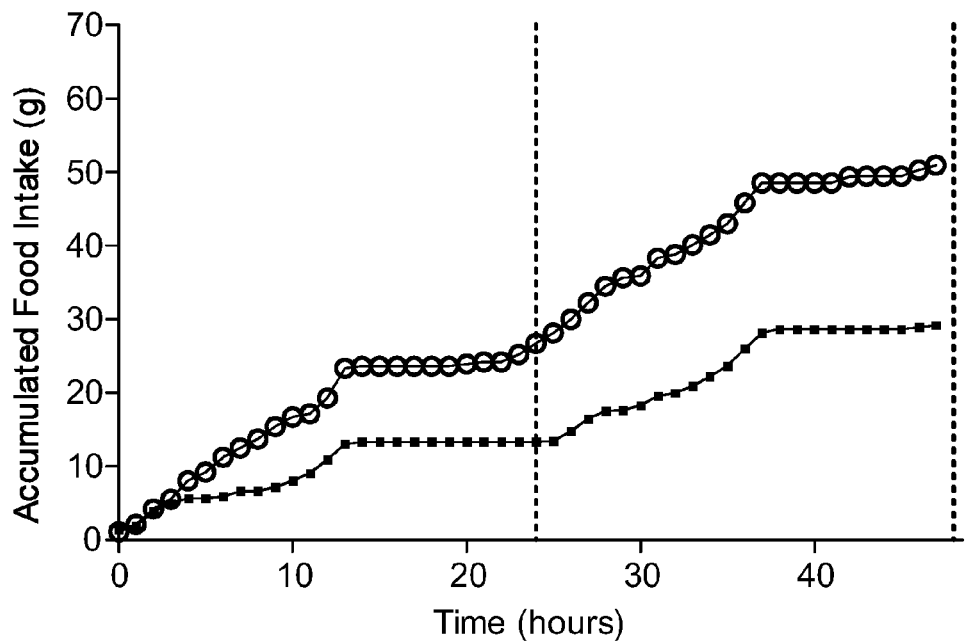
FIG. 42a shows food intake during 48 hours according to Pharmacological Assay (I). Data=mean. n=5-7. Open circle: vehicle. Black squares: 30 nmol/kg of compound 67.
Figure 42B:
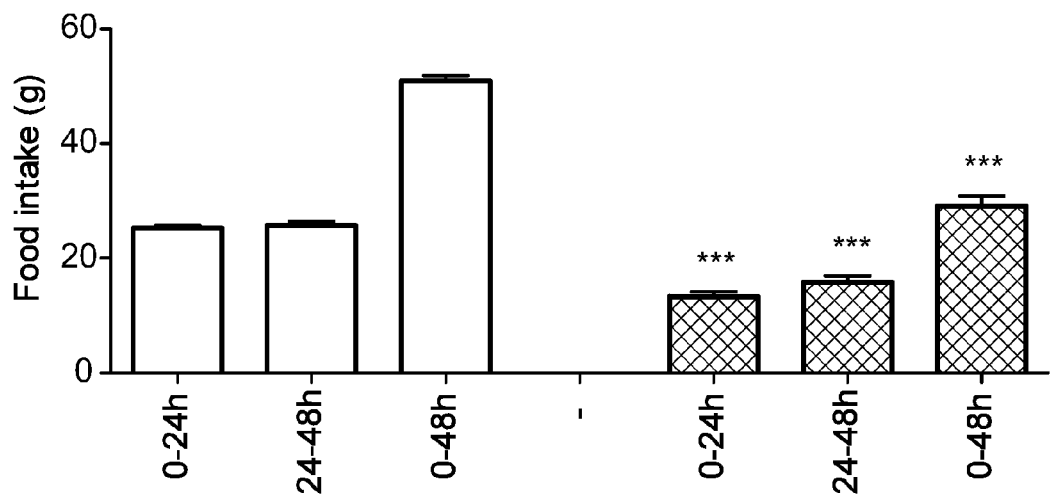
FIG. 42b shows accumulated food intake according to Pharmacological Assay (I) in the first 24 hours, the period from 24 to 48 hours, and the whole 48 hour period. Data=mean. n=5-7. Grey bars: vehicle. Black bars: 30 nmol/kg of compound 67.

From the FIG. 42a showing food intake over a period of 48 hours, it is seen that compound 67 is effectively reducing food intake. This is also illustrated in FIG. 42b, showing accumulated food intake in the periods 0-24 hours, 24-48 hours, and 0-48 hours, respectively. Food intake was compared using two-sided Student's t-test, alpha=0.05.

Example 68

N-alpha-[(S)-4-Carboxy-4-(19-carboxynonade-canoylamino)butyryl]-Glu-His-His-[Arg1,Arg17,Gln21]-pramlintide

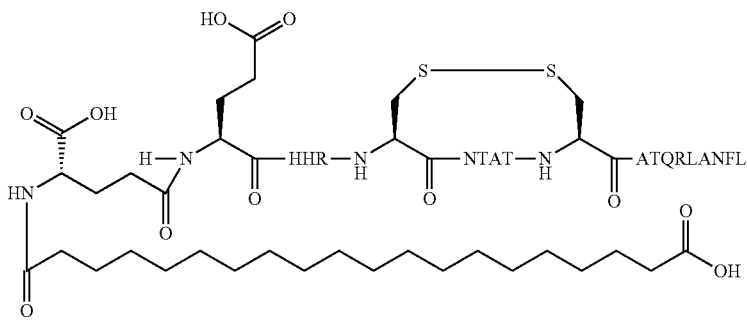
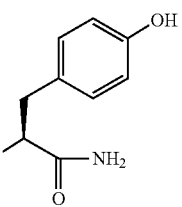

Example 69

N-alpha-[(S)-4-Carboxy-4-(19-carboxynonade-canoylamino)butyryl]-Glu-Arg-His-[Arg1,His17]-pramlintide

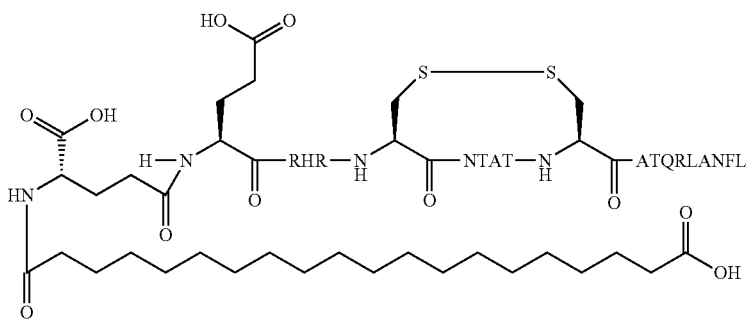
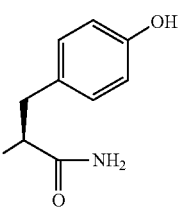

Example 70
N-alpha-[(S)-4-Carboxy-4-(19-carboxynonade-canoylamino)butyryl]-Arg-His[Arg1,His17]-pramlintide
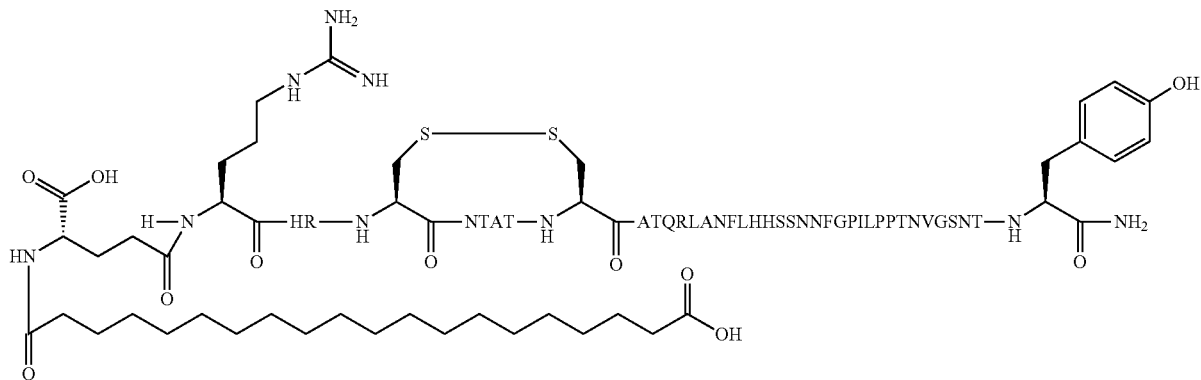
Example 71
N-alpha-[(S)-4-Carboxy-4-(19-carboxynonadecanoyl-amino)butyryl]-His-His-[Arg1,His17]-pramlintide
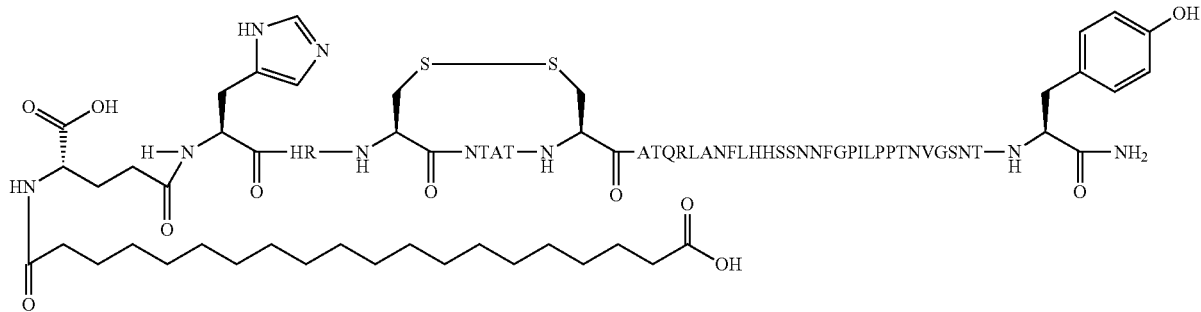
Example 72
N-alpha-[(S)-4-Carboxy-4-(19-carboxynonade-canoylamino)butyryl]-His-Arg-[His1,His17]-pramlintide
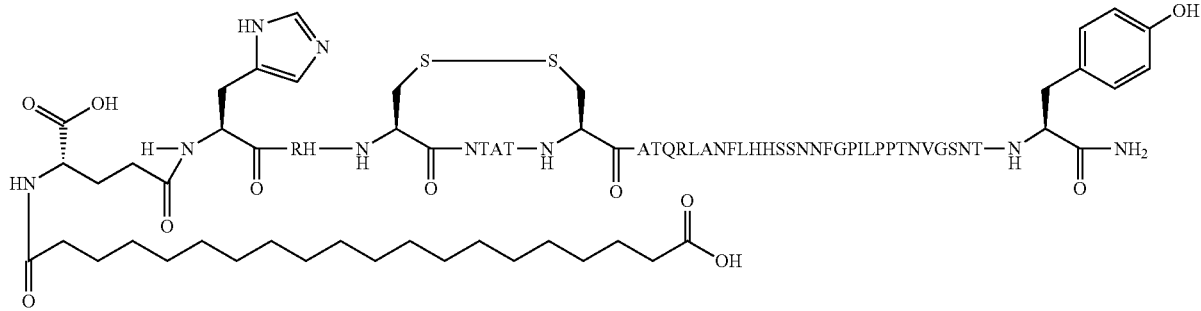

The amylin derivatives according to examples 1-72 were tested in the "Luciferase assay" as described below and results are shown in table 1 together with the molecular weight MW of the amylin derivatives

TABLE 1

| Example | MW | Potency Luciferase pmol/l |
|---|---|---|
| 1 | 4757.4 | 900 |
| 2 | 4870.6 | 900 |
| 3 | 4730.4 | 400 |
| 4 | 4843.5 | 2000 |
| 5 | 4312.9 | 100 |
| 6 | 4469.1 | 300 |
| 7 | 4441.1 | 200 |
| 8 | 4597.3 | 70 |
| 9 | 4725.5 | 60 |
| 10 | 4284.9 | 80 |
| 11 | 4262.9 | 100 |
| 12 | 4246.9 | 100 |
| 13 | 4232.8 | 400 |
| 14 | 4332.0 | 200 |
| 15 | 4279.9 | 8000 |
| 16 | 4458.1 | 100 |
| 17 | 4597.3 | 80 |
| 18 | 4517.2 | 100 |
| 19 | 4531.2 | 100 |
| 20 | 4547.2 | 100 |
| 21 | 4557.3 | 2000 |
| 22 | 4616.3 | 100 |
| 23 | 4761.5 | 100 |
| 24 | 4676.4 | 80 |
| 25 | 4572.3 | 30 |
| 26 | 4588.3 | 50 |
| 27 | 4587.2 | 100 |
| 28 | 4578.2 | 100 |
| 29 | 4450.1 | 70 |
| 30 | 4268.9 | 60 |
| 31 | 4559.2 | 20 |
| 32 | 4422.0 | 80 |
| 33 | 4589.3 | 100 |
| 34 | 4751.4 | 200 |
| 35 | 4606.3 | 100 |
| 36 | 4469.1 | 100 |
| 37 | 4595.2 | 90 |
| 38 | 4732.4 | 100 |
| 39 | 4724.4 | 60 |
| 40 | 4734.4 | 100 |
| 41 | 4679.2 | 100 |
| 42 | 4666.2 | 600 |
| 43 | 4313.9 | 100 |
| 44 | 4385.0 | 100 |
| 45 | 4731.4 | 30 |
| 46 | 4684.2 | 200 |
| 47 | 4606.3 | 200 |
| 48 | 4680.2 | 60 |
| 49 | 4590.2 | 300 |
| 50 | 4571.2 | 300 |
| 51 | 4442.0 | 200 |
| 52 | 4864.6 | 80 |
| 53 | 4313.9 | 60 |
| 54 | 4853.5 | 100 |
| 55 | 4891.6 | 200 |
| 56 | 4888.6 | 90 |
| 57 | 4907.6 | 300 |
| 58 | 4891.6 | 200 |
| 59 | 4902.6 | 60 |
| 60 | 4696.3 | 50 |
| 61 | 4528.0 | 40 |
| 62 | 4575.2 | 40 |
| 63 | 4888.6 | 100 |
| 64 | 4603.2 | 70 |
| 65 | 4921.6 | 100 |
| 66 | 4872.5 | 100 |
| 67 | 4872.5 | 100 |

TABLE 1-continued

| Example | MW | Potency Luciferase pmol/l |
|---|---|---|
| 68 | 4905.6 | 100 |
| 69 | 4891.6 | 100 |
| 70 | 4762.5 | 100 |
| 71 | 4743.4 | 90 |
| 72 | 4743.4 | 50 |

The half life of the amylin derivatives of the inventions were tested in mini pigs and rats as described in the assays below. The data are given in table 2.

TABLE 2

| Example | T½ in mini pigs, hours | T½ in rats, hours |
|---|---|---|
| 5 | 70 | 16 |
| 10 | 66 | 11 |
| 20 | 41 | 10 |
| 22 | 34 | 13 |
| 23 | 53 | |
| 27 | 64 | |
| 29 | 110 | |
| 31 | 41 | |
| 37 | 66 | |
| 39 | 60 | 14 |
| 40 | 31 | |
| 47 | 30 | |
| 54 | 53 | |
| 55 | 38 | |
| 56 | 31 | |

Assays
Pharmacological Assay (I)—Experimental Protocol for Efficacy Testing on Appetite with an Amylin Derivative, Using an Ad Libitum Fed Rat Model.

Sprague Dawley (SD) rats from Taconic Europe, Denmark are used for the experiments. The rats have a body weight 200-250 g at the start of experiment. The rats arrive at least 10-14 days before start of experiment to allow acclimatization to experimental settings. During this period the animals are handled at least 2 times. After arrival rats are housed individually for one week in a reversed light/dark phase (meaning that lights are off during daytime and on during nighttime) for two weeks. Since rats are normally active and eat their major part of their daily food intake during the dark period, rats are dosed in the morning right before lights are turned off. This set-up results in the lowest data variation and highest test sensitivity. The experiment is conducted in the rats' home cages and rats have free access to food and water throughout the acclimatization period and the experiment period. Each dose of derivative is tested in a group of 5-8 rats. A vehicle group of 6-8 rats is included in each set of testing. Rats are dosed once according to body weight with a 0.01-3 mg/kg solution administered intraperitoneally (ip), orally (po) or subcutaneously (sc). The time of dosing is recorded for each group. After dosing, the rats are returned to their home cages, where they then have access to food and water. The food consumption is recorded individually continuously by on-line registration or manually every hour for 7 hours, and then after 24 h and sometimes 48 h. At the end of the experimental session, the animals are euthanized.

The individual data are recorded in Microsoft excel sheets. Outliers are excluded after applying the Grubbs statistical evaluation test for outliers, and the result is presented graphically using the GraphPad Prism program.

Pharmacological Assay (II)—Experimental Protocol for Efficacy Testing on Appetite with an Amylin Derivative, Using a Schedule Fed Rat Model.

TAC:SPRD @mol rats or Wistar rats from M&B Breeding and Research Centre A/S, Denmark are used for the experiments. The rats have a body weight 200-250 g at the start of experiment. The rats arrive at least 10-14 days before start of experiment with a body weight of 180-200 g. Each dose of derivative is tested in a group of 6-8 rats. A vehicle group of 6-8 rats is included in each set of testing.

When the animals arrive they are housed individually. At least 7 days prior to onset of study the will start training to a feeding schedule allowing them to have free access to food and water in a scheduled time period between 3 and 7 h. In the remaining period of the day, the rats will not have access to food, but only water. Within a week rats will eat the complete daily ration in the set schedule. Since rats normally initiate food intake when light is removed, and eat the major part of their daily food intake during the night, this set up results allow for monitoring of food intake during day time and will typically mean less variation in the vehicle group compared to an ad libitum fed rat. During the acclimatization period of 10-14 days, the rats have free access to food and water. During this period the animals are handled at least 3 times. The experiment is conducted in the rats' home cages. Immediately before dosing the rats are randomised to the various treatment groups (n=6-8) by body weight. They are dosed according to body weight at between 15 to 30 min prior to given access to food with a 0.01-3 mg/kg solution administered intraperitoneally (ip), orally (po) or subcutaneously (sc). The time of dosing is recorded for each group. After dosing, the rats are returned to their home cages, where they then have access to food and water. The food consumption is recorded individually continuously by on-line registration or manually every hour during the schedule. At the end of the experimental session, the animals are euthanized.

The individual data are recorded in Microsoft excel sheets. Outliers are excluded after applying the Grubbs statistical evaluation test for outliers, and the result is presented graphically using the GraphPad Prism program.

Luciferase Assay (III)

1. Amylin Assay Outline

It has previously been published (Poyner D R et al 2002, Pharmacological Reviews 54(2) 233-246) that activation of Amylin receptors (coexpression of Calcitonin receptor and receptor activity modifying peptides RAMPs) by Amylin leads to an increase in the intracellular concentration of cAMP. Consequently, transcription is activated at promoters containing multiple copies of the cAMP response element (CRE). It is thus possible to measure Amylin activity by use of a CRE luciferase reporter gene introduced into BHK cells also expressing an Amylin receptor.

2. Construction of an Amylin 3(a)/CRE-luc Cell Line

A BHK570 cell line stably transfected with the human calcitonin receptor (CTa) and a CRE-responsive luciferase reportergene. The cell line was further transfected with RAMP-3, using standard methods. This turns the Calcitonin receptor into an Amylin 3(a) receptor. Methotrexate, Neomycin, and Hygromycin are selection markers for luciferase, the Calcitonin receptor, and RAMP-3, respectively.

3. Amylin Luciferase Assay

To perform activity assays, BHK Amylin 3(a)//CRE-luc cells were seeded in white 96 well culture plates at a density of about 20,000 cells/well. The cells were in 100 µl growth medium (DMEM with 10% FBS, 1% Pen/Strep, 1 mM Na-pyruvate, 250 nM Methotrexate, 500 µg/ml Neomycin, and 400 µg/ml Hygromycin). After incubation overnight at 37° C. and 5% $CO_2$, the growth medium was replaced by 50 µl/well assay medium (DMEM (without phenol red), Glumamax™, 10% FBS, and 10 mM Hepes, pH 7,4). Further, 50 µl/well of standard or sample in assay buffer were added. After 4 hours incubation at 37° C. and 5% $CO_2$, the assay medium with standard or sample were removed and replaced by 100 µl/well PBS. Further, 100 µl/well LucLite™ was added. The plates were sealed and incubated at room temperature for 30 minutes. Finally, luminescence was measured on a TopCounter (Packard) in SPC (single photon counting) mode.

Assay (IV) General Introduction to Tht Fibrillation Assays for the Assessment of Physical Stability of Protein Formulations Low physical stability of a peptide may lead to amyloid fibril formation, which is observed as well-ordered, thread-like macromolecular structures in the sample eventually resulting in gel formation. This has traditionally been measured by visual inspection of the sample. However, that kind of measurement is very subjective and depending on the observer. Therefore, the application of a small molecule indicator probe is much more advantageous. Thioflavin T (ThT) is such a probe and has a distinct fluorescence signature when binding to fibrils [Naiki et al. (1989) Anal. Biochem. 177, 244-249; LeVine (1999) Methods. Enzymol. 309, 274-284].

The time course for fibril formation can be described by a sigmoidal curve with the following expression [Nielsen et al. (2001) Biochemistry 40, 6036-6046]:

$$F = f_i + m_i t + \frac{f_f + m_f t}{1 + e^{-[(t-t_0)/\tau]}} \qquad \text{Eq. (1)}$$

Figure 43:
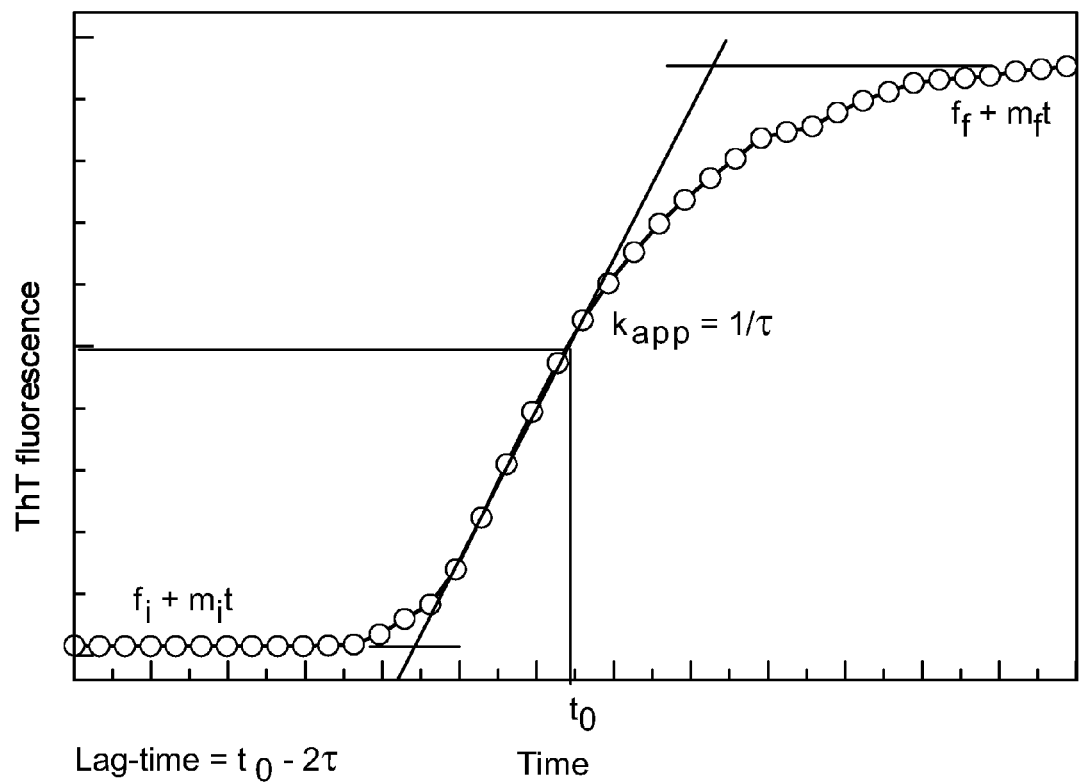
FIG. 43 shows Thioflavin T (ThT) fluorescence according to Pharmacological Assay (IV) as a function of time.

Here, F is the ThT fluorescence at the time t, as shown in FIG. 43. The constant $t_0$ is the time needed to reach 50% of maximum fluorescence. The two important parameters describing fibril formation are the lag-time calculated by $t_0 - 2\tau$ and the apparent rate constant $k_{app} = 1/\tau$.

Formation of a partially folded intermediate of the peptide is suggested as a general initiating mechanism for fibrillation. Few of those intermediates nucleate to form a template onto which further intermediates may assembly and the fibrillation proceeds. The lag-time corresponds to the interval in which the critical mass of nucleus is built up and the apparent rate constant is the rate with which the fibril itself is formed.

Sample Preparation

Samples were prepared freshly before each assay. Each sample composition is described in each example. The pH of the sample was adjusted to the desired value using appropriate amounts of concentrated NaOH and $HClO_4$ or HCl. Thioflavin T was added to the samples from a stock solution in $H_2O$ to a final concentration of 1 µM.

Sample aliquots of 200 µl were placed in a 96 well microtiter plate (Packard OptiPlate™-96, white polystyrene). Usually, four or eight replica of each sample (corresponding to one test condition) were placed in one column of wells. The plate was sealed with Scotch Pad (Qiagen).

Incubation and Fluorescence Measurement

Incubation at given temperature, shaking and measurement of the ThT fluorescence emission were done in a Fluoroskan Ascent FL fluorescence platereader or Varioskan platereader (Thermo Labsystems). The temperature was adjusted to 37° C. The orbital shaking was adjusted to 960 rpm with an amplitude of 1 mm in all the presented data. Fluorescence measurement was done using excitation through a 444 nm filter and measurement of emission through a 485 nm filter.

Each run was initiated by incubating the plate at the assay temperature for 10 min. The plate was measured every 20 minutes for a desired period of time. Between each measurement, the plate was shaken and heated as described.

Data Handling

The measurement points were saved in Microsoft Excel format for further processing and curve drawing and fitting was performed using Graph Pad Prism. The background emission from ThT in the absence of fibrils was negligible. The data points are typically a mean of four or eight samples and shown with standard deviation error bars. Only data obtained in the same experiment (i.e. samples on the same plate) are presented in the same graph ensuring a relative measure of fibrillation between experiments.

The data set may be fitted to Eq. (1). However, since full sigmodial curves in this case are not always achieved during the measurement time, the degree of fibrillation is expressed as ThT fluorescence tabulated as the mean of the samples and shown with the standard deviation at various time points.

Assay (V) PK—Determination OF T½ in Mini-Pig

T½ is the terminal half-life=ln $2/\lambda_z$ of a compound in plasma. $\lambda_z$ is the first order rate constant associated with the terminal (log-linear) portion of the plasma concentration-time curve and is estimated by linear regression of time vs. log concentration.

T½ values of the amylin analogues of the invention is determined by pharmacokinetic studies in male Göttingen mini-pigs from Ellegaard Göttingen Minipigs ApS and the principles of laboratory animal care are followed.

An acclimatization period of approximately 6-10 days was allowed before the animals entered the study. At start of the acclimatization period the mini-pigs were about 5 to 12 months old and in the weight range of 7-35 kg. The mini-pigs had two central venous catheters inserted which were used for blood sampling.

The studies were conducted in an animal room which was illuminated to give a cycle of approx 12 hours light and 12 hours darkness. The animals were housed individually.

The animals had free access to domestic quality drinking water during the study, but were typically fasted from overnight before dosing until approx 6-12 hours after dosing. The animals were weighed on arrival and on the days of dosing.

In the present studies the test substances were administered subcutaneously in approx 2 nmol/kg dose. The animals received a single subcutaneous injection. The subcutaneous injection was given on the right side of the neck, approximately 5-7 cm from the ear and 7-9 cm from the middle of the neck. The injections were given with a stopper on the needle, allowing approx 0.5 cm of the needle to be introduced. Each test substance was given to typically three but in some cases two or four animals.

A full plasma concentration-time profile, employing 12-16 sampling points, was obtained from each animal. In example blood samples were collected according to the following schedule:

After subcutaneous administration:

Predose (0), 0.5, 1, 2, 4, 6, 8, 12, 24, 48, 72, 96, 120, 168 and 240 hours after injection. In some cases also additional blood samples up to 288 hours post injection were taken.

At each sampling time, 0.5 to 2 ml of blood was drawn from each animal. The blood samples were taken via the central venous catheter.

The blood samples were collected into EDTA test tubes (i.e. Sarstedt Micro tube 1.3 mL K3E). Blood samples were kept on ice for max 20 min. before centrifugation. Plasma was separated using centrifugation (i.e. at 4° C., 10 min., 1500 G) and was immediately transferred to Micronic tubes. Approximately 200 µl plasma was transferred to each Micronic tube. The plasma was stored at −20° C. until assayed. The plasma samples were assayed for the content of amylin using an ELISA assay.

The plasma concentration-time profiles were analysed by a non-compartmental pharmacokinetic analysis (NCA) using WinNonlin Professional 5.0 (Pharsight Inc., Mountain View, Calif., USA). NCA was performed using the individual plasma concentration-time profiles from each animal. T½ is the terminal half-life=ln $2/\lambda_z$ and was determined from $\lambda_z$, the first order rate constant associated with the terminal (log-linear) portion of the curve, estimated by linear regression of time vs. log concentration.

ELISA Plasma Assay for Amylin Quantification

The human amylin ELISA is a monoclonal antibody-based sandwich immunoassay for determining amylin levels in human plasma. The capture antibody recognizes human amylin, amylin acid (deamidated amylin), a 1-20 fragment of amylin, but not reduced amylin.

The detection antibody binds to reduced or unreduced human amylin but not amylin acid and is complexed with streptavidin-alkaline phosphatase. The substrate, 4-methylumbelliferyl phosphate, is applied to the completed sandwich and the fluorescent signal, monitored at 355 nm/460 nm, is proportional to the amount of amylin present in the sample.

Assay (VI) PK—Determination OF T½ in Rat

T½ is the terminal half-life=ln $2/\lambda_z$ of a compound in plasma. $\lambda_z$ is the first order rate constant associated with the terminal (log-linear) portion of the plasma concentration-time curve and is estimated by linear regression of time vs. log concentration.

T½ values of the amylin analogues of the invention is determined by pharmacokinetic studies in Sprague Dawley male rats, from Taconic Europe and the principles of laboratory animal care are followed.

An acclimatization period of approximately 7 days was allowed before the animals entered the study. At start of the acclimatization period the rats were in the weight range of 300-400 g. The rats had permanent catheters inserted in a. carotis which were used for blood sampling.

The studies were conducted in an animal room which was illuminated to give a cycle of approx 12 hours light and 12 hours darkness. The animals were housed individually due to the catheters and had food and water ad lib. The animals were weighed on the days of dosing.

In the present studies the test substances were administered subcutaneously in approx 20 nmol/kg dose. The animals received a single subcutaneous injection to the neck using a 25 G needle with syringe. Each test substance was given to typically three but in some cases two or four animals.

A full plasma concentration-time profile, employing 8-10 sampling points, was obtained from each animal. In example blood samples were collected according to the following schedule:

After subcutaneous administration:

Predose (0), 0.5, 1, 1.5, 2, 4, 6, 12, 24, 48 and 72 hours after injection. At each sampling time, 0.08 to 0.10 ml of blood was drawn from each animal. The blood samples were taken via the catheter.

The blood samples were collected into EDTA test tubes. Blood samples were kept on ice for max 20 min. before centrifugation. Plasma was separated using centrifugation (i.e. at 4° C., 10 min., 1500 G) and was immediately transferred to Micronic tubes or PCR plates. Approximately 40 µl plasma was transferred and was stored at −20° C. until assayed. The plasma samples were assayed for the content of amylin using an ELISA assay.

The plasma concentration-time profiles were analysed by a non-compartmental pharmacokinetic analysis (NCA) using WinNonlin Professional 5.0 (Pharsight Inc., Mountain View, Calif., USA). NCA was performed using the individual plasma concentration-time profiles from each animal. T½ is the terminal half-life=ln 2/$\lambda_z$ and was determined from $\lambda_z$, the first order rate constant associated with the terminal (log-linear) portion of the curve, estimated by linear regression of time vs. log concentration.

ELISA Plasma Assay for Amylin Quantification

The human amylin ELISA is a monoclonal antibody-based sandwich immunoassay for determining amylin levels in human plasma. The capture antibody recognizes human amylin, amylin acid (deamidated amylin), a 1-20 fragment of amylin, but not reduced amylin. The detection antibody binds to reduced or unreduced human amylin but not amylin acid and is complexed with streptavidin-alkaline phosphatase. The substrate, 4-methylumbelliferyl phosphate, is applied to the completed sandwich and the fluorescent signal, monitored at 355 nm/460 nm, is proportional to the amount of amylin present in the sample.

Assay (VII)—Determination of Solubility

Solubility versus pH curves were measured in the following way. A formulation was prepared and aliquotes were adjusted to pH values in the desired range by adding $HClO_4$ or HCl and NaOH. These samples were left equilibrating at room temperature for 2-3 days. Then the samples were centrifuged. A small aliquot of each sample was withdrawn for reverse HPLC analysis for determination of the concentration of the proteins in solution. The pH of each sample was measured after the centrifugation, and the concentration of each protein was depicted versus the measured pH.

The invention claimed is:

1. A derivative of amylin, which is a human amylin analogue, wherein the human amylin analogue comprises an amino acid sequence of formula 1:

$Xaa_1$-Cys- $Xaa_3$-Thr-Ala-Thr-Cys-Ala-Thr-Gln-Arg-Leu-Ala- $Xaa_{14}$-Phe-Leu- $Xaa_{17}$-$Xaa_{18}$-Ser-Ser-$Xaa_{21}$-Asn- Phe- $Xaa_{24}$- $Xaa_{25}$- $Xaa_{26}$-Leu-$Xaa_{28}$-$Xaa_{29}$-Thr- $Xaa_{31}$-Val-Gly-Ser-Asn-Thr-Tyr    Formula (1) (SEQ ID No:2)

wherein $Xaa_1$ is deleted or independently selected from Lys, Arg, His and Glu;

$Xaa_3$ is independently selected from Asn and Lys;

$Xaa_{14}$ is independently selected from Glu, Asn, Gln and Asp;

$Xaa_{17}$ is independently selected from His, Ser, Gly, Arg and Pro;

$Xaa_{18}$ is independently selected from His or Arg;

$Xaa_{21}$ is independently selected from Asp, Asn and Gln;

$Xaa_{24}$ is independently selected from Glu and Gly;

$Xaa_{25}$ is independently selected from Ala and Pro;

$Xaa_{26}$ is independently selected from Pro and Ile;

$Xaa_{28}$ is independently selected from Ser and Pro;

$Xaa_{29}$ is independently selected from Ser and Pro;

$Xaa_{31}$ is independently selected from Glu and Asn;

the C-terminal may optionally be derivatized as an amide;

wherein a substituent is connected to the amino acid residue $Xaa_1$ or to Cys in position 2, which substituent comprises an albumin binding moiety.

2. A pharmaceutical composition comprising a derivative according to claim 1, and a pharmaceutically acceptable excipient.

3. A process for preparing a pharmaceutical composition comprising mixing a derivative according to claim 1 with at least one pharmaceutically acceptable excipient.

4. The derivative according to claim 1, wherein the amino acids in position 25, 28 and 29 are Pro.

5. The derivative according to claim 1, wherein the substituent comprises a linker.

6. The derivative according to claim 5, wherein the linker comprises amino acids selected from the group consisting of γGlu, Arg, γGlu-Arg, γGlu-His, Trx-γGlu, γGlu-His, Glu-Lys, Glu-Glu, Glu-Arg, γGlu-His-His, γGlu-Arg-His, γGlu-His-Arg, γGlu-Glu-Arg, Glu-Glu-Arg, Glu-Lys-Arg, γGlu-Glu-His-His (SEQ ID: 36), γGlu-Glu-His-Arg (SEQ ID: 37), Glu-Glu-Arg-Glu (SEQ ID: 38) and Glu-Glu-Glu-Glu (SEQ ID: 39).

7. The derivative according to 6, wherein the linker comprises —C(O)—$(CH_2)_l$—O—[$CH_2CH_2$—O]$_m$—$(CH_2)_p$-[NHC(O)—$(CH_2)_l$—O—[$(CH_2)_n$—O]$_m$—$(CH_2)_p$]$_q$—NH— wherein l, m, n, and p independently are 1-7, and q is 0-5.

8. The derivative according to claim 1, wherein the albumin binding moiety is an acyl group selected from the group comprising HOOC$(CH_2)_s$CO—, wherein s is an integer from 17 to 21.

9. The derivative according to claim 8, wherein s is 18.

10. The derivative according to claim 8, wherein s is 19.

11. The derivative according to claim 8, wherein s is 20.

* * * * *

```
                        SEQUENCE LISTING

<160> NUMBER OF SEQ ID NOS: 39

<210> SEQ ID NO 1
<211> LENGTH: 37
<212> TYPE: PRT
<213> ORGANISM: Homo sapiens

<400> SEQUENCE: 1

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Ser Thr Asn Val
            20                  25                  30

Gly Ser Asn Thr Tyr
        35

<210> SEQ ID NO 2
<211> LENGTH: 37
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Xaa1 is deleted or independently selected from
      Lys, Arg, His and Glu
<220> FEATURE:
<221> NAME/KEY: MISC_FEATURE
<222> LOCATION: (3)..(3)
<223> OTHER INFORMATION: Xaa3 is independently selected from Asn and Lys
<220> FEATURE:
<221> NAME/KEY: MISC_FEATURE
<222> LOCATION: (14)..(14)
<223> OTHER INFORMATION: Xaa14 is independently selected from Glu, Asn,
      Gln and Asp
<220> FEATURE:
<221> NAME/KEY: MISC_FEATURE
<222> LOCATION: (17)..(17)
<223> OTHER INFORMATION: Xaa17 is independently selected from His, Ser,
      Gly, Arg and Pro
<220> FEATURE:
<221> NAME/KEY: MISC_FEATURE
<222> LOCATION: (18)..(18)
<223> OTHER INFORMATION: Xaa18 is independently selected from His or Arg
<220> FEATURE:
<221> NAME/KEY: MISC_FEATURE
<222> LOCATION: (21)..(21)
<223> OTHER INFORMATION: Xaa21 is independently selected from Asp, Asn
      and Gln
<220> FEATURE:
<221> NAME/KEY: MISC_FEATURE
<222> LOCATION: (24)..(24)
<223> OTHER INFORMATION: Xaa24 is independently selected from Glu and
```

```
                Gly
<220> FEATURE:
<221> NAME/KEY: MISC_FEATURE
<222> LOCATION: (25)..(25)
<223> OTHER INFORMATION: Xaa25 is independently selected from Ala and
      Pro
<220> FEATURE:
<221> NAME/KEY: MISC_FEATURE
<222> LOCATION: (26)..(26)
<223> OTHER INFORMATION: Xaa26 is independently selected from Pro and
      Ile
<220> FEATURE:
<221> NAME/KEY: MISC_FEATURE
<222> LOCATION: (28)..(28)
<223> OTHER INFORMATION: Xaa28 is independently selected from Ser and
      Pro
<220> FEATURE:
<221> NAME/KEY: MISC_FEATURE
<222> LOCATION: (29)..(29)
<223> OTHER INFORMATION: Xaa29 is independently selected from Ser and
      Pro
<220> FEATURE:
<221> NAME/KEY: MISC_FEATURE
<222> LOCATION: (31)..(31)
<223> OTHER INFORMATION: Xaa31 is independently selected from Glu and
      Asn

<400> SEQUENCE: 2

Xaa Cys Xaa Thr Ala Thr Cys Ala Thr Gln Arg Leu Ala Xaa Phe Leu
1               5                   10                  15

Xaa Xaa Ser Ser Xaa Asn Phe Xaa Xaa Xaa Leu Xaa Xaa Thr Xaa Val
            20                  25                  30

Gly Ser Asn Thr Tyr
            35

<210> SEQ ID NO 3
<211> LENGTH: 36
<212> TYPE: PRT
<213> ORGANISM: Artificial Sequence
<220> FEATURE:
<223> OTHER INFORMATION: synthetic peptide

<400> SEQUENCE: 3

Cys Asn Thr Ala Thr Cys Ala Thr Gln Arg Leu Ala Asp Phe Leu His
1               5                   10                  15

His Ser Ser Asn Asn Phe Gly Pro Ile Leu Pro Pro Thr Asn Val Gly
            20                  25                  30

Ser Asn Thr Tyr
            35

<210> SEQ ID NO 4
<211> LENGTH: 36
<212> TYPE: PRT
<213> ORGANISM: Artificial Sequence
<220> FEATURE:
<223> OTHER INFORMATION: synthetic peptide

<400> SEQUENCE: 4

Cys Asn Thr Ala Thr Cys Ala Thr Gln Arg Leu Ala Asn Phe Leu Ala
1               5                   10                  15

His Ser Ser Asn Asn Phe Gly Pro Ile Leu Pro Pro Thr Asn Val Gly
            20                  25                  30

Ser Asn Thr Tyr
            35

<210> SEQ ID NO 5
<211> LENGTH: 36
```

```
<212> TYPE: PRT
<213> ORGANISM: Artificial Sequence
<220> FEATURE:
<223> OTHER INFORMATION: synthetic peptide

<400> SEQUENCE: 5

Cys Asn Thr Ala Thr Cys Ala Thr Gln Arg Leu Ala Asn Phe Leu Gly
1               5                   10                  15

His Ser Ser Asn Asn Phe Gly Pro Ile Leu Pro Pro Thr Asn Val Gly
            20                  25                  30

Ser Asn Thr Tyr
        35

<210> SEQ ID NO 6
<211> LENGTH: 36
<212> TYPE: PRT
<213> ORGANISM: Artificial Sequence
<220> FEATURE:
<223> OTHER INFORMATION: synthetic peptide

<400> SEQUENCE: 6

Cys Asn Thr Ala Thr Cys Ala Thr Gln Arg Leu Ala Asn Phe Leu His
1               5                   10                  15

His Ser Ser Asn Asn Phe Glu Pro Ile Leu Pro Pro Thr Asn Val Gly
            20                  25                  30

Ser Asn Thr Tyr
        35

<210> SEQ ID NO 7
<211> LENGTH: 36
<212> TYPE: PRT
<213> ORGANISM: Artificial Sequence
<220> FEATURE:
<223> OTHER INFORMATION: synthetic peptide

<400> SEQUENCE: 7

Cys Asn Thr Ala Thr Cys Ala Thr Gln Arg Leu Ala Asn Phe Leu His
1               5                   10                  15

His Ser Ser Asn Asn Phe Gly Pro Ile Leu Pro Pro Thr Asp Val Gly
            20                  25                  30

Ser Asn Thr Tyr
        35

<210> SEQ ID NO 8
<211> LENGTH: 37
<212> TYPE: PRT
<213> ORGANISM: Artificial Sequence
<220> FEATURE:
<223> OTHER INFORMATION: synthetic peptide

<400> SEQUENCE: 8

Lys Cys Asn Thr Ala Thr Cys Ala Thr Gln Arg Leu Ala Asn Phe Leu
1               5                   10                  15

Ser His Ser Ser Asn Asn Phe Gly Pro Ile Leu Pro Pro Thr Asn Val
            20                  25                  30

Gly Ser Asn Thr Tyr
        35

<210> SEQ ID NO 9
<211> LENGTH: 36
<212> TYPE: PRT
<213> ORGANISM: Artificial Sequence
<220> FEATURE:
```

<223> OTHER INFORMATION: synthetic peptide

<400> SEQUENCE: 9

Cys Asn Thr Ala Thr Cys Ala Thr Gln Arg Leu Ala Asn Phe Leu His
1               5                   10                  15

His Ser Ser Asn Asn Phe Gly Pro Ile Leu Pro Pro Thr Asn Val Gly
            20                  25                  30

Ser Asn Thr Tyr
        35

<210> SEQ ID NO 10
<211> LENGTH: 36
<212> TYPE: PRT
<213> ORGANISM: Artificial Sequence
<220> FEATURE:
<223> OTHER INFORMATION: synthetic peptide

<400> SEQUENCE: 10

Cys Asn Thr Ala Thr Cys Ala Thr Gln Arg Leu Ala Asn Phe Leu His
1               5                   10                  15

His Ser Ser Asn Asn Phe Gly Pro Ile Leu Pro Pro Thr Asn Val Gly
            20                  25                  30

Ser Asn Thr Tyr
        35

<210> SEQ ID NO 11
<211> LENGTH: 36
<212> TYPE: PRT
<213> ORGANISM: Artificial Sequence
<220> FEATURE:
<223> OTHER INFORMATION: synthetic peptide

<400> SEQUENCE: 11

Cys Asn Thr Ala Thr Cys Ala Thr Gln Arg Leu Ala Asn Phe Leu Pro
1               5                   10                  15

His Ser Ser Asn Asn Phe Gly Pro Ile Leu Pro Pro Thr Asn Val Gly
            20                  25                  30

Ser Asn Thr Tyr
        35

<210> SEQ ID NO 12
<211> LENGTH: 36
<212> TYPE: PRT
<213> ORGANISM: Artificial Sequence
<220> FEATURE:
<223> OTHER INFORMATION: synthetic peptide

<400> SEQUENCE: 12

Cys Asn Thr Ala Thr Cys Ala Thr Gln Arg Leu Ala Asn Phe Leu Arg
1               5                   10                  15

His Ser Ser Asn Asn Phe Gly Pro Ile Leu Pro Pro Thr Asn Val Gly
            20                  25                  30

Ser Asn Thr Tyr
        35

<210> SEQ ID NO 13
<211> LENGTH: 36
<212> TYPE: PRT
<213> ORGANISM: Artificial Sequence
<220> FEATURE:
<223> OTHER INFORMATION: synthetic peptide

<400> SEQUENCE: 13

Cys Asn Thr Ala Thr Cys Ala Thr Gln Arg Leu Ala Asn Phe Leu Ser
1               5                   10                  15

His Ser Ser Asn Asn Phe Gly Pro Ile Leu Pro Pro Thr Asn Val Gly
            20                  25                  30

Ser Asn Thr Tyr
        35

<210> SEQ ID NO 14
<211> LENGTH: 37
<212> TYPE: PRT
<213> ORGANISM: Artificial Sequence
<220> FEATURE:
<223> OTHER INFORMATION: synthetic peptide

<400> SEQUENCE: 14

Glu Cys Asn Thr Ala Thr Cys Ala Thr Gln Arg Leu Ala Asp Phe Leu
1               5                   10                  15

His His Ser Ser Asn Asn Phe Gly Ala Pro Leu Ser Ser Thr Asn Val
            20                  25                  30

Gly Ser Asn Thr Tyr
            35

<210> SEQ ID NO 15
<211> LENGTH: 37
<212> TYPE: PRT
<213> ORGANISM: Artificial Sequence
<220> FEATURE:
<223> OTHER INFORMATION: synthetic peptide

<400> SEQUENCE: 15

Glu Cys Asn Thr Ala Thr Cys Ala Thr Gln Arg Leu Ala Asp Phe Leu
1               5                   10                  15

His His Ser Ser Gln Asn Phe Gly Ala Pro Leu Ser Ser Thr Asn Val
            20                  25                  30

Gly Ser Asn Thr Tyr
            35

<210> SEQ ID NO 16
<211> LENGTH: 37
<212> TYPE: PRT
<213> ORGANISM: Artificial Sequence
<220> FEATURE:
<223> OTHER INFORMATION: synthetic peptide

<400> SEQUENCE: 16

Glu Cys Asn Thr Ala Thr Cys Ala Thr Gln Arg Leu Ala Glu Phe Leu
1               5                   10                  15

His His Ser Ser Asn Asn Phe Gly Pro Ile Leu Pro Pro Thr Glu Val
            20                  25                  30

Gly Ser Asn Thr Tyr
            35

<210> SEQ ID NO 17
<211> LENGTH: 37
<212> TYPE: PRT
<213> ORGANISM: Artificial Sequence
<220> FEATURE:
<223> OTHER INFORMATION: synthetic peptide

<400> SEQUENCE: 17

Glu Cys Asn Thr Ala Thr Cys Ala Thr Gln Arg Leu Ala Asn Phe Leu
1               5                   10                  15

His His Ser Ser Asn Asn Phe Gly Pro Ile Leu Pro Pro Thr Asn Val
            20                  25                  30

Gly Ser Asn Thr Tyr
        35

<210> SEQ ID NO 18
<211> LENGTH: 37
<212> TYPE: PRT
<213> ORGANISM: Artificial Sequence
<220> FEATURE:
<223> OTHER INFORMATION: synthetic peptide

<400> SEQUENCE: 18

Glu Cys Asn Thr Ala Thr Cys Ala Thr Gln Arg Leu Ala Asn Phe Leu
1               5                   10                  15

His His Ser Ser Gln Asn Phe Gly Ala Pro Leu Ser Ser Thr Asn Val
            20                  25                  30

Gly Ser Asn Thr Tyr
        35

<210> SEQ ID NO 19
<211> LENGTH: 37
<212> TYPE: PRT
<213> ORGANISM: Artificial Sequence
<220> FEATURE:
<223> OTHER INFORMATION: synthetic peptide

<400> SEQUENCE: 19

Glu Cys Asn Thr Ala Thr Cys Ala Thr Gln Arg Leu Ala Asn Phe Leu
1               5                   10                  15

Arg His Ser Ser Asn Asn Phe Gly Ala Pro Leu Ser Ser Thr Asn Val
            20                  25                  30

Gly Ser Asn Thr Tyr
        35

<210> SEQ ID NO 20
<211> LENGTH: 37
<212> TYPE: PRT
<213> ORGANISM: Artificial Sequence
<220> FEATURE:
<223> OTHER INFORMATION: synthetic peptide

<400> SEQUENCE: 20

Glu Cys Asn Thr Ala Thr Cys Ala Thr Gln Arg Leu Ala Asn Phe Leu
1               5                   10                  15

Arg His Ser Ser Asn Asn Phe Gly Pro Ile Leu Pro Pro Thr Asn Val
            20                  25                  30

Gly Ser Asn Thr Tyr
        35

<210> SEQ ID NO 21
<211> LENGTH: 37
<212> TYPE: PRT
<213> ORGANISM: Artificial Sequence
<220> FEATURE:
<223> OTHER INFORMATION: synthetic peptide

<400> SEQUENCE: 21

His Cys Asn Thr Ala Thr Cys Ala Thr Gln Arg Leu Ala Asn Phe Leu
1               5                   10                  15

His His Ser Ser Asn Asn Phe Gly Pro Ile Leu Pro Pro Thr Asn Val
            20                  25                  30

Gly Ser Asn Thr Tyr
        35

<210> SEQ ID NO 22
<211> LENGTH: 37
<212> TYPE: PRT
<213> ORGANISM: Artificial Sequence
<220> FEATURE:
<223> OTHER INFORMATION: synthetic peptide

<400> SEQUENCE: 22

His Cys Asn Thr Ala Thr Cys Ala Thr Gln Arg Leu Ala Asn Phe Leu
1               5                   10                  15

His Arg Ser Ser Asn Asn Phe Gly Pro Ile Leu Pro Pro Thr Asn Val
            20                  25                  30

Gly Ser Asn Thr Tyr
        35

<210> SEQ ID NO 23
<211> LENGTH: 37
<212> TYPE: PRT
<213> ORGANISM: Artificial Sequence
<220> FEATURE:
<223> OTHER INFORMATION: synthetic peptide

<400> SEQUENCE: 23

His Cys Asn Thr Ala Thr Cys Ala Thr Gln Arg Leu Ala Asn Phe Leu
1               5                   10                  15

Arg His Ser Ser Asn Asn Phe Gly Pro Ile Leu Pro Pro Thr Asn Val
            20                  25                  30

Gly Ser Asn Thr Tyr
        35

<210> SEQ ID NO 24
<211> LENGTH: 37
<212> TYPE: PRT
<213> ORGANISM: Artificial Sequence
<220> FEATURE:
<223> OTHER INFORMATION: synthetic peptide

<400> SEQUENCE: 24

Lys Cys Lys Thr Ala Thr Cys Ala Thr Gln Arg Leu Ala Asn Phe Leu
1               5                   10                  15

His His Ser Ser Asp Asn Phe Gly Pro Ile Leu Pro Pro Thr Asn Val
            20                  25                  30

Gly Ser Asn Thr Tyr
        35

<210> SEQ ID NO 25
<211> LENGTH: 37
<212> TYPE: PRT
<213> ORGANISM: Artificial Sequence
<220> FEATURE:
<223> OTHER INFORMATION: synthetic peptide

<400> SEQUENCE: 25

Lys Cys Asn Thr Ala Thr Cys Ala Thr Gln Arg Leu Ala Asn Phe Leu
1               5                   10                  15

Ala His Ser Ser Asn Asn Phe Gly Pro Ile Leu Pro Pro Thr Asn Val
            20                  25                  30

Gly Ser Asn Thr Tyr
        35

```
<210> SEQ ID NO 26
<211> LENGTH: 37
<212> TYPE: PRT
<213> ORGANISM: Artificial Sequence
<220> FEATURE:
<223> OTHER INFORMATION: synthetic peptide

<400> SEQUENCE: 26

Lys Cys Asn Thr Ala Thr Cys Ala Thr Gln Arg Leu Ala Asn Phe Leu
1               5                   10                  15

Gly His Ser Ser Asn Asn Phe Gly Pro Ile Leu Pro Pro Thr Asn Val
            20                  25                  30

Gly Ser Asn Thr Tyr
        35

<210> SEQ ID NO 27
<211> LENGTH: 37
<212> TYPE: PRT
<213> ORGANISM: Artificial Sequence
<220> FEATURE:
<223> OTHER INFORMATION: synthetic peptide

<400> SEQUENCE: 27

Lys Cys Asn Thr Ala Thr Cys Ala Thr Gln Arg Leu Ala Asn Phe Leu
1               5                   10                  15

His His Ser Ser Asn Asn Phe Gly Pro Ile Leu Pro Pro Thr Asn Val
            20                  25                  30

Gly Ser Asn Thr Tyr
        35

<210> SEQ ID NO 28
<211> LENGTH: 37
<212> TYPE: PRT
<213> ORGANISM: Artificial Sequence
<220> FEATURE:
<223> OTHER INFORMATION: synthetic peptide

<400> SEQUENCE: 28

Lys Cys Asn Thr Ala Thr Cys Ala Thr Gln Arg Leu Ala Asn Phe Leu
1               5                   10                  15

Arg His Ser Ser Asn Asn Phe Gly Pro Ile Leu Pro Pro Thr Asn Val
            20                  25                  30

Gly Ser Asn Thr Tyr
        35

<210> SEQ ID NO 29
<211> LENGTH: 37
<212> TYPE: PRT
<213> ORGANISM: Artificial Sequence
<220> FEATURE:
<223> OTHER INFORMATION: synthetic peptide

<400> SEQUENCE: 29

Arg Cys Asn Thr Ala Thr Cys Ala Thr Gln Arg Leu Ala Asn Phe Leu
1               5                   10                  15

Ala His Ser Ser Asn Asn Phe Gly Pro Ile Leu Pro Pro Thr Asn Val
            20                  25                  30

Gly Ser Asn Thr Tyr
        35

<210> SEQ ID NO 30
```

```
<211> LENGTH: 37
<212> TYPE: PRT
<213> ORGANISM: Artificial Sequence
<220> FEATURE:
<223> OTHER INFORMATION: synthetic peptide

<400> SEQUENCE: 30

Arg Cys Asn Thr Ala Thr Cys Ala Thr Gln Arg Leu Ala Asn Phe Leu
1               5                  10                  15

His His Ser Ser Asn Asn Phe Gly Pro Ile Leu Pro Pro Thr Asn Val
            20                  25                  30

Gly Ser Asn Thr Tyr
        35

<210> SEQ ID NO 31
<211> LENGTH: 37
<212> TYPE: PRT
<213> ORGANISM: Artificial Sequence
<220> FEATURE:
<223> OTHER INFORMATION: synthetic peptide

<400> SEQUENCE: 31

Arg Cys Asn Thr Ala Thr Cys Ala Thr Gln Arg Leu Ala Asn Phe Leu
1               5                  10                  15

His His Ser Ser Gln Asn Phe Gly Pro Ile Leu Pro Pro Thr Asn Val
            20                  25                  30

Gly Ser Asn Thr Tyr
        35

<210> SEQ ID NO 32
<211> LENGTH: 37
<212> TYPE: PRT
<213> ORGANISM: Artificial Sequence
<220> FEATURE:
<223> OTHER INFORMATION: synthetic peptide

<400> SEQUENCE: 32

Lys Cys Asn Thr Ala Thr Cys Ala Thr Gln Arg Leu Ala Asn Phe Leu
1               5                  10                  15

Pro His Ser Ser Asn Asn Phe Gly Pro Ile Leu Pro Pro Thr Asn Val
            20                  25                  30

Gly Ser Asn Thr Tyr
        35

<210> SEQ ID NO 33
<211> LENGTH: 37
<212> TYPE: PRT
<213> ORGANISM: Artificial Sequence
<220> FEATURE:
<223> OTHER INFORMATION: synthetic peptide

<400> SEQUENCE: 33

Arg Cys Asn Thr Ala Thr Cys Ala Thr Gln Arg Leu Ala Asn Phe Leu
1               5                  10                  15

Arg His Ser Ser Asn Asn Phe Gly Pro Ile Leu Pro Pro Thr Asn Val
            20                  25                  30

Gly Ser Asn Thr Tyr
        35

<210> SEQ ID NO 34
<211> LENGTH: 37
<212> TYPE: PRT
<213> ORGANISM: Artificial Sequence
```

```
<220> FEATURE:
<223> OTHER INFORMATION: synthetic peptide

<400> SEQUENCE: 34

Arg Cys Asn Thr Ala Thr Cys Ala Thr Gln Arg Leu Ala Asn Phe Leu
1               5                   10                  15

Arg His Ser Ser Gln Asn Phe Gly Pro Ile Leu Pro Pro Thr Asn Val
            20                  25                  30

Gly Ser Asn Thr Tyr
        35

<210> SEQ ID NO 35
<211> LENGTH: 37
<212> TYPE: PRT
<213> ORGANISM: Artificial Sequence
<220> FEATURE:
<223> OTHER INFORMATION: synthetic peptide

<400> SEQUENCE: 35

Arg Cys Asn Thr Ala Thr Cys Ala Thr Gln Arg Leu Ala Asn Phe Leu
1               5                   10                  15

Ser His Ser Ser Asn Asn Phe Gly Pro Ile Leu Pro Pro Thr Asn Val
            20                  25                  30

Gly Ser Asn Thr Tyr
        35

<210> SEQ ID NO 36
<211> LENGTH: 4
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Xaa is gamma-Glu which forms the amide bonds to
      the two neighboring residues by alpha-nitrogen and gamma-carboxy
      group

<400> SEQUENCE: 36

Xaa Glu His His
1

<210> SEQ ID NO 37
<211> LENGTH: 4
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Xaa is gamma-Glu which forms the amide bonds to
      the two neighboring residues by alpha-nitrogen and gamma-carboxy
      group

<400> SEQUENCE: 37

Xaa Glu His Arg
1

<210> SEQ ID NO 38
<211> LENGTH: 4
<212> TYPE: PRT
<213> ORGANISM: Artificial Sequence
<220> FEATURE:
<223> OTHER INFORMATION: synthetic peptide
```

```
<400> SEQUENCE: 38

Glu Glu Arg Glu
1

<210> SEQ ID NO 39
<211> LENGTH: 4
<212> TYPE: PRT
<213> ORGANISM: Artificial Sequence
<220> FEATURE:
<223> OTHER INFORMATION: synthetic peptide

<400> SEQUENCE: 39

Glu Glu Glu Glu
1
```